United States Patent
Nissink et al.

(10) Patent No.: US 10,590,132 B2
(45) Date of Patent: *Mar. 17, 2020

(54) SELECTIVE ESTROGEN RECEPTOR DOWN-REGULATORS

(71) Applicant: AstraZeneca AB, Södertälje (SE)

(72) Inventors: Johannes Wilhelmus Maria Nissink, Cambridge (GB); James Stewart Scott, Cambridge (GB); Thomas Andrew Moss, Cambridge (GB); Samantha Jayne Hughes, Cambridge (GB); Bernard Christophe Barlaam, Cambridge (GB); Bin Yang, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/263,683

(22) Filed: Jan. 31, 2019

(65) Prior Publication Data

US 2019/0233413 A1 Aug. 1, 2019

Related U.S. Application Data

(63) Continuation of application No. 15/881,962, filed on Jan. 29, 2018, now Pat. No. 10,221,173.

(60) Provisional application No. 62/592,485, filed on Nov. 30, 2017, provisional application No. 62/560,304, filed on Sep. 19, 2017, provisional application No. 62/523,695, filed on Jun. 22, 2017, provisional application No. 62/451,971, filed on Jan. 30, 2017.

(51) Int. Cl.
| | |
|---|---|
| *C07D 471/04* | (2006.01) |
| *A61K 31/437* | (2006.01) |
| *A61K 31/407* | (2006.01) |
| *A61P 35/00* | (2006.01) |

(52) U.S. Cl.
CPC .......... *C07D 471/04* (2013.01); *A61K 31/407* (2013.01); *A61K 31/437* (2013.01); *A61P 35/00* (2018.01)

(58) Field of Classification Search
CPC ...... C07D 471/04; A61P 35/00; A61K 31/407
USPC ......................................................... 546/87
See application file for complete search history.

(56) References Cited

U.S. PATENT DOCUMENTS

| | | | |
|---|---|---|---|
| 2012/0157402 A1 | 6/2012 | Cao et al. | |
| 2014/0357661 A1* | 12/2014 | Bradbury | C07C 57/145 514/292 |
| 2016/0175289 A1* | 6/2016 | Labadie | A61K 31/565 514/171 |
| 2018/0021316 A1* | 1/2018 | Scott | A61K 31/407 514/411 |
| 2018/0111931 A1 | 4/2018 | Barlaam et al. | |

FOREIGN PATENT DOCUMENTS

| | | |
|---|---|---|
| CN | 106518768 A | 3/2017 |
| CN | 107814798 A | 3/2018 |
| WO | 2010138695 A1 | 12/2010 |
| WO | 2010138758 A1 | 12/2010 |
| WO | 2011156518 A2 | 12/2011 |
| WO | 2011159769 A2 | 12/2011 |
| WO | 2013090829 A1 | 6/2013 |
| WO | 2013090836 A1 | 6/2013 |
| WO | 2014191726 A1 | 12/2014 |
| WO | 2014205136 A1 | 12/2014 |
| WO | 2014205138 A1 | 12/2014 |
| WO | 2015092634 A1 | 6/2015 |
| WO | 2016097071 A1 | 6/2016 |
| WO | 2016097072 A1 | 6/2016 |
| WO | 2016097073 A1 | 6/2016 |
| WO | 2016174551 A1 | 11/2016 |
| WO | 2016189011 A1 | 12/2016 |
| WO | 2016202161 A1 | 12/2016 |
| WO | 2017059139 A1 | 4/2017 |
| WO | 2017080338 A1 | 5/2017 |
| WO | 2017080966 A1 | 5/2017 |
| WO | 2017107754 A1 | 6/2017 |
| WO | 2017174757 A1 | 10/2017 |
| WO | 2017192991 A1 | 11/2017 |
| WO | 2018001232 A1 | 1/2018 |
| WO | 2018053354 A1 | 3/2018 |

OTHER PUBLICATIONS

Chesworth et al., "Tetrahydroisoquinolines as subtype selective estrogen agonists/antagonists", Bioorg. and Med. Chem. Lett, 2004, 14(11), 2729-2733.
International Search Report for International Application No. PCT/EP2018/052040, dated Mar. 20, 2018.

* cited by examiner

*Primary Examiner* — Rita J Desai

(57) ABSTRACT

The specification relates to compounds of Formula (I):

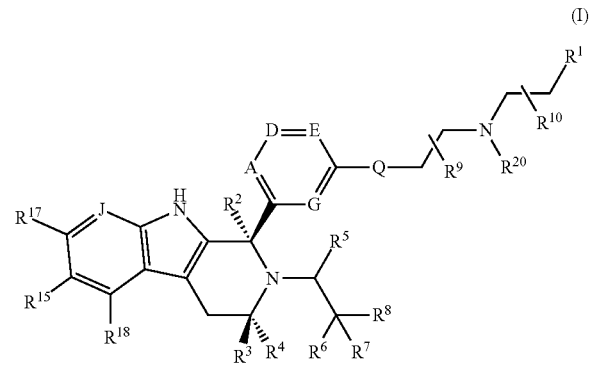

and to pharmaceutically acceptable salts thereof, to processes and intermediates used for their preparation, to pharmaceutical compositions containing them and to their use in the treatment of cell proliferative disorders.

12 Claims, No Drawings

SELECTIVE ESTROGEN RECEPTOR DOWN-REGULATORS

This specification relates to certain indole compounds and pharmaceutically acceptable salts thereof that selectively down-regulate the estrogen receptor and possess anti-cancer activity. This specification also relates to use of said indole compounds and pharmaceutically acceptable salts thereof in methods of treatment of the human or animal body, for example in prevention or treatment of cancer. This specification also relates to processes and intermediate compounds involved in the preparation of said indole compounds and to pharmaceutical compositions containing them.

Estrogen receptor alpha (ERα, ESR1, NR3A) and estrogen receptor beta (ERβ, ESR2, NR3b) are steroid hormone receptors which are members of the large nuclear receptor family.

Structured similarly to all nuclear receptors, ERα is composed of six functional domains (named A-F) (Dahlman-Wright, et al., *Pharmacol. Rev.*, 2006, 58:773-781) and is classified as a ligand-dependent transcription factor because after its association with the specific ligand, (the female sex steroid hormone 17b estradiol (E2)), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains a N-terminal (A/B) domain, a hinge (D) domain that links the C and E domains and a C-terminal extension (F domain). While the C and E domains of ERα and ERβ are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerisation, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., *Pure Applied Chemistry* 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., *Mol. Endocrinology*, 1994, 8:21-30). Although ERs are considered transcription factors they can also act through non-genomic mechanisms as evidenced by rapid ER effects in tissues following E2 administration in a timescale that is considered too fast for a genomic action. It is still unclear if receptors responsible for the rapid actions of estrogen are the same nuclear ERs or distinct G-protein coupled steroid receptors (Warner, et al., *Steroids* 2006 71:91-95) but an increasing number of E2 induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser 118 by MAPK in response to growth factors such as IGF-1 and EGF (Kato, et al., *Science*, 1995, 270:1491-1494).

A large number of structurally distinct compounds have been shown to bind to ER. Some compounds such as endogenous ligand E2, act as receptor agonists whereas others competitively inhibit E2 binding and act as receptor antagonists. These compounds can be divided into 2 classes depending on their functional effects. Selective estrogen receptor modulators (SERMs) such as tamoxifen have the ability to act as both receptor agonists and antagonists depending on the cellular and promoter context as well as the ER isoform targeted. For example tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., *Cancer Res.*, 1991, 51:3867-3873; Pike, et al., *Structure*, 2001, 9:145-153).

Intracellular levels of ERα are down-regulated in the presence of E2 through the ubiquitin/proteasome (Ub/26S) pathway. Polyubiquitinylation of liganded ERα is catalysed by at least three enzymes; the ubiquitin-activating enzyme E1 activated ubiquitin is conjugated by E2 with lysine residues through an isopeptide bond by E3 ubiquitin ligase and polyubiquitinated ERα is then directed to the proteasome for degradation. Although ER-dependent transcription regulation and proteasome-mediated degradation of ER are linked (Lonard, et al., *Mol. Cell,* 2000 5:939-948), transcription in itself is not required for ERα degradation and assembly of the transcription initiation complex is sufficient to target ERα for nuclear proteasomal degradation. This E2 induced degradation process is believed to necessary for its ability to rapidly activate transcription in response to requirements for cell proliferation, differentiation and metabolism (Stenoien, et al., *Mol. Cell Biol.*, 2001, 21:4404-4412). Fulvestrant is also classified as a selective estrogen receptor down-regulator (SERD), a subset of antagonists that can also induce rapid down-regulation of ERα via the 26S proteasomal pathway. In contrast a SERM such as tamoxifen can increase ERα levels although the effect on transcription is similar to that seen for a SERD.

Approximately 70% of breast cancers express ER and/or progesterone receptors implying the hormone dependence of these tumour cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre and post menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumours express ER display de novo resistance to existing ER therapies or develop resistance to these therapies over time. Several distinct mechanisms have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex.

Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumour samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 *Nature* 490: 61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking to agonist activated wild type ER. Published data has shown that endocrine therapies such as tamoxifen and fulvestrant can still bind to ER mutant and inhibit transcriptional activation to some extent and that fulvestrant is capable of degrading Try537Ser but that higher doses may be needed for full receptor inhibition (Toy et al., *Nat. Genetics* 2013, 45: 1439-1445; Robinson et al., *Nat. Genetics* 2013, 45: 144601451; Li, S. et al. *Cell Rep.* 4, 1116-1130 (2013). It is therefore feasible that certain compounds of the Formula (I) or pharmaceutically acceptable salts thereof (as described hereinafter) will be capable of down-regulating and antagonising mutant ER although it is not known at this stage whether ESR1 mutations are associated with an altered clinical outcome.

Regardless of which resistance mechanism or combination of mechanisms takes place, many are still reliant on ER-dependent activities and removal of the receptor through a SERD mechanism offers the best way of removing the ERα receptor from the cell. Fulvestrant is currently the only SERD approved for clinical use, yet despite its mechanistic properties, the pharmacological properties of the drug have limited its efficacy due to the current limitation of a 500 mg monthly dose which results in less than 50% turnover of the receptor in patient samples compared to the complete downregulation of the receptor seen in in vitro breast cell line experiments (Wardell, et al., *Biochem. Pharm.*, 2011, 82:122-130). Hence there is a need for new ER targeting agents that have the required pharmaceutical properties and SERD mechanism to provide enhanced benefit in the early, metastatic and acquired resistance setting.

The compounds of the specification have been found to possess potent anti-tumour activity, being useful in inhibiting the uncontrolled cellular proliferation which arises from malignant disease. The compounds of the specification provide an anti-tumour effect by, as a minimum, acting as SERDs. For example, the compounds of the specification may exhibit anti-tumour activity via the ability to down-regulate the estrogen receptor in a number of different breast cancer cell-lines, for example against the MCF-7, CAMA-1, BT474 and/or MDA-MB-134 breast cancer cell-lines. Such compounds may be expected to be more suitable as therapeutic agents, particularly for the treatment of cancer.

The compounds of the specification may also exhibit advantageous physical properties (for example, lower lipophilicity, higher aqueous solubility, higher permeability, lower plasma protein binding, and/or greater chemical stability), and/or favourable toxicity profiles (for example a decreased activity at hERG), and/or favourable metabolic or pharmacokinetic profiles, in comparison with other known SERDs. Such compounds may therefore be especially suitable as therapeutic agents, particularly for the treatment of cancer.

According to one aspect of the specification there is provided a compound of Formula (I):

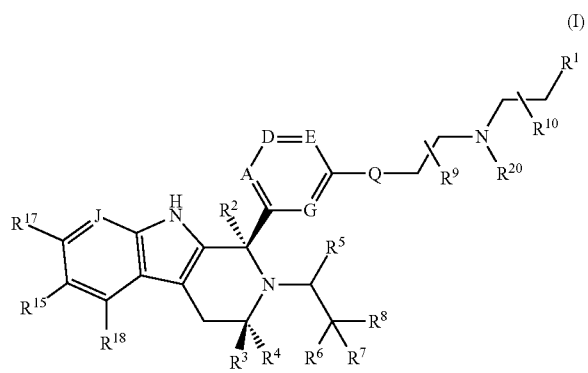

wherein:
A is $CR^{11}$ or N;
G is $CR^{12}$ or N;
D is $CR^{13}$ or N;

E is CR$^{14}$ or N;
J is CR$^{19}$ or N;
Q is O, NH or NMe;
R$^1$ is CH$_2$F, CHF$_2$ or CF$_3$;
R$^2$ is H, Me, CH$_2$F, CHF$_2$ or CF$_3$;
R$^3$ is H or Me;
R$^4$ is C$_{1-3}$ alkyl, CH$_2$F, CHF$_2$, CF$_3$, CH$_2$CH=CH$_2$, cyclopropyl or cyclobutyl;
R$^5$ is H, Me, CH$_2$F, CHF$_2$, CF$_3$, CN, CH$_2$CN, CH$_2$OMe, CH$_2$OH, COOH or CH$_2$SO$_2$Me;
R$^6$ is H, Me, F, CH$_2$F, CHF$_2$, CF$_3$, CN, CH$_2$CN, CH$_2$OMe, CH$_2$OH, COOH or SO$_2$Me;
R$^7$ is H, Me or F;
R$^8$ is H, Me or F; or
R$^7$ and R$^8$ taken together with the carbon atom to which they are attached form a cyclopropyl ring, a cyclobutyl ring, or an oxetane ring;
R$^9$ is H, Me, CH$_2$OH, CH$_2$OMe or F;
R$^{10}$ is H, Me, CH$_2$OH, CH$_2$OMe or F;
R$^{11}$ is H, F, Cl, CN, C$_{1-3}$ alkyl or O—C$_{1-3}$ alkyl (wherein the said C$_{1-3}$ alkyl groups are optionally substituted by a further group selected from OMe, OH, F and CN);
R$^{12}$ is H, F, Cl, CN, Me, OMe or CHF$_2$;
R$^{13}$ is H, F, Cl, CN, Me or OMe;
R$^{14}$ is H, F, Cl, CN, Me or OMe;
R$^{15}$ is H, F, Cl or Me;
R$^{17}$ is H, F, Cl or Me;
R$^{18}$ is H, F, Cl or Me;
R$^{19}$ is H or F; and
R$^{20}$ is H or Me;
or a pharmaceutically acceptable salt thereof.

This specification also describes pharmaceutical compositions which comprise a compound of Formula (I), or a pharmaceutically acceptable salt thereof, in association with a pharmaceutically acceptable excipient.

This specification also describes a compound of Formula (I), or a pharmaceutically acceptable salt thereof, for use as a medicament.

This specification also describes a compound of Formula (I), or a pharmaceutically acceptable salt thereof, for use in the treatment of cancer.

This specification also describes combinations of a compound of Formula (I), or a pharmaceutically acceptable salt thereof, with another anti-tumour agent, for use in the treatment of cancer.

Further aspects of the specification will be apparent to one skilled in the art from reading this specification.

In one embodiment there is provided a compound of Formula (I) as defined above.

In one embodiment there is provided a pharmaceutically acceptable salt of a compound of Formula (I).

In one embodiment D is CH.
In one embodiment E is CH.
In one embodiment both D and E are CH.
In one embodiment both D and E are N.
In one embodiment one of D or E is CH and the other of D or E is N.
In one embodiment A is CR$^{11}$.
In one embodiment G is CR$^{12}$.
In one embodiment A is CR$^{11}$ and G is CR$^{12}$.
In one embodiment A is CR$^{11}$ and G is CH.
In one embodiment A is CH and G is CR$^{12}$.
In one embodiment A is CR$^{11}$ and D, E and G are all CH;
In one embodiment R$^{11}$ is independently selected from Me, Cl, F or OMe.
In one embodiment R$^{11}$ is independently selected from H, F, CN or OMe.
In one embodiment R$^{11}$ is independently selected from H or OMe.
In one embodiment R$^{11}$ is independently selected from H or F.
In one embodiment R$^{11}$ is independently selected from F, Cl or OMe.
In one embodiment R$^{11}$ is H.
In one embodiment R$^{11}$ is OMe.
In one embodiment R$^{11}$ is F.
In one embodiment R$^{11}$ is Me.
In one embodiment R$^{11}$ is Cl.
In one embodiment R$^{12}$ is independently selected from Me, Cl, F or CHF$_2$.
In one embodiment R$^{12}$ is independently selected from H, F, CN or OMe.
In one embodiment R$^{12}$ is independently selected from H or OMe.
In one embodiment R$^{12}$ is independently selected from H or F.
In one embodiment R$^{12}$ is independently selected from H, Me or F.
In one embodiment R$^{12}$ is H.
In one embodiment R$^{12}$ is OMe.
In one embodiment R$^{12}$ is Me.
In one embodiment R$^{12}$ is F.
In one embodiment A is CR$^{11}$ and R$^{11}$ is H, F, CN or OMe.
In one embodiment G is CR$^{12}$ and R$^{12}$ is H, F, CN or OMe.
In one embodiment A is CR$^{11}$ and R$^{11}$ is Cl, F or OMe.
In one embodiment G is CR$^{12}$ and R$^{12}$ is H, Me or F.
In one embodiment A is CH and G is CH.
In one embodiment A is C—F and G is C—F.
In one embodiment A is C—F and G is CH.
In one embodiment A is C—OMe and G is CH.
In one embodiment A is CH and G is C—OMe.
In one embodiment A is C—F and G is C-Me.
In one embodiment A is C—Cl and G is C—F.
In one embodiment Q is O or NH.
In one embodiment Q is O.
In one embodiment Q is NH.
In one embodiment Q is NMe.
In one embodiment R$^1$ is CH$_2$F or CHF$_2$.
In one embodiment R$^1$ is CH$_2$F.
In one embodiment R$^1$ is CHF$_2$.
In one embodiment R$^1$ is CF$_3$.
In one embodiment R$^2$ is H or Me.
In one embodiment R$^2$ is H.
In one embodiment R$^2$ is Me.
In one embodiment R$^3$ is H.
In one embodiment R$^3$ is Me.
In one embodiment R$^4$ is C$_{1-3}$ alkyl, CHF$_2$ or cyclopropyl.
In one embodiment R$^4$ is C$_{1-3}$ alkyl or CHF$_2$.
In one embodiment R$^4$ is C$_{1-3}$ alkyl, CF$_3$ or CHF$_2$.
In one embodiment R$^4$ is C$_{1-3}$ alkyl.
In one embodiment R$^4$ is Me.
In one embodiment R$^3$ is H and R$^4$ is Me.
In one embodiment R$^4$ is CHF$_2$.
In one embodiment R$^4$ is CF$_3$.
In one embodiment R$^5$ is H or Me.
In one embodiment R$^5$ is H.
In one embodiment R$^5$ is Me.
In one embodiment R$^6$ is H, Me, F, CH$_2$F, CH$_2$OMe, CH$_2$OH, COOH or SO$_2$Me.
In one embodiment R$^6$ is H, F or CH$_2$OH.
In one embodiment R$^6$ is F.
In one embodiment R$^6$ is CH$_2$OH.
In one embodiment R$^6$ is COOH.

In one embodiment $R^7$ is H.
In one embodiment $R^7$ is Me.
In one embodiment $R^7$ is F.
In one embodiment $R^8$ is Me or F.
In one embodiment $R^8$ is Me.
In one embodiment $R^8$ is F.
In one embodiment $R^8$ is H.
In one embodiment $R^6$ is F or CH$_2$OH and $R^7$ is H.
In one embodiment $R^6$ is F or CH$_2$OH and $R^7$ is F.
In one embodiment $R^7$ is H and $R^8$ is F.
In one embodiment $R^7$ is F and $R^8$ is F.
In one embodiment $R^6$ is F and $R^7$ and $R^8$ taken together with the carbon atom to which they are attached form a cyclopropyl ring, or a cyclobutyl ring, or an oxetane ring.
In one embodiment $R^6$ is F and $R^7$ and $R^8$ taken together with the carbon atom to which they are attached form a cyclopropyl ring or an oxetane ring.
In one embodiment $R^6$ is F and $R^7$ and $R^8$ taken together with the carbon atom to which they are attached form a cyclopropyl ring.
In one embodiment $R^6$ is F and $R^7$ and $R^8$ taken together with the carbon atom to which they are attached form a cyclobutyl ring.
In one embodiment $R^6$ is F and $R^7$ and $R^8$ taken together with the carbon atom to which they are attached form an oxetane ring.

In one embodiment the group —CH($R^5$)—C($R^6$)($R^7$)($R^8$) in the compound of Formula (I) is selected from the group consisting of:

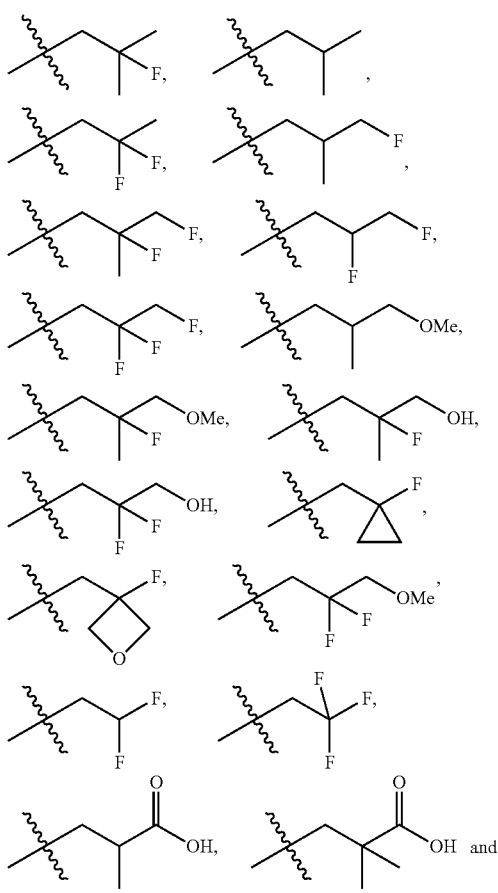

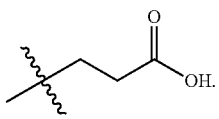

In one embodiment the group —CH($R^5$)—C($R^6$)($R^7$)($R^8$) in the compound of Formula (I) is selected from the group consisting of:

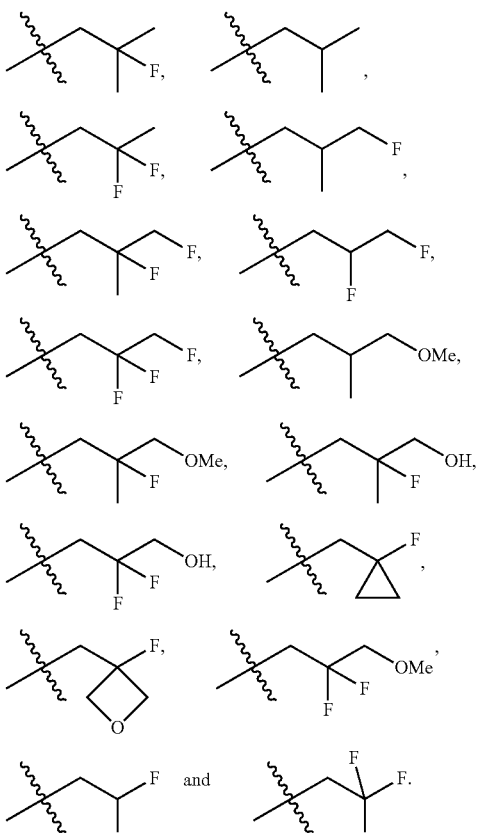

In one embodiment the group —CH($R^5$)—C($R^6$)($R^7$)($R^8$) in the compound of Formula (I) is selected from the group consisting of:

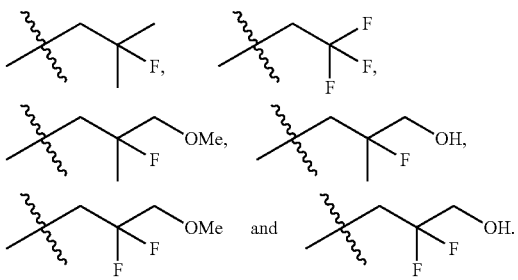

In one embodiment the group —CH($R^5$)—C($R^6$)($R^7$)($R^8$) in the compound of Formula (I) is selected from the group consisting of:

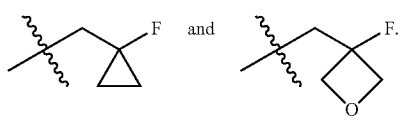 [SMILES: *CC1(F)CC1 ; "and" ; *CC1(F)COC1]

In one embodiment the group —CH(R⁵)—C(R⁶)(R⁷)(R⁸) in the compound of Formula (I) is selected from the group consisting of:

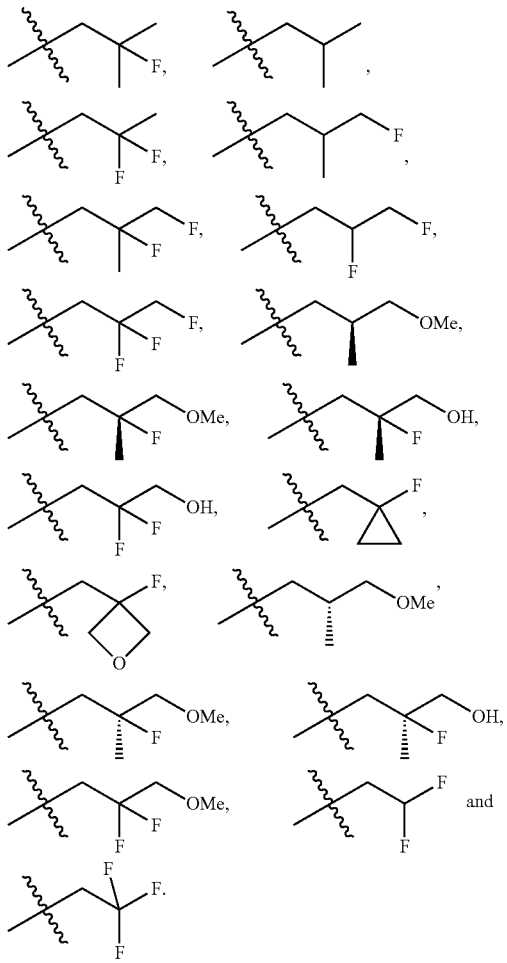

In one embodiment the group —CH(R⁵)—C(R⁶)(R⁷)(R⁸) in the compound of Formula (I) is selected from the group consisting of:

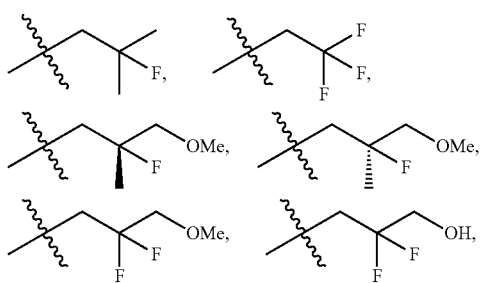

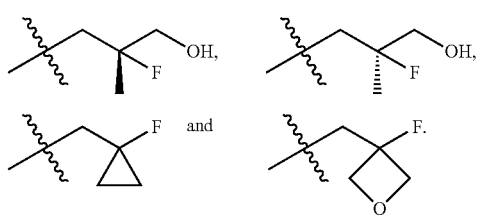

In one embodiment the group —CH(R⁵)—C(R⁶)(R⁷)(R⁸) in the compound of Formula (I) is selected from the group consisting of:

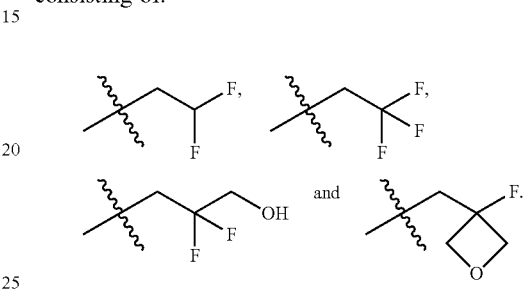

In one embodiment the group —CH(R⁵)—C(R⁶)(R⁷)(R⁸) in the compound of Formula (I) is selected from the group consisting of:

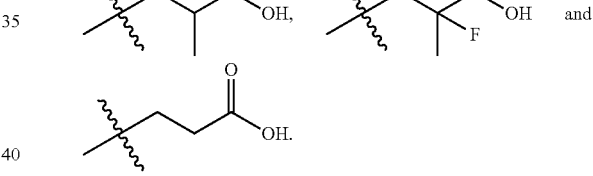

In one embodiment the group —CH(R⁵)—C(R⁶)(R⁷)(R⁸) in the compound of Formula (I) is selected from the group consisting of:

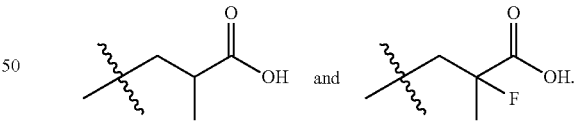

In one embodiment the group —CH(R⁵)—C(R⁶)(R⁷)(R⁸) in the compound of Formula (I) is selected from the group consisting of:

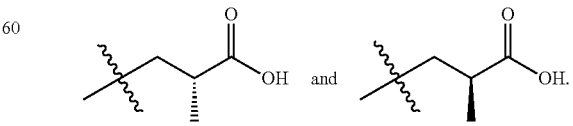

In one embodiment the group —CH(R⁵)—C(R⁶)(R⁷)(R⁸) in the compound of Formula (I) is:

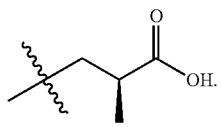 [SMILES: *C[C@H](C)C(=O)O]

In one embodiment both $R^9$ and $R^{10}$ are H.

In one embodiment one of $R^9$ and $R^{10}$ is H, the other of $R^9$ and $R^{10}$ is Me, F, $CH_2OH$ or $CH_2OMe$.

In one embodiment one of $R^9$ and $R^{10}$ is Me, the other of $R^9$ and $R^{10}$ is H.

In one embodiment J is N.

In one embodiment J is C—$R^{19}$.

In one embodiment $R^{15}$ is H, F or Me.

In one embodiment $R^{15}$ is F.

In one embodiment $R^{15}$ is H.

In one embodiment $R^{17}$ is H or F.

In one embodiment $R^{17}$ is F.

In one embodiment $R^{17}$ is H.

In one embodiment $R^{18}$ is H or F.

In one embodiment $R^{18}$ is F.

In one embodiment $R^{18}$ is H.

In one embodiment $R^{19}$ is H or F.

In one embodiment $R^{19}$ is F.

In one embodiment $R^{19}$ is H.

In one embodiment, each of $R^{17}$, $R^{18}$ and $R^{19}$ is H.

In one embodiment $R^{20}$ is H.

In one embodiment $R^{20}$ is Me.

In one embodiment there is provided a compound of Formula (I) wherein:

$R^2$, $R^3$, $R^9$, $R^{10}$, $R^{17}$ and $R^{18}$ are each H;

$R^{15}$ is H or F;

A is $CR^{11}$ and $R^1$ is H, F, CN or OMe;

G is $CR^{12}$ and $R^{12}$ is H, Me or F;

D is CH;

E is CH or N;

J is CH; and the group —CH($R^5$)—C($R^6$)($R^7$)($R^8$) in the compound of Formula (I) is selected from the group consisting of:

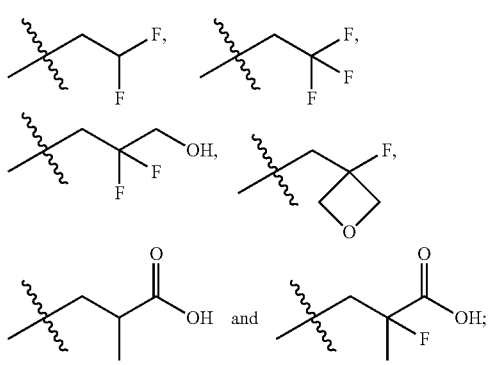

or a pharmaceutically acceptable salt thereof.

In a further embodiment of the specification there is provided a compound of Formula (IA):

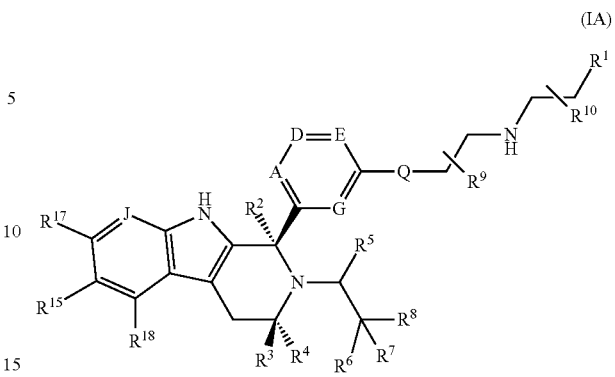

wherein:

A is $CR^{11}$ or N;
G is $CR^{12}$ or N;
D is $CR^{13}$ or N;
E is $CR^{14}$ or N;
J is $CR^{19}$ or N;
Q is O, NH or NMe;
$R^1$ is $CH_2F$, $CHF_2$ or $CF_3$;
$R^2$ is H, Me, $CH_2F$, $CHF_2$ or $CF_3$;
$R^3$ is H or Me;
$R^4$ is $C_{1-3}$ alkyl, $CH_2F$, $CHF_2$, $CF_3$, $CH_2CH=CH_2$, cyclopropyl or cyclobutyl;
$R^5$ is H, Me, $CH_2F$, $CHF_2$, $CF_3$, CN, $CH_2CN$, $CH_2OMe$, $CH_2OH$, COOH or $CH_2SO_2Me$;
$R^6$ is H, Me, F, $CH_2F$, $CHF_2$, $CF_3$, CN, $CH_2CN$, $CH_2OMe$, $CH_2OH$, COOH or $SO_2Me$;
$R^7$ is H, Me or F;
$R^8$ is H, Me or F; or
$R^7$ and $R^8$ taken together with the carbon atom to which they are attached form a cyclopropyl ring, a cyclobutyl ring, or an oxetane ring;
$R^9$ is H, Me, $CH_2OH$, $CH_2OMe$ or F;
$R^{10}$ is H, Me, $CH_2OH$, $CH_2OMe$ or F;
$R^1$ is H, F, Cl, CN, $C_{1-3}$ alkyl or O—$C_{1-3}$ alkyl (wherein the said $C_{1-3}$ alkyl groups are optionally substituted by a further group selected from OMe, OH, F and CN);
$R^{12}$ is H, F, Cl, CN, Me, OMe or $CHF_2$;
$R^{13}$ is H, F, Cl, CN, Me or OMe;
$R^{14}$ is H, F, Cl, CN, Me or OMe;
$R^{15}$ is H, F, Cl or Me;
$R^{17}$ is H, F, Cl or Me;
$R^{18}$ is H, F, Cl or Me; and
$R^{19}$ is H or F;
or a pharmaceutically acceptable salt thereof.

In one embodiment D is CH.

In one embodiment E is CH.

In one embodiment both D and E are CH.

In one embodiment both D and E are N.

In one embodiment one of D or E is CH and the other of D or E is N.

In one embodiment A is $CR^{11}$.

In one embodiment G is $CR^{12}$.

In one embodiment A is $CR^{11}$ and G is $CR^{12}$.

In one embodiment A is $CR^{11}$ and G is CH.

In one embodiment A is CH and G is $CR^{12}$.

In one embodiment A is $CR^{11}$ and D, E and G are all CH;

In one embodiment $R^{11}$ is independently selected from Me, Cl, F or OMe.

In one embodiment $R^{11}$ is independently selected from H, F, CN or OMe.

In one embodiment $R^{11}$ is independently selected from H or OMe.
In one embodiment $R^{11}$ is independently selected from H or F.
In one embodiment $R^{11}$ is independently selected from F, Cl or OMe.
In one embodiment $R^{11}$ is H.
In one embodiment $R^{11}$ is OMe.
In one embodiment $R^{11}$ is F.
In one embodiment $R^{11}$ is Me.
In one embodiment $R^{11}$ is Cl.
In one embodiment $R^{12}$ is independently selected from Me, Cl, F or $CHF_2$.
In one embodiment $R^{12}$ is independently selected from H, F, CN or OMe.
In one embodiment $R^{12}$ is independently selected from H or OMe.
In one embodiment $R^{12}$ is independently selected from H or F.
In one embodiment $R^{12}$ is independently selected from H, Me or F.
In one embodiment $R^{12}$ is H.
In one embodiment $R^{12}$ is OMe.
In one embodiment $R^{12}$ is Me.
In one embodiment $R^{12}$ is F.
In one embodiment A is $CR^{11}$ and $R^{11}$ is H, F, CN or OMe.
In one embodiment G is $CR^{12}$ and $R^{12}$ is H, F, CN or OMe.
In one embodiment A is $CR^{11}$ and $R^{11}$ is Cl, F or OMe.
In one embodiment G is $CR^{12}$ and $R^{12}$ is H, Me or F.
In one embodiment A is CH and G is CH.
In one embodiment A is C—F and G is C—F.
In one embodiment A is C—F and G is CH.
In one embodiment A is C—OMe and G is CH.
In one embodiment A is CH and G is C—OMe.
In one embodiment A is C—F and G is C-Me.
In one embodiment A is C—Cl and G is C—F.
In one embodiment Q is O or NH.
In one embodiment Q is O.
In one embodiment Q is NH.
In one embodiment Q is NMe.
In one embodiment $R^1$ is $CH_2F$ or $CHF_2$.
In one embodiment $R^1$ is $CH_2F$.
In one embodiment $R^1$ is $CHF_2$.
In one embodiment $R^1$ is $CF_3$.
In one embodiment $R^2$ is H or Me.
In one embodiment $R^2$ is H.
In one embodiment $R^2$ is Me.
In one embodiment $R^3$ is H.
In one embodiment $R^3$ is Me.
In one embodiment $R^4$ is $C_{1-3}$ alkyl, $CHF_2$ or cyclopropyl.
In one embodiment $R^4$ is $C_{1-3}$ alkyl or $CHF_2$.
In one embodiment $R^4$ is $C_{1-3}$ alkyl, $CF_3$ or $CHF_2$.
In one embodiment $R^4$ is $C_{1-3}$ alkyl.
In one embodiment $R^4$ is Me.
In one embodiment $R^3$ is H and $R^4$ is Me.
In one embodiment $R^4$ is $CHF_2$.
In one embodiment $R^4$ is $CF_3$.
In one embodiment $R^5$ is H or Me.
In one embodiment $R^5$ is H.
In one embodiment $R^5$ is Me.
In one embodiment $R^6$ is H, Me, F, $CH_2F$, $CH_2OMe$, $CH_2OH$, COOH or $SO_2Me$.
In one embodiment $R^6$ is H, F or $CH_2OH$.
In one embodiment $R^6$ is F.
In one embodiment $R^6$ is $CH_2OH$.
In one embodiment $R^6$ is COOH.

In one embodiment $R^7$ is H.
In one embodiment $R^7$ is Me.
In one embodiment $R^7$ is F.
In one embodiment $R^8$ is Me or F.
In one embodiment $R^8$ is Me.
In one embodiment $R^8$ is F.
In one embodiment $R^8$ is H.
In one embodiment $R^6$ is F or $CH_2OH$ and $R^7$ is H.
In one embodiment $R^6$ is F or $CH_2OH$ and $R^7$ is F.
In one embodiment $R^7$ is H and $R^8$ is F.
In one embodiment $R^7$ is F and $R^8$ is F.
In one embodiment $R^6$ is F and $R^7$ and $R^8$ taken together with the carbon atom to is which they are attached form a cyclopropyl ring, or a cyclobutyl ring, or an oxetane ring.
In one embodiment $R^6$ is F and $R^7$ and $R^8$ taken together with the carbon atom to which they are attached form a cyclopropyl ring or an oxetane ring.
In one embodiment $R^6$ is F and $R^7$ and $R^8$ taken together with the carbon atom to which they are attached form a cyclopropyl ring.
In one embodiment $R^6$ is F and $R^7$ and $R^8$ taken together with the carbon atom to which they are attached form a cyclobutyl ring.
In one embodiment $R^6$ is F and $R^7$ and $R^8$ taken together with the carbon atom to which they are attached form an oxetane ring.
In one embodiment the group —$CH(R^5)$—$C(R^6)(R^7)(R^8)$ in the compound of Formula (IA) is selected from the group consisting of:

In one embodiment the group —$CH(R^5)$—$C(R^6)(R^7)(R^8)$ in the compound of Formula (IA) is selected from the group consisting of:

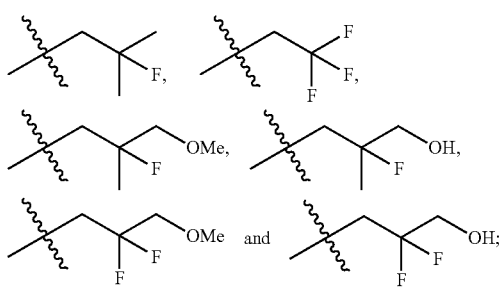

In one embodiment the group —CH($R^5$)—C($R^6$)($R^7$)($R^8$) in the compound of Formula (IA) is selected from the group consisting of:

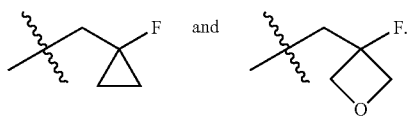 [SMILES: *CC1(F)CC1 ; *CC1(F)COC1]

In one embodiment the group —CH($R^5$)—C($R^6$)($R^7$)($R^8$) in the compound of Formula (IA) is selected from the group consisting of:

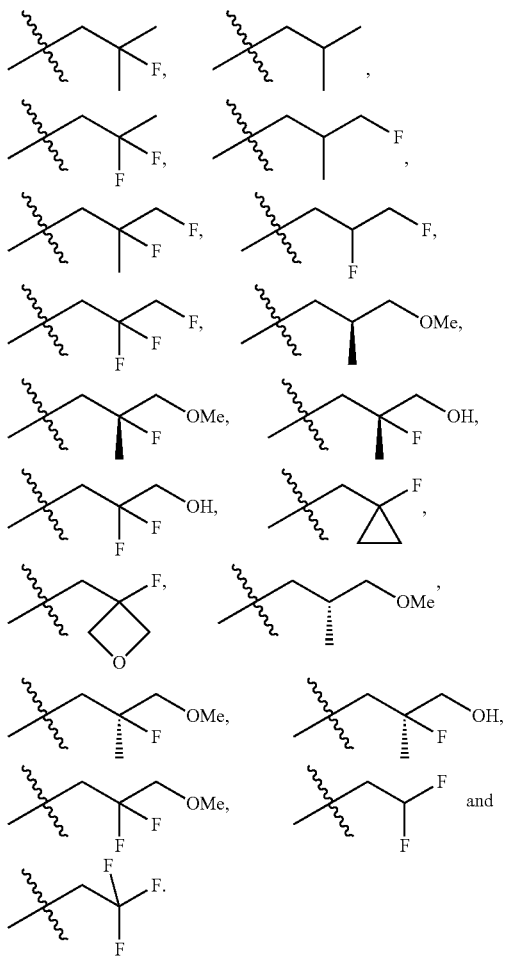

In one embodiment the group —CH($R^5$)—C($R^6$)($R^7$)($R^8$) in the compound of Formula (IA) is selected from the group consisting of:

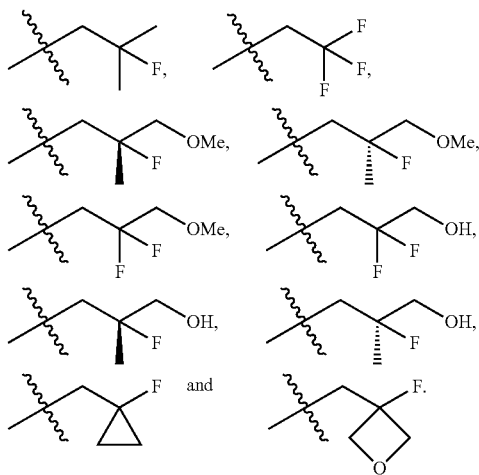

In one embodiment the group —CH($R^5$)—C($R^6$)($R^7$)($R^8$) in the compound of Formula (IA) is selected from the group consisting of:

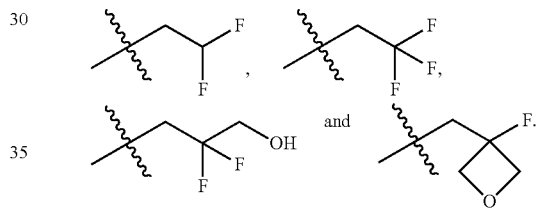

In one embodiment the group —CH($R^5$)—C($R^6$)($R^7$)($R^8$) in the compound of Formula (IA) is selected from the group consisting of:

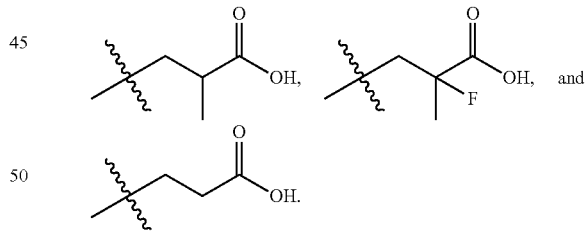

In one embodiment the group —CH($R^5$)—C($R^6$)($R^7$)($R^8$) in the compound of Formula (IA) is selected from the group consisting of:

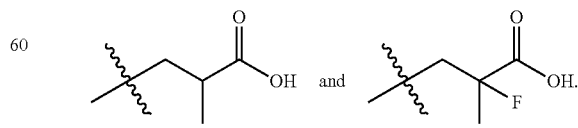

In one embodiment the group —CH($R^5$)—C($R^6$)($R^7$)($R^8$) in the compound of Formula (IA) is selected from the group consisting of:

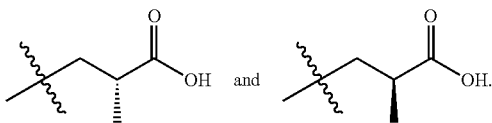

In one embodiment the group —CH(R$^5$)—C(R$^6$)(R$^7$)(R$^8$) in the compound of Formula (IA) is:

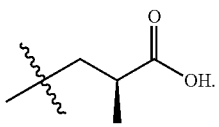 [SMILES: *C[C@H](C)C(=O)O]

In one embodiment both R$^9$ and R$^{10}$ are H.
In one embodiment one of R$^9$ and R$^{10}$ is H, the other of R$^9$ and R$^{10}$ is Me, F, CH$_2$OH or CH$_2$OMe.
In one embodiment one of R$^9$ and R$^{10}$ is Me, the other of R$^9$ and R$^{10}$ is H.
In one embodiment J is N.
In one embodiment J is C—R$^{19}$.
In one embodiment R$^{15}$ is H, F or Me.
In one embodiment R$^{15}$ is F.
In one embodiment R$^{15}$ is H.
In one embodiment R$^{17}$ is H or F.
In one embodiment R$^{17}$ is F.
In one embodiment R$^{17}$ is H.
In one embodiment R$^{18}$ is H or F.
In one embodiment R$^{18}$ is F.
In one embodiment R$^{18}$ is H.
In one embodiment R$^{19}$ is H or F.
In one embodiment R$^{19}$ is F.
In one embodiment R$^{19}$ is H.
In one embodiment, each of R$^{17}$, R$^{18}$ and R$^{19}$ is H.

In a further embodiment of the specification there is provided a compound of Formula (IB):

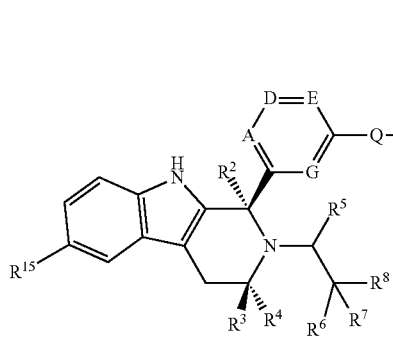

(IB)

wherein:
A is CR$^{11}$ or N;
G is CR$^{12}$ or N;
D is CR$^{13}$ or N;
E is CR$^{14}$ or N;
Q is O, NH or NMe;
R$^1$ is CH$_2$F, CHF$_2$ or CF$_3$;
R$^2$ is H, Me, CH$_2$F, CHF$_2$ or CF$_3$;
R$^3$ is H or Me;
R$^4$ is C$_{1-3}$ alkyl, CH$_2$F, CHF$_2$, CF$_3$, CH$_2$CH=CH$_2$, cyclopropyl or cyclobutyl;

R$^5$ is H, Me, CH$_2$F, CHF$_2$, CF$_3$, CN, CH$_2$CN, CH$_2$OMe, CH$_2$OH, COOH or CH$_2$SO$_2$Me;
R$^6$ is H, Me, F, CH$_2$F, CHF$_2$, CF$_3$, CN, CH$_2$CN, CH$_2$OMe, CH$_2$OH, COOH or SO$_2$Me;
R$^7$ is H, Me or F;
R$^8$ is H, Me or F; or
R$^7$ and R$^8$ taken together with the carbon atom to which they are attached form a cyclopropyl ring or an oxetane ring;
R$^9$ is H, Me, CH$_2$OH, CH$_2$OMe or F;
R$^{10}$ is H, Me, CH$_2$OH, CH$_2$OMe or F;
R$^{11}$ is H, F, Cl, CN, C$_{1-3}$ alkyl or O—C$_{1-3}$ alkyl (wherein the said C$_{1-3}$ alkyl groups are optionally substituted by a further group selected from OMe, OH, F and CN);
R$^{12}$ is H, F, Cl, CN, Me or OMe;
R$^{13}$ is H, F, Cl, CN, Me or OMe;
R$^{14}$ is H, F, Cl, CN, Me or OMe; and
R$^{15}$ is H or F;
or a pharmaceutically acceptable salt thereof.

In one embodiment there is provided a compound of Formula (IC):

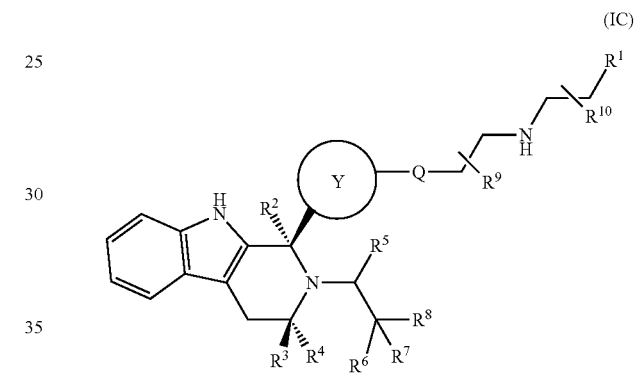

(IC)

wherein:
Q is O, NH or NMe;
R$^1$ is CH$_2$F, CHF$_2$ or CF$_3$;
R$^2$ is H, Me, CH$_2$F, CHF$_2$, or CF$_3$;
R$^3$ is H or Me;
R$^4$ is C$_{1-3}$ alkyl, CH$_2$F, CHF$_2$, CF$_3$, CH$_2$CH=CH$_2$, cyclopropyl or cyclobutyl;
R$^5$ is H, Me, CH$_2$F, CHF$_2$, CF$_3$, CN, CH$_2$CN, CH$_2$OMe, CH$_2$OH, COOH or CH$_2$SO$_2$Me;
R$^6$ is H, Me, F, CH$_2$F, CHF$_2$, CF$_3$, CN, CH$_2$CN, CH$_2$OMe, CH$_2$OH, COOH or SO$_2$Me;
R$^7$ is H, Me or F;
R$^8$ is H, Me or F; or
R$^7$ and R$^8$ taken together with the carbon atom to which they are attached form a cyclopropyl ring or an oxetane ring;
R$^9$ and R$^{10}$ are each independently selected from H, Me, CH$_2$OH, CH$_2$OMe or F; and
Ring Y is selected from the group consisting of:

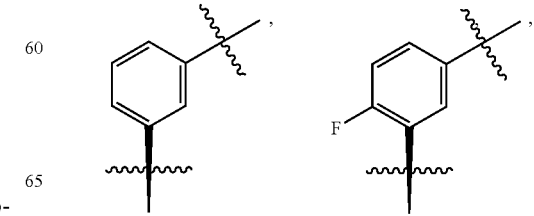

-continued

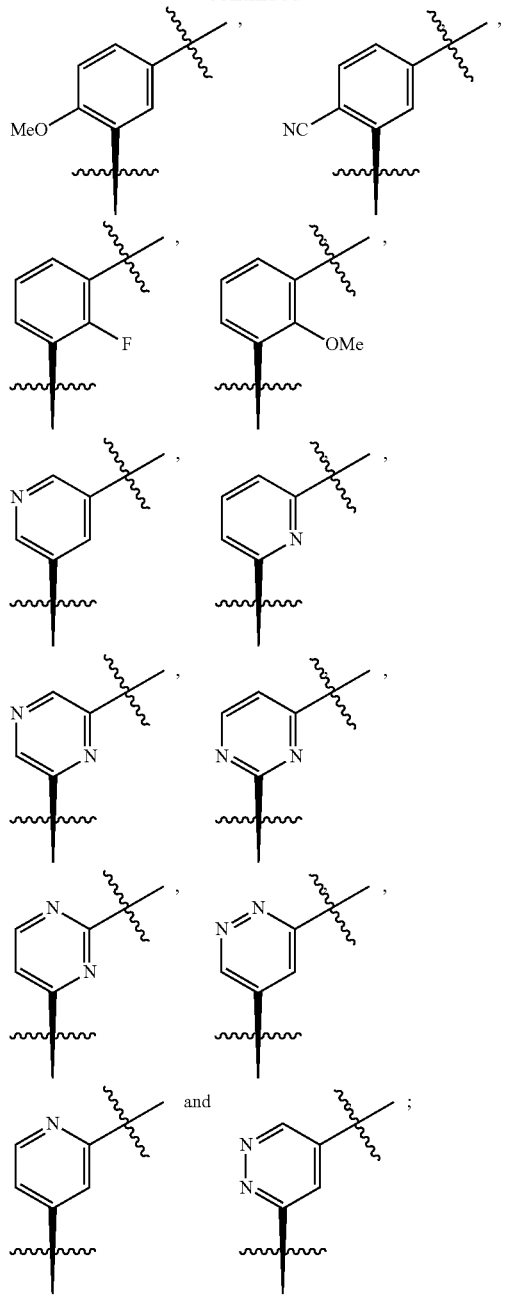

or a pharmaceutically acceptable salt thereof.

In one embodiment there is provided a compound of Formula (IC), or a pharmaceutically acceptable salt thereof, wherein Ring Y is selected from the group consisting of:

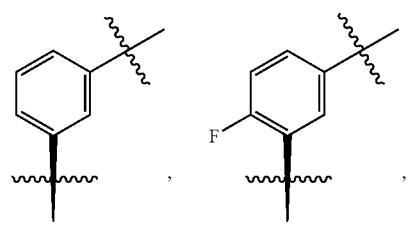

-continued

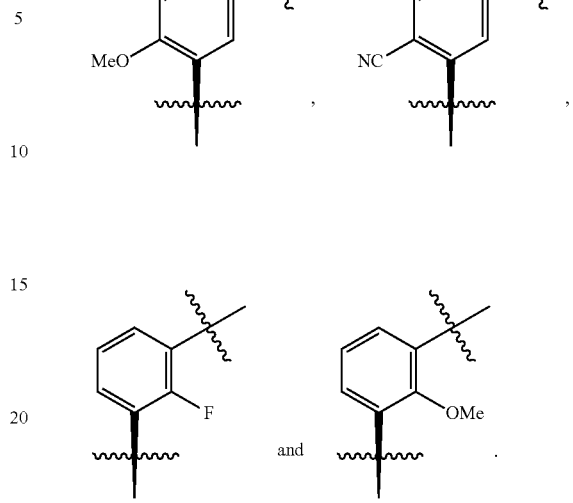

In one embodiment there is provided a compound of Formula (IC), or a to pharmaceutically acceptable salt thereof, wherein Ring Y is selected from the group consisting of:

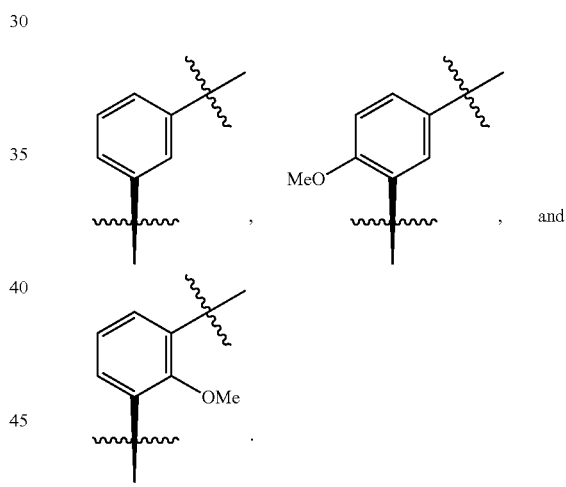

In one embodiment there is provided a compound of Formula (IC), or a pharmaceutically acceptable salt thereof, wherein Ring Y is selected from the group consisting of:

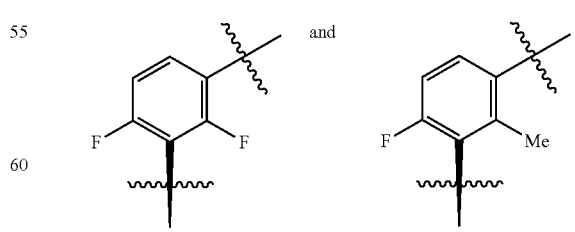

In one embodiment there is provided a compound of Formula (IC), or a pharmaceutically acceptable salt thereof, wherein Ring Y is selected from the group consisting of:

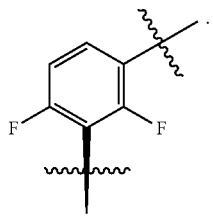

In one embodiment there is provided a compound of Formula (IC), or a pharmaceutically acceptable salt thereof, wherein Ring Y is selected from the group consisting of:

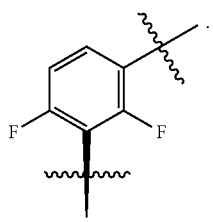

In one embodiment there is provided a compound of Formula (IC), or a pharmaceutically acceptable salt thereof, wherein Q is NH.

In one embodiment there is provided a compound of Formula (IC), or a pharmaceutically acceptable salt thereof, wherein Q is NMe.

In one embodiment there is provided a compound of Formula (IC), or a pharmaceutically acceptable salt thereof, wherein Q is O.

In one embodiment there is provided a compound of Formula (IC), or a pharmaceutically acceptable salt thereof, wherein $R^1$ is $CH_2F$.

In one embodiment there is provided a compound of Formula (IC), or a pharmaceutically acceptable salt thereof, wherein $R^1$ is $CHF_2$.

In one embodiment there is provided a compound of Formula (IC), or a pharmaceutically acceptable salt thereof, wherein $R^2$ is H.

In one embodiment there is provided a compound of Formula (IC), or a pharmaceutically acceptable salt thereof, wherein $R^3$ is H.

In one embodiment there is provided a compound of Formula (IC), or a pharmaceutically acceptable salt thereof, wherein $R^4$ is Me.

In one embodiment there is provided a compound of Formula (IC), or a pharmaceutically acceptable salt thereof, wherein $R^3$ is H and $R^4$ is Me.

In one embodiment there is provided a compound of Formula (IC), or a pharmaceutically acceptable salt thereof, wherein $R^5$ is H.

In one embodiment there is provided a compound of Formula (IC), or a pharmaceutically acceptable salt thereof, wherein $R^6$ is H, F or $CH_2OH$.

In one embodiment there is provided a compound of Formula (IC), or a pharmaceutically acceptable salt thereof, wherein $R^6$ is F and $R^7$ and $R^8$ taken together with the carbon atom to which they are attached form a cyclopropyl ring, or a cyclobutyl ring, or an oxetane ring. In a further embodiment $R^7$ and $R^8$ taken together with the carbon atom to which they are attached form a cyclopropyl ring. In a further embodiment $R^7$ and $R^8$ taken together with the carbon atom to which they are attached form a cyclobutyl ring. In a further embodiment $R^7$ and $R^8$ taken together with the carbon atom to which they are attached form an oxetane ring.

In one embodiment there is provided a compound of Formula (IC), or a pharmaceutically acceptable salt thereof, wherein both $R^9$ and $R^{10}$ are H.

In one embodiment the group —CH($R^5$)—C($R^6$)($R^7$)($R^8$) in the compound of Formula (IC) is selected from the group consisting of:

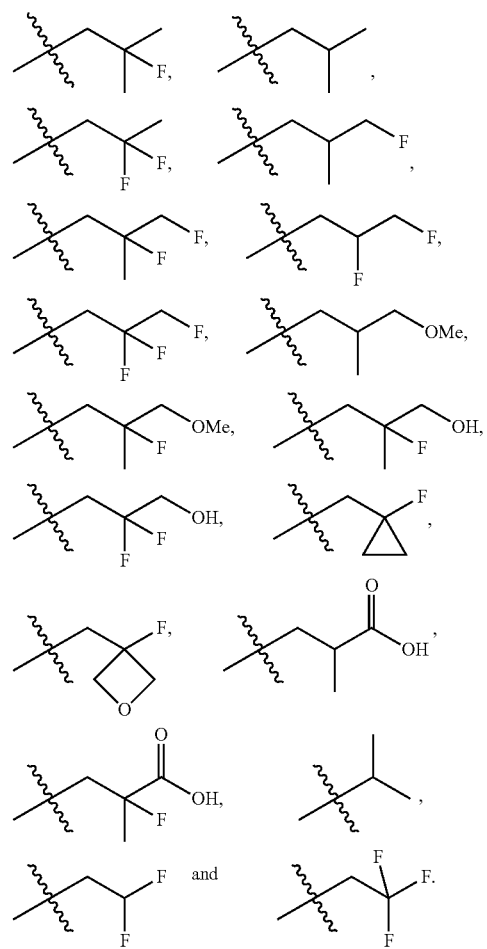

In one embodiment the group —CH($R^5$)—C($R^6$)($R^7$)($R^8$) in the compound of Formula (IC) is selected from the group consisting of:

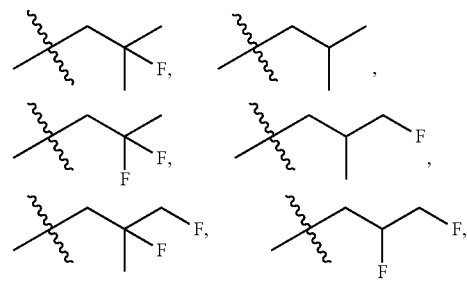

-continued

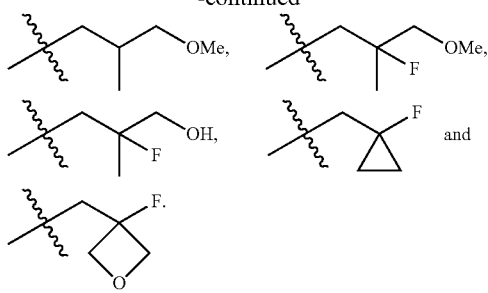

In one embodiment the group —CH(R$^5$)—C(R$^6$)(R$^7$)(R$^8$) in the compound of Formula (IC) is selected from the group consisting of:

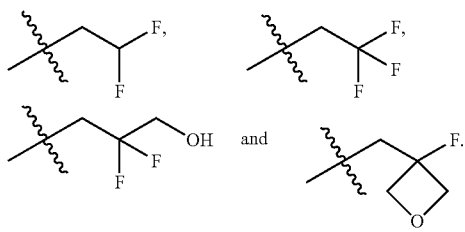

In one embodiment the group —CH(R$^5$)—C(R$^6$)(R$^7$)(R$^8$) in the compound of Formula (IC) is selected from the group consisting of:

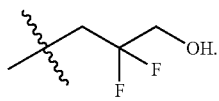

In one embodiment the group —CH(R$^5$)—C(R$^6$)(R$^7$)(R$^8$) in the compound of Formula (IC) is selected from the group consisting of:

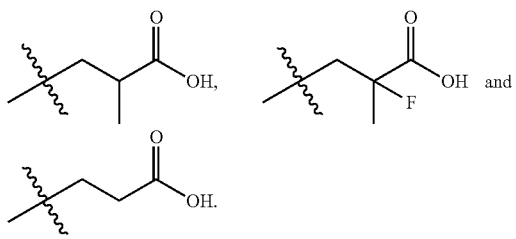

In one embodiment the group —CH(R$^5$)—C(R$^6$)(R$^7$)(R$^8$) in the compound of Formula (IC) is selected from the group consisting of:

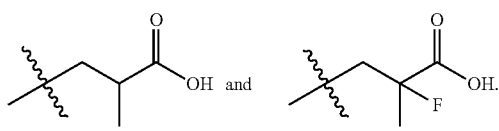

In one embodiment the group —CH(R$^5$)—C(R$^6$)(R$^7$)(R$^8$) in the compound of Formula (IC) is selected from the group consisting of:

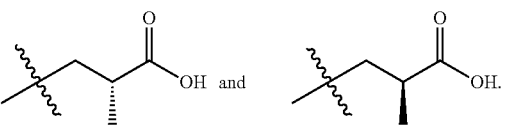

In one embodiment the group —CH(R$^5$)—C(R$^6$)(R$^7$)(R$^8$) in the compound of Formula (IC) is:

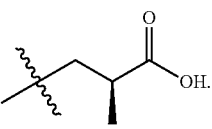 [SMILES: *C[C@H](C)C(=O)O]

In one embodiment there is provided a compound of Formula (ID):

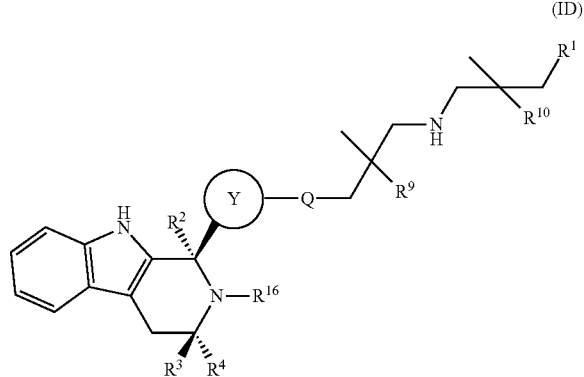

(ID)

wherein:
Q is O, NH or NMe;
R$^1$ is CH$_2$F, CHF$_2$ or CF$_3$;
R$^2$ is H or Me;
R$^3$ is H or Me;
R$^4$ is C$_{1-3}$ alkyl;
R$^9$ is H or Me;
R$^{10}$ is H or Me;
R$^{16}$ is selected from the group consisting of:

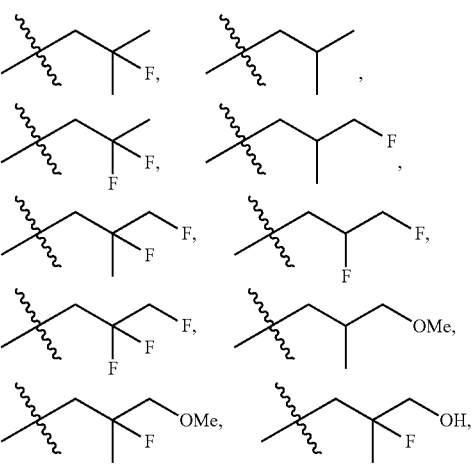

-continued

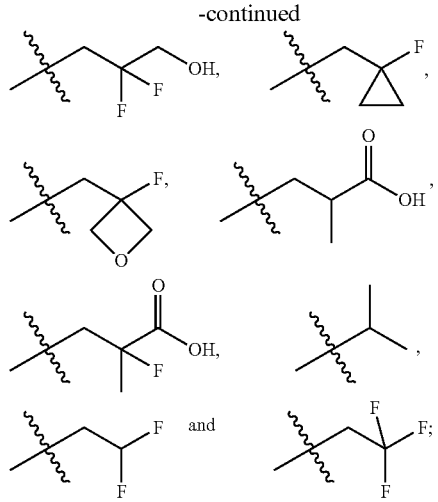

and
Ring Y is selected from the group consisting of:

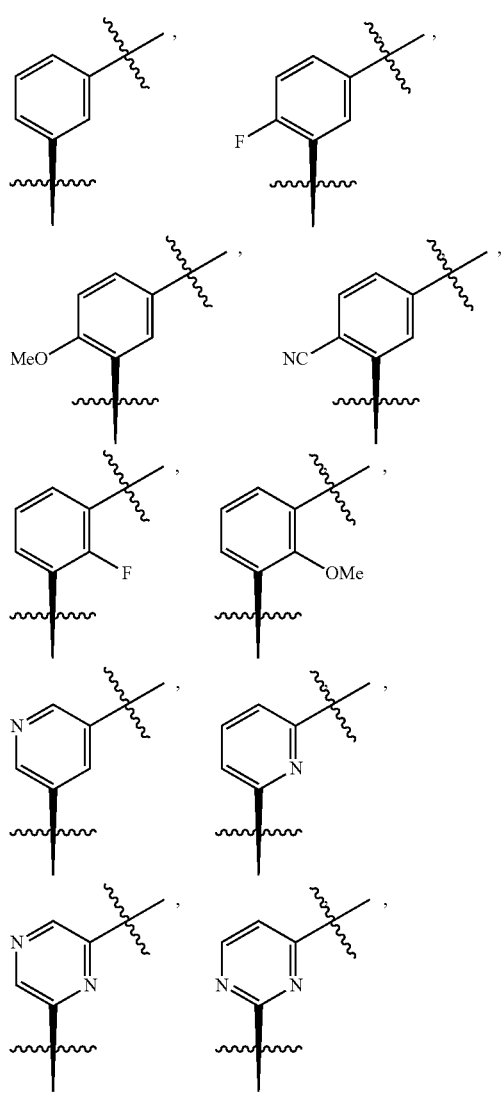

-continued

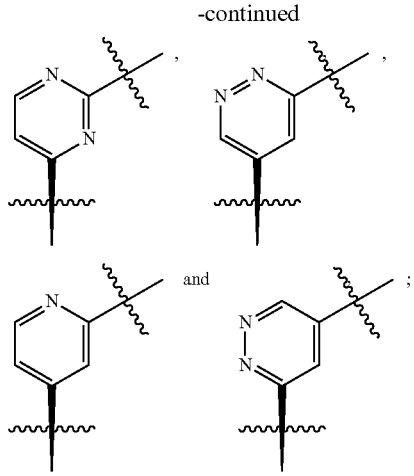

or a pharmaceutically acceptable salt thereof.

In one embodiment there is provided a compound of Formula (ID), or a pharmaceutically acceptable salt thereof, wherein Ring Y is selected from the group consisting of:

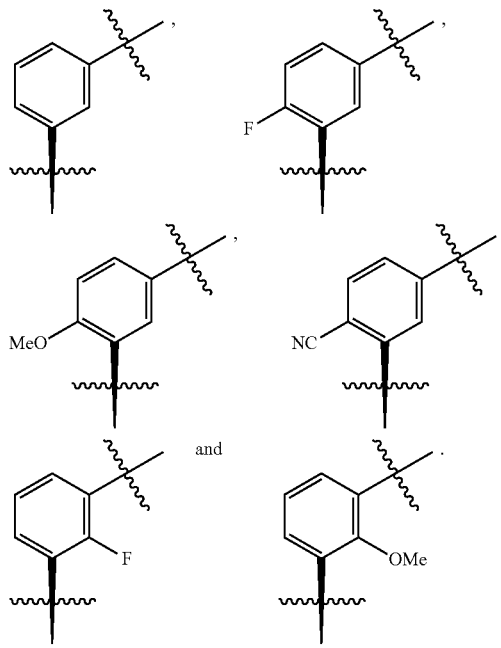

In one embodiment there is provided a compound of Formula (ID), or a pharmaceutically acceptable salt thereof, wherein Ring Y is selected from the group consisting of:

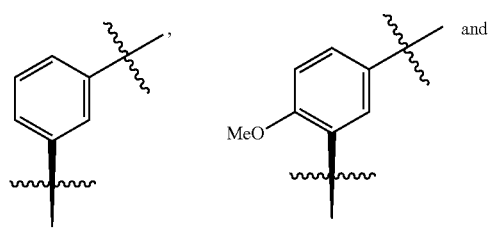

-continued

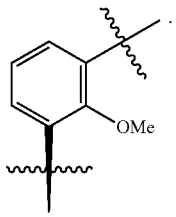

In one embodiment there is provided a compound of Formula (ID), or a pharmaceutically acceptable salt thereof, wherein Ring Y is selected from the group consisting of:

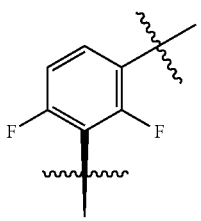 and 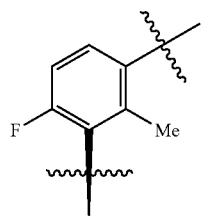

In one embodiment there is provided a compound of Formula (ID), or a pharmaceutically acceptable salt thereof, wherein Ring Y is selected from the group consisting of:

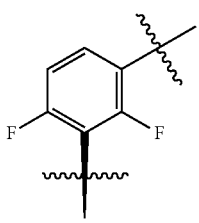

In one embodiment there is provided a compound of Formula (ID), or a to pharmaceutically acceptable salt thereof, wherein Ring Y is selected from the group consisting of:

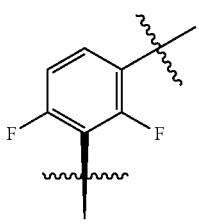

In one embodiment there is provided a compound of Formula (ID), or a pharmaceutically acceptable salt thereof, wherein Q is NH.

In one embodiment there is provided a compound of Formula (ID), or a pharmaceutically acceptable salt thereof, wherein Q is NMe.

In one embodiment there is provided a compound of Formula (ID), or a pharmaceutically acceptable salt thereof, wherein Q is O.

In one embodiment there is provided a compound of Formula (ID), or a pharmaceutically acceptable salt thereof, wherein $R^1$ is $CH_2F$.

In one embodiment there is provided a compound of Formula (ID), or a pharmaceutically acceptable salt thereof, wherein $R^1$ is $CHF_2$.

In one embodiment there is provided a compound of Formula (ID), or a pharmaceutically acceptable salt thereof, wherein $R^2$ is H.

In one embodiment there is provided a compound of Formula (ID), or a pharmaceutically acceptable salt thereof, wherein $R^3$ is H.

In one embodiment there is provided a compound of Formula (ID), or a pharmaceutically acceptable salt thereof, wherein $R^4$ is Me.

In one embodiment the group $R^{16}$ in the compound of Formula (ID) is selected from the group consisting of:

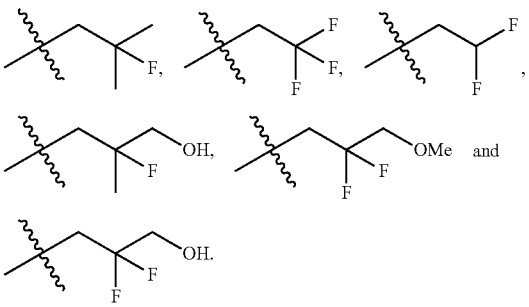

In one embodiment the group R in the compound of Formula (ID) is selected from the group consisting of:

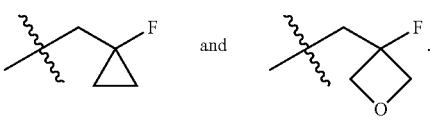 [SMILES: *CC1(F)CC1 ; *CC1(F)COC1]

In one embodiment the group $R^{16}$ in the compound of Formula (ID) is selected from the group consisting of:

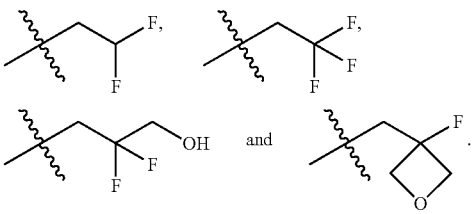

In one embodiment the group $R^{16}$ in the compound of Formula (ID) is selected from the group consisting of:

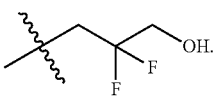 [SMILES: *CC(F)(F)CO]

In one embodiment the group $R^{16}$ in the compound of Formula (ID) is selected from the group consisting of:

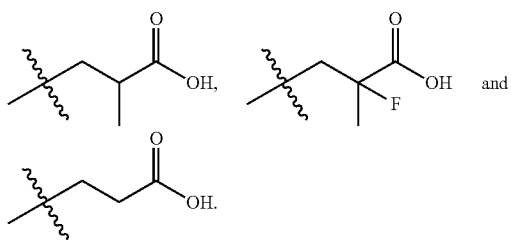

In one embodiment the group $R^{16}$ in the compound of Formula (ID) is selected from the group consisting of:

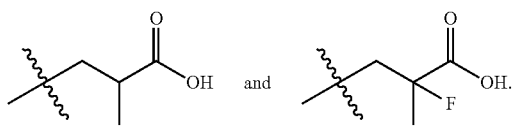

In one embodiment the group $R^{16}$ in the compound of Formula (ID) is selected from the group consisting of:

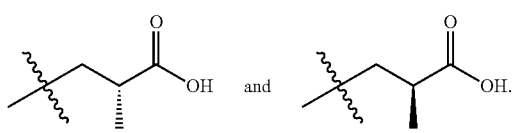

In one embodiment the group $R^{16}$ in the compound of Formula (ID) is:

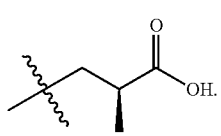 [SMILES: *C[C@H](C)C(=O)O]

In one embodiment there is provided a compound of Formula (IE):

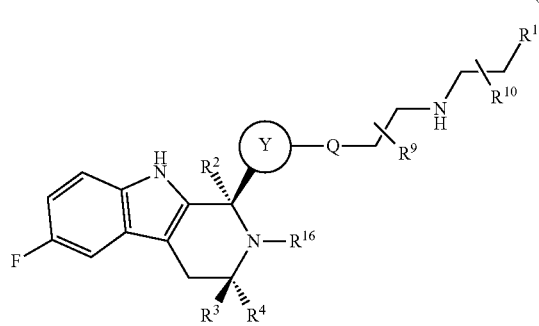

(IE)

wherein:
Q is O, NH or NMe;
$R^1$ is $CH_2F$, $CHF_2$ or $CF_3$;
$R^2$ is H or Me;
$R^3$ is H or Me;
$R^4$ is $C_{1-3}$ alkyl;
$R^9$ is H or Me;
$R^{10}$ is H or Me;
$R^{16}$ is selected from the group consisting of:

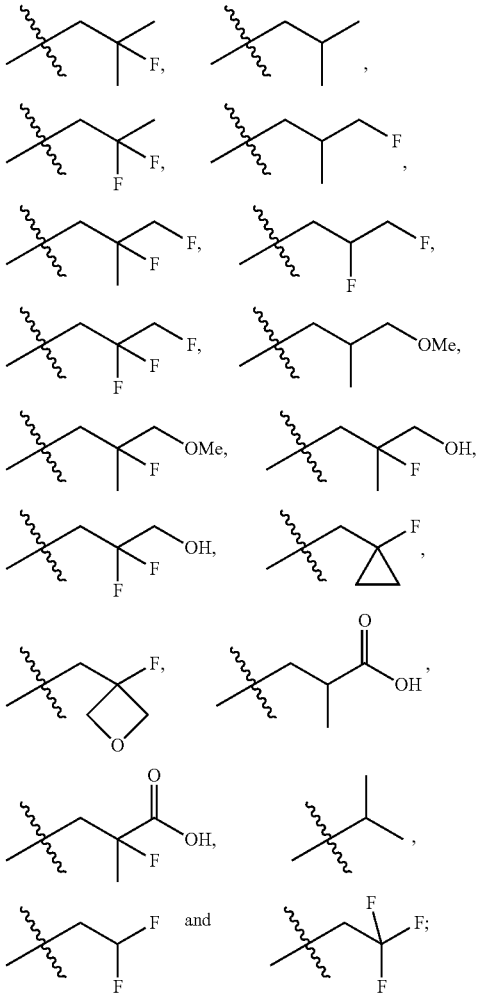

and
Ring Y is selected from the group consisting of:

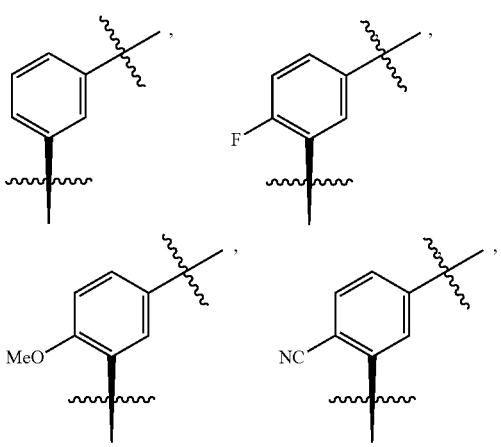

-continued

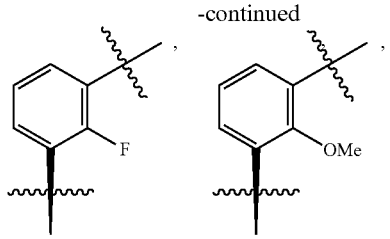

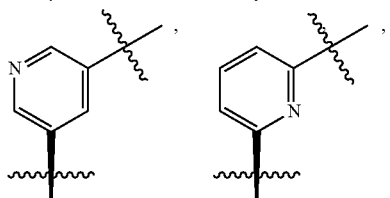

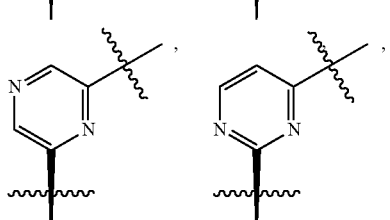

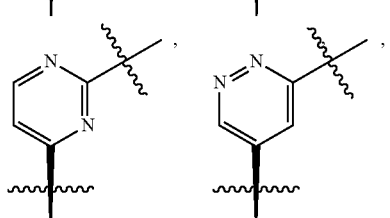

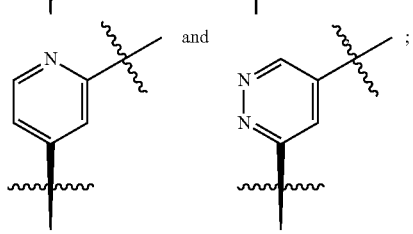

or a pharmaceutically acceptable salt thereof.

In one embodiment there is provided a compound of Formula (IE), or a pharmaceutically acceptable salt thereof, wherein Ring Y is selected from the group consisting of:

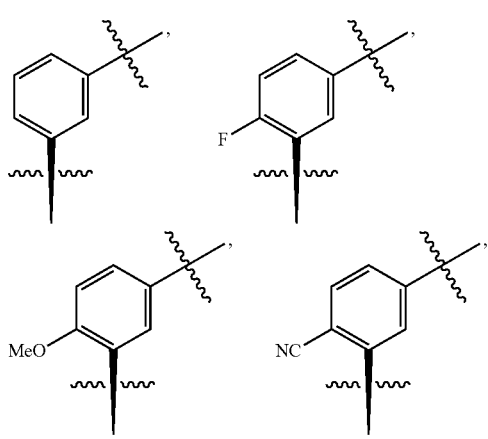

-continued

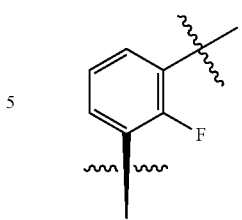 and 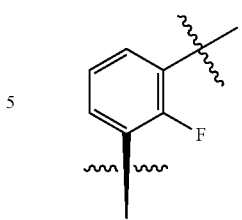,

In one embodiment there is provided a compound of Formula (IE), or a pharmaceutically acceptable salt thereof, wherein Ring Y is selected from the group consisting of:

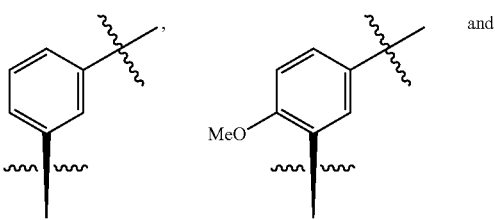

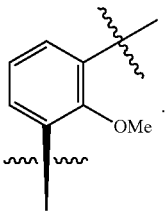

In one embodiment there is provided a compound of Formula (IE), or a pharmaceutically acceptable salt thereof, wherein Ring Y is selected from the group consisting of:

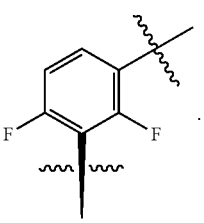

In one embodiment there is provided a compound of Formula (IE), or a pharmaceutically acceptable salt thereof, wherein Q is NH.

In one embodiment there is provided a compound of Formula (IE), or a pharmaceutically acceptable salt thereof, wherein Q is NMe.

In one embodiment there is provided a compound of Formula (IE), or a pharmaceutically acceptable salt thereof, wherein Q is O.

In one embodiment there is provided a compound of Formula (IE), or a pharmaceutically acceptable salt thereof, wherein $R^1$ is $CH_2F$.

In one embodiment there is provided a compound of Formula (IE), or a pharmaceutically acceptable salt thereof, wherein $R^1$ is $CHF_2$.

In one embodiment there is provided a compound of Formula (IE), or a pharmaceutically acceptable salt thereof, wherein $R^2$ is H.

In one embodiment there is provided a compound of Formula (IE), or a pharmaceutically acceptable salt thereof, wherein $R^3$ is H.

In one embodiment there is provided a compound of Formula (IE), or a pharmaceutically acceptable salt thereof, wherein $R^4$ is Me.

In one embodiment the group $R^{16}$ in the compound of Formula (IE) is selected from the group consisting of:

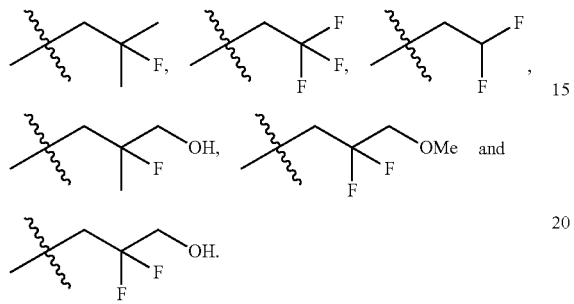

In one embodiment the group $R^{16}$ in the compound of Formula (IE) is selected from the group consisting of:

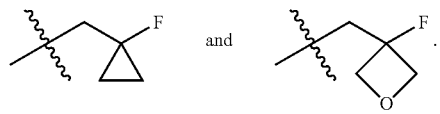 [SMILES: *CC1(F)CC1 ; *CC1(F)COC1]

In one embodiment the group $R^{16}$ in the compound of Formula (IE) is selected from the group consisting of:

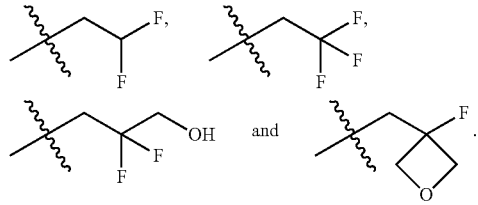

In one embodiment the group $R^{16}$ in the compound of Formula (IE) is selected from the group consisting of:

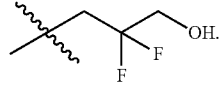 [SMILES: *CC(F)(F)CO]

In one embodiment the group $R^{16}$ in the compound of Formula (IE) is selected from the group consisting of:

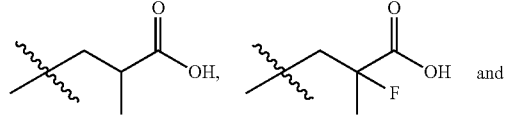

-continued

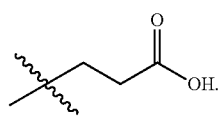

In one embodiment the group $R^{16}$ in the compound of Formula (IE) is selected from the group consisting of:

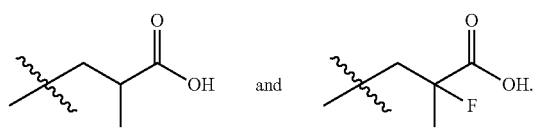

In one embodiment there is provided a compound of Formula (IF):

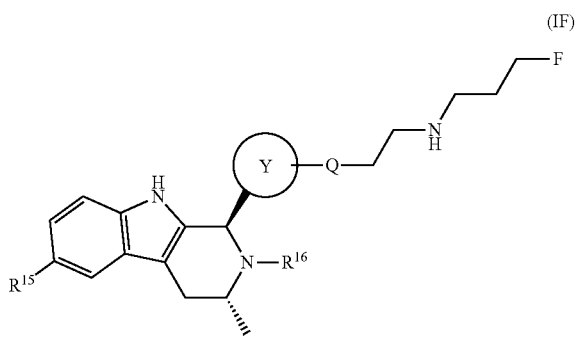

(IF)

wherein:

Q is O or NH;

$R^{15}$ is H or F;

$R^{16}$ is selected from the group consisting of:

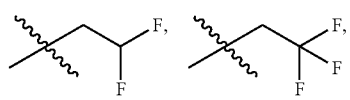

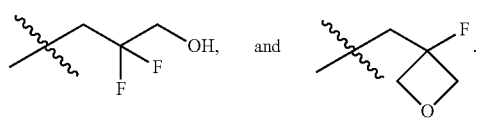

and Ring Y is selected from the group consisting of:

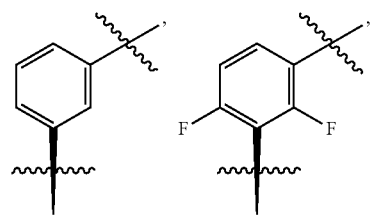

-continued

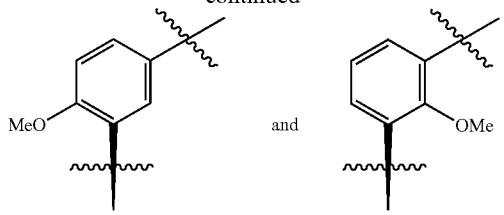

or a pharmaceutically acceptable salt thereof.

In one embodiment there is provided a compound of Formula (IF), or a pharmaceutically acceptable salt thereof, wherein Q is NH.

In one embodiment there is provided a compound of Formula (IF), or a pharmaceutically acceptable salt thereof, wherein Q is O.

In one embodiment there is provided a compound of Formula (IF), or a pharmaceutically acceptable salt thereof, wherein $R^{15}$ is H;

In one embodiment there is provided a compound of Formula (IF), or a pharmaceutically acceptable salt thereof, wherein $R^{15}$ is F;

In one embodiment there is provided a compound of Formula (IF), or a pharmaceutically acceptable salt thereof, wherein $R^{16}$ is:

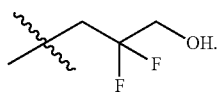

In one embodiment there is provided a compound of Formula (IF), or a pharmaceutically acceptable salt thereof, wherein Ring Y is:

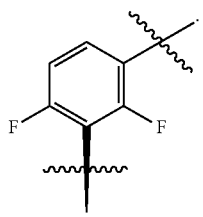

In one embodiment there is provided a compound of Formula (IF) wherein:
Q is O or NH;
$R^{15}$ is H or F;
$R^{16}$ is selected from the group consisting of:

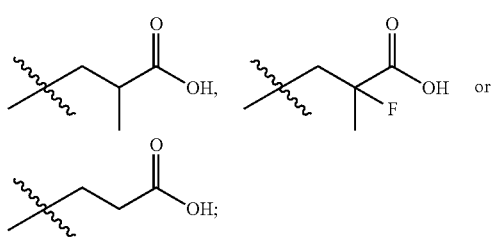

and Ring Y is selected from the group consisting of:

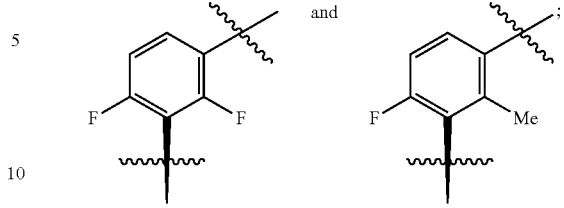

or a pharmaceutically acceptable salt thereof.

In a further embodiment, there is provided a compound of Formula (IG):

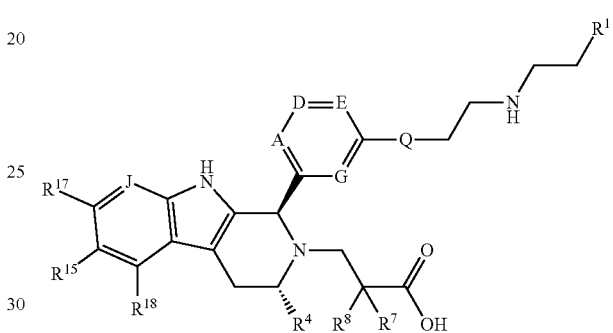

(IG)

wherein:
A is $CR^{11}$ or N;
G is $CR^{12}$;
D is $CR^{13}$ or N;
E is $CR^{14}$ or N;
J is $CR^{19}$;
Q is O or NH;
$R^1$ is $CH_2F$, $CHF_2$ or $CF_3$;
$R^4$ is Me, $CHF_2$ or $CF_3$;
$R^7$ is H or Me;
$R^8$ is H or Me; or
$R^7$ and $R^8$ taken together with the carbon atom to which they are attached form a cyclopropyl ring, or a cyclobutyl ring;
$R^{11}$ is H, Me, F, Cl or OMe;
$R^{12}$ is H, Me, F, Cl, or $CHF_2$;
$R^{13}$ is H or F;
$R^{14}$ is H or F;
$R^{15}$ is H, F, or Me;
$R^{17}$ is H or F;
$R^{18}$ is H or F; and
$R^{19}$ is H or F;
or a pharmaceutically acceptable salt thereof.

In one embodiment there is provided a compound of Formula (IG), or a pharmaceutically acceptable salt thereof, wherein A is C—F, C—OMe or C—Cl.

In one embodiment there is provided a compound of Formula (IG), or a pharmaceutically acceptable salt thereof, wherein G is C—H, C—F or C-Me.

In one embodiment there is provided a compound of Formula (IG), or a pharmaceutically acceptable salt thereof, wherein D and E are both C—H.

In one embodiment there is provided a compound of Formula (IG), or a pharmaceutically acceptable salt thereof, wherein D is C—H and E is N.

In one embodiment there is provided a compound of Formula (IG), or a pharmaceutically acceptable salt thereof, wherein J is C—H.

In one embodiment there is provided a compound of Formula (IG), or a pharmaceutically acceptable salt thereof, wherein $R^{17}$ is H.

In one embodiment there is provided a compound of Formula (IG), or a pharmaceutically acceptable salt thereof, wherein $R^{18}$ is H.

In one embodiment there is provided a compound of Formula (IG), or a pharmaceutically acceptable salt thereof, wherein $R^{15}$ is H or F.

In one embodiment there is provided a compound of Formula (IG), or a pharmaceutically acceptable salt thereof, wherein $R^1$ is $CH_2F$.

In one embodiment there is provided a compound of Formula (IG), or a pharmaceutically acceptable salt thereof, wherein $R^4$ is Me.

In one embodiment there is provided a compound of Formula (IG), or a pharmaceutically acceptable salt thereof, wherein $R^7$ is Me and $R^8$ is H.

In one embodiment there is provided a compound of Formula (IG), or a pharmaceutically acceptable salt thereof, wherein Q is O.

In one embodiment there is provided a compound of Formula (IG), or a pharmaceutically acceptable salt thereof, wherein:
A is C—F, C—Cl or C—OMe;
G is C—H, C-Me or C—F;
D and E are both C—H; or D is C—H and E is N;
J is C—H;
Q is O;
$R^1$ is $CH_2F$;
$R^4$ is Me;
$R^7$ is H;
$R^8$ is Me;
$R^{15}$ is H or F; and
$R^{17}$ and $R^{18}$ are both H.

According to a further embodiment of the specification there is provided a compound of Formula (IH):

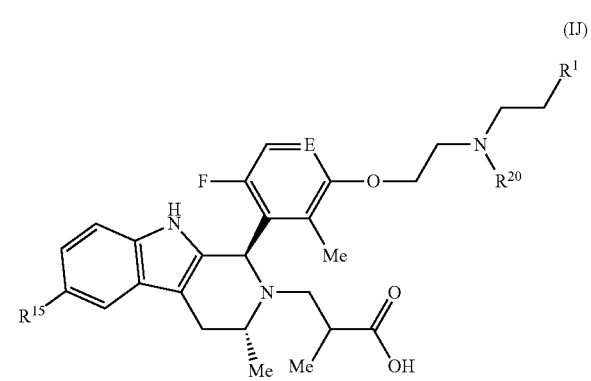

(IH)

wherein:
E is CH or N;
Q is O, NH or NMe;
$R^1$ is $CH_2F$ or $CHF_2$;
$R^3$ is H or Me;
$R^4$ is $C_{1-3}$ alkyl, $CHF_2$ or $CF_3$;
$R^7$ is H, Me or F;
$R^8$ is H, Me or F; or
$R^7$ and $R^8$ taken together with the carbon atom to which they are attached form a cyclobutyl ring;
$R^{11}$ is H, F, Cl, or OMe;
$R^{12}$ is H, F, Cl, $CHF_2$, or Me;
$R^{15}$ is H or F; and
$R^{20}$ is H or Me;
or a pharmaceutically acceptable salt thereof.

In a further embodiment, E in the compound of Formula (IH) is CH and $R^1$ is $CH_2F$ or $CHF_2$; or E in the compound of Formula (IH) is N and R1 is $CH_2F$.

According to a further embodiment of the specification there is provided a compound of Formula (IJ):

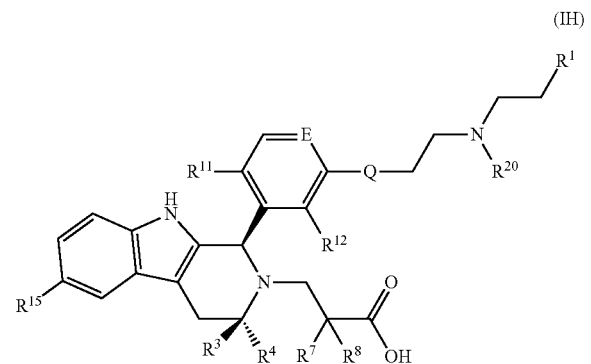

(IJ)

wherein:
E is CH or N;
$R^1$ is $CH_2F$ or $CHF_2$;
$R^{15}$ is H or F; and
$R^{20}$ is H or Me;
or a pharmaceutically acceptable salt thereof.

In a further embodiment, $R^{15}$ in the compound of Formula (IJ) is H.

In a further embodiment, E in the compound of Formula (IJ) is N.

In a further embodiment, E in the compound of Formula (IJ) is CH and $R^1$ is $CH_2F$ or $CHF_2$; or E in the compound of Formula (IJ) is N and R1 is $CH_2F$.

In a further embodiment, $R^1$ in the compound of Formula (IJ) is $CH_2F$.

In a further embodiment, $R^1$ in the compound of Formula (IJ) is $CHF_2$.

In a further aspect, there is provided a compound of Formula (IZ):

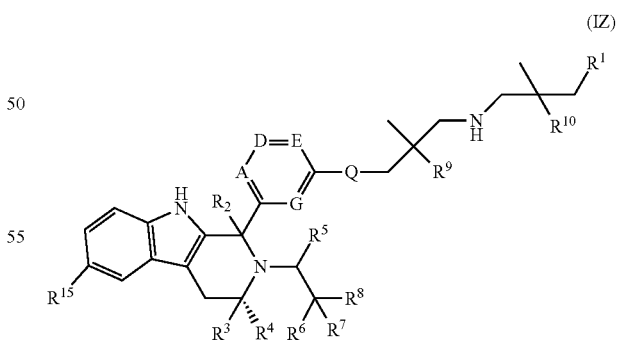

(IZ)

wherein:
A is $CR^{11}$ or N;
G is $CR^{12}$ or N;
D is $CR^{13}$ or N;
E is $CR^{14}$ or N;
Q is O, NH or NMe;
$R^1$ is $CH_2F$, $CHF_2$ or $CF_3$;

$R^2$ is H, Me, $CH_2F$, $CHF_2$ or $CF_3$;
$R^3$ is H or Me;
$R^4$ is $C_{1-3}$ alkyl, $CH_2F$, $CHF_2$, $CF_3$, $CH_2CH=CH_2$, cyclopropyl or cyclobutyl;
$R^5$ is H, Me, $CH_2F$, $CHF_2$, $CF_3$, CN, $CH_2CN$, $CH_2OMe$, $CH_2OH$, COOH or $CH_2SO_2Me$;
$R^6$ is H, Me, F, $CH_2F$, $CHF_2$, $CF_3$, CN, $CH_2CN$, $CH_2OMe$, $CH_2OH$, COOH or $SO_2Me$;
$R^7$ is H, Me or F;
$R^8$ is H, Me or F; or
$R^7$ and $R^8$ taken together with the carbon atom to which they are attached form a cyclopropyl ring or an oxetane ring;
$R^9$ is H, Me, $CH_2OH$, $CH_2OMe$ or F;
$R^{10}$ is H, Me, $CH_2OH$, $CH_2OMe$ or F;
$R^{11}$ is H, F, Cl, CN, $C_{1-3}$ alkyl or O—$C_{1-3}$ alkyl (wherein the said $C_{1-3}$ alkyl groups are optionally substituted by a further group selected from OMe, OH, F and CN);
$R^{12}$ is H, F, Cl, CN, Me or OMe;
$R^{13}$ is H, F, Cl, CN, Me or OMe;
$R^{14}$ is H, F, Cl, CN, Me or OMe; and
$R^{15}$ is H or F;
or a pharmaceutically acceptable salt thereof.

In a further aspect, there is provided a compound of Formula (IZA):

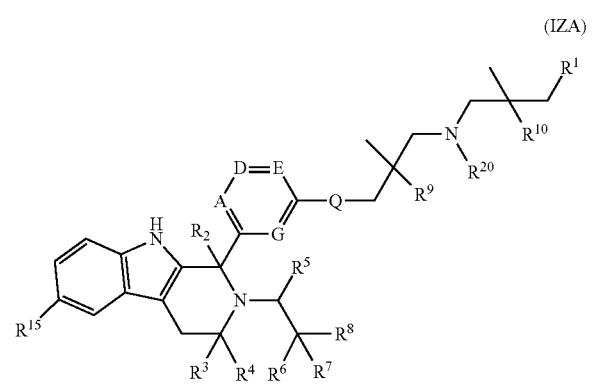

(IZA)

wherein:
A is $CR^{11}$ or N;
G is $CR^{12}$ or N;
D is $CR^{13}$ or N;
E is $CR^{14}$ or N;
Q is O, NH or NMe;
$R^1$ is $CH_2F$, $CHF_2$ or $CF_3$;
$R^2$ is H, Me, $CH_2F$, $CHF_2$ or $CF_3$;
$R^3$ is H or Me;
$R^4$ is $C_{1-3}$ alkyl, $CH_2F$, $CHF_2$, $CF_3$, $CH_2CH=CH_2$, cyclopropyl or cyclobutyl;
$R^5$ is H, Me, $CH_2F$, $CHF_2$, $CF_3$, CN, $CH_2CN$, $CH_2OMe$, $CH_2H$, COOH or $CH_2SO_2Me$;
$R^6$ is H, Me, F, $CH_2F$, $CHF_2$, $CF_3$, CN, $CH_2CN$, $CH_2OMe$, $CH_2OH$, COOH or $SO_2Me$;
$R^7$ is H, Me or F;
$R^8$ is H, Me or F; or
$R^7$ and $R^8$ taken together with the carbon atom to which they are attached form a cyclopropyl ring or an oxetane ring;
$R^9$ is H, Me, $CH_2OH$, $CH_2OMe$ or F;
$R^{10}$ is H, Me, $CH_2OH$, $CH_2OMe$ or F;
$R^{11}$ is H, F, Cl, CN, $C_{1-3}$ alkyl or O—$C_{1-3}$ alkyl (wherein the said $C_{1-3}$ alkyl groups are optionally substituted by a further group selected from OMe, OH, F and CN);
$R^{12}$ is H, F, Cl, CN, Me or OMe;
$R^{13}$ is H, F, Cl, CN, Me or OMe;
$R^{14}$ is H, F, Cl, CN, Me or OMe;
$R^{15}$ is H or F; and
$R^{20}$ is H or Me;
or a pharmaceutically acceptable salt thereof.

In a further embodiment there is provided the compound of Formula (IZ), (IZA), or a is pharmaceutically acceptable salt thereof wherein the stereochemistry at the 1-position of the tetrahydro-1H-pyrido[3,4-b]indol-1-yl ring is S.

In a further embodiment there is provided the compound of Formula (IZ), (IZA), or a pharmaceutically acceptable salt thereof wherein the stereochemistry at the 1-position of the tetrahydro-1H-pyrido[3,4-b]indol-1-yl ring is R.

In a further embodiment there is provided the compound of Formula (IZ), (IZA), or a pharmaceutically acceptable salt thereof wherein the stereochemistry at the 3-position of the tetrahydro-1H-pyrido[3,4-b]indol-1-yl ring is S.

In a further embodiment there is provided the compound of Formula (IZ), (IZA), or a pharmaceutically acceptable salt thereof wherein the stereochemistry at the 3-position of the tetrahydro-1H-pyrido[3,4-b]indol-1-yl ring is R.

In one embodiment there is provided a compound of Formula (I), wherein the compound is selected from the group consisting of:
3-Fluoro-N-(2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)propan-1-amine;
N-1-(3-((1R,3R)-2-((3-fluorooxetan-3-yl)methyl)-3-methyl-2,3,4,9-tetrahydro-1H-pyrido[3,4-b]indol-1-yl)phenyl)-N-2-(3-fluoropropyl)ethane-1,2-diamine;
N-1-(3-((1R,3R)-2-((3-fluorooxetan-3-yl)methyl)-3-methyl-2,3,4,9-tetrahydro-1H-pyrido[3,4-b]indol-1-yl)phenyl)-N-2-(3-fluoropropyl)-N-1-methylethane-1,2-diamine;
3-Fluoro-N-(2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)propan-1-amine;
3-fluoro-N-(2-(3-((1R,3R)-2-((3-fluorooxetan-3-yl)methyl)-3-methyl-2,3,4,9-tetrahydro-1H-pyrido[3,4-b]indol-1-yl)-2-methoxyphenoxy)ethyl)propan-1-amine;
N-(2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)-3-fluoropropan-1-amine;
3-Fluoro-N-(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine; and
2,2-Difluoro-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)propan-1-ol;
or a pharmaceutically acceptable salt thereof.

In one embodiment there is provided a compound of Formula (I), wherein the compound is selected from the group consisting of:
N-(2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;
3-fluoro-N-(2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;
3-fluoro-N-(2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;
3-fluoro-N-(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

N-(2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)-3-fluoropropan-1-amine;

3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol;

3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2,2-difluoropropan-1-ol;

3-fluoro-N-(2-(3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(4-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(3-methyl-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(2-methyl-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

N-(2-(4-ethyl-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

N-(2-(4-chloro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

4-(2-((3-fluoropropyl)amino)ethoxy)-2-((1R,3R)-3-methyl-2-(2,2,2-trifluoroethyl)-2,3,4,9-tetrahydro-1H-pyrido[3,4-b]indol-1-yl)benzonitrile;

3-fluoro-N-(2-(2-fluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

N-(2-(2-chloro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

3-fluoro-N-(2-(4-methoxy-2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(3-fluoro-4-methoxy-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(2-fluoro-4-methoxy-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

N-(2-(2,5-difluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

N-(2-(3,4-difluoro-5-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

N-(2-(2,5-difluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

3-fluoro-N-(2-(2,4,5-trifluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(4-fluoro-2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-((6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

3-fluoro-N-(2-((2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)propan-1-amine;

3-fluoro-N-(2-((6-methoxy-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine;

3-fluoro-N-(2-((6-methyl-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine;

3-fluoro-N-(2-((4-methyl-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine;

3-fluoro-N-(2-((5-fluoro-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

N1-(3-fluoropropyl)-N2-(4-methoxy-3-((1R,3R)-3-methyl-2-(2,2,2-trifluoroethyl)-2,3,4,9-tetrahydro-1H-pyrido[3,4-b]indol-1-yl)phenyl)ethane-1,2-diamine;

N1-(3-fluoropropyl)-N2-(6-methoxy-5-((1R,3R)-3-methyl-2-(2,2,2-trifluoroethyl)-2,3,4,9-tetrahydro-1H-pyrido[3,4-b]indol-1-yl)pyridin-3-yl)ethane-1,2-diamine;

N1-(3-fluoropropyl)-N2-(5-methoxy-4-((1R,3R)-3-methyl-2-(2,2,2-trifluoroethyl)-2,3,4,9-tetrahydro-1H-pyrido[3,4-b]indol-1-yl)pyridin-2-yl)ethane-1,2-diamine;

N1-(3-fluoropropyl)-N2-(5-methoxy-6-((1S,3R)-3-methyl-2-(2,2,2-trifluoroethyl)-2,3,4,9-tetrahydro-1H-pyrido[3,4-b]indol-1-yl)pyridin-2-yl)ethane-1,2-diamine;

3-((1R,3R)-1-(2-chloro-5-(2-((3-fluoropropyl)amino)ethoxy)phenyl)-3-methyl-1,3,4,9-tetrahydro-2H-pyrido[3,4-b]indol-2-yl)-2,2-difluoropropan-1-ol;

2,2-difluoro-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propan-1-ol;

2,2-difluoro-3-((1R,3R)-6-fluoro-1-(5-(2-((3-fluoropropyl)amino)ethoxy)-2-methoxyphenyl)-3-methyl-1,3,4,9-tetrahydro-2H-pyrido[3,4-b]indol-2-yl)propan-1-ol;

2,2-difluoro-3-((1R,3R)-1-(5-(((R)-1-((3-fluoropropyl)amino)propan-2-yl)oxy)-2-methoxyphenyl)-3-methyl-1,3,4,9-tetrahydro-2H-pyrido[3,4-b]indol-2-yl)propan-1-ol;

2,2-difluoro-3-((1R,3R)-1-(5-(((S)-1-((3-fluoropropyl)amino)propan-2-yl)oxy)-2-methoxyphenyl)-3-methyl-1,3,4,9-tetrahydro-2H-pyrido[3,4-b]indol-2-yl)propan-1-ol;

2,2-difluoro-3-((1R,3R)-1-(5-((S)-2-((3-fluoropropyl)amino)propoxy)-2-methoxyphenyl)-3-methyl-1,3,4,9-tetrahydro-2H-pyrido[3,4-b]indol-2-yl)propan-1-ol;

2,2-difluoro-3-((1R,3R)-1-(5-((R)-2-((3-fluoropropyl)amino)propoxy)-2-methoxyphenyl)-3-methyl-1,3,4,9-tetrahydro-2H-pyrido[3,4-b]indol-2-yl)propan-1-ol;

N-(2-(3-((1R,3R)-2-(2,2-difluoroethyl)-3-methyl-2,3,4,9-tetrahydro-1H-pyrido[3,4-b]indol-1-yl)-2,4-difluorophenoxy)ethyl)-3-fluoropropan-1-amine;

3-fluoro-N-(2-(3-((1R,3R)-2-((1-fluorocyclopropyl)methyl)-3-methyl-2,3,4,9-tetrahydro-1H-pyrido[3,4-b]indol-1-yl)-4-methoxyphenoxy)ethyl)propan-1-amine;

(S)-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)-2-methylpropanoic acid;

(S)-3-((1R,3R)-1-(6-chloro-2-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid; and 3-fluoro-N-(2-((5-methoxy-6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

or a pharmaceutically acceptable salt thereof.

In one embodiment there is provided a compound of Formula (I), wherein the compound is selected from the group consisting of:

(S)-3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid;

3-((1R,3R)-1-(2,6-difluoro-3-(2-((3-fluoropropyl)amino)ethoxy)phenyl)-8-fluoro-3-methyl-1,3,4,9-tetrahydro-2H-pyrido[3,4-b]indol-2-yl)-2,2-difluoropropan-1-ol;

3-((1R,3R)-1-(2,6-difluoro-3-(2-((3-fluoropropyl)amino)ethoxy)phenyl)-7-fluoro-3-methyl-1,3,4,9-tetrahydro-2H-pyrido[3,4-b]indol-2-yl)-2,2-difluoropropan-1-ol;

3-((1R,3R)-1-(2,6-difluoro-3-(2-((3-fluoropropyl)amino)ethoxy)phenyl)-5-fluoro-3-methyl-1,3,4,9-tetrahydro-2H-pyrido[3,4-b]indol-2-yl)-2,2-difluoropropan-1-ol;

3-((1R,3R)-1-(2,6-difluoro-3-(2-((3-fluoropropyl)amino)ethoxy)phenyl)-3,6-dimethyl-1,3,4,9-tetrahydro-2H-pyrido[3,4-b]indol-2-yl)-2,2-difluoropropan-1-ol;

3-((R,3R)-1-(3,5-difluoro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol;

3-((R,3R)-1-(3,5-difluoro-2-(2-((3-fluoropropyl)amino)ethoxy)pyridin-4-yl)-6-fluoro-3-methyl-1,3,4,9-tetrahydro-2H-pyrido[3,4-b]indol-2-yl)-2,2-difluoropropan-1-ol;

3-((R,3R)-1-(3,5-difluoro-2-(2-((3-fluoropropyl)amino)ethoxy)pyridin-4-yl)-3,6-dimethyl-1,3,4,9-tetrahydro-2H-pyrido[3,4-b]indol-2-yl)-2,2-difluoropropan-1-ol;

3-((1R,3R)-1-(3,5-difluoro-2-(2-((3-fluoropropyl)(methyl)amino)ethoxy)pyridin-4-yl)-6-fluoro-3-methyl-1,3,4,9-tetrahydro-2H-pyrido[3,4-b]indol-2-yl)-2,2-difluoropropan-1-ol;

3-((1R,3R)-1-(2-(difluoromethyl)-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol;

2-(2-((3-fluoropropyl)amino)ethoxy)-6-((1R,3R)-3-methyl-2-(2,2,2-trifluoroethyl)-2,3,4,9-tetrahydro-1H-pyrido[3,4-b]indol-1-yl)benzonitrile;

(4-(2-((3-fluoropropyl)amino)ethoxy)-2-((1R,3R)-3-methyl-2-(2,2,2-trifluoroethyl)-2,3,4,9-tetrahydro-1H-pyrido[3,4-b]indol-1-yl)phenyl)methanol;

3-fluoro-N-(2-(4-(methoxymethyl)-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3,3,3-trifluoro-N-(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(3-fluoro-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

3-fluoro-N-(2-(2-fluoro-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

N-(2-(3-((1R,3R)-1,3-dimethyl-2-(2,2,2-trifluoroethyl)-2,3,4,9-tetrahydro-1H-pyrido[3,4-b]indol-1-yl)phenoxy)ethyl)-3-fluoropropan-1-amine;

N-(2-(2,4-difluoro-3-((1R,3R)-2-((1-fluorocyclopropyl)methyl)-3-methyl-2,3,4,9-tetrahydro-1H-pyrido[3,4-b]indol-1-yl)phenoxy)ethyl)-3-fluoropropan-1-amine;

N-(2-(2,4-difluoro-3-((1R,3R)-3-methyl-2-((1-(methylsulfonyl)cyclopropyl)methyl)-2,3,4,9-tetrahydro-1H-pyrido[3,4-b]indol-1-yl)phenoxy)ethyl)-3-fluoropropan-1-amine;

N-(2-(4-chloro-2-fluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

N-(2-(2,4-dimethyl-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine;

3-fluoro-N-(2-(2-fluoro-4-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine;

2,2-difluoro-3-((1R,3R)-1-(2-fluoro-3-(2-((3-fluoropropyl)amino)ethoxy)-6-methoxyphenyl)-3-methyl-1,3,4,9-tetrahydro-2H-pyrido[3,4-b]indol-2-yl)propan-1-ol;

N-(2-(3-((1R,3R)-2-(2,2-difluoroethyl)-3-methyl-2,3,4,9-tetrahydro-1H-pyrido[3,4-b]indol-1-yl)-2-fluoro-4-methoxyphenoxy)ethyl)-3-fluoropropan-1-amine;

3-fluoro-N-(2-(2-fluoro-3-((1R,3R)-2-((1-fluorocyclopropyl)methyl)-3-methyl-2,3,4,9-tetrahydro-1H-pyrido[3,4-b]indol-1-yl)-4-methoxyphenoxy)ethyl)propan-1-amine;

3-fluoro-N-(2-(2-fluoro-3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)propan-1-amine;

3-((1R,3R)-1-(2-chloro-6-fluoro-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol;

2,2-difluoro-3-((1R,3R)-6-fluoro-1-(2-fluoro-3-(2-((3-fluoropropyl)amino)ethoxy)-6-methoxyphenyl)-3-methyl-1,3,4,9-tetrahydro-2H-pyrido[3,4-b]indol-2-yl)propan-1-ol;

3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanenitrile;

N1-(2,4-difluoro-3-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine;

3-((1R,3R)-1-(2,6-difluoro-3-((2-((3-fluoropropyl)amino)ethyl)amino)phenyl)-6-fluoro-3-methyl-1,3,4,9-tetrahydro-2H-pyrido[3,4-b]indol-2-yl)-2,2-difluoropropan-1-ol;

N1-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine;

N1-(2-fluoro-4-methoxy-5-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine;

3-fluoro-N-(2-((3-fluoro-2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)propan-1-amine;

N-(2-((3-chloro-2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)-3-fluoropropan-1-amine;

N1-(3-fluoro-2-((1S,3R)-3-methyl-2-(2,2,2-trifluoroethyl)-2,3,4,9-tetrahydro-1H-pyrido[3,4-b]indol-1-yl)pyridin-4-yl)-N2-(3-fluoropropyl)ethane-1,2-diamine;

N1-(3-fluoropropyl)-N2-(3-methyl-2-((1S,3R)-3-methyl-2-(2,2,2-trifluoroethyl)-2,3,4,9-tetrahydro-1H-pyrido[3,4-b]indol-1-yl)pyridin-4-yl)ethane-1,2-diamine;

2,2-difluoro-3-((1S,3R)-1-(4-(2-((3-fluoropropyl)amino)ethoxy)-3-methylpyridin-2-yl)-3-methyl-1,3,4,9-tetrahydro-2H-pyrido[3,4-b]indol-2-yl)propan-1-ol;

2,2-difluoro-3-((1S,3R)-1-(3-fluoro-4-(2-((3-fluoropropyl)amino)ethoxy)pyridin-2-yl)-3-methyl-1,3,4,9-tetrahydro-2H-pyrido[3,4-b]indol-2-yl)propan-1-ol;

N-(2-((2-((1S,3R)-2-(2,2-difluoroethyl)-3-methyl-2,3,4,9-tetrahydro-1H-pyrido[3,4-b]indol-1-yl)-3-fluoropyridin-4-yl)oxy)ethyl)-3-fluoropropan-1-amine;

3-fluoro-N-(2-((3-fluoro-2-((1S,3R)-2-((1-fluorocyclopropyl)methyl)-3-methyl-2,3,4,9-tetrahydro-1H-pyrido[3,4-b]indol-1-yl)pyridin-4-yl)oxy)ethyl)propan-1-amine;

3-fluoro-N-(2-((3-fluoro-2-((1S,3R)-2-((3-fluorooxetan-3-yl)methyl)-3-methyl-2,3,4,9-tetrahydro-1H-pyrido[3,4-b]indol-1-yl)pyridin-4-yl)oxy)ethyl)propan-1-amine;

3-fluoro-N-(2-((5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine;

3-fluoro-N-(2-((4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

2,2-difluoro-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)propan-1-ol;

3-((1R,3R)-1-(3-chloro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol;

3-fluoro-N-(2-((5-methyl-6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

3-fluoro-N-(2-((3-methyl-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine;

N-(2-((3,5-difluoro-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)-3-fluoropropan-1-amine;

N-(2-((3,5-difluoro-4-((1R,3R)-2-((1-fluorocyclopropyl)methyl)-3-methyl-2,3,4,9-tetrahydro-1H-pyrido[3,4-b]indol-1-yl)pyridin-2-yl)oxy)ethyl)-3-fluoropropan-1-amine;

N-(2-((3,5-difluoro-4-((1R,3R)-6-fluoro-2-((1-fluorocyclopropyl)methyl)-3-methyl-2,3,4,9-tetrahydro-1H-pyrido[3,4-b]indol-1-yl)pyridin-2-yl)oxy)ethyl)-3-fluoropropan-1-amine;

2,2-difluoro-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)propan-1-ol;

3-((1R,3R)-1-(3-chloro-5-fluoro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol;

3-fluoro-N-(2-((6-methoxy-5-((1R,3R)-3-methyl-2-(2,2,2-trifluoroethyl)-2,3,4,9-tetrahydro-1H-pyrido[3,4-b]indol-1-yl)pyridazin-3-yl)oxy)ethyl)propan-1-amine;

3-fluoro-N-(2-((6-((1S,3R)-3-methyl-2-(2,2,2-trifluoroethyl)-2,3,4,9-tetrahydro-1H-pyrido[3,4-b]indol-1-yl)pyrimidin-4-yl)oxy)ethyl)propan-1l-amine;

3-fluoro-N-(2-((5-methyl-6-((1S,3R)-3-methyl-2-(2,2,2-trifluoroethyl)-2,3,4,9-tetrahydro-1H-pyrido[3,4-b]indol-1-yl)pyrimidin-4-yl)oxy)ethyl)propan-1-amine;

2,2-difluoro-3-((1S,3R)-1-(6-(2-((3-fluoropropyl)amino)ethoxy)-5-methylpyrimidin-4-yl)-3-methyl-1,3,4,9-tetrahydro-2H-pyrido[3,4-b]indol-2-yl)propan-1-ol;

3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid;

(R)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid;

2,2-difluoro-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid;

3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2,2-dimethylpropanoic acid;

1-(((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)methyl)cyclobutane-1-carboxylic acid;

(R)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid;

(S)-3-((1R,3R)-3-ethyl-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid;

(R)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid;

(S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid;

(S)-3-((1R,3R)-1-(2-(difluoromethyl)-6-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid;

(R)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid;

(S)-3-((1R,3R)-1-(2,6-dichloro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(2,6-dichloro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid;

(R)-3-((1R,3R)-1-(2,6-dichloro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid;

3-((1R,3R)-1-(2-chloro-6-fluoro-3-(2-((3-fluoropropyl)amino)ethoxy)phenyl)-3-methyl-1,3,4,9-tetrahydro-2H-pyrido[3,4-b]indol-2-yl)-2,2-dimethylpropanoic acid;

(S)-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid;

(S)-3-((1R,3R)-1-(3-chloro-5-fluoro-2-(2-((3-fluoropropyl)amino)ethoxy)pyridin-4-yl)-3-methyl-1,3,4,9-tetrahydro-2H-pyrido[3,4-b]indol-2-yl)-2-methylpropanoic acid;

(S)-3-((R)-1-(6-fluoro-3-(2-((3-fluoropropyl)amino)ethoxy)-2-methylphenyl)-3,3-dimethyl-1,3,4,9-tetrahydro-2H-pyrido[3,4-b]indol-2-yl)-2-methylpropanoic acid;

(S)-3-((1R,3R)-1-(6-fluoro-3-((2-((3-fluoropropyl)amino)ethyl)amino)-2-methylphenyl)-3-methyl-1,3,4,9-tetrahydro-2H-pyrido[3,4-b]indol-2-yl)-2-methylpropanoic acid;

(S)-3-((1R,3R)-1-(6-fluoro-3-((2-((3-fluoropropyl)amino)ethyl)(methyl)amino)-2-methylphenyl)-3-methyl-1,3,4,9-tetrahydro-2H-pyrido[3,4-b]indol-2-yl)-2-methylpropanoic acid;

(S)-3-((1R,3S)-3-(difluoromethyl)-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid;

(S)-3-((1R,3S)-1-(2-chloro-6-fluoro-3-(2-((3-fluoropropyl)amino)ethoxy)phenyl)-3-(difluoromethyl)-1,3,4,9-tetrahydro-2H-pyrido[3,4-b]indol-2-yl)-2-methylpropanoic acid;

(S)-3-((1R,3S)-1-(3-chloro-5-fluoro-2-(2-((3-fluoropropyl)amino)ethoxy)pyridin-4-yl)-3-(difluoromethyl)-1,3,4,9-tetrahydro-2H-pyrido[3,4-b]indol-2-yl)-2-methylpropanoic acid;

(S)-3-((1R,3S)-1-(6-fluoro-3-(2-((3-fluoropropyl)amino)ethoxy)-2-methylphenyl)-3-(trifluoromethyl)-1,3,4,9-tetrahydro-2H-pyrido[3,4-b]indol-2-yl)-2-methylpropanoic acid;

(S)-3-((1R,3S)-1-(2-chloro-6-fluoro-3-(2-((3-fluoropropyl)amino)ethoxy)phenyl)-3-(trifluoromethyl)-1,3,4,9-tetrahydro-2H-pyrido[3,4-b]indol-2-yl)-2-methylpropanoic acid;

(S)-3-((1R,3S)-1-(3-chloro-5-fluoro-2-(2-((3-fluoropropyl)amino)ethoxy)pyridin-4-yl)-3-(trifluoromethyl)-1,3,4,9-tetrahydro-2H-pyrido[3,4-b]indol-2-yl)-2-methylpropanoic acid;

(S)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;

(S)-3-((1R,3R)-1-(2,6-difluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;

(S)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;

(S)-3-((1R,3R)-1-(6-fluoro-3-((2-((3-fluoropropyl)(methyl)amino)ethyl)(methyl)amino)-2-methylphenyl)-3-methyl-1,3,4,9-tetrahydro-2H-pyrido[3,4-b]indol-2-yl)-2-methylpropanoic acid;

(S)-3-((1R,3R)-1-(2-(difluoromethyl)-6-fluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid;

(S)-3-((1R,3S)-1-(6-fluoro-3-(2-((3-fluoropropyl)(methyl)amino)ethoxy)-2-methylphenyl)-3-(trifluoromethyl)-1,3,4,9-tetrahydro-2H-pyrido[3,4-b]indol-2-yl)-2-methylpropanoic acid;

(S)-3-((1R,3R)-1-(6-fluoro-3-(2-((3-fluoropropyl)(methyl-d3)amino)ethoxy)-2-methylphenyl)-3-methyl-1,3,4,9-tetrahydro-2H-pyrido[3,4-b]indol-2-yl)-2-methylpropanoic acid;

(R)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;

(R)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;

(R)-3-((1R,3R)-1-(5-fluoro-2-(2-((3-fluoropropyl)(methyl-d3)amino)ethoxy)-3-methylpyridin-4-yl)-3-methyl-1,3,4,9-tetrahydro-2H-pyrido[3,4-b]indol-2-yl)-2-methylpropanoic acid; and N-(2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)-3-fluoro-N-methylpropan-1-amine;

or a pharmaceutically acceptable salt thereof.

In one embodiment there is provided a compound of Formula (I), wherein the compound is selected from the group consisting of:

(2R)-3-[(1R,3R)-6-fluoro-1-[5-fluoro-2-[2-[3-fluoropropyl(methyl)amino]ethoxy]-3-methyl-4-pyridyl]-3-methyl-1,3,4,9-tetrahydropyrido[3,4-b]indol-2-yl]-2-methyl-propanoic acid;

3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid;

3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid;

3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)butanoic acid;

(3R)-3-((1R,3R)-1-(5-fluoro-2-(2-((3-fluoropropyl)(methyl)amino) ethoxy)-3-methyl pyridin-4-yl)-3-methyl-1,3,4,9-tetrahydro-2H-pyrido[3,4-b]indol-2-yl) butanoic acid;

(3S)-3-((1R,3R)-1-(5-fluoro-2-(2-((3-fluoropropyl)(methyl)amino) ethoxy)-3-methyl pyridin-4-yl)-3-methyl-1,3,4,9-tetrahydro-2H-pyrido[3,4-b]indol-2-yl)butanoic acid;

(R)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;

(R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;

(R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoic acid; and 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoic acid;

or a pharmaceutically acceptable salt thereof.

In one embodiment there is provided a compound of Formula (I), (IA), (IB), (IC), (ID), (IE), (IF), (IH), (IJ), (IZ), or (IZA), or a pharmaceutically acceptable salt thereof, wherein the compound is selected from any of the Examples in the specification. A further feature is any of the embodiments described in the specification with the proviso that any of the specific Examples are individually disclaimed. A further feature is any of the embodiments described in the specification with the proviso that any one or more of the compounds selected from the above list of examples of compounds of the specification are individually disclaimed.

The $C_{1-3}$ alkyl group may be branched or unbranched. Examples of suitable $C_{1-3}$ alkyl groups are methyl (Me), ethyl (Et), n-propyl (n-Pr) or i-propyl (i-Pr).

For the avoidance of doubt, in the compound of Formula (I), (IA), (IB), (IC), (ID), (IE), (IF), (IH), (IJ), (IZ), or (IZA), the substituents $R^9$ and $R^{10}$ may each be substituted at either position of the respective ethyl chain with which they are associated. Therefore, by way of example only, the $R^9$ substituent may be attached in the two possible positions as shown below:

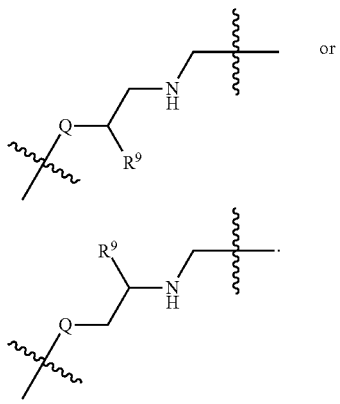

For the further avoidance of doubt, the use of "∼∼" in formulae of this specification denotes the point of attachment between different groups.

For the further avoidance of doubt, where multiple substituents are independently selected from a given group, the selected substituents may comprise the same substituents or different substituents from within the given group.

The compounds of Formula (I), (IA), (IB), (IC), (ID), (IE), (IF), (IH), (IJ), (IZ), or (IZA), have two or more chiral centres and it will be recognised that the compounds of Formula (I), (IA), (IB), (IC), (ID), (IE), (IF), (IH), (IJ), (IZ), or (IZA), may be prepared, isolated and/or supplied with or without the presence, in addition, of one or more of the other possible enantiomeric and/or diastereomeric isomers of the compounds of Formula (I), (IA), (IB), (IC), (ID), (IE), (IF), (IH), (IJ), (IZ), or (IZA), in any relative proportions. The preparation of enantioenriched/enantiopure and/or diastereoenriched/diastereopure compounds may be carried out by standard techniques of organic chemistry that are well known in the art, for example by synthesis from enantioenriched or enantiopure starting materials, use of an appropriate enantioenriched or enantiopure catalyst during synthesis, and/or by resolution of a racemic or partially enriched mixture of stereoisomers, for example via chiral chromatography.

For use in a pharmaceutical context it may be preferable to provide a compound of Formula (I), (IA), (IB), (IC), (ID), (IE), (IF), (IH), (IJ), (IZ), or (IZA), or a pharmaceutically acceptable salt thereof without large amounts of the other stereoisomeric forms being present.

Accordingly, in one embodiment there is provided a composition comprising a compound of Formula (I), (IA), (IB), (IC), (ID), (IE), (IF), (IH), (IJ), (IZ), or (IZA), or a pharmaceutically acceptable salt thereof, optionally together with one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In a further embodiment there is provided a composition comprising a compound of Formula (I), (IA), (IB), (IC), (ID), (IE), (IF), (IH), (IJ), (IZ), or (IZA), or a pharmaceutically acceptable salt thereof, optionally together with one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In a further embodiment there is provided a composition comprising a compound of Formula (I), (IA), (IB), (IC), (ID), (IE), (IF), (IH), (IJ), (IZ), or (IZA), or a pharmaceutically acceptable salt thereof, optionally together with one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with an enantiomeric excess (% ee) of ≥90% and a diastereomeric excess (% de) of ≥90%.

In further embodiments of the above-mentioned composition the % ee and % de may take any combination of values as listed below:

The % ee is ≤5% and the % de is ≥80%.
The % ee is ≤5% and the % de is ≥90%.
The % ee is ≤5% and the % de is ≥95%.
The % ee is ≤5% and the % de is ≥98%.
The % ee is ≥95% and the % de is ≥95%.
The % ee is ≥98% and the % de is ≥98%.
The % ee is ≥99% and the % de is ≥99%.

In a further embodiment there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in association with a pharmaceutically acceptable excipient.

In one embodiment there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in association with a pharmaceutically acceptable excipient, optionally further comprising one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In one embodiment there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in association with a pharmaceutically acceptable excipient, optionally further comprising one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In one embodiment there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in association with a pharmaceutically acceptable excipient, optionally further comprising one or more of the other stereoisomeric forms of the compound of Formula (I), (IA), (IB), (IC), (ID), (IE), (IF), (IH), (IJ), (IZ), or (IZA), or pharmaceutically acceptable salt thereof, wherein the compound of Formula (I), (IA), (IB), (IC), (ID), (IE), (IF), (IH), (IJ), (IZ), or (IZA), or pharmaceutically acceptable salt thereof is present within the composition with an enantiomeric excess (% ee) of ≥90% and a diastereomeric excess (% de) of ≥90%.

In further embodiments of the above-mentioned pharmaceutical composition the % ee and % de may take any combination of values as listed below:

The % ee is ≥95% and the % de is ≥95%.
The % ee is ≥98% and the % de is ≥98%.
The % ee is ≥99% and the % de is ≥99%.

The compounds of Formula (I), (IA), (IB), (IC), (ID), (IE), (IF), (IH), (IJ), (IZ), or (IZA), and pharmaceutically acceptable salts thereof may be prepared, used or supplied in amorphous form, crystalline form, or semicrystalline form and any given compound of Formula (I), (IA), (IB), (IC), (ID), (IE), (IF), (IH), (IJ), (IZ), or (IZA), or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I), (IA), (IB), (IC), (ID), (IE), (IF), (IH), (IJ), (IZ), or (IZA), and pharmaceutically acceptable salts thereof.

In further embodiments there is provided a compound of Formula (I), (IA), (IB), (IC), (ID), (IE), (IF), (IH), (IJ), (IZ), or (IZA), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopes of nitrogen include $^{15}N$. In a particular embodiment there is provided a compound of Formula (I), (IA), (IB), (IC), (ID), (IE), (IZ), or (IZA), wherein $R^2$ is deuterium. In a further embodiment there is provided a compound of Formula (I), (IH), (IJ) or (IZA) where $R^{20}$ is $CD_3$.

A suitable pharmaceutically acceptable salt of a compound of the Formula (I), (IA), (IB), (IC), (ID), (IE), (IF), (IH), (IJ), (IZ), or (IZA), is, for example, an acid addition salt. A suitable pharmaceutically acceptable salt of a compound of Formula (I), (IA), (IB), (IC), (ID), (IE), (IF), (IH), (IJ), (IZ), or (IZA), may be, for example, an acid-addition salt of a compound of the Formula (I), (IA), (IB), (IC), (ID), (IE), (IF), (IH), (IJ), (IZ), or (IZA), for example an acid-addition salt with an inorganic or organic acid such as acetic acid, adipic acid, benzene sulfonic acid, benzoic acid, cinnamic acid, citric acid, D,L-lactic acid, ethane disulfonic acid, ethane sulfonic acid, fumaric acid, hydrochloric acid, L-tartaric acid, maleic acid, malic acid, malonic acid, methane sulfonic acid, napadisylic acid, phosphoric acid, saccharin, succinic acid, sulfuric acid, p-toluenesulfonic acid, toluene sulfonic acid or trifluoroacetic acid.

A further suitable pharmaceutically acceptable salt of a compound of the Formula (I), (IA), (IB), (IC), (ID), (IE), (IF), (IH), (IJ), (IZ), or (IZA), is, for example, a salt formed within is the human or animal body after administration of a compound of the Formula (I), (IA), (IB), (IC), (ID), (IE), (IF), (IH), (IJ), (IZ), or (IZA), to said human or animal body.

The compound of Formula (I), (IA), (IB), (IC), (ID), (IE), (IF), (IH), (IJ), (IZ), or (IZA), or pharmaceutically acceptable salt thereof may be prepared as a co-crystal solid form.

It is to be understood that a pharmaceutically acceptable co-crystal of a compound of the Formula (I), (IA), (IB), (IC), (ID), (IE), (IF), (IH), (IJ), (IZ), or (IZA), or pharmaceutically acceptable salts thereof, form an aspect of the present specification.

It is to be understood that a suitable pharmaceutically acceptable pro-drug of a compound of the Formula (I), (IA), (IB), (IC), (ID), (IE), (IF), (IH), (IJ), (IZ), or (IZA), also forms an aspect of the present specification. Accordingly, the compounds of the specification may be administered in the form of a pro-drug, which is a compound that is broken down in the human or animal body to release a compound of the specification. A pro-drug may be used to alter the physical properties and/or the pharmacokinetic properties of a compound of the specification. A pro-drug can be formed when the compound of the specification contains a suitable group or substituent to which a property-modifying group can be attached. Examples of pro-drugs include in-vivo cleavable ester or amide derivatives of the compound of the Formula (I), (IA), (IB), (IC), (ID), (IE), (IF), (IH), (IJ), (IZ), or (IZA).

Accordingly, one aspect of the present specification includes those compounds of Formula (I), (IA), (IB), (IC), (ID), (IE), (IF), (IH), (IJ), (IZ), or (IZA), as defined hereinbefore when made available by organic synthesis and when made available within the human or animal body by way of cleavage of a pro-drug thereof. Accordingly, the present specification includes those compounds of the Formula (I), (IA), (IB), (IC), (ID), (IE), (IF), (IH), (IJ), (IZ), or (IZA), that are produced by organic synthetic means and also such compounds that are produced in the human or animal body by way of metabolism of a precursor compound, that is a compound of the Formula (I), (IA), (IB), (IC), (ID), (IE), (IF), (IH), (IJ), (IZ), or (IZA), may be a synthetically-produced compound or a metabolically-produced compound.

A suitable pharmaceutically acceptable pro-drug of a compound of the Formula (I), (IA), (IB), (IC), (ID), (IE), (IF), (IH), (IJ), (IZ), or (IZA), is one that is based on reasonable medical judgement as being suitable for administration to the human or animal body without is undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in-vivo effects of a compound of the Formula (I), (IA), (IB), (IC), (ID), (IE), (IF), (IH), (IJ), (IZ), or (IZA), may be exerted in part by one or more metabolites that are formed within the human or animal body after administration of a compound of the Formula (I), (IA), (IB), (IC), (ID), (IE), (IF), (IH), (IJ), (IZ), or (IZA). As stated hereinbefore, the in-vivo effects of a compound of the Formula (I), (IA), (IB), (IC), (ID), (IE), (IF), (IH), (IJ), (IZ), or (IZA), may also be exerted by way of metabolism of a precursor compound (a pro-drug).

For the avoidance of doubt it is to be understood that where in this specification a group is qualified by 'hereinbefore defined' or 'defined herein' the said group encompasses the first occurring and broadest definition as well as each and all of the alternative definitions for that group.

Another aspect of the present specification provides a process for preparing a compound of the Formula (I), (IA), (IB), (IC), (ID), (IE), (IF), (IH), (IJ), (IZ), or (IZA), or a pharmaceutically acceptable salt thereof. A suitable process is illustrated by the following representative process variants in which, unless otherwise stated, A, D, E, G, Q and $R^1$ to $R^{10}$ is have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Compounds of Formula (I) may be made by, for example:
a) Reaction of a compound of formula (II) with a compound of formula (III) under conditions known in the art as suitable for Pictet-Spengler reactions (such as in the presence of acid (such as acetic acid) and in a suitable solvent (for example toluene) and a suitable temperature (such as 80-100° C.) with or without a protecting group (P) on the nitrogen that may be removed under conditions known to the art.

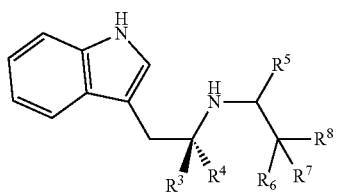

(II)

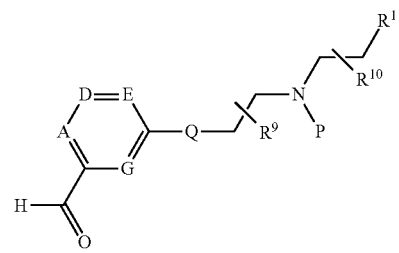

(III)

b) Where Q is O, NH or NMe, by etherification or amination of a suitable aryl halide of formula (IV), where L is for example a halogen (such as Br) or a trifluoromethanesulfonyl (triflate) group or a boronic acid or boronate ester, with an alcohol or amine of formula (V) using a suitable metal catalyst (for example RockPhos 3rd Generation Precatalyst or BrettPhos 3rd Generation Precatalyst) in a suitable solvent (for example toluene, THF or DME) in the presence of a suitable base (for example cesium carbonate or potassium carbonate) and a suitable temperature (such as 90-120° C.) with or without a protecting group (P) on the nitrogen that may be removed under conditions known to the art.

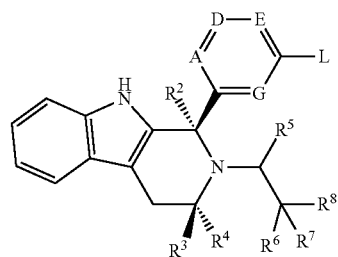

(IV)

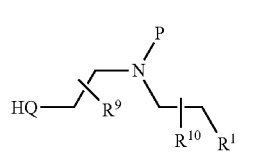

(V)

c) Where Q is O, by alkylation of a suitable phenol or hydroxyl heteroaryl compound of formula (VI) with an alcohol of formula (V) via Mitsunobu reaction using appropriate reagents (such as triphenylphosphine and diisopropyl (E)-diazene-1,2-dicarboxylate) in a suitable solvent (such as DCM) with or without a protecting group (P) on the nitrogen that may be removed under conditions known to the art.

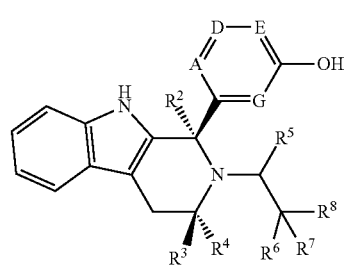

(VI)

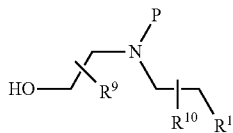
(V)

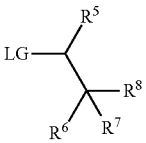
(XII)

d) Alkylation of a suitable compound of formula (VII), where LG is a leaving group known to the art, for example halide (such as Br), trifluoromethanesulfonate (triflate) or methanesulfonate (mesylate), with an amine of formula (VIII) in a suitable solvent (for example acetonitrile) in the presence of a suitable base (for example potassium carbonate) and a suitable temperature (such as 80-90° C.). with or without a protecting group (P) on the nitrogen that may be removed under conditions known to the art.

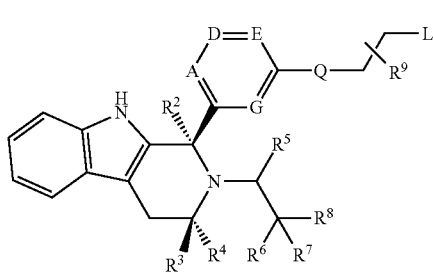
(VII)

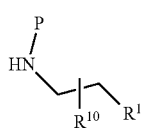
(VIII)

Compounds of formula (II) may be prepared by, for example:

a) Reaction of a compound of formula (IX) with an aldehyde of formula (X), in a suitable solvent (for example THF) in the presence of a suitable reducing agent (such as sodium triacetoxyborohydride) and at a suitable temperature (such as 20-30° C.);

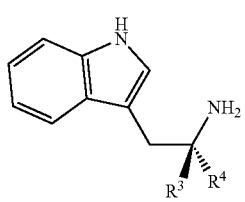
(IX)

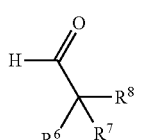
(X)

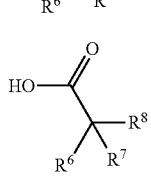
(XI)

b) (i) reaction of a compound of formula (IX) with an acid of formula (XI) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);

c) reaction of a compound of formula (IX) with a compound of formula (XII), wherein LG is a suitable leaving group (for example a halogen atom (such as bromo or chloro) or trifluoromethanesulfonate), in the presence of a suitable base (such as diisopropylethylamine) in a suitable solvent (for example DCM or dioxane) and at a suitable temperature (such as 20-85° C.).

Compounds of formula (III) may be prepared by reaction of a compound of formula (XIII) with an alcohol of formula (V) under conditions known in the art as suitable for Mitsunobu reactions (such as in the presence of an azodicarboxylate reagent (such as DEAD) and triphenylphosphine and in a suitable solvent (such as THF) and at a suitable temperature (such as 20-30° C.).

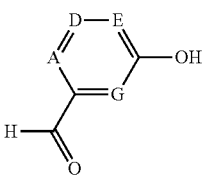
(XIII)

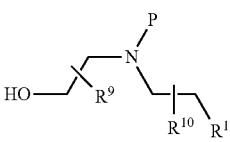
(V)

Compounds of formula (IV) may be prepared by reaction of a compound of formula (II) with a compound of formula (XIV), where L is a suitable functional group such as halide (for example bromide or chloride), triflate, boronic acid or boronic ester, under conditions known in the art as suitable for Pictet-Spengler reactions, such as in the presence of acid (such as acetic acid) and in a suitable solvent (for example toluene) and a suitable temperature (such as 80-100° C.).

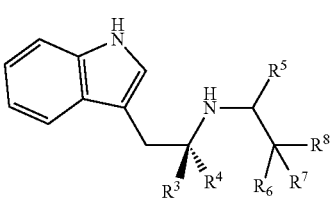
(II)

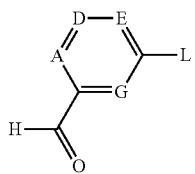

(XIV)

Compounds of formula (VI) may be prepared by reaction of a compound of formula (II) with a compound of formula (XV), under conditions known in the art as suitable for Pictet-Spengler reactions (such as in the presence of acid (such as acetic acid) and in a suitable solvent (for example toluene) and a suitable temperature (such as 80-100° C.). In certain aspects X equals OH (optionally with a protecting group) or X equals a boronic acid or boronic ester that may be converted to an OH using a suitable oxidant (such as hydrogen peroxide) in the presence of a suitable base (such as sodium hydroxide) in a suitable solvent (such as THF).

Alternatively, compounds of formula (VII) may be prepared by reaction of a compound of formula (IV) using standard functional group manipulations for example, an etherification, where L is for example a halogen (such as Br) or a trifluoromethanesulfonyl (triflate) group or a boronic acid or boronate ester, with an appropriate diol (with optional mono-protection) using a suitable metal catalyst (for example RockPhos 3rd Generation Precatalyst) in a suitable solvent (for example toluene or DME) in the presence of a suitable base (for example cesium carbonate). Subsequently, (with removal of protection if required) the alcohol may be converted into an appropriate leaving group (for example halide (such as Br), trifluoromethanesulfonate (triflate) or methanesulfonate (mesylate)) under standard conditions.

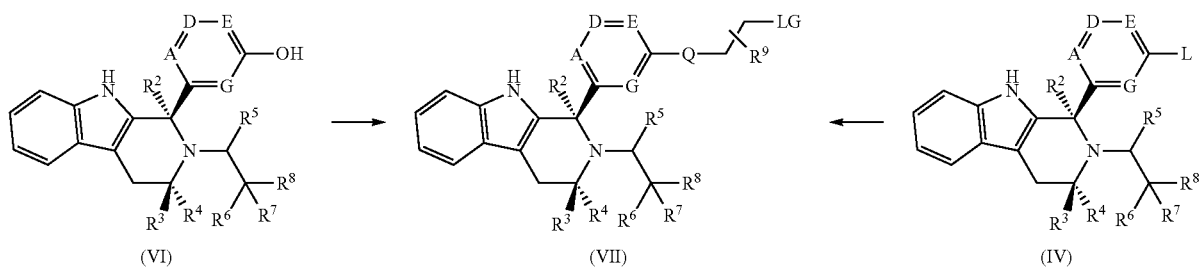

(VI)            (VII)            (IV)

It is to be understood that other permutations of the process steps in the process variants described above are also possible.

When a pharmaceutically acceptable salt of a compound of Formula (I), (IA), (IB), (IC), (ID), (IE), (IF), (IH), (IJ), (IZ), or (IZA), is required it may be obtained by, for example, reaction of said compound with a suitable acid or suitable base. When a pharmaceutically acceptable pro-drug of a compound of Formula (I), (IA), (IB), (IC), (ID), (IE), (IF), (IH), (IJ), (IZ), or (IZA), is required, it may be obtained using a conventional procedure.

It will also be appreciated that, in some of the reactions mentioned hereinbefore, it may be necessary or desirable to protect any sensitive functionalities in the compounds. The instances where protection is necessary or desirable, and suitable methods for protection, are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for

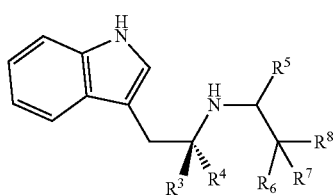

(II)

(XV)

Compounds of formula (VII) may be prepared by reaction of a compound of formula (VI) using standard functional group manipulations for example, a Mitsunobu reaction using appropriate reagents (such as triphenylphosphine and diisopropyl (E)-diazene-1,2-dicarboxylate) with 2-haloethanol (such as 2-bromoethan-1-ol) in a suitable solvent (such as DCM).

example, by hydrolysis with a suitable base such as an alkali metal hydroxide, for example lithium or sodium hydroxide. Alternatively an alkoxycarbonyl group such as a t-butoxycarbonyl group may be removed, for example, by treatment with a suitable acid as hydrochloric, sulfuric, formic, phosphoric or trifluoroacetic acid, and an arylmethoxycarbonyl group such as a benzyloxycarbonyl group may be removed, for example, by hydrogenation over a catalyst such as palladium-on-carbon, or by treatment with a Lewis acid, such as boron tris(trifluoroacetate). A suitable alternative protecting group for a primary amino group is, for example, a phthaloyl group, which may be removed by treatment with an alkylamine, for example dimethylaminopropylamine, or hydrazine.

A suitable protecting group for a hydroxy group is, for example, an acyl group, for example an alkanoyl group such as acetyl, an aroyl group, for example benzoyl, an arylmethyl group, for example benzyl, or a trialkyl or diarylalkyl silane, such as TBDMS or TBDPS. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates defined herein are novel and these are provided as further features of the specification.

Biological Assays

The following assays were used to measure the effects of the compounds of the present specification.

ERα Binding Assay

The ability of compounds to bind to isolated Estrogen Receptor Alpha Ligand binding domain (ER alpha-LBD (GST)) was assessed in competition assays using a LanthaScreen is Time-Resolved Fluorescence Resonance Energy Transfer (TR-FRET) detection end-point. For the LanthaScreen TR-FRET endpoint, a suitable fluorophore (Fluormone ES2, ThermoFisher, Product code P2645) and recombinant human Estrogen Receptor alpha ligand binding domain, residues 307-554 (expressed and purified in-house) were used to measure compound binding. The assay principle is that ER alpha-LBD (GST) is added to a fluorescent ligand to form a receptor/fluorophore complex. A terbium-labelled anti-GST antibody (Product code PV3551) is used to indirectly label the receptor by binding to its GST tag, and competitive binding is detected by a test compound's ability to displace the fluorescent ligand, resulting in a loss of TR-FRET signal between the Tb-anti-GST antibody and the tracer. The assay was performed as follows with all reagent additions carried out using the Beckman Coulter BioRAPTR FRD microfluidic workstation:

1. Acoustic dispense 120 nL of the test compound into a black low volume 384 well assay plates.
2. Prepare 1×ER alpha-LBD/Tb-antiGST Ab in ES2 screening buffer and incubate for 15 minutes.
3. Dispense 6 μL of the 1×AR-LBD/Tb-anti-GST Ab reagent into each well of the assay plate followed by 6 μL of Fluorophore reagent into each well of the assay plate
4. Cover the assay plate to protect the reagents from light and evaporation, and incubate at room temperature for 4 hours.
5. Excite at 337 nm and measure the fluorescent emission signal of each well at 490 nm and 520 nm using the BMG PheraSTAR.

Compounds were dosed directly from a compound source microplate containing serially diluted compound (4 wells containing 10 mM, 0.1 mM, 1 μM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range.

In total 120 nL of compound plus DMSO were added to each well and compounds were tested in a 12-point concentration response format over a final compound concentration range of 10, 2.917, 1.042, 0.2083, 0.1, 0.0292, 0.0104, 0.002083, 0.001, 0.0002917, 0.0001042, and 0.00001 μM respectively. TR-FRET dose response data obtained with each compound was exported into a suitable software package (such as Origin or Genedata) to perform curve fitting analysis. Competitive ER alpha binding was expressed as an $IC_{50}$ value. This was determined by calculation of the concentration of compound that was required to give a 50% reduction in tracer compound binding to ER alpha-LBD.

MCF-7 ER Down-Regulation Assay

The ability of compounds to down-regulate Estrogen Receptor (ER) numbers was assessed in a cell based immuno-fluorescence assay using the MCF-7 human ductal carcinoma breast cell line. MCF-7 cells were revived directly from a cryovial (approx $5 \times 10^6$ cells) in Assay Medium (phenol red free Dulbecco's Modified Eagle's medium (DMEM); Sigma D5921) containing 2 mM L-Glutamine and 5% (v/v) Charcoal/Dextran treated foetal calf serum. Cells were syringed once using a sterile 18G×1.5 inch (1.2×40 mm) broad gauge needle and cell density was measured using a Coulter Counter (Beckman). Cells were further diluted in Assay Medium to a density of $3.75 \times 10^4$ cells per mL and 40 μL per well added to transparent bottomed, black, tissue culture-treated 384 well plates (Costar, No. 3712) using a Thermo Scientific Matrix WellMate or Thermo Multidrop. Following cell seeding, plates were incubated overnight at 37° C., 5% $CO_2$ (Liconic carousel incubator). Test data was generated using the LabCyte Echomodel 555 compound reformatter which is part of an automated workcell (Integrated Echo 2 workcell). Compound stock solutions (10 mM) of the test compounds were used to generate a 384 well compound dosing plate (Labcyte P-05525-CV1). 40 μL of each of the 10 mM compound stock solutions was dispensed into the first quadrant well and then 1:100 step-wise serial dilutions in DMSO were performed using a Hydra II (MATRIX UK) liquid handling unit to give 40 μL of diluted compound into quadrant wells 2 (0.1 mM), 3 (1 μM) and 4 (0.01 μM), respectively. 40 μL of DMSO added to wells in row P on the source plate allowed for DMSO normalisation across the dose range. To dose the control wells 40 µL of DMSO was added to row O1 and 40 µL of 100 µM fulvestrant in DMSO was added to row O3 on the compound source plate.

The Echo uses acoustic technology to perform direct microplate-to-microplate transfers of DMSO compound solutions to assay plates. The system can be programmed to transfer volumes as low as 2.5 nL in multiple increments between microplates and in so doing generates a serial dilution of compound in the assay plate which is then back-filled to normalise the DMSO concentration across the dilution range. Compounds were dispensed onto the cell plates with a compound source plate prepared as above producing a 12 point duplicate 3 µM to 3 pM dose range with 3-fold dilutions and one final 10-fold dilution using the Integrated Echo 2 workcell. The maximum signal control wells were dosed with DMSO to give a final concentration of 0.3%, and the minimum signal control wells were dosed with fulvestrant to give a final concentration of 100 nM accordingly. Plates were further incubated for 18-22 hours at 37° C., 5% $CO_2$ and then fixed by the addition of 20 µL of 11.1% (v/v) formaldehyde solution (in phosphate buffered saline (PBS)) giving a final formaldehyde concentration of 3.7% (v/v). Cells were fixed at room temperature for 20 mins before being washed two times with 250 µL PBS/Proclin (PBS with a Biocide preservative) using a BioTek platewasher, 40 µL of PBS/Proclin was then added to all wells and the plates stored at 4° C. The fixing method described above was carried out on the Integrated Echo 2 workcell. Immunostaining was performed using an automated AutoElisa workcell. The PBS/Proclin was aspirated from all wells and the cells permeabilised with 40 µL PBS containing 0.5% Tween™ 20 (v/v) for 1 hour at room temperature. The plates were washed three times in 250 µL of PBS/0.05% (v/v) Tween 20 with Proclin (PBST with a Biocide preservative) and then 20 µL of ERα (SP1) Rabbit monoclonal antibody (Thermofisher) 1:1000 in PBS/Tween™/3% (w/v) Bovine Serum Albumin was added. The plates were incubated overnight at 4° C. (Liconic carousel incubator) and then washed three times in 250 µL of PBS/0.05% (v/v) Tween™ 20 with Proclin (PBST). The plates were then incubated with 20 µL/well of a goat anti-rabbit IgG AlexaFluor 594 or goat anti-rabbit AlexaFluor 488 antibody (Molecular Probes) with Hoechst at 1:5000 in PBS/Tween™/3% (w/v) Bovine Serum Albumin for 1 hour at room temperature. The plates were then washed three times in 250 µL of PBS/0.05% (v/v) Tween™ 20 with Proclin (PBST with a Biocide preservative). 20 µL of PBS was added to each well and the plates covered with a black plate seal and stored at 4° C. before being read. Plates were read using a Cellomics Arrayscan reading the 594 nm (24 hr time point) or 488 nm (5 hr timepoint) fluorescence to measure the ERα receptor level in each well. The mean total intensity was normalized for cell number giving the total intensity per cell. The data was exported into a suitable software package (such as Origin) to perform curve fitting analysis. Down-regulation of the ERα receptor was expressed as an $IC_{50}$ value and was determined by calculation of the concentration of compound that was required to give a 50% reduction of the average maximum Total Intensity signal.

The data shown in Table A were generated (the data below may be a result from a single experiment or an average of two or more experiments):

TABLE A

| Example | ER binding $IC_{50}$ value (nM) | ER down regulation $IC_{50}$ value (nM) |
|---|---|---|
| 1 | 12 | 3.7 |
| 2 | 34 | 49 |
| 3 | 180 | 98 |
| 4 | 2.6 | 0.28 |
| 5 | 45 | 25 |
| 6 | 2.1 | 0.19 |
| 7 | 1.5 | 0.12 |
| 8 | 1.4 | 0.20 |
| 9 | 1.2 | 0.088 |
| 10 | 2.9 | 0.23 |
| 11 | 1.2 | 0.14 |
| 12 | 0.62 | 0.059 |
| 13 | 1.6 | 0.22 |
| 14 | 0.69 | 0.092 |
| 15 | 0.55 | 0.079 |
| 16 | 1.7 | 3.7 |
| 17 | 3.8 | 1.6 |
| 18 | 10 | 6.2 |
| 19 | 360 | 110 |
| 20 | 1.0 | 0.29 |
| 21 | 2.6 | 1.6 |
| 22 | 1.4 | 0.12 |
| 23 | 2.7 | 0.5 |
| 24 | 2.0 | 0.85 |
| 25 | 0.88 | 0.25 |
| 26 | 0.85 | 0.16 |
| 27 | 2.7 | 1.6 |
| 28 | 2.8 | 0.8 |
| 29 | 2.0 | 0.44 |
| 30 | 2.1 | 0.32 |
| 31 | 5.4 | 7.2 |
| 32 | 2.7 | 0.38 |
| 33 | 1.6 | 0.081 |
| 34 | 190 | — (41%) |
| 35 | 1.9 | 1.1 |
| 36 | 2.6 | 0.35 |
| 37 | 12 | 35 |
| 38 | NT | 0.19 |
| 39 | 1.4 | 0.26 |
| 40 | 7.9 | 0.53 |
| 41 | 12 | 6.0 |
| 42 | 3.7 | 1.9 |
| 43 | 82 | 220 |
| 44 | 1.0 | 0.14 |
| 45 | 0.78 | 0.034 |
| 46 | 1.0 | 0.22 |
| 47 | 2.5 | 11 (81%) |
| 48 | 4.4 | 13 |
| 49 | 1.2 | 0.15 |
| 50 | 1.0 | 0.81 (81%) |
| 51 | 1.2 | 0.12 |
| 52 | 0.58 | 0.34 |
| 53 | 150 | — (40%) |
| 54 | 5.9 | 1.0 |
| 55 | 4.0 | 0.53 |
| 56 | 39 | 14 |
| 57 | 2.6 | 0.34 |
| 58 | 7.9 | 1.9 |
| 59 | 2.3 | 3.1 |
| 60 | 0.84 | 0.12 |
| 61 | 0.79 | 0.19 |
| 62 | 0.71 | 0.076 |
| 63 | 1.1 | 0.32 |
| 64 | 0.96 | 0.071 |
| 65 | 0.64 | 0.058 |
| 66 | 0.71 | 0.34 |
| 67 | 0.70 | 0.099 |
| 68 | 0.69 | 0.095 |
| 69 | 1.4 | 1.5 |
| 70 | 1300 | 180 |
| 71 | 3.4 | 2.0 (90%) |
| 72 | 1.4 | 0.49 |
| 73 | 9.4 | 18 |
| 74 | 31 | 59 |
| 75 | 52 | 58 |
| 76 | 1.0 | 0.21 |
| 77 | 7.3 | 6.2 |

TABLE A-continued

| Example | ER binding IC$_{50}$ value (nM) | ER down regulation IC$_{50}$ value (nM) |
|---|---|---|
| 78 | 1.3 | 0.12 |
| 79 | 1.4 | 0.16 |
| 80 | 2.0 | 1.2 |
| 81 | >110 | 0.17 |
| 82 | 0.80 | 0.042 |
| 83 | 1.7 | 0.28 (90%) |
| 84 | 0.94 | 0.16 (83%) |
| 85 | 1.3 | 0.089 |
| 86 | 0.86 | 0.17 |
| 87 | 0.54 | 0.065 |
| 88 | 2.2 | 0.28 |
| 89 | 0.91 | 0.14 |
| 90 | 0.65 | 0.3 |
| 91 | 9.4 | 15 |
| 92 | 1.6 | 0.4 |
| 93 | 1.4 | 0.39 |
| 94 | 3.6 | 9.2 |
| 95 | 5.6 | 3.3 |
| 96 | 1.4 | 0.2 |
| 97 | 2.2 | 0.66 |
| 98 | 1.9 | 1.2 |
| 99 | 3.4 | 3.8 |
| 100 | 5.2 | 11 |
| 101 | 9.2 | 27 |
| 102 | 2.0 | 2.9 |
| 103 | 0.56 | 0.084 |
| 104 | 0.72 | 0.17 |
| 105 | 42 | 39 |
| 106 | 0.92 | 0.095 |
| 107 | 1.3 | 0.21 |
| 108 | 1.0 | 0.3 |
| 109 | 1.2 | 0.41 |
| 110 | 0.43 | 0.045 |
| 111 | 0.60 | 0.07 |
| 112 | 2.0 | 0.95 |
| 113 | 17 | >300 |
| 114 | 0.74 | 0.2 |
| 115 | 1.0 | 0.31 |
| 116 | 15 | 1.1 |
| 117 | 9.2 | 0.92 |
| 118 | 1.2 | 5.5 |
| 119 | 6.9 | 1.0 |
| 120 | 11 | 2.5 |
| 121 | 2.8 | 0.53 |
| 122 | 4.9 | 0.39 |
| 123 | 11 | 0.96 |
| 124 | 3.9 | 0.68 |
| 125 | 1.3 | 0.62 |
| 126 | 1.2 | 0.43 |
| 127 | 1.8 | 0.49 |
| 128 | 3.4 | 1.1 |
| 129 | 8.9 | 2.6 |
| 130 | 1.8 | 1.3 |
| 131 | 13 | 2.4 |
| 132 | 2.0 | 0.98 |
| 133 | 1.5 | 1.5 |
| 134 | 5.8 | 1.6 (85%) |
| 135 | 160 | 16 |
| 136 | 2.0 | >300 |
| 137 | 1.7 | 0.52 |
| 138 | 1.6 | 1.6 |
| 139 | 1.5 | 0.9 |
| 140 | 1.4 | 1.0 |
| 141 | 2.8 | 0.98 |
| 142 | 1.5 | 0.95 |
| 143 | 2.1 | 0.39 |
| 144 | 5.6 | 7.9 (88%) |
| 145 | 1.1 | 0.35 |
| 146 | 1.1 | 0.4 |
| 147 | 51 | NT |
| 148 | 1.1 | 0.42 (68%) |
| 149 | 1.5 | 0.85 (86%) |
| 150 | 5.2 | 0.53 |
| 151 | 8.2 | 1.1 |
| 152 | 1.5 | 0.38 |
| 153 | 2.2 | 0.44 |
| 154 | 1.2 | 0.89 (79%) |
| 155 | 1.0 | 0.21 |
| 156 | 1.2 | 1.4 |
| 157 | 1.8 | 1.0 |
| 158 | 1.5 | 1.0 |
| 159 | 0.9 | 0.18 |
| 160 | 1.9 | 0.36 |
| 161 | 1.7 | 1.1 |
| 162 | 1.4 | 0.48 |
| 163 | 3.3 | 1.2 |

[1]Compounds tested in the ER down regulation assay show downregulation values (>90%) in the assay unless otherwise stated, in which case the % downregulation is shown in brackets.
(NT = not tested).

Western Blotting Assay

The ability of compounds to down-regulate estrogen receptor (ER) was assessed by western blotting using human breast cancer cell lines (MCF-7 and CAMA-1). Cells were plated into 12-well tissue culture-treated plates at 0.5×10$^6$/well in phenol red-free RPMI containing 2 mM L-glutamine and 5% (v/v) charcoal treated foetal calf serum (F6765, Sigma). Cells were incubated with compounds (100 nM) or vehicle control (0.1% DMSO) for 48 h at 37° C., 5% $CO_2$ before washing once with PBS and lysing with 80 µl lysis buffer (25 mM Tris/HCl, 3 mM EDTA, 3 mM EGTA, 50 mM NaF, 2 mM sodium orthovanadate, 0.27 M sucrose, 10 mM 3-glycerophosphate, 5 mM sodium pyrophosphate, 0.5% TritonX-100, pH 6.8) on ice.

Cells were scraped, sonicated and centrifuged prior to performing a protein assay (DC Bio-Rad Protein kit, 500-0116) and making samples to a protein concentration of 1-2 mg/mL in lysis buffer containing 1×LDS Sample Buffer (NP0007, Invitrogen) and 1× NuPAGE sample reducing agent (NP0009, Invitrogen). Samples were boiled for 10 min at 95° C. and then frozen at −20° C. until ready for use.

10-20 µg protein was loaded onto 26-well Criterion gels (BioRad 345-0034). Gels were run at 125 V for 1 hr 25 min in running buffer (24 mM Tris Base Sigma, 192 mM Glycine, 3.5 mM SDS, made up in distilled water). Gels were then transferred at 30V for 2 hr in transfer is buffer (25 mM Tris, 192 mM Glycine, 20% (v/v) methanol, pH 8.3, made up in distilled water) onto nitrocellulose membrane. The blot was stained with Ponceau S (P7170, Sigma) and cut according to appropriate molecular weight markers.

Membranes were blocked for 1 hour at room temp in 5% Marvel (w/v) in phosphate-buffered saline containing 0.05% Tween™ 20 (PBS/Tween). Blots were then incubated with anti-ERα (SP1) rabbit monoclonal antibody (Thermofisher) diluted 1:1000 at 4° C. overnight (with gentle shaking) followed by several washes with PBS/Tween. Secondary anti-rabbit HRP antibody (7074, CST) diluted 1:2000 dilution was incubated for 2 h at room temperature (with gentle shaking) followed by several washes with PBS/Tween. All antibodies were made up in 5% Marvel (w/v) in PBS/Tween.

The immunoblots were developed using Pierce WestDura chemiluminescent reagents (Thermo Scientific 34076) and developed/quantified on the G-box using Syngene software. Down-regulation of the ERα receptor was normalised to the vehicle control (0% down-regulation) and the 100 nM fulvestrant control (100% down-regulation) run within the same gel.

Table B shows the data generated for selected Examples (the data below may be a result from a single experiment or an average of two or more experiments):

TABLE B

| Example | CAMA1 Western % ER deg vs Fv | MCF7 Western % ER deg vs Fv |
|---|---|---|
| 1 | 66 | 79 |
| 4 | 75 | 56 |
| 6 | 81 | 97 |
| 7 | 90 | 100 |
| 8 | 93 | 98 |
| 9 | 101 | 97 |
| 10 | 101 | 94 |
| 11 | 92 | 94 |
| 12 | 89 | 92 |
| 13 | 92 | 83 |
| 14 | 95 | 95 |
| 15 | 91 | 94 |
| 16 | 83 | 89 |
| 19 | 103 | 101 |
| 20 | 91 | 88 |
| 21 | 95 | 99 |
| 22 | 96 | 96 |
| 23 | 95 | 95 |
| 35 | 92 | 94 |
| 40 | 70 | 86 |
| 44 | 94 | 95 |
| 45 | 93 | 89 |
| 46 | 89 | 83 |
| 51 | 93 | 92 |
| 55 | 94 | 89 |
| 57 | 88 | 93 |
| 58 | 83 | 76 |
| 60 | 97 | 92 |
| 61 | 83 | 94 |
| 62 | 96 | 95 |
| 63 | 85 | 94 |
| 64 | 98 | 96 |
| 65 | 97 | 94 |
| 76 | 85 | 92 |
| 88 | 93 | 90 |
| 90 | 93 | 76 |
| 92 | 91 | 93 |
| 96 | 100 | 94 |
| 97 | 84 | 89 |
| 107 | 98 | 95 |
| 110 | 83 | 91 |
| 111 | 92 | 84 |
| 117 | 92 | 96 |
| 121 | 107 | 85 |
| 123 | 90 | 91 |
| 124 | 82 | 93 |
| 126 | 89 | 93 |
| 127 | 100 | 96 |
| 133 | 86 | 88 |
| 137 | 95 | 90 |
| 140 | 86 | 84 |
| 141 | NT | 79 |
| 142 | 80 | 85 |
| 143 | 71 | 87 |
| 145 | 87 | 94 |
| 152 | 90 | 93 |

Human Hepatocyte Assay

The metabolic stability of compounds in human hepatocytes was assessed using the following protocol:

1. Prepare 10 mM stock solutions of compound and control compounds in appropriate solvent (DMSO). Place incubation medium (L-15Medium) in a 37° C. water bath, and allow warming for at least 15 minutes prior to use.
2. Add 80 µL of acetonitrile to each well of the 96-well deep well plate (quenching plate).
3. In a new 96-well plate, dilute the 10 mM test compounds and the control compounds to 100 µM by combining 198 µL of acetonitrile and 2 µL of 10 mM stock.
4. Remove a vial of cryopreserved (less than −150° C.) human hepatocytes (LiverPool 10 Donor Human hepatocytes obtained from Celsis IVT. Chicago, Ill. (Product No. S01205)) from storage, ensuring that vials remain at cryogenic temperatures until thawing process ensues. As quickly as possible, thaw the cells by placing the vial in a 37° C. water bath and gently shaking the vials. Vials should remain in water bath until all ice crystals have dissolved and are no longer visible. After thawing is complete, spray vial with 70% ethanol, transfer the vial to a bio-safety cabinet.
5. Open the vial and pour the contents into the 50 mL conical tube containing thawing medium. Place the 50 mL conical tube into a centrifuge and spin at 100 g for 10 minutes. Upon completion of spin, aspirate thawing medium and resuspend hepatocytes in enough incubation medium to yield ~$1.5 \times 10^6$ cells/mL.
6. Using Cellometer Vision, count cells and determine the viable cell density. Cells with poor viability (<80% viability) are not acceptable for use. Dilute cells with incubation medium to a working cell density of $1.0 \times 10^6$ viable cells/mL.
7. Transfer 247.5 µL of hepatocytes into each well of a 96-well cell culture plate. Place the plate on Eppendorf Thermomixer Comfort plate shaker to allow the hepatocytes to warm for 10 minutes.
8. Add 2.5 µL of 100 µM test compound or control compounds into an incubation well containing cells, mix to achieve a homogenous suspension at 0.5 min, which when achieved, will define the 0.5 min time point. At the 0.5 min time, transfer 20 µL of incubated mixture to wells in a "Quenching plate" followed by vortexing.
9. Incubate the plate at 37° C. at 900 rpm on an Eppendorf Thermomixer Comfort plate shaker. At 5, 15, 30, 45, 60, 80, 100 and 120 min, mix the incubation system and transfer samples of 20 µL incubated mixture at each time point to wells in a separate "Quenching plate" followed by vortexing.
10. Centrifuge the quenching plates for 20 minutes at 4,000 rpm. 4 different compounds are pooled into one cassette and used for LC/MS/MS analysis.

All calculations were carried out using Microsoft Excel. Peak areas were determined from extracted ion chromatograms. In vitro intrinsic clearance (in vitro $Cl_{int}$, in L/min/$10^6$ cells) of parent compound was determined by regression analysis of the Ln percent parent disappearance vs. time curve. The in vitro intrinsic clearance (in vitro $Cl_{int}$, in L/min/$10^6$ cells) was determined from the slope value using the following equation and is shown in Table C:

in vitro $Cl_{int}$=kV/N

V=incubation volume (0.25 mL);

N=number of hepatocytes per well ($0.25 \times 10^6$ cells).

TABLE C

| Example | $Cl_{int}$ (µL/min/$10^6$ cells) |
|---|---|
| 9 | 4 |
| 14 | 6 |
| 55 | <1 |
| 57 | 2 |
| 121 | <1 |
| 123 | <1 |
| 126 | <1 |
| 127 | <1 |
| 143 | 4 |
| 145 | 5 |
| 151 | <1 |
| 152 | 2 |

TABLE C-continued

| Example | $Cl_{int}$ (μL/min/10⁶ cells) |
|---|---|
| 157 | 2 |
| 160 | 1 |

Physical Properties
Log D

The lipophilicity of a drug is an important physical property which may influence many biological and metabolic properties of a compound, for example the absorption, distribution, metabolism, excretion and toxicity profiles of a compound. The distribution coefficient between 1-octanol and aqueous buffer, Log DO/W, at pH 7.4, is the most commonly used measurement of the lipophilicity of a compound. The current method for measurement of Log DO/W is based on the traditional shake flask technique, but with the modification of measuring compounds in mixtures of ten at a time using UPLC with quantitative mass spectrometry (MS) as a method to measure the relative octanol and aqueous concentrations. The maximum capacity is 379 project compounds (48 pools with 10 compounds incl. three QC compounds) per experiment. 2 quality control (QC) samples, Cyclobenzaprine with moderate Log D and Nicardipine high Log D is used in all pools to ensure good quality. An additional QC sample Caffeine, with low Log D, are is used and randomly placed in all runs. The method has been thoroughly validated against the previous shake flask methodologies.

Solubility

In order for an oral compound to reach the site of action, and in order for oral absorption from the gut to occur, that compound must be in solution, and therefore compounds which possess high intrinsic solubility may be more suitable for pharmaceutical use. The thermodynamic solubility of a research compound is measured under standard conditions. It is a shake-flask approach that uses 10 mM DMSO solutions which are supplied from the Compound Managements liquid store and is a high throughput method. The dried compounds are equilibrated in an aqueous phosphate buffer (pH 7.4) for 24 hours at 25° C., the portion with the dissolved compound is then separated from the remains. The solutions are analyzed and quantified using UPLC/MS/MS, QC-samples are incorporated in each assay-run to ensure the quality of the assay.

Human Plasma Protein Binding

Human plasma protein binding is a key factor in controlling the amount of free (unbound) drug available for binding to target and hence plays an important role in the observed efficacy of is drugs in vivo. Therefore, compounds which possess high free fraction (low levels of plasma protein binding) may exhibit enhanced efficacy relative to a compound with similar potency and exposure levels. The automated equilibrium dialysis assay in human plasma uses the RED (Rapid Equilibrium Dialysis) Device and sample handling. The assay generally runs over two to three days including delivery of results. After dialysis for 18 hours, plasma and buffer samples are prepared for analysis by liquid chromatography and mass spectrometry. Samples are generally tested in singlicates and quantified by LC/MSMS by using a 7-point calibration curve in plasma. The compounds are pooled together in plasma pools up to 10 compounds. Three reference compounds are used in each run, Propranolol, Metoprolol and Warfarin. Warfarin is used as a control in each pool and Propranolol and Metoprolol are placed randomly in each run. An in-house Excel macro is used for preparation of files for the robot and the mass spectrometer and is also used for the calculations of fraction unbound (fu %) in plasma.

Table D shows the data for log D, solubility and plasma protein binding generated for selected Examples (the data below may be a result from a single experiment or an average of two or more experiments):

TABLE D

| Example | LogD pH 7.4 | Solubility (μM) | Human plasma protein binding (% free) |
|---|---|---|---|
| 1 | 3.0 | 303 | 6.5 |
| 2 | 3.1 | 895 | 3.8 |
| 3 | 3.0 | 712 | 2.6 |
| 4 | 2.5 | 543 | 10 |
| 5 | 3.0 | 357 | 2.8 |
| 6 | 3.2 | 154 | 2.2 |
| 7 | 3.7 | 35 | 1.5 |
| 8 | 2.6 | 617 | 5.6 |
| 9 | 3.6 | 100 | 1.6 |
| 10 | 3.6 | 67 | 2.0 |
| 11 | 3.4 | 102 | 0.85 |
| 13 | 2.6 | 493 | 3.5 |
| 14 | 2.4 | 606 | 4.0 |
| 15 | 2.9 | 571 | 3.2 |
| 16 | 4.1 | 74 | 1.2 |
| 17 | 4.0 | 68 | 0.36 |
| 18 | 4.5 | 27 | 0.55 |
| 19 | 4.6 | 5 | 0.49 |
| 20 | 4.6 | 11 | 0.24 |
| 21 | 4.6 | 3 | 0.10 |
| 22 | 4.2 | 0.7 | 0.61 |
| 23 | 3.4 | 73 | 3.7 |
| 24 | 3.7 | 88 | 0.84 |
| 25 | 4.3 | 19 | 0.080 |
| 26 | 4.6 | 8 | 0.22 |
| 27 | 4.2 | 6 | 0.42 |
| 28 | 3.8 | 40 | 1.2 |
| 29 | >3.2 | 58 | <3.2 |
| 30 | 4.1 | 39 | 0.72 |
| 31 | 4.1 | 40 | 0.41 |
| 32 | 4.1 | 55 | 0.52 |
| 33 | 4.5 | 8 | 0.090 |
| 34 | 3.7 | 151 | 2.2 |
| 35 | 3.1 | 222 | 5.4 |
| 36 | 3.5 | 183 | 2 |
| 37 | 3.6 | 434 | 2.3 |
| 38 | NT | NT | 0.91 |
| 39 | 3.6 | 259 | NT |
| 40 | 3.0 | 366 | 0.89 |
| 41 | 2.9 | 242 | 1.8 |
| 42 | 2.9 | 349 | NT |
| 43 | 2.2 | 358 | 2.8 |
| 44 | 3.3 | 278 | 2.3 |
| 45 | 3.3 | 227 | 1.2 |
| 46 | 2.8 | 462 | 2.4 |
| 47 | 2.7 | 488 | 6.1 |
| 48 | 2.8 | 307 | NT |
| 49 | 2.8 | 335 | NT |
| 50 | 2.8 | 461 | 7.1 |
| 51 | 3.2 | 122 | 2.3 |
| 52 | 3.0 | 426 | 3.3 |
| 53 | 0.1 | >1000 | 80 |
| 54 | 0.9 | >1000 | 18 |
| 55 | 0.9 | 875 | 26 |
| 56 | 2.7 | 445 | 4.6 |
| 57 | 1.3 | >1000 | 17 |
| 58 | 0.4 | >1000 | 38 |
| 59 | 0.9 | >1000 | 28 |
| 60 | 3.0 | 351 | 1.9 |
| 61 | 3.0 | 446 | 2.0 |
| 62 | 3.3 | 302 | 1.2 |
| 63 | 3.1 | 273 | 0.97 |
| 64 | 2.7 | 944 | 5.4 |
| 65 | 3.0 | 462 | 1.9 |
| 66 | 3.0 | 441 | 1.3 |

TABLE D-continued

| Example | LogD pH 7.4 | Solubility (µM) | Human plasma protein binding (% free) |
|---|---|---|---|
| 67 | 4.0 | 80.6 | 1.6 |
| 68 | 3.2 | 56.6 | 1.2 |
| 69 | 3.6 | 150 | 2.2 |
| 70 | 2.2 | 231 | 23 |
| 71 | 3.8 | <1.6 | 0.44 |
| 72 | 5.2 | <0.2 | <0.1 |
| 73 | 4.4 | 7 | 0.24 |
| 74 | 4.1 | 0.9 | 0.61 |
| 75 | 4.5 | 0.9 | 0.08 |
| 76 | 3.1 | 147 | 4.6 |
| 77 | 2.4 | 410 | 5.5 |
| 78 | 4.0 | 26 | 0.21 |
| 79 | 4.8 | 3.9 | <0.4 |
| 80 | 4.5 | 13 | 0.12 |
| 81 | 2.6 | 736 | 2.9 |
| 82 | 2.9 | 475 | 1.9 |
| 83 | 2.9 | 595 | 2.5 |
| 84 | 2.4 | 640 | 6 |
| 85 | 3.1 | 224 | 1.0 |
| 86 | 2.9 | 385 | 2.6 |
| 87 | 3.1 | 71 | 1.6 |
| 88 | 3.4 | 118 | 0.58 |
| 89 | 2.7 | 670 | <3.4 |
| 90 | 2.8 | 365 | 1.1 |
| 91 | 2.9 | 280 | 0.93 |
| 92 | 2.7 | 468 | NT |
| 93 | 4.3 | 0.5 | 0.34 |
| 94 | 2.4 | 698 | 7 |
| 95 | 2.5 | 869 | 4.6 |
| 96 | 2.4 | 960 | 7.1 |
| 97 | 1.8 | >1000 | 6.8 |
| 98 | 2.3 | 594 | NT |
| 99 | 2.1 | 285 | NT |
| 100 | 2.5 | >1000 | NT |
| 101 | 3.3 | 329 | 8.4 |
| 102 | 3.8 | 251 | 1.4 |
| 103 | 2.9 | 660 | 2 |
| 104 | 3.0 | 431 | 2.8 |
| 105 | 3.4 | 136 | 1 |
| 106 | 3.9 | 264 | 0.34 |
| 107 | 3.6 | 120 | 1 |
| 108 | 3.2 | 375 | 2.3 |
| 109 | >3.6 | 176 | 1.9 |
| 110 | 3.1 | 939 | NT |
| 111 | 3.1 | 469 | 1.4 |
| 112 | 3.2 | 92 | 1.5 |
| 113 | 4.1 | <1.6 | NT |
| 114 | 3.3 | 276 | 1.7 |
| 115 | 2.1 | 983 | 11 |
| 116 | 0.3 | >1000 | 58 |
| 117 | 0.8 | 948 | 46 |
| 118 | 1.8 | 111 | 8.4 |
| 119 | 1.3 | >1000 | 31 |
| 120 | NT | NT | NT |
| 121 | 1.4 | >1000 | 30 |
| 122 | 1.1 | >1000 | 18 |
| 123 | 1.1 | 954 | 36 |
| 124 | 1.3 | 958 | 14 |
| 125 | 0.9 | 978 | 7.4 |
| 126 | 1.2 | 966 | 15 |
| 127 | 1.8 | 952 | 24 |
| 128 | 1.0 | 973 | 15 |
| 129 | 1.5 | 953 | 23 |
| 130 | 1.5 | 854 | 7.8 |
| 131 | 1.2 | >1000 | 32 |
| 132 | 0.6 | 914 | 34 |
| 133 | 1.2 | 772 | 16 |
| 134 | 0.6 | >1000 | 36 |
| 135 | 0.5 | >1000 | 32 |
| 136 | 1.1 | 328 | 2.1 |
| 137 | 1.4 | >1000 | 11 |
| 138 | 1.6 | 995 | 8.3 |
| 139 | 1.0 | 916 | 13 |
| 140 | 1.7 | 775 | 5.7 |
| 141 | 1.5 | 638 | 5.2 |
| 142 | 1.4 | 796 | 6.2 |
| 143 | 1.5 | >1000 | 28 |
| 144 | NT | NT | NT |
| 145 | 1.8 | >1000 | 15 |
| 146 | 1.9 | 887 | 14 |
| 147 | NT | NT | 19 |
| 148 | 1.5 | 788 | 10 |
| 149 | 2.2 | 523 | 5.3 |
| 150 | 1.3 | 924 | 32 |
| 151 | 1.0 | >1000 | 45 |
| 152 | 1.9 | 860 | 20 |
| 153 | 1.9 | >1000 | 22 |
| 154 | 3.5 | 49 | 2.7 |
| 155 | 2.3 | 978 | 9.2 |
| 156 | 1.7 | 882 | 18 |
| 157 | 1.2 | 943 | 29 |
| 158 | 1.8 | >1000 | 21 |
| 159 | 1.7 | >1000 | 13 |
| 160 | 1.7 | 951 | 32 |
| 161 | 1.3 | >1000 | 6.3 |
| 162 | 1.8 | >1000 | 27 |
| 163 | 0.7 | >1000 | 49 |

(NT = Not tested)

hERG Binding Assay hERG (human ether a go go-related gene) potassium channels are essential for normal electrical activity in the heart. Arrhythmia can be induced by a blockage of hERG channels by a diverse group of drugs. This side effect is a common reason for drug failure in preclinical safety trials [Sanguinetti et al., Nature., 2006, 440, 463-469.] and therefore minimisation of hERG channel blocking activity may be a desirable property for drug candidates.

The purpose of the hERG binding assay is to evaluate the effects of test compounds on the voltage-dependent potassium channel encoded by the human ether go go-related gene (hERG) using a constitutively expressing CHO cell line on the Nanion Syncropatch 384PE automated patch clamp system.

The assay was conducted as follows with all reagents used at room temperature unless otherwise stated.

Reagent Preparations Include:

1. Internal "IC700" solution used to perfuse the underside of chip (in mM), KF 130, KCl 20, MgCl2 1, EGTA 10 and HEPES 10, (all Sigma-Aldrich; pH 7.2-7.3 using 10 M KOH, 320 mOsm) and supplemented with 25 µM escin.

2. External and cell buffer (in mM), NaCl 137, KCl 4, HEPES 10, D-glucose 10, CaCl2 2, MgCl2 1 (pH7.4, NaOH)

3. NMDG "reference" buffer used to establish a stable baseline prior to the addition of test compounds, NaCl 80, KCl 4, CaCl2 2, MgCl2 1, NMDG Cl 60, D-Glucose monohydrate 5, HEPES 10 (pH7.4 NaOH 298 mOsm)

4. Seal enhancer used to improve seal quality of cells, NaCl 80, KCl 3, CaCl2 10, HEPES 10, MgCl2 1 (pH7.4 NaOH)

Cell Preparations:

1. If using cell culture; cells to be incubated at 30° C. for approximately 4-6 days prior to being used. Day of assay lift cells using accutase and re-suspend in 20 ml cell buffer to a density of 0.8 to 1e6 cells/ml.

2. If using assay ready cryovials; rapidly thaw two cryovials at 37° C. and slowly pipette into 23 ml external solution 3. All cell preps to be incubated for 15 min on the shaking cell hotel set to 10° C. prior to starting assay Compound Preparations:

All compounds were acoustically dispensed in quadruplicate using a Labcyte Echo. A 10 mM stock solution is used to generate 6 compound source plates each at a different concentration to allow cumulative dosing onto cells (0.03167 mM, followed by 0.1 mM, then 0.3167 mM, 1 mM, 3.167 mM, 10 mM). 90 µl of reference buffer is added to each well of the source plates containing 600 nl of compound for a final compound concentration of 0.1 µM, 0.39 µM, 1.2 µM, 3.9 µM, 12.5 µM and 39.6 µM respectively.

hERG Assay (all Dispense Steps are Performed Using the Liquid Handling Set Up on the Nanion Syncropatch)

1. Fill 384 well medium resistance 4 hole chips with 40 µl external buffer and perfuse internal buffer to the underside of plate.
2. Dispense 20 µl of cells into each well of the chip followed by 20 µl of seal enhancer.
3. Remove 40 µl of reagent from each well to the wash station, leaving a residual volume of 40 µl
4. Dispense 40 µl of reference buffer with a removal step of 40 µl after 3 min, repeat this step.
5. Dispense 40 µl of compound plate 1 (0.03167 mM), 'real time' recordings for 3 min exposure prior to removal of 40 µl. This step is repeated for 5 further subsequent compound plates in increasing concentrations to generate a cumulative concentration-effect curve in each well of the Syncropatch chip.

hERG-mediated currents were elicited using a voltage step protocol consisting of a continuous holding voltage of −80 mV, with a 500 ms step to 60 mV followed by a 500 ms step to −40 mV every 15 seconds. hERG current magnitude was measured automatically from the leak-subtracted traces by the Nanion software by taking the peak of the hERG "tail" current at −40 mV every 15 seconds and taking the last three of these responses for each concentration to generate the concentration-effect curve.

Calculation of results is performed using APC package within Genedata. For the routine normalization of well data with Neutral and Inhibitor control well groups as reference, GeneData Assay Analyzer uses the following equation to normalize the signal values to the desired signal range:

$$N(x) = CR + \frac{x - \langle cr \rangle}{\langle sr \rangle - \langle cr \rangle}(SR - CR)$$

x is the measured raw signal value of a well
⟨cr⟩ is the median of the measured signal values for the Central Reference (Neutral) wells on a plate
⟨sr⟩ is the median of the measured signal values for the Scale Reference (Inhibitor) wells on a plate
CR is the desired median normalized value for the Central Reference (Neutral)
SR is the desired median normalized value for the Scale Reference (Inhibitor)

Table E shows the hERG binding data for selected Examples (the data below may be a result from a single experiment or an average of two or more experiments):

TABLE E

| Example | hERG IC$_{50}$ (µM) |
|---|---|
| 1 | 4.4 |
| 6 | 5.4 |
| 7 | 3.8 |
| 8 | 4.6 |
| 9 | 9.6 |
| 10 | 3.6 |
| 11 | 5.4 |
| 12 | 8.2 |
| 13 | 2.6 |
| 14 | 5.1 |
| 15 | 4.6 |
| 17 | 4.1 |
| 18 | 4.5 |
| 20 | 3.8 |
| 22 | 4.2 |
| 23 | 5.4 |
| 24 | 7 |
| 25 | 5.2 |
| 26 | 4.1 |
| 27 | 4.8 |
| 28 | 3.6 |
| 29 | 5.1 |
| 30 | 2.3 |
| 31 | 11 |
| 32 | 5.8 |
| 33 | 5.3 |
| 34 | 3.4 |
| 35 | 5.6 |
| 36 | 8.7 |
| 37 | 3.5 |
| 38 | 5 |
| 39 | 3.9 |
| 40 | 4.1 |
| 41 | 4.9 |
| 42 | 7.1 |
| 43 | 3.1 |
| 44 | 2.9 |
| 45 | 1.5 |
| 46 | 2.7 |
| 47 | 3.2 |
| 48 | 2.7 |
| 49 | 5.6 |
| 50 | 5.3 |
| 51 | 4.1 |
| 52 | 5.5 |
| 53 | >40 |
| 54 | >40 |
| 55 | >40 |
| 57 | >40 |
| 58 | >40 |
| 59 | >40 |
| 60 | 4.4 |
| 61 | 2.7 |
| 62 | 5 |
| 63 | 4.7 |
| 64 | 6.1 |
| 65 | 9.4 |
| 66 | 5.4 |
| 67 | 5.7 |
| 68 | 2 |
| 69 | 2.7 |
| 70 | 6.3 |
| 71 | 5.8 |
| 73 | 6.7 |
| 74 | 12 |
| 75 | 7.7 |
| 76 | 4.2 |
| 77 | 5.4 |
| 79 | 10 |
| 80 | 10 |
| 81 | 3.9 |
| 82 | 4.3 |
| 83 | 4 |
| 84 | 2.8 |
| 85 | 4.2 |
| 86 | 3.9 |
| 87 | 2.4 |
| 88 | 4.8 |

TABLE E-continued

| Example | hERG IC$_{50}$ (µM) |
|---|---|
| 89 | 6.1 |
| 90 | 5 |
| 91 | 2.6 |
| 92 | 23 |
| 93 | 6.6 |
| 94 | 9.9 |
| 95 | 7.2 |
| 96 | 10 |
| 97 | 18 |
| 98 | >32 |
| 99 | 20 |
| 100 | 19 |
| 101 | 7.1 |
| 102 | 7.2 |
| 103 | 4.3 |
| 104 | 4.3 |
| 105 | 3.5 |
| 106 | 7.3 |
| 107 | 8.1 |
| 108 | 6 |
| 110 | 2.8 |
| 111 | 5.1 |
| 112 | 19 |
| 114 | 5.9 |
| 115 | 11 |
| 117 | >40 |
| 119 | >40 |
| 121 | >40 |
| 123 | >40 |
| 125 | >40 |
| 126 | >40 |
| 128 | >40 |
| 132 | >40 |
| 133 | >40 |
| 137 | >40 |
| 138 | >40 |
| 140 | >40 |
| 143 | >40 |
| 145 | >40 |
| 149 | >40 |
| 151 | >40 |
| 152 | >40 |
| 154 | 4.3 |
| 156 | >40 |
| 157 | >40 |
| 158 | >40 |
| 159 | >40 |
| 161 | >40 |
| 162 | >40 |

Permeability

In order to maximize oral absorption, a drug must have sufficient transmembrane flux as well as avoid efflux by P-glycoprotein. The most widely used system for predicting oral absorption is by determination of the permeation rate of compounds through monolayers of a human colon adenocarcinoma cell line Caco-2.

Human Caco-2 Bidirectional Permeability A to B and B to A

An automated assay was used to determine the bidirectional permeability (efflux and uptake) of compounds in Caco-2 cells carried out over 2 hours at pH 7.4. Samples were analyzed through LC/MS/MS to estimate the apparent permeability coefficients (Papp) of compounds across Caco-2 cell monolayers and results are quoted in units of ×10$^{-6}$ cm/s.

The efflux ratio (ER) can be determined using the following equation:

$$ER = P_{app(B-A)} / P_{app(A-B)}$$

Where $P_{app(B-A)}$ indicates the apparent permeability coefficient in basolateral to apical direction, and $P_{app(A-B)}$ indicates the apparent permeability coefficient in apical to basolateral direction.

Human Caco-2 Passive Permeability A to B Papp

An automated assay was used to determine the passive permeability of compounds in Caco-2 cell monolayers carried out over 2 hours with an apical pH of 6.5 and basolateral pH of 7.4. The Caco-2 AB inhibition assay is carried out with chemical inhibition of the three major efflux transporters ABCB1 (P-gp), ABCG2 (BCRP) and ABCC2 (MRP2) in Caco-2 cells. Incubation of both apical and basolateral is carried out with a cocktail of inhibitors (50 µM quinidine, 20 M sulfasalazine and 100 µM benzbromarone). Samples were analyzed through LC/MS/MS to estimate the apparent permeability coefficients (Papp) of compounds across Caco-2 cell monolayers and results are quoted in units of ×10$^{-6}$ cm/s.

Table F shows the data for permeability generated for selected Examples (the data below may be a result from a single experiment or an average of two or more experiments):

TABLE F

| Example | Bidirectional Caco-2 Papp (×10$^{-6}$ cm/s) | Bidirectional Caco-2 efflux ratio | Passive Caco-2 Papp (×10$^{-6}$ cm/s) |
|---|---|---|---|
| 9 | 1.0 | 1.0 | NT |
| 10 | 1.4 | 1.6 | NT |
| 11 | 3.6 | 1.4 | NT |
| 14 | 4.4 | 1.3 | 13 |
| 52 | 8.8 | 1.0 | NT |
| 55 | 0.55 | 23 | <0.7 |
| 57 | 0.15 | 105 | <1.2 |
| 59 | 0.035 | 480 | <0.3 |
| 64 | 2.6 | 6.1 | NT |
| 76 | 6.4 | 0.55 | NT |
| 117 | 0.27 | 34 | <0.3 |
| 119 | 0.85 | 25 | 3.5 |
| 121 | 0.20 | 58 | NT |
| 122 | 0.58 | 40 | <1.0 |
| 123 | 1.1 | 16 | <1.0 |
| 124 | 1.1 | 23 | 1.9 |
| 125 | 0.13 | 130 | <0.6 |
| 126 | 0.46 | 52 | 1.2 |
| 127 | 0.43 | 48 | 2.0 |
| 133 | 0.29 | 51 | 2.5 |
| 137 | 0.35 | 64 | 4.6 |
| 138 | 0.16 | 94 | 1.8 |
| 139 | 0.26 | 54 | <0.9 |
| 140 | 0.51 | 36 | 4.0 |
| 141 | 0.54 | 36 | 3.4 |
| 142 | 0.34 | 40 | 3.2 |
| 143 | 3.2 | 11 | 3.3 |
| 144 | 0.50 | 35 | 4.0 |
| 145 | 5.6 | 3.4 | 17 |
| 151 | 2.2 | 9.5 | 4.3 |
| 152 | 11 | 2.2 | 16 |
| 155 | 7.3 | 2.6 | 23 |
| 156 | 4.6 | 4.2 | 9.2 |
| 157 | 3.6 | 5.6 | 12 |
| 160 | 4.4 | 6.4 | 4.2 |

(NT = Not Tested)

According to a further aspect of the specification there is provided a pharmaceutical composition, which comprises a compound of the Formula (I), (IA), (IB), (IC), (ID), (IE), (IF), (IH), (IJ), (IZ), or (IZA), or a pharmaceutically acceptable salt thereof, as defined hereinbefore in association with a pharmaceutically acceptable excipient.

Suitable pharmaceutically acceptable excipients for a tablet formulation include, for example, inert diluents, granulating and disintegrating agents, binding agents, lubricating agents, preservative agents and antioxidants. A further suitable pharmaceutically acceptable excipient may be a chelating agent. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the specification may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent system.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. Dry powder inhalers may also be suitable.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to Ig) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of is active ingredient divided conveniently between them. Typically, unit dosage forms will contain about 10 mg to 0.5 g of a compound of this specification, although a unit dosage form may contain up to 1 g. Conveniently, a single solid dosage form may contain between 1 and 300 mg of active ingredient.

The size of the dose for therapeutic or prophylactic purposes of compounds of the present specification will naturally vary according to the nature and severity of the disease state, the age and sex of the animal or patient and the route of administration, according to well known principles of medicine.

In using compounds of the present specification for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form.

In one aspect of the specification, compounds of the present specification or pharmaceutically acceptable salts thereof, are administered as tablets comprising 10 mg to 100 mg of the compound of the specification (or a pharmaceutically acceptable salt thereof), wherein one or more tablets are administered as required to achieve the desired dose.

As stated above, it is known that signalling through ERα causes tumourigenesis by one or more of the effects of mediating proliferation of cancer and other cells, mediating angiogenic events and mediating the motility, migration and invasiveness of cancer cells. We have found that the compounds of the present specification possess potent anti-tumour activity which it is believed is obtained by way of antagonism and down-regulation of ERα that is involved in the signal transduction steps which lead to the proliferation and survival of tumour cells and the invasiveness and migratory ability of metastasising tumour cells.

Accordingly, the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of ERα and that are involved in the signal transduction steps which lead to the proliferation and survival of tumour cells and the migratory ability and invasiveness of metastasising tumour cells. Further, the compounds of the present specification may be useful in the prevention or treatment of those tumours which are mediated alone or in part by antagonism and down-regulation of ERα, i.e. the compounds may be used to produce an ERα inhibitory effect in a warm-blooded animal in need of such treatment.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore for use as a medicament in a warm-blooded animal such as man.

According to a further aspect of the specification, there is provided a compound of the Formula (I), (IA), (IB), (IC), (ID), (IE), (IF), (IH), (IJ), (IZ), or (IZA), or a pharmaceutically acceptable salt thereof, as defined hereinbefore for use in the production of an anti-proliferative effect in a warm-blooded animal such as man.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore for use in a warm-blooded animal such as man as an anti-invasive agent in the containment and/or treatment of solid tumour disease.

According to a further aspect of the specification, there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, for the production of an anti-proliferative effect in a warm-blooded animal such as man.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the production of an anti-proliferative effect in a warm-blooded animal such as man.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further aspect of the specification there is provided a method for producing an anti-proliferative effect in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a method for producing an anti-invasive effect by the containment and/or treatment of solid tumour disease in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification, there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the prevention or treatment of cancer in a warm-blooded animal such as man.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore in the manufacture of a medicament for use in the prevention or treatment of cancer in a warm-blooded animal such as man.

According to a further aspect of the specification there is provided a method for the prevention or treatment of cancer in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification, there is provided a compound of the Formula (I), (IA), (IB), (IC), (ID), (IE), (IF), (IH), (IJ), (IZ), or (IZA), or a pharmaceutically acceptable salt thereof, as defined hereinbefore for use in the prevention or treatment of solid tumour disease in a warm-blooded animal such as man.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the prevention or treatment of solid tumour disease in a warm-blooded animal such as man.

According to a further aspect of the specification there is provided a method for the prevention or treatment of solid tumour disease in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided a method for the prevention or treatment of those tumours which are sensitive to inhibition of ERα that are involved in the signal transduction steps which lead to the proliferation, survival, invasiveness and migratory ability of tumour cells which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore for use in providing an inhibitory effect on ERα.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore in the manufacture of a medicament for use in providing an inhibitory effect on ERα.

According to a further aspect of the specification there is also provided a method for providing an inhibitory effect on ERα which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in providing a selective inhibitory effect on ERα.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in providing a selective inhibitory effect on ERα.

According to a further aspect of the specification there is also provided a method for providing a selective inhibitory effect on ERα which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

Described herein are compounds that can bind to ERα ligand binding domain and are selective estrogen receptor degraders. In biochemical and cell based assays the compounds of the present specification are shown to be potent estrogen receptor binders and reduce cellular levels of ERα and may therefore be useful in the treatment of estrogen sensitive diseases or conditions (including diseases that have developed resistance to endocrine therapies), i.e. for use in the treatment of cancer of the breast and gynaecological cancers (including endometrial, ovarian and cervical) and cancers expressing ERα mutated proteins which may be de novo mutations or have arisen as a result of treatment with a prior endocrine therapy such as an aromatase inhibitor.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the treatment of breast or gynaecological cancers.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the treatment of cancer of the breast, endometrium, ovary or cervix.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the treatment of cancer of the breast.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the treatment of cancer of the breast, wherein the cancer has developed resistance to one or more other endocrine therapies.

According to a further aspect of the specification there is provided a method for treating breast or gynaecological cancers, which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a method for treating cancer of the breast, endometrium, ovary or cervix, which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a method for treating breast cancer, which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided a method for treating breast cancer, wherein the cancer has developed resistance to one or more other endocrine therapies, which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the treatment of breast or gynaecological cancers.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the treatment of cancer of the breast, endometrium, ovary or cervix.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the treatment of breast cancer.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined hereinbefore, in the manufacture of a medicament for use in the treatment of breast cancer, wherein the cancer has developed resistance to one or more other endocrine therapies.

In one feature of the specification, the cancer to be treated is breast cancer. In a further aspect of this feature, the breast cancer is Estrogen Receptor+ve (ER+ve). In one embodiment of this aspect, the compound of Formula (I), (IA), (IB), (IC), (ID), (IE), (IF), (IH), (IJ), (IZ), or (IZA), or a pharmaceutically acceptable salt thereof, is dosed in combination with another anticancer agent, such as an anti-hormonal agent as defined herein.

According to a further aspect of the specification there is provided a compound of the Formula (I), (IA), (IB), (IC), (ID), (IE), (IF), (IH), (IJ), (IZ), or (IZA), or a pharmaceutically acceptable salt thereof, as defined hereinbefore, for use in the treatment of ER+ve breast cancer.

According to a further aspect of the specification there is provided a method for treating ER+ve breast cancer, which comprises administering an effective amount of a compound of the Formula (I), (IA), (IB), (IC), (ID), (IE), (IF), (IH), (IJ), (IZ), or (IZA), or a pharmaceutically acceptable salt thereof, as defined hereinbefore.

According to a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, as defined herein before in the manufacture of a medicament for use in the treatment of ER+ve breast cancer.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolomide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polo kinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and idoxifene), progestogens (for example megestrol acetate), aromatase inhibitors (for example as anastrozole, letrozole, vorozole and exemestane);

(iii) inhibitors of growth factor function and their downstream signalling pathways: included are Ab modulators of any growth factor or growth factor receptor targets, reviewed by Stern et al. *Critical Reviews in Oncology/Haematology*, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK7, CDK9 and CDK4/6 such as palbociclib;

iv) modulators of DNA damage signalling pathways, for example PARP inhibitors (e.g. Olaparib), ATR inhibitors or ATM inhibitors;

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab);

(x) Antisense or RNAi based therapies, for example those which are directed to the targets listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Accordingly, in one embodiment there is provided a compound of Formula (I), (IA), (IB), (IC), (ID), (IE), (IF), (IH), (IJ), (IZ), or (IZA), or a pharmaceutically acceptable salt thereof, and an additional anti-tumour substance for the conjoint treatment of cancer.

According to this aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect of the specification there is provided a compound of the Formula (I), (IA), (IB), (IC), (ID), (IE), (IF), (IH), (IJ), (IZ), or (IZA), or a pharmaceutically acceptable salt thereof, in combination with another anti-tumour agent, in particular an anti-tumour agent selected from one listed under (i)-(xi) herein above.

In a further aspect of the specification there is provided a compound of the Formula (I), (IA), (IB), (IC), (ID), (IE), (IF), (IH), (IJ), (IZ), or (IZA), or a pharmaceutically acceptable salt thereof, in combination with another anti-tumour agent, in particular an anti-tumour agent selected from one listed under (i) above.

In a further aspect of the specification there is provided a compound of the Formula (I), (IA), (IB), (IC), (ID), (IE), (IF), (IH), (IJ), (IZ), or (IZA), or a pharmaceutically acceptable salt thereof, and any one of the anti-tumour agents listed under (i) above.

In a further aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof, and a taxoid, such as for example taxol or taxotere, conveniently taxotere.

In a further aspect of the specification there is provided a compound of the Formula (I), (IA), (IB), (IC), (ID), (IE), (IF), (IH), (IJ), (IZ), or (IZA), or a pharmaceutically acceptable salt thereof, in combination with another anti-tumour agent, in particular an anti-tumour agent selected from one listed under (ii) herein above.

In a further aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof, and any one of the antihormonal agents listed under (ii) above, for example any one of the anti-oestrogens listed in (ii) above, or for example an aromatase inhibitor listed in (ii) above.

In a further aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof, and an mTOR inhibitor, such as AZD2014.

In a further aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, or a pharmaceutically-acceptable salt thereof.

In a further aspect of the specification there is provided a combination suitable for use in the treatment of cancer comprising a compound of the Formula (I), (IA), (IB), (IC), (ID), (IE), (IF), (IH), (IJ), (IZ), or (IZA), or a pharmaceutically acceptable salt thereof, and a CDK4/6 inhibitor, such as palbociclib.

In one aspect the above combination of a compound of the Formula (I), (IA), (IB), (IC), (ID), (IE), (IF), (IH), (IJ), (IZ), or (IZA), or a pharmaceutically acceptable salt thereof, with an anti-tumour agent listed in (ii) above, or an mTOR inhibitor (such as AZD2014), or a PI3K-a inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the treatment of breast or gynaecological cancers, such as cancer of the breast, endometrium, ovary or cervix, particularly breast cancer, such as ER+ve breast cancer.

Herein, where the term "combination" is used it is to be understood that this refers to simultaneous, separate or sequential administration. In one aspect of the specification "combination" refers to simultaneous administration. In another aspect of the specification "combination" refers to separate administration. In a further aspect of the specification "combination" refers to sequential administration. Where the administration is sequential or separate, the delay in administering the second component should not be such as to lose the beneficial effect of the combination. Where a combination of two or more components is administered separately or sequential, it will be understood that the dosage regime for each component may be different to and independent of the other components. Conveniently, the compounds of the present specification are dosed once daily.

According to a further aspect of the specification there is provided a pharmaceutical composition which comprises a compound of Formula (I), (IA), (IB), (IC), (ID), (IE), (IF), (IH), (IJ), (IZ), or (IZA), or a pharmaceutically acceptable salt thereof in combination with an anti-tumour agent selected from one listed under (i)-(xi) herein above, in association with a pharmaceutically acceptable excipient.

According to a further aspect of the specification there is provided a pharmaceutical composition which comprises a compound of Formula (I), (IA), (IB), (IC), (ID), (IE), (IF), (IH), (IJ), (IZ), or (IZA), or a pharmaceutically acceptable salt thereof in combination with any one of antihormonal agents listed under (ii) above, for example any one of the anti-oestrogens listed in (ii) above, or for example an aromatase inhibitor listed in (ii) above in association with a pharmaceutically acceptable excipient.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and an mTOR inhibitor, such as AZD2014, in association with a pharmaceutically acceptable excipient.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and a CDK4/6 inhibitor (such as palbociclib) in association with a pharmaceutically acceptable excipient.

According to a further aspect of the specification there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in combination with an anti-tumour agent selected from one listed under (i)-(xi) herein above, in association with a pharmaceutically acceptable excipient for use in treating cancer.

According to a further aspect of the specification there is provided a pharmaceutical composition which comprises a compound of the Formula (I), (IA), (IB), (IC), (ID), (IE), (IF), (IH), (IJ), (IZ), or (IZA), or a pharmaceutically acceptable salt thereof, in combination with any one of antihormonal agents listed under (ii) above, for example any one of the anti-oestrogens listed in (ii) above, or for example an aromatase inhibitor listed in (ii) above in association with a pharmaceutically acceptable excipient for use in treating cancer.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and an mTOR inhibitor, such as AZD2014, in association with a pharmaceutically acceptable excipient for use in treating cancer.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient for use in treating cancer.

In a further aspect of the specification there is provided a pharmaceutical composition comprising a compound of the Formula (I), (IA), (IB), (IC), (ID), (IE), (IF), (IH), (IJ), (IZ), or (IZA), or a pharmaceutically acceptable salt thereof, and a CDK4/6 inhibitor (such as palbociclib) in association with a pharmaceutically acceptable excipient for use in treating cancer.

In one aspect the above pharmaceutical compositions of a compound of the Formula (I), (IA), (IB), (IC), (ID), (IE), (IF), (IH), (IJ), (IZ), or (IZA), or a pharmaceutically acceptable salt thereof, with an anti-tumour agent listed in (ii) above, or an mTOR inhibitor (such as AZD2014), or a PI3K-a inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the treatment of breast or gynaecological cancers, such as cancer of the breast, endometrium, ovary or cervix, particularly breast cancer, such as ER+ve breast cancer.

According to another feature of the specification there is provided the use of a compound of the Formula (I), (IA), (IB), (IC), (ID), (IE), (IF), (IH), (IJ), (IZ), or (IZA), or a pharmaceutically acceptable salt thereof in combination with an anti-tumour agent selected from one listed under (i)-(xi) herein above, in the manufacture of a medicament for use in the treatment of cancer in a warm-blooded animal, such as man.

According to a further aspect of the specification there is provided the use of a compound of Formula (I), (IA), (IB), (IC), (ID), (IE), (IF), (IH), (IJ), (IZ), or (IZA), or a pharmaceutically acceptable salt thereof in combination with any one of antihormonal agents listed under (ii) above, for example any one of the anti-oestrogens listed in (ii) above, or for example an aromatase inhibitor listed in (ii) above in the manufacture of a medicament for use in the treatment of cancer in a warm-blooded animal, such as man.

In a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, in combination with an mTOR inhibitor, such as AZD2014, in the manufacture of a medicament for use in the treatment of cancer in a warm-blooded animal, such as man.

In a further aspect of the specification there is provided the use of a compound of the Formula (I), (IA), (IB), (IC), (ID), (IE), (IF), (IH), (IJ), (IZ), or (IZA), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in the manufacture of a medicament for use in the treatment of cancer in a warm-blooded animal, such as man.

In a further aspect of the specification there is provided the use a compound of the Formula (I), (IA), (IB), (IC), (ID), (IE), (IF), (IH), (IJ), (IZ), or (IZA), or a pharmaceutically acceptable salt thereof, in combination with a CDK4/6 inhibitor (such as palbociclib) in the manufacture of a medicament for use in the treatment of cancer in a warm-blooded animal, such as man.

In one aspect the above uses of a compound of the Formula (I), (IA), (IB), (IC), (ID), (IE), (IF), (IH), (IJ), (IZ), or (IZA), or a pharmaceutically acceptable salt thereof, in combination with an anti-tumour agent listed in (ii) above, or an mTOR inhibitor (such as AZD2014), or a PI3K-a inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the manufacture of a medicament for the treatment of breast or gynaecological cancers, such as cancer of the breast, endometrium, ovary or cervix, particularly breast cancer, such as ER+ve breast cancer.

Therefore in an additional feature of the specification, there is provided a method of treating cancer in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, in combination with an anti-tumour agent selected from one listed under (i)-(xi) herein above.

According to a further aspect of the specification there is provided a method of treating cancer in a warm-blooded animal, such as man, in need of such treatment which comprises administering to said animal an effective amount of a compound of Formula (I), (IA), (IB), (IC), (ID), (IE), (IF), (IH), (IJ), (IZ), or (IZA), or a pharmaceutically acceptable salt thereof in combination with any one of antihormonal agents listed under (ii) above, for example any one of the anti-oestrogens listed in (ii) above, or for example an aromatase inhibitor listed in (ii) above.

In a further aspect of the specification there is provided a method of treating cancer in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, in combination with an mTOR inhibitor, such as AZD2014.

In a further aspect of the specification there provided a method of treating cancer in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one.

In a further aspect of the specification there is provided a method of treating cancer in a warm-blooded animal, such as man, in need of such treatment which comprises administering to said animal an effective amount of a compound of the Formula (I), (IA), (IB), (IC), (ID), (IE), (IF), (IH), (IJ), (IZ), or (IZA), or a pharmaceutically acceptable salt thereof, in combination with a CDK4/6 inhibitor (such as palbociclib).

In one aspect the above combinations, pharmaceutical compositions, uses and methods of treating cancer, are methods for the treatment of breast or gynaecological cancers, such as cancer of the breast, endometrium, ovary or cervix, particularly breast cancer, such as ER+ve breast cancer.

According to a further aspect of the present specification there is provided a kit comprising a compound of Formula (I), (IA), (IB), (IC), (ID), (IE), (IF), (IH), (IJ), (IZ), or (IZA), or a pharmaceutically acceptable salt thereof in combination with an anti-tumour agent selected from one listed under (i)-(xi) herein above.

According to a further aspect of the present specification there is provided a kit comprising a compound of Formula (I), (IA), (IB), (IC), (ID), (IE), (IF), (IH), (IJ), (IZ), or (IZA), or a pharmaceutically acceptable salt thereof in combination with an anti-tumour agent selected from one listed under (i) or (ii) herein above.

According to a further aspect of the present specification there is provided a kit comprising:
a) a compound of Formula (I), (IA), (IB), (IC), (ID), (IE), (IF), (IH), (IJ), (IZ), or (IZA), or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present specification there is provided a kit comprising:
a) a compound of Formula (I), (IA), (IB), (IC), (ID), (IE), (IF), (IH), (IJ), (IZ), or (IZA), or a pharmaceutically acceptable salt thereof in a first unit dosage form;
b) an anti-tumour agent selected from one listed under (i)-(ii) herein above in a second unit dosage form; and
c) container means for containing said first and second dosage forms.

According to a further aspect of the present specification there is provided a kit comprising:
a) a compound of the Formula (I), (IA), (IB), (IC), (ID), (IE), (IF), (IH), (IJ), (IZ), or (IZA), or a pharmaceutically acceptable salt thereof, in a first unit dosage form;
b) an anti-tumour agent selected from an anti-tumour agent listed in (ii) above, an mTOR inhibitor (such as AZD2014), a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, and a CDK4/6 inhibitor, such as palbociclib, in a second unit dosage form; and
c) container means for containing said first and second dosage forms.

Combination therapy as described above may be added on top of standard of care therapy typically carried out according to its usual prescribing schedule.

Although the compounds of the Formula (I), (IA), (IB), (IC), (ID), (IE), (IF), (IH), (IJ), (IZ), or (IZA), are primarily of value as therapeutic agents for use in warm-blooded animals (including man), they are also useful whenever it is required to inhibit ER-c. Thus, they are useful as pharmacological standards for use in the development of new biological tests and in the search for new pharmacological agents.

Personalised Healthcare

Another aspect of the present specification is based on identifying a link between the status of the gene encoding ERα and potential susceptibility to treatment with a compound of Formula (I), (IA), (IB), (IC), (ID), (IE), (IF), (IH), (IJ), (IZ), or (IZA). In particular, ERα gene status may indicate that a patient is less likely to respond to existing hormone therapy (such as aromatase inhibitors), in part at least because some ERα mutations are though to arise as resistance mechanisms to existing treatments. A SERD, particularly a SERD which can be administered orally in potentially larger doses without excessive inconvenince, may then advantageously be used to treat patients with ERα mutations who may be resistant to other therapies. This therefore provides opportunities, methods and tools for selecting patients for treatment with a compound of Formula (I), (IA), (IB), (IC), (ID), (IE), (IF), (IH), (IJ), (IZ), or (IZA), particularly cancer patients. The present specification relates to patient selection tools and methods (including personalised medicine). The selection is based on whether the tumour cells to be treated possess wild-type or mutant ERα gene. The ERα gene status could therefore be used as a biomarker to indicate that selecting treatment with a SERD may be advantageous. For the avoidance of doubt, compounds of the Formula (I), (IA), (IB), (IC), (ID), (IE), (IF), (IH), (IJ), (IZ), or (IZA), as described herein are thought to be similarly active against wild-type and mutant ERα genes, at least those mutations in ERα gene identified at the date of filing this application.

There is a clear need for biomarkers that will enrich for or select patients whose tumours will respond to treatment with a SERD, such as a compound of Formula (I), (IA), (IB), (IC), (ID), (IE), (IF), (IH), (IJ), (IZ), or (IZA). Patient selection biomarkers that identify the patients most likely to respond to one agent over another are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present specification is the identification of means for stratification of patients for treatment with a compound of Formula (I), (IA), (IB), (IC), (ID), (IE), (IF), (IH), (IJ), (IZ), or (IZA). The technical problem is solved by provision of the embodiments characterized in the claims and/or description herein.

Tumours which contain wild type ERα are believed to be susceptible to treatment with a compound of Formula (I), (IA), (IB), (IC), (ID), (IE), (IF), (IH), (IJ), (IZ), or (IZA), for example as a first-line treatment. Tumours may also respond to treatment with a compound of Formula (I), (IA), (IB), (IC), (ID), (IE), (IF), (IH), (IJ), (IZ), or (IZA), as a second-line, third-line or subsequent therapy and this may be useful, in particular, where the tumours contain mutant ERα and may thus be resistant to existing therapies such as AIs. A higher dosage of a compound of Formula (I), (IA), (IB), (IC), (ID), (IE), (IF), (IH), (IJ), (IZ), or (IZA), may be required in the resistant setting than in wild type tumours).

The specification provides a method of determining sensitivity of cells to a compound of Formula (I), (IA), (IB), (IC), (ID), (IE), (IF), (IH), (IJ), (IZ), or (IZA). The method comprises determining the status of ERα gene in said cells. A cell is defined as sensitive to a compound of Formula (I), (IA), (IB), (IC), (ID), (IE), (IF), (IH), (IJ), (IZ), or (IZA), if it inhibits the increase in cell number in a cell growth assay (either through inhibition of cell proliferation and/or through increased cell death). Methods of the specification are useful for predicting which cells are more likely to respond to a compound of Formula (I), (IA), (IB), (IC), (ID), (IE), (IF), (IH), (IJ), (IZ), or (IZA), by growth inhibition.

A sample "representative of the tumour" can be the actual tumour sample isolated, or may be a sample that has been further processed, e.g. a sample of PCR amplified nucleic acid from the tumour sample.

Definitions

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense is variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonymous variants, are generally considered to be included in the definition of wild-type gene sequence. A catalog of human polymorphisms and associated annotation, including validation, observed frequencies, and disease association, is maintained by NCBI (dbSNP: http://www.ncbi.nlm.nih.gov/projects/SNP/). Please note that the term "polymorphism" when used in the context of gene sequences should not be confused with the term "polymorphism" when used in the context of solid state form of a compound that is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 pg/mL denatured, sheared salmon sperm DNA, followed by washing the filters in 0.1×SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect of the specification there is provided a method for selecting a patient for treatment with a compound of Formula (I), (IA), (IB), (IC), (ID), (IE), (IF), (IH), (IJ), (IZ), or (IZA), the method comprising providing a tumour cell containing sample from a patient; determining whether the ERα gene in the patient's tumour cell containing sample is wild type or mutant; and selecting a patient for treatment with a compound of Formula (I), (IA), (IB), (IC), (ID), (IE), (IF), (IH), (IJ), (IZ), or (IZA), based thereon.

The method may include or exclude the actual patient sample isolation step. Thus, according to one aspect of the specification there is provided a method for selecting a patient for treatment with a compound of Formula (I), (IA), (IB), (IC), (ID), (IE), (IF), (IH), (IJ), (IZ), or (IZA), the method comprising determining whether the ERα gene in a tumour cell containing sample previously isolated from the patient is wild type or mutant; and selecting a patient for treatment with a compound of Formula (I), (IA), (IB), (IC), (ID), (IE), (IF), (IH), (IJ), (IZ), or (IZA), based thereon.

In one embodiment, the patient is selected for treatment with a compound of Formula (I), (IA), (IB), (IC), (ID), (IE), (IF), (IH), (IJ), (IZ), or (IZA), if the tumour cell DNA has a mutant ERα gene. In other embodiments, a patient whose tumour cell DNA possesses a wild type ERα gene is selected for treatment with a compound of Formula (I), (IA), (IB), (IC), (ID), (IE), (IF), (IH), (IJ), (IZ), or (IZA).

For the purpose of this specification, a gene status of wild-type is meant to indicate normal or appropriate expression of the gene and normal function of the encoded protein. In contrast, mutant status is meant to indicate expression of a protein with altered function, consistent with the known roles of mutant ERα genes in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonymous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the ERα gene is determined by the presence or absence of non-synonymous nucleic acid variations in the genes. Observed non-synonymous variations corresponding to known common polymorphisms with no annotated functional effects do not contribute to a gene status of mutant.

Other variations in the ERα gene that signify mutant status include splice site variations that decrease recognition of an intron/exon junction during processing of pre-mRNA to mRNA. This can result in exon skipping or the inclusion of normally intronic sequence in spliced mRNA (intron retention or utilization of cryptic splice junctions). This can, in turn, result in the production of aberrant protein with insertions and/or deletions is relative to the normal protein. Thus, in other embodiments, the gene has a mutant status if there is a variant that alters splice site recognition sequence at an intron/exon junction.

For ESR1, reference sequences are available for the gene (GenBank accession number: NG_008493), mRNA (GenBank accession number: NM_000125), and protein (GenBank accession number: NP_000116 or Swiss-Prot accession: P03372). A person of skill in the art will be able to determine the ESR1 gene status, i.e. whether a particular ESR1gene is wild type or mutant, based on comparison of DNA or protein sequence with wild type.

It will be apparent that the gene and mRNA sequences disclosed for ERα gene are representative sequences. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

There are numerous techniques available to the person skilled in the art to determine the gene status of ERα. The gene status can be determined by determination of the nucleic acid sequence. This could be via direct sequencing of the full-length gene or analysis of specific sites within the gene, e.g. commonly mutated sites.

Samples

The patient's sample to be tested for the gene status can be any tumour tissue or tumour-cell containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.)

The diagnostic methods of the specification can be undertaken using a sample previously taken from the individual or patient. Such samples may be preserved by freezing or fixed and embedded in formalin-paraffin or other media. Alternatively, a fresh tumour cell containing sample may be obtained and used.

The methods of the specification can be applied using cells from any tumour. Suitable tumours for treatment with a compound of Formula (I), (IA), (IB), (IC), (ID), (IE), (IF), (IH), (IJ), (IZ), or (IZA), have been described hereinbefore.

Methods for Detection of Nucleic Acids

The detection of mutant ERα nucleic acids can be employed, in the context of the present specification, to select drug treatment. Since mutations in these genes occur at the DNA level, the methods of the specification can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation is requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.,* 1997, 43, 1114-1120; Anderson SM. *Expert Rev Mol Diagn.,* 2011, 11, 635-642; Meyerson M. et al., *Nat Rev Genet.,* 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the ERα gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS), amplification refractory mutation system linear extension (ALEX), competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)—such as amplification refractory mutation system (ARMS), sequencing, allelic discrimination assay, hybridisation, restriction fragment length polymorphism (RFLP) or oligonucleotide ligation assay (OLA).

In particular embodiments, hybridization with allele specific probes can be conducted by: (1) allele specific oligonucleotides bound to a solid phase (e.g. glass, silicon, nylon membranes) with the labelled sample in solution, for example as in many DNA chip applications; or, (2) bound sample (often cloned DNA or PCR amplified DNA) and labelled oligonucleotides in solution (either allele specific or short so as to allow sequencing by hybridization). Diagnostic tests may involve a panel of variances, often on a solid support, which enables the simultaneous determination of more than one variance. Such hybridization probes are well known in the art (see, e.g., Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) and may span two or more variance sites.

Thus, in one embodiment, the detection of the presence or absence of at least one mutation provides for contacting ERα nucleic acid containing a putative mutation site with at least one nucleic acid probe. The probe preferentially hybridizes with a nucleic acid sequence including a variance site and containing complementary nucleotide bases at the variance site under selective hybridization conditions. Hybridization can be detected with a detectable label using labels known to one skilled in the art. Such labels include, but are not limited to radioactive, fluorescent, dye, and enzymatic labels.

In another embodiment, the detection of the presence or absence of at least one mutation provides for contacting ERα nucleic acid containing a putative mutation site with at least one nucleic acid primer. The primer preferentially hybridizes with a nucleic acid sequence including a variance site and containing complementary nucleotide bases at the variance site under selective hybridization conditions.

Oligonucleotides used as primers for specific amplification may carry the complementary nucleotide base to the mutation of interest in the centre of the molecule (so that amplification depends on differential hybridization; see, e.g., Gibbs, et al., 1989. *Nucl. Acids Res.,* 17, 2437-248) or at the extreme 3'-terminus of one primer where, under appropriate conditions, mismatch can prevent, or reduce polymerase extension (see, e.g., Prossner, 1993, *Tibtech,* 11 238).

In yet another embodiment, the detection of the presence or absence of at least one is mutation comprises sequencing at least one nucleic acid sequence and comparing the obtained sequence with the known wild type nucleic acid sequence.

Alternatively, the presence or absence of at least one mutation comprises mass spectrometric determination of at least one nucleic acid sequence.

In one embodiment, the detection of the presence or absence of at least one nucleic acid variance comprises performing a polymerase chain reaction (PCR). The target nucleic acid sequence containing the hypothetical variance is amplified and the nucleotide sequence of the amplified nucleic acid is determined. Determining the nucleotide sequence of the amplified nucleic acid comprises sequencing at least one nucleic acid segment. Alternatively, amplification products can be analysed using any method capable of separating the amplification products according to their size, including automated and manual gel electrophoresis, and the like.

Mutations in genomic nucleic acid are advantageously detected by techniques based on mobility shift in amplified nucleic acid fragments. For instance, Chen et al., *Anal Biochem* 1996, 239, 61-9, describe the detection of single-base mutations by a competitive mobility shift assay. Moreover, assays based on the technique of Marcelino et al., *BioTechniques* 1999, 26, 1134-1148 are available commercially.

In a particular example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the specification is an exponential amplification, as exhibited by for example the polymerase chain reaction.

Many target and signal amplification methods have been described in the literature, for example, general reviews of these methods in Landegren, U., et al., *Science*, 1988 242, 229-237 and Lewis, R., *Genetic Engineering News* 1990, 10, 54-55. These amplification methods can be used in the methods of our specification, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology*, 1994, 52: 247-252).

An allele specific amplification technique such as Amplification Refractory Mutation System (ARMS™) (Newton et al., *Nucleic Acids Res.*, 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3'-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR (Basics: From Background to Bench)* by M. J. McPherson, S. G. Mailer, R. Beynon, C. Howe, Springer Verlag; 1st edition (Oct. 15, 2000), ISBN: 0387916008.

The present specification also provides predictive and diagnostic kits comprising degenerate primers to amplify a target nucleic acid in the ERα gene and instructions comprising; amplification protocol and analysis of the results. The kit may alternatively also comprise buffers, enzymes, and containers for performing the amplification and analysis of the amplification products. The kit may also be a component of a screening, or diagnostic kit comprising other tools such as DNA microarrays, or other supports. Preferably, the kit also provides one or more control templates, such as nucleic acids isolated from normal tissue sample, and/or a series of samples representing different variances in the reference genes.

In one embodiment, the kit provides two or more primer pairs, each pair capable of amplifying a different region of the reference (ERα) gene (each region a site of potential variance) thereby providing a kit for analysis of expression of several gene variances in a biological sample in one reaction or several parallel reactions.

Primers in the kits may be labelled, for example fluorescently labelled, to facilitate detection of the amplification products and consequent analysis of the nucleic acid variances. The kit may also allow for more than one variance to be detected in one analysis. A combination kit will therefore comprise of primers capable of amplifying different segments of the reference gene. The primers may be differentially labelled, for example using different fluorescent labels, so as to differentiate between the variances.

In another aspect, the specification provides a method of treating a patient suffering from cancer comprising: determining the mutant or wild type status of the ERα gene in the patient's tumour cells and if the ERα gene is mutant, administering to the patient an effective amount of a compound of Formula (I), (IA), (IB), (IC), (ID), (IE), (IF), (IH), (IJ), (IZ), or (IZA).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

According to another aspect of the specification there is provided the use of a compound of Formula (I), (IA), (IB), (IC), (ID), (IE), (IF), (IH), (IJ), (IZ), or (IZA), or a pharmaceutically acceptable salt thereof to treat a cancer patient whose tumour cells have been identified as possessing a mutant ERα gene.

According to another aspect of the specification there is provided a compound of Formula (I), (IA), (IB), (IC), (ID), (IE), (IF), (IH), (IJ), (IZ), or (IZA), or a pharmaceutically acceptable salt thereof for treating cancers with tumour cells identified as harbouring mutant ERα gene.

According to another aspect of the specification there is provided a method of treating cancers with tumour cells identified as harbouring mutant ERα gene comprising administering an effective amount of a compound of Formula (I), (IA), (IB), (IC), (ID), (IE), (IF), (IH), (IJ), (IZ), or (IZA), or a pharmaceutically acceptable salt thereof.

In still further embodiments, the specification relates to a pharmaceutical composition comprising a compound of Formula (I), (IA), (IB), (IC), (ID), (IE), (IF), (IH), (IJ), (IZ), or (IZA), for use in the prevention and treatment of cancer with tumour cells identified as harbouring a mutant ERα gene.

For all the aspects above, mutant forms of ERα determined/identified are at all positions across the gene.

For all the aspects above, using tumours such as breast cancer as an example, particular mutant forms of ERα determined/identified are those at positions Ser463Pro, Val543Glu, Leu536Arg, Tyr537Ser, Tyr537Asn and Asp538Gly.

EXAMPLES

The specification will now be illustrated in the following Examples in which, generally:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash Rf or Teledyne Isco CombiFlash Companion using prepacked RediSep Rf Gold Silica Columns (20-40 μm, spherical particles), GraceeResolv Cartridges (Davisil silica) or Silicycle cartridges (40-63 μm).

(iv) preparative chromatography was performed on a Gilson prep HPLC instrument with UV collection or via supercritical fluid chromatography performed on a Waters Prep 100 SFC-MS instrument with MS- and UV-triggered collection or a Thar MultiGram III SFC instrument with UV collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection;

(vi) yields, where present, are not necessarily the maximum attainable;

(vii) in general, the structures of end-products of the Formula (I) were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal (viii) in general, end-products of the Formula (I) were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1ml/min using a solvent system of 97% A+3% B to 3% A to 97% B over 1.50 mins (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8 μm 2.1×50 mm, for base analysis the column used was Waters Acquity BEH 1.7 μm 2.1×50 mm; LCMS was carried out using a Waters Alliance HT (2795) fitted with a Waters ZQ ESCi mass spectrometer and a Phenomenex Gemini-NX (50×2.1 mm 5 μm) column at a flow rate of 1.1 ml/min 95% A to 95% B over 4 min with a 0.5 min hold. The modifier is kept at a constant 5% C (50:50 acetonitrile:water 0.1% formic acid) or D (50:50 acetonitrile:water 0.1% ammonium hydroxide (0.88 SG) depending on whether it is an acidic or basic method.

(ix) ion exchange purification was generally performed using a SCX-2 (Biotage, Propylsulfonic acid functionalized silica. Manufactured using a trifunctional silane. Non endcapped) cartridge.

(x) intermediate purity was assessed by thin layer chromatographic, mass spectral, HPLC (high performance liquid chromatography) and/or NMR analysis;

(xi) RockPhos $3^{rd}$ Generation Precatalyst was sourced from Strem Chemicals Inc. and from Sigma-Aldrich.

(xii) the following abbreviations have been used:—

AcOH acetic acid aq. aqueous

Brettphos $3^{rd}$ Generation [(2-Di-cyclohexylphosphino-3,6-dimethoxyprecatalyst 2',4',6'-triisopropyl-1,1'-biphenyl)-2-(2'-amino-1,1'-biphenyl)]palladium(II) methanesulfonate Cbz Benzyloxycarbamate CDCl$_3$ deutero-chloroform Conc. concentrated DCM dichloromethane DIPEA diisopropylethylamine DMF N,N-dimethylformamide DMSO dimethyl sulfoxide EtOAc ethyl acetate HPLC high performance liquid chromatography MeCN acetonitrile MeOH methanol RockPhos 3rd Generation [(2-Di-tert-butylphosphino-3-methoxy-6- precatalyst methyl-2',4',6'-triisopropyl-1,1'-biphenyl)-2-(2-aminobiphenyl)]palladium(II) methanesulfonate rt/RT room temperature sat. saturated sol. Solution TBAF Tetra-N-butylammonium fluoride TBDMS tert-butyldimethylsilyl TFA trifluoroacetic acid THF tetrahydrofuran XPhos 2nd generation chloro(2-dicyclohexylphosphino-2',4',6'- precatalyst triisopropyl-1,1'-biphenyl) [2-(2'-amino-1,1'-biphenyl)]palladium(II)

Example 1

3-Fluoro-N-(2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)propan-1-amine

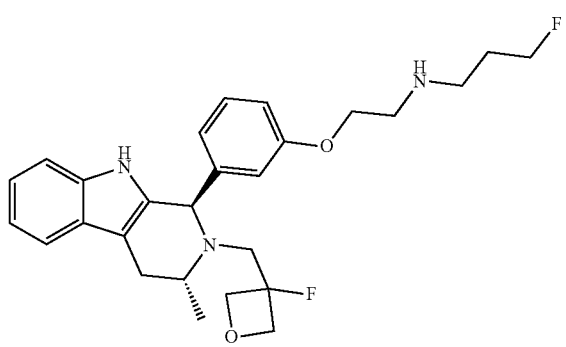 [SMILES: C[C@@H]1Cc2c([nH]c3ccccc23)[C@@H](c2cccc(OCCNCCCF)c2)N1CC1(F)COC1]

2,2,2-Trifluoroacetic acid (0.33 mL, 4.35 mmol) was added to a stirred solution of tert-butyl (2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate (67 mg, 0.12 mmol) in DCM (3.3 mL) at −5° C. under nitrogen. The resulting mixture was stirred at −5° C. for 1 hour. Saturated NaHCO₃ (5 mL) was added carefully and the mixture was extracted with DCM (3×10 mL). The combined organics were dried and concentrated to give the crude product. The crude product was purified by preparative HPLC (Waters SunFire column, 5μ silica, 19 mm diameter, 100 mm length), using decreasingly polar mixtures of water (containing 1% NH₃) and MeCN as eluents. Fractions containing the desired compounds were evaporated to dryness to give 3-fluoro-N-(2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)propan-1-amine (35 mg, 63%) as a white solid. ¹H NMR (500 MHz, CDCl₃, 22° C.): 1.16 (3H, d), 1.83-1.95 (2H, m), 2.60 (1H, dd), 2.77-2.86 (3H, m), 2.88-3 (3H, m), 3.10-3.21 (1H, m), 3.29-3.39 (1H, m), 3.98-4.05 (2H, m), 4.40 (1H, dd), 4.48 (1H, t), 4.58 (1H, t), 4.59-4.74 (2H, m), 4.82 (1H, dd), 4.97 (1H, s), 6.78-6.83 (2H, m), 6.87 (1H, d), 7.10-7.23 (3H, m), 7.27-7.30 (1H, m), 7.54 (1H, d), 7.61 (1H, s). m/z: ES+ [M+H]+ 470.

The tert-butyl (2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate used as starting material was prepared as follows:

Preparation of (3-fluorooxetan-3-yl)methyl Trifluoromethanesulfonate

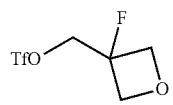

2,6-Lutidine (0.441 mL, 3.79 mmol) was added to a stirred solution of (3-fluorooxetan-3-yl)methanol (335 mg, 3.16 mmol) in anhydrous DCM (15 mL) at −10° C. Trifluoromethanesulfonic anhydride (0.560 mL, 3.32 mmol) was then added dropwise via syringe over 3 minutes, and the reaction was allowed to stir at −10° C. for 40 minutes. The cooling bath was removed, and the solution was washed successively with cold aqueous HCl (1 N; 2×5 mL) and saturated aqueous NaHCO₃ (2×5 mL), then dried over MgSO₄, filtered and concentrated under reduced pressure. Drying under vacuum afforded (3-fluorooxetan-3-yl)methyl trifluoromethanesulfonate (431 mg, 57%) as a pale yellow oil, which was used without further purification. ¹H NMR (300 MHz, CDCl₃, 27° C.) 4.53-4.67 (2H, m), 4.79-4.95 (4H, m).

Preparation of (R)—N-((3-fluorooxetan-3-yl)methyl)-1-(1H-indol-3-yl)propan-2-amine

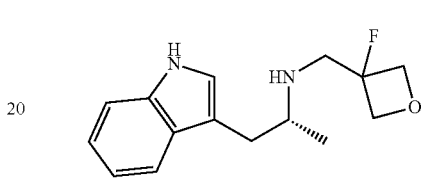

A solution of (3-fluorooxetan-3-yl)methyl trifluoromethanesulfonate (431 mg, 1.81 mmol) in DCM (3 mL) was added dropwise to a stirred solution of (R)-1-(1H-indol-3-yl)propan-2-amine (287 mg, 1.65 mmol) and diisopropylethylamine (0.345 mL, 1.97 mmol) in DCM (7 mL) at ambient temperature. The reaction was stirred for 8 hours and then diluted with DCM and washed with water. The phases were separated, and the organic layer was dried over MgSO₄, filtered, and concentrated under reduced pressure. The resulting residue was purified by flash silica chromatography, elution gradient 30 to 100% EtOAc in hexanes. Product fractions were combined and concentrated under reduced pressure to afford (R)—N-((3-fluorooxetan-3-yl)methyl)-1-(1H-indol-3-yl)propan-2-amine (384 mg, 89%) as a colorless gum. 1H NMR (300 MHz, CDCl₃, 27° C.) 1.12 (3H, d), 2.82 (2H, dd), 2.95-3.07 (3H, m), 3.12 (1H, t), 4.49 (2H, ddd), 4.67 (1H, dd), 4.70-4.78 (1H, m), 6.92 (1H, d), 7.05-7.14 (1H, m), 7.18 (1H, td), 7.29 (1H, d), 7.59 (1H, d), 8.34 (1H, br s). m/z: ES+ [M+H]+ 263.

Preparation of (1R,3R)-1-(3-bromophenyl)-2-((3-fluorooxetan-3-yl)methyl)-3-methyl-2,3,4,9-tetrahydro-1H-pyrido[3,4-b]indole

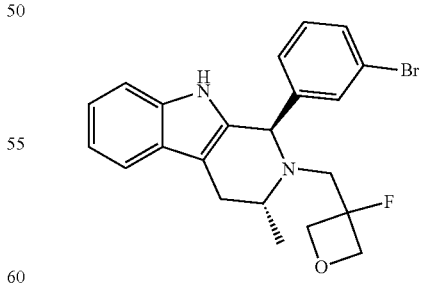

Acetic acid (1.0 mL) was added to a stirred solution of (R)—N-((3-fluorooxetan-3-yl)methyl)-1-(1H-indol-3-yl)propan-2-amine (700 mg, 2.67 mmol) and 3-bromobenzaldehyde (311 μL, 2.67 mmol) in toluene (9.3 mL). The resulting mixture was heated to 90° C. and stirred for 16 hours. The mixture was concentrated under reduced pressure and the residue was partitioned between DCM (50 mL) from 1M NaOH (25 mL). The layers were separated and the aqueous layer was extracted with DCM (50 mL). The combined organic layers were washed with saturated aqueous sodium chloride (25 mL), dried over MgSO$_4$, filtered, and concentrated under reduced pressure. The crude product was purified by flash silica chromatography, elution gradient 0 to 40% EtOAc in heptane. Pure fractions were evaporated to dryness to afford (1R,3R)-1-(3-bromophenyl)-2-((3-fluorooxetan-3-yl)methyl)-3-methyl-2,3,4,9-tetrahydro-1H-pyrido[3,4-b]indole (809 mg, 71%) as a white solid. $^1$H NMR (500 MHz, CDCl$_3$, 27° C.): 1.18 (3H, d), 2.60 (1H, dd), 2.79 (1H, dd), 2.92 (1H, t), 3.18 (1H, dd), 3.23-3.30 (1H, m), 4.37 (1H, dd), 4.69 (2H, ddd), 4.86 (1H, dd), 5.02 (1H, s), 7.11-7.23 (4H, m), 7.31 (1H, d), 7.35 (1H, s), 7.40 (1H, dd), 7.55 (1H, d), 7.64 (1H, s). m/z: ES+ [M+H]+ 429.

Preparation of tert-butyl 3-fluoropropyl(2-hydroxyethyl)carbamate

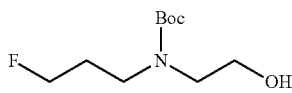

A solution of 1-iodo-3-fluoropropane (7.0 g, 37 mmol) in acetonitrile (10 mL) was added to a suspension of ethanolamine (4.50 mL, 74.5 mmol) and potassium carbonate (25.7 g, 186 mmol) in acetonitrile (60 mL). The mixture was stirred at room temperature for 5 hours and then diluted with DCM (20 ml). The mixture was cooled to 0° C. and di-tert-butyl dicarbonate (19.0 mL, 81.9 mmol) was added. The mixture was stirred at room temperature for 3 hours and filtered. The filtrate was concentrated under reduced pressure, and the resulting residue was purified by flash silica chromatography, elution gradient 0 to 4% methanol in DCM to afford tert-butyl (3-fluoropropyl)(2-hydroxyethyl)carbamate (3.82 g, 46%) as a colorless oil. $^1$H NMR (300 MHz, DMSO-d$_6$): 1.4 (9H, s), 1.70-2.00 (2H, m), 3.10-3.20 (2H, m), 3.30 (2H, d), 3.50 (2H, d), 4.30-4.60 (2H, m), 4.60 (1H, br t). m/z: ES+ [M+Na]+244.

Preparation of tert-butyl (2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate

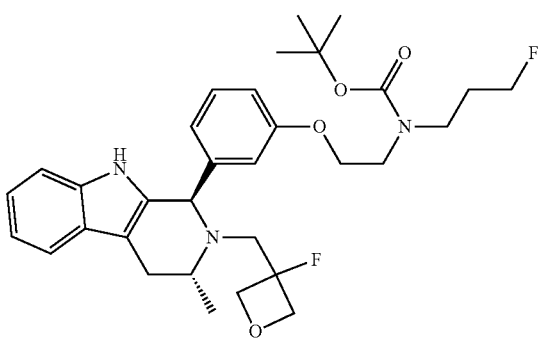 [SMILES: C[C@@H]1Cc2c([nH]c3ccccc23)[C@@H](c2cccc(OCCN(CCCF)C(=O)OC(C)(C)C)c2)N1CC1(F)COC1]

(1R,3R)-1-(3-bromophenyl)-2-((3-fluorooxetan-3-yl)methyl)-3-methyl-2,3,4,9-tetrahydro-1H-pyrido[3,4-b]indole (100 mg, 0.23 mmol), cesium carbonate (190 mg, 0.58 mmol) and RockPhos 3rd generation (19.75 mg, 0.02 mmol) were charged to a flask and the flask was evacuated and back filled with nitrogen 3 times. A solution of tert-butyl (3-fluoropropyl)(2-hydroxyethyl)carbamate (103 mg, 0.47 mmol) in degassed toluene (0.78 mL) was added and the reaction heated to 90° C. for 16 hours. After cooling, the reaction was partitioned between water (20 mL) and EtOAc (20 mL). The layers were separated and the aqueous was extracted with EtOAc (2×20 mL). The combined organic layers were washed with saturated aqueous sodium chloride (20 mL), dried over Na$_2$SO$_4$, filtered and concentrated under reduced pressure. The crude product was purified by silica gel column chromatography eluting with 0-50% ethyl acetate in heptane. Fractions containing product were combined and concentrated in vacuo to give tert-butyl (2-(3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate (77 mg, 58%) as a white solid. $^1$H NMR (500 MHz, CDCl$_3$, 27° C.): 1.16 (3H, d), 1.35-1.51 (9H, m), 1.97 (2H, s), 2.52-2.65 (1H, m), 2.84 (1H, dd), 2.88-2.98 (1H, m), 3.15 (1H, dd), 3.32-3.44 (3H, m), 3.49-3.60 (2H, m), 3.97-4.09 (2H, m), 4.40 (2H, dd), 4.50 (1H, s), 4.57-4.66 (1H, m), 4.65-4.73 (1H, m), 4.75-4.84 (1H, m), 4.95 (1H, s), 6.76-6.84 (2H, m), 6.86 (1H, d), 7.09-7.18 (2H, m), 7.20 (1H, t), 7.28 (1H, d), 7.53 (1H, d), 7.66 (1H, s). m/z: ES+ [M+H]+ 570.

Example 2

N-1-(3-((1R,3R)-2-((3-fluorooxetan-3-yl)methyl)-3-methyl-2,3,4,9-tetrahydro-1H-pyrido[3,4-b]indol-1-yl)phenyl)-N-2-(3-fluoropropyl)ethane-1,2-diamine

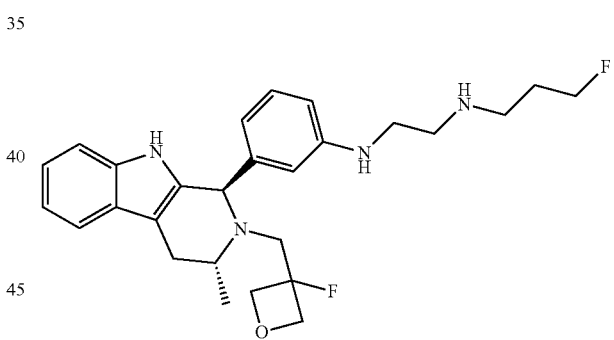

Benzyl (2-((3-((1R,3R)-2-((3-fluorooxetan-3-yl)methyl)-3-methyl-2,3,4,9-tetrahydro-1H-pyrido[3,4-b]indol-1-yl)phenyl)amino)ethyl)(3-fluoropropyl)carbamate (55 mg, 0.09 mmol) and 10% palladium on carbon (19.4 mg, 0.02 mmol) in ethanol (1 mL) were stirred under an atmosphere of hydrogen at 21° C. for 30 minutes. The mixture was diluted with DCM (20 mL) and the solids were filtered through celite, washing the filtercake with DCM (10 mL). The combined organics were combined and concentrated under reduced pressure to give the crude product. The crude product was purified by preparative HPLC (Waters SunFire column, 5 silica, 19 mm diameter, 100 mm length), using decreasingly polar mixtures of water (containing 1% NH$_3$) and MeCN as eluents. Fractions containing the desired compounds were evaporated to dryness to give N1-(3-((1R,3R)-2-((3-fluorooxetan-3-yl)methyl)-3-methyl-2,3,4,9-tetrahydro-1H-pyrido[3,4-b]indol-1-yl)phenyl)-N2-(3-fluoropropyl)ethane-1,2-diamine (25 mg, 59%) as a white solid. $^1$H NMR (500 MHz, CDCl$_3$, 27° C.): 1.15 (3H, d), 1.79-1.92

(2H, m), 2.59 (1H, dd), 2.75 (2H, t), 2.82-3.00 (4H, m), 3.06-3.20 (3H, m), 3.36-3.45 (1H, m), 4.05 (1H, s), 4.39-4.49 (2H, m), 4.54-4.64 (2H, m), 4.69 (1H, dd), 4.78 (1H, dd), 4.88 (1H, s), 6.51-6.57 (2H, m), 6.62 (1H, d), 7.08-7.18 (3H, m), 7.26 (1H, s), 7.53 (1H, d), 7.57 (1H, s). m/z: ES+ [M+H]+ 469.

The benzyl (2-((3-((1R,3R)-2-((3-fluorooxetan-3-yl)methyl)-3-methyl-2,3,4,9-tetrahydro-1H-pyrido[3,4-b]indol-1-yl)phenyl)amino)ethyl)(3-fluoropropyl)carbamate used as starting material was prepared as follows:

Preparation of benzyl (2-((tert-butoxycarbonyl)amino)ethyl)(3-fluoropropyl)carbamate

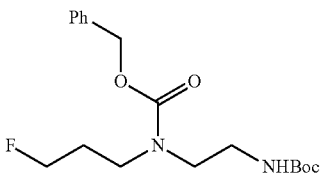 [SMILES: CC(C)(C)OC(=O)NCCN(CCCF)C(=O)OCc1ccccc1]

A solution of 1-iodo-3-fluoropropane (3.52 g, 18.7 mmol) in acetonitrile (5 mL) was added to a suspension of tert-butyl (2-aminoethyl)carbamate (5.0 g, 31 mmol) and potassium carbonate (8.63 g, 62.4 mmol) in acetonitrile (30 mL). The mixture was stirred at room temperature for 3 hours and then filtered. The filtrate was concentrated under reduced pressure and then DCM (50 mL) was added. The solution was cooled to 0° C., and DIPEA (7.10 mL, 40.7 mmol) was added followed by slow dropwise addition of benzyl chloroformate (4.56 mL, 32.0 mmol). Once addition was complete, the ice bath was removed, and the reaction mixture was stirred at room temperature for 6 hours. The reaction was diluted with water and extracted with ethyl acetate. The organic layer was dried over sodium sulfate, filtered and concentrated under reduced pressure. The resulting residue was purified by flash silica chromatography, elution gradient 0 to 80% ethyl acetate in hexane, to give benzyl (2-((tert-butoxycarbonyl)amino)ethyl)(3-fluoropropyl)carbamate (2.1 g, 21%) as an oil. ¹H NMR (300 MHz, DMSO-d₆, 27° C.): 1.37 (9H, s), 1.74-1.98 (2H, m), 3.01-3.13 (2H, m), 3.19-3.41 (4H, m), 4.29-4.63 (2H, m), 5.07 (2H, s), 6.88 (1H, br. s), 7.30-7.39 (5H, m).

Preparation of benzyl (2-aminoethyl)(3-fluoropropyl)carbamate

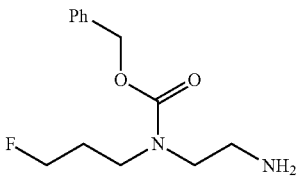

Trifluoroacetic acid (3.48 mL, 45.1 mmol) was added to a solution of benzyl (2-((tert-butoxycarbonyl)amino)ethyl)(3-fluoropropyl)carbamate (1.6 g, 4.5 mmol) in DCM (16 mL) and stirred at room temperature for 1 hour. The reaction was then concentrated under reduced pressure, diluted with ethyl acetate, and washed with saturated aqueous sodium bicarbonate. The organic layer was dried over sodium sulfate, filtered and, concentrated under reduced pressure to give benzyl (2-aminoethyl)(3-fluoropropyl)carbamate (1.1 g, 98%) as a light yellow solid. ¹H NMR (300 MHz, DMSO-d₆, 27° C.): 1.73-1.98 (2H, m), 2.88 (2H, br. s), 3.37 (4H, q), 4.45 (2H, dt), 5.09 (2H, s), 6.43 (2H, br. s), 7.25-7.49 (5H, m).

Preparation of benzyl (2-((3-((1R,3R)-2-((3-fluorooxetan-3-yl)methyl)-3-methyl-2,3,4,9-tetrahydro-1H-pyrido[3,4-b]indol-1-yl)phenyl)amino)ethyl)(3-fluoropropyl)carbamate

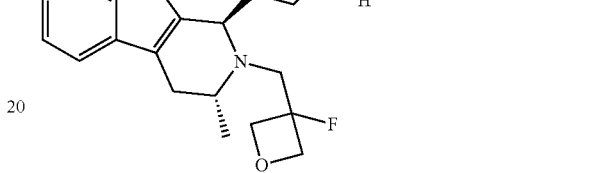

BrettPhos Pd G3 (42.2 mg, 0.05 mmol) was added to a degassed mixture of (1R,3R)-1-(3-bromophenyl)-2-((3-fluorooxetan-3-yl)methyl)-3-methyl-2,3,4,9-tetrahydro-1H-pyrido[3,4-b]indole (200 mg, 0.47 mmol), benzyl (2-aminoethyl)(3-fluoropropyl)carbamate (154 mg, 0.61 mmol) and potassium carbonate (129 mg, 0.93 mmol) in THF (4.3 mL) at 21° C. The resulting mixture was heated to 70° C. and stirred at 70° C. for 16 hours. The mixture was allowed to cool to room temperature, concentrated under reduced pressure to give the crude product. The crude product was purified by flash silica chromatography, elution gradient 0 to 80% EtOAc in heptane. Pure fractions were evaporated to dryness to afford benzyl (2-((3-((1R,3R)-2-((3-fluorooxetan-3-yl)methyl)-3-methyl-2,3,4,9-tetrahydro-1H-pyrido[3,4-b]indol-1-yl)phenyl)amino)ethyl)(3-fluoropropyl)carbamate (110 mg, 39%) as a yellow oil. ¹H NMR (500 MHz, CDCl₃, 27° C.) 1.15 (3H, d), 1.90 (2H, s), 2.59 (1H, dd), 2.81-2.99 (2H, m), 3.04-3.17 (1H, m), 3.19-3.61 (8H, m), 4.33-4.62 (4H, m), 4.66-4.91 (3H, m), 5.14 (2H, d), 6.32-6.70 (3H, m), 7.07-7.15 (2H, m), 7.23 (1H, d), 7.28-7.39 (6H, m), 7.49-7.56 (1H, m), 7.66 (1H, d). m/z: ES+ [M+H]+ 603.

Example 3

N-1-(3-((1R,3R)-2-((3-fluorooxetan-3-yl)methyl)-3-methyl-2,3,4,9-tetrahydro-1H-pyrido[3,4-b]indol-1-yl)phenyl)-N-2-(3-fluoropropyl)-N-1-methylethane-1,2-diamine

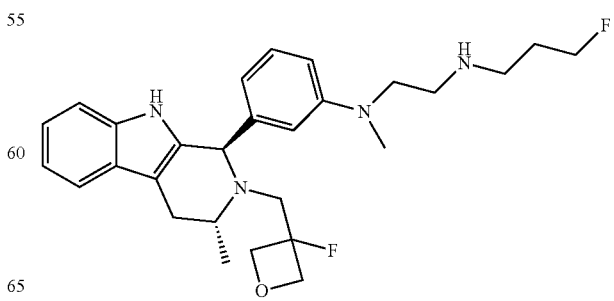

A solution of benzyl (2-((3-((1R,3R)-2-((3-fluorooxetan-3-yl)methyl)-3-methyl-2,3,4,9-tetrahydro-1H-pyrido[3,4-b]indol-1-yl)phenyl)(methyl)amino)ethyl)(3-fluoropropyl)carbamate (55.5 mg, 0.09 mmol) in ethanol (2 mL) was hydrogenated in the H-Cube hydrogenation cell using a 30 mm 10% palladium on carbon cartridge, at 21° C., 30 bar and a flow rate of 1 ml/minute for 30 minutes. The mixture was concentrated under reduced pressure to give the crude product. The crude product was purified by preparative HPLC (Waters SunFire column, 5μ silica, 19 mm diameter, 100 mm length), using decreasingly polar mixtures of water (containing 1% NH$_3$) and MeCN as eluents. Fractions containing the desired compounds were evaporated to dryness to give N1-(3-((1R,3R)-2-((3-fluorooxetan-3-yl)methyl)-3-methyl-2,3,4,9-tetrahydro-1H-pyrido[3,4-b]indol-1-yl)phenyl)-N2-(3-fluoropropyl)-N1-methylethane-1,2-diamine (1.5 mg, 3%) as a white solid. $^1$H NMR (500 MHz, CDCl$_3$, 27° C.): 1.16 (3H, d), 1.74-1.88 (2H, m), 2.60 (1H, dd), 2.70 (2H, t), 2.78 (2H, t), 2.87 (1H, dd), 2.91 (3H, s), 2.92-2.99 (1H, m), 3.06-3.18 (1H, m), 3.35-3.45 (3H, m), 4.40-4.49 (2H, m), 4.53 (1H, t), 4.60 (1H, dd), 4.69 (1H, dd), 4.78 (1H, dd), 4.90 (1H, s), 6.56 (1H, d), 6.67 (1H, dd), 6.75 (1H, s), 7.07-7.17 (3H, m), 7.26 (1H, s), 7.52 (1H, d), 7.61 (1H, s). m/z: ES+ [M+H]+ 483.

The benzyl (2-((3-((1R,3R)-2-((3-fluorooxetan-3-yl)methyl)-3-methyl-2,3,4,9-tetrahydro-1H-pyrido[3,4-b]indol-1-yl)phenyl)(methyl)amino)ethyl)(3-fluoropropyl)carbamate used as starting material was prepared as follows:

Preparation of benzyl (2-((3-((1R,3R)-2-((3-fluorooxetan-3-yl)methyl)-3-methyl-2,3,4,9-tetrahydro-1H-pyrido[3,4-b]indol-1-yl)phenyl)(methyl)amino)ethyl)(3-fluoropropyl)carbamate

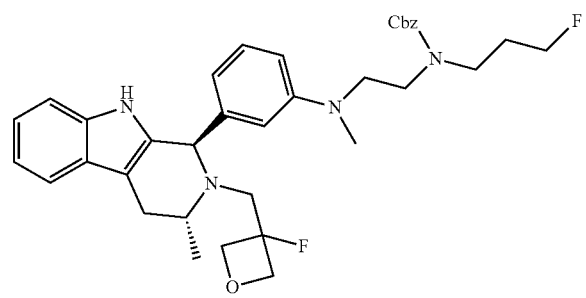 [SMILES: C[C@@H]1Cc2c([nH]c3ccccc23)[C@@H](c2cccc(N(C)CCN(CCCF)C(=O)OCc3ccccc3)c2)N1CC1(F)COC1]

Iodomethane (6.25 μL, 0.10 mmol) was added to a suspension of potassium carbonate (18.9 mg, 0.14 mmol) in a solution of benzyl (2-((3-((1R,3R)-2-((3-fluorooxetan-3-yl)methyl)-3-methyl-2,3,4,9-tetrahydro-1H-pyrido[3,4-b]indol-1-yl)phenyl)amino)ethyl)(3-fluoropropyl)carbamate (55 mg, 0.09 mmol) in DMF (1 mL). The resulting mixture was heated at 50° C. for 3 hours. Further iodomethane (6.25 μL, 0.10 mmol) was added and the mixture was stirred at 50° C. for 16 hours. The mixture was diluted with EtOAc (20 mL) and water (10 mL). The layers were separated and the organic layer was washed with water (2×10 mL) and saturated aqueous sodium chloride (10 mL). The organic layer was dried and concentrated to give benzyl (2-((3-((1R,3R)-2-((3-fluorooxetan-3-yl)methyl)-3-methyl-2,3,4,9-tetrahydro-1H-pyrido[3,4-b]indol-1-yl)phenyl)(methyl)amino)ethyl)(3-fluoropropyl)carbamate (56 mg, 100%) as an orange oil, which was used without further purification. m/z: ES+ [M+H]+ 617.

Example 4

3-Fluoro-N-(2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)propan-1-amine

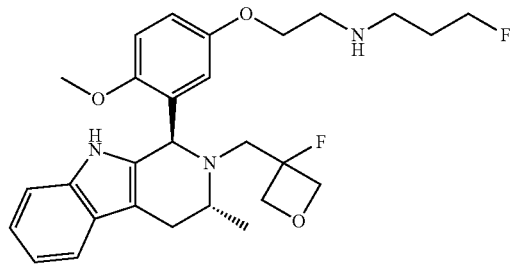 [SMILES: COc1ccc(OCCNCCCF)cc1[C@@H]1c2[nH]c3ccccc3c2C[C@@H](C)N1CC1(F)COC1]

Tert-butyl (2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)(3-fluoropropyl)carbamate (220 mg, 0.37 mmol) was dissolved in DCM (3.5 mL) and treated with TFA (0.28 mL, 3.7 mmol) dropwise. The reaction was allowed to stir at room temperature for 5 hours and then concentrated under reduced pressure. The resulting residue was dissolved in EtOAc, washed with saturated aqueous NaHCO$_3$, dried over sodium sulfate, filtered and concentrated under reduced pressure. The resulting residue was purified by HPLC (Xbridge C18 column, 5 μm silica, 19 mm diameter, 100 mm length, 20 mL/min) eluting with 50 to 80% acetonitrile in water containing 0.2% NH$_4$OH (pH 10) over 6 minutes. Product fractions were combined and concentrated under reduced pressure to afford 3-fluoro-N-(2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)propan-1-amine (183 mg, 60%) as a white foam. $^1$H NMR (300 MHz, DMSO-d$_6$, 27° C.): 1.07 (3H, d), 1.53-1.79 (3H, m), 2.52-2.60 (2H, m), 2.62-2.89 (4H, m), 3.03-3.36 (3H, m), 3.75 (2H, t), 3.80 (3H, s), 4.38-4.74 (4H, m), 4.42 (2H, dt), 5.36 (1H, s), 6.13 (1H, d), 6.82 (1H, dd), 6.94 (3H, s), 7.16-7.23 (1H, m), 7.43 (1H, d), 10.50 (1H, s). m/z: ES+ [M+H]+ 500.

The tert-butyl (2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)(3-fluoropropyl)carbamate used as starting material was prepared as follows:

Preparation of (1R,3R)-1-(5-bromo-2-methoxyphenyl)-2-((3-fluorooxetan-3-yl)methyl)-3-methyl-2,3,4,9-tetrahydro-1H-pyrido[3,4-b]indole

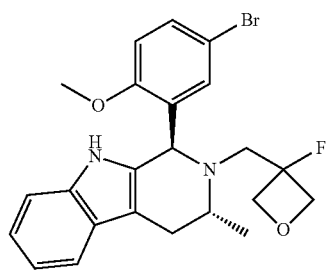 [SMILES: COc1ccc(Br)cc1[C@@H]1c2[nH]c3ccccc3c2C[C@@H](C)N1CC1(F)COC1]

(R)—N-((3-fluorooxetan-3-yl)methyl)-1-(1H-indol-3-yl) propan-2-amine (346 mg, 1.32 mmol; prepared according to the procedure of Example 1) and 5-bromo-2-methoxybenzaldehyde (265 mg, 1.23 mmol) were dissolved in toluene (6.0 mL). Acetic acid (0.67 mL) was added, and the reaction was heated at 80° C. for 18 hours. The reaction was then diluted with EtOAc and neutralized with saturated aqueous NaHCO$_3$. The layers were separated, and the organic layer was dried over sodium sulfate, filtered, and concentrated under reduced pressure. The resulting is residue was purified by flash silica chromatography, elution gradient 0 to 50% EtOAc in hexanes. Fractions containing the desired product were combined and concentrated under reduced pressure to give (1R,3R)-1-(5-bromo-2-methoxyphenyl)-2-((3-fluorooxetan-3-yl)methyl)-3-methyl-2,3,4,9-tetrahydro-1H-pyrido[3,4-b]indole (513 mg, 91%) as a light yellow foam. $^1$H NMR (300 MHz, DMSO-d$_6$, 27° C.): 1.09 (3H, d), 2.52-2.61 (1H, m) 2.62-2.88 (2H, m), 3.06-3.29 (2H, m), 3.87 (3H, s), 4.34-4.79 (4H, m), 5.38 (1H, s), 6.61 (1H, d), 6.94-7.09 (3H, m), 7.19-7.27 (1H, m), 7.39-7.51 (2H, m), 10.56 (1H, s). m/z: ES+ [M+H]+ 459.

Preparation of tert-butyl (2-(3-((1R,3R)-2-((3-fluorooxetan-3-yl)methyl)-3-methyl-2,3,4,9-tetrahydro-1H-pyrido[3,4-b]indol-1-yl)-4-methoxyphenoxy) ethyl)(3-fluoropropyl)carbamate

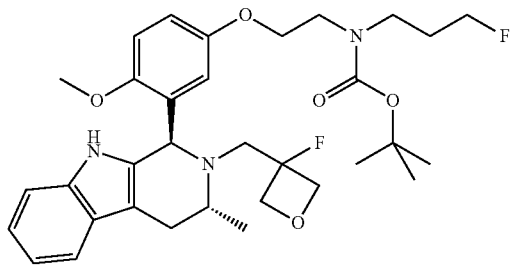 [SMILES: COc1ccc(OCCN(CCCF)C(=O)OC(C)(C)C)cc1[C@@H]1c2[nH]c3ccccc3c2C[C@@H](C)N1CC1(F)COC1]

(1R,3R)-1-(5-Bromo-2-methoxyphenyl)-2-((3-fluorooxetan-3-yl)methyl)-3-methyl-2,3,4,9-tetrahydro-1H-pyrido [3,4-b]indole (250 mg, 0.54 mmol), tert-butyl (3-fluoropropyl)(2-hydroxyethyl)carbamate (181 mg, 0.82 mmol), and cesium carbonate (355 mg, 1.09 mmol) were suspended in toluene (3 mL) in a 25 mL oven-dried pear-shaped flask. The suspension was degassed (evacuated and backfilled with nitrogen), and then RockPhos 3$^{rd}$ Generation Precatalyst (18 mg, 0.02 mmol) was added. The reaction was fitted with a condenser and heated at 90° C. for 3 hours. The mixture was diluted with water and extracted with EtOAc. The organic layer was dried over sodium sulfate, filtered and concentrated under reduced pressure. The resulting residue was purified by flash silica chromatography, elution gradient 0 to 50% EtOAc in hexanes. Fractions containing the desired product were combined and concentrated under is reduced pressure to give tert-butyl (2-(3-((1R,3R)-2-((3-fluorooxetan-3-yl)methyl)-3-methyl-2,3,4,9-tetrahydro-1H-pyrido [3,4-b]indol-1-yl)-4-methoxyphenoxy)ethyl)(3-fluoropropyl)carbamate (220 mg, 67%) as a yellow foam. $^1$H NMR (300 MHz, DMSO-d$_6$, 27° C.): 1.08 (3H, d) 1.17-1.39 (9H, m), 1.61-1.86 (2H, m), 2.53-2.63 (1H, m), 2.65-2.90 (2H, m), 3.06-3.30 (4H, m), 3.32-3.45 (2H, m), 3.75-3.90 (5H, m), 4.31 (2H, dt), 4.42-4.76 (4H, m), 5.37 (1H, s), 6.13 (1H, d), 6.72-6.91 (1H, m), 6.91-7.10 (3H, m), 7.13-7.28 (1H, m), 7.44 (1H, d), 10.50 (1H, s). m/z: ES+ [M+H]+ 600.

Example 5

3-fluoro-N-(2-(3-((1R,3R)-2-((3-fluorooxetan-3-yl) methyl)-3-methyl-2,3,4,9-tetrahydro-1H-pyrido[3,4-b]indol-1-yl)-2-methoxyphenoxy)ethyl)propan-1-amine

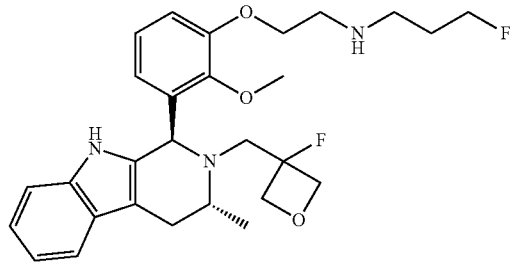 [SMILES: COc1c(OCCNCCCF)cccc1[C@@H]1c2[nH]c3ccccc3c2C[C@@H](C)N1CC1(F)COC1]

Tert-butyl (2-(3-((1R,3R)-2-((3-fluorooxetan-3-yl) methyl)-3-methyl-2,3,4,9-tetrahydro-1H-pyrido[3,4-b]indol-1-yl)-2-methoxyphenoxy)ethyl)(3-fluoropropyl)carbamate (168 mg, 0.28 mmol) was dissolved in DCM (2.5 mL) and treated with TFA (0.22 mL, 2.8 mmol) dropwise. The reaction was stirred at room temperature for 2 hours and then concentrated under reduced pressure. The resulting residue was dissolved in EtOAc, washed with saturated aqueous NaHCO$_3$, dried over sodium sulfate, filtered, and the filtrate was concentrated under reduced pressure. The resulting residue was purified by reverse phase HPLC (Xbridge C18 column, 5 m silica, 19 mm diameter, 100 mm length, 20 mL/min), eluting with 50 to 80% acetonitrile in water containing 0.2% NH$_4$OH (pH 10) over 6 minutes. Product fractions were combined and concentrated under reduced pressure to afford 3-fluoro-N-(2-(3-((1R,3R)-2-((3-fluorooxetan-3-yl)methyl)-3-methyl-2,3,4,9-tetrahydro-1H-pyrido[3,4-b]indol-1-yl)-2-methoxyphenoxy)ethyl)propan-1-amine (63 mg, 45%) as a white foam. $^1$H NMR (300 MHz, DMSO-d$_6$, 27° C.): 1.08 (3H, d), 1.67-1.92 (3H, m), 2.52-2.63 (1H, m), 2.63-2.88 (4H, m), 2.91-2.99 (2H, br m), 3.07-3.35 (2H, m), 3.85 (3H, s), 3.97-4.12 (2H, m), 4.30-4.70 (6H, m), 5.32 (1H, s), 6.21 (1H, dd), 6.86 (1H, t), 6.91-7.07 (3H, m), 7.17-7.26 (1H, m), 7.42 (1H, d), 10.50 (1H, s). m/z: ES+ [M+H]+ 500.

The tert-butyl (2-(3-((1R,3R)-2-((3-fluorooxetan-3-yl) methyl)-3-methyl-2,3,4,9-tetrahydro-1H-pyrido[3,4-b]indol-1-yl)-2-methoxyphenoxy)ethyl)(3-fluoropropyl)carbamate used as starting material was prepared as follows:

Preparation of (1R,3R)-1-(3-bromo-2-methoxyphenyl)-2-((3-fluorooxetan-3-yl)methyl)-3-methyl-2,3,4, 9-tetrahydro-1H-pyrido[3,4-b]indole

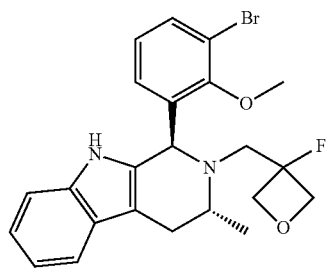 [SMILES: COc1c(Br)cccc1[C@@H]1c2[nH]c3ccccc3c2C[C@@H](C)N1CC1(F)COC1]

(R)—N-((3-Fluorooxetan-3-yl)methyl)-1-(1H-indol-3-yl)propan-2-amine (345 mg, 1.32 mmol) and 3-bromo-2-methoxybenzaldehyde (297 mg, 1.38 mmol) were dissolved in toluene (6 mL) and treated with AcOH (0.67 mL). The reaction was heated at 80° C. for 18 hours and then diluted with ethyl acetate. The mixture was washed with saturated aqueous sodium hydrogencarbonate, the layers were separated, and the organic layer was dried over sodium sulfate, filtered, and concentrated at reduced pressure. The resulting residue was purified by flash silica chromatography, elution gradient 0 to 50% EtOAc in hexanes. Fractions containing desired product were combined and concentrated under reduced pressure to give (1R,3R)-1-(3-bromo-2-methoxyphenyl)-2-((3-fluorooxetan-3-yl)methyl)-3-methyl-2,3,4,9-tetrahydro-1H-pyrido[3,4-b]indole (438 mg, 73%) as a yellow foam. $^1$H NMR (300 MHz, DMSO-$d_6$, 27° C.): 1.11 (3H, d) 2.53-2.66 (1H, m) 2.70-2.93 (2H, m) 3.16-3.35 (2H, m) 3.91 (3H, s) 4.33-4.75 (4H, m) 5.36 (1H, s) 6.63 (1H, dd) 6.89-7.09 (3H, m) 7.20-7.28 (1H, m) 7.46 (1H, d) 7.56 (1H, dd) 10.59 (1H, s). m/z: ES+ [M+H]+ 459.

Preparation of tert-butyl (2-(3-((1R,3R)-2-((3-fluorooxetan-3-yl)methyl)-3-methyl-2,3,4,9-tetrahydro-1H-pyrido[3,4-b]indol-1-yl)-2-methoxyphenoxy)ethyl)(3-fluoropropyl)carbamate

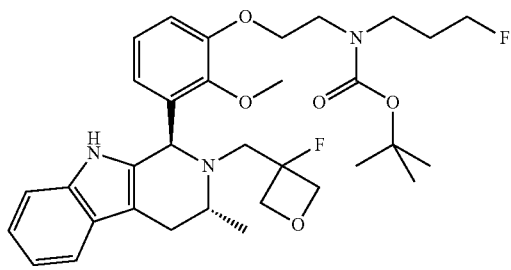 [SMILES: COc1c(OCCN(CCCF)C(=O)OC(C)(C)C)cccc1[C@@H]1c2[nH]c3ccccc3c2C[C@@H](C)N1CC1(F)COC1]

(1R,3R)-1-(3-bromo-2-methoxyphenyl)-2-((3-fluorooxetan-3-yl)methyl)-3-methyl-2,3,4,9-tetrahydro-1H-pyrido[3,4-b]indole (240 mg, 0.52 mmol), tert-butyl (3-fluoropropyl)(2-hydroxyethyl)carbamate (173 mg, 0.78 mmol; prepared according to the procedure of Example 1), and cesium carbonate (340 mg, 1.04 mmol) were suspended in toluene (3 mL) in a 25 mL oven-dried pear-shaped flask. The suspension was degassed (evacuation and back-filled with nitrogen) and then treated with RockPhos 3$^{rd}$ Generation Precatalyst (18 mg, 0.02 mmol). The reaction flask was fitted with a condenser and heated at 90° C. for 3 hrs. The mixture was then diluted with water and extracted with EtOAc. The organic layer was dried over sodium sulfate, filtered, and concentrated under reduced pressure. The resulting residue was purified by flash silica chromatography, elution gradient 0 to 50% EtOAc in hexanes. Fractions containing desired product were combined and concentrated under reduced pressure to give tert-butyl (2-(3-((1R,3R)-2-((3-fluorooxetan-3-yl)methyl)-3-methyl-2,3,4,9-tetrahydro-1H-pyrido[3,4-b]indol-1-yl)-2-methoxyphenoxy)ethyl)(3-fluoropropyl)carbamate (168 mg, 54%) as a yellow foam. $^1$H NMR (300 MHz, DMSO-$d_6$, 27° C.): 1.09 (3H, d), 1.41 (9H, s), 1.80-1.99 (2H, m), 2.53-2.65 (1H, m), 2.66-2.90 (2H, m), 3.10-3.36 (2H, m), 3.42 (2H, t), 3.53-3.70 (2H, m), 3.84 (3H, s), 4.06-4.20 (2H, br m), 4.31-4.72 (6H, m), 5.33 (1H, s), 6.23 (1H, dd), 6.86 (1H, t), 6.92-7.09 (3H, m), 7.17-7.28 (1H, m), 7.39-7.49 (1H, m), 10.52 (1H, s). m/z: ES+ [M+H]+ 600.

Example 6

N-(2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)-3-fluoropropan-1-amine

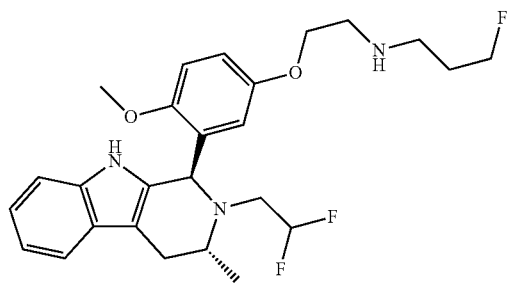 [SMILES: COc1ccc(OCCNCCCF)cc1[C@@H]1c2[nH]c3ccccc3c2C[C@@H](C)N1CC(F)F]

2,2,2-Trifluoroacetic acid (0.5 mL, 0.13 mmol) was added to a solution of tert-butyl (2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)(3-fluoropropyl)carbamate (76 mg, 0.13 mmol) in DCM (5 mL). The mixture was stirred at room temperature for 16 hours. The reaction was concentrated under vacuum, redissolved in MeOH and applied to a pre-wetted (MeOH) SCX-2 cartridge. The cartridge was washed with MeOH (50 mL) and the product eluted with 1M NH$_3$ in MeOH solution (30 mL). The resulting residue was purified by preparative HPLC (Waters XSelect CSH C18 column, 5µ silica, 30 mm diameter, 100 mm length), using decreasingly polar mixtures of water (containing 1% NH$_3$) and MeCN as eluents. Fractions containing the desired compound were evaporated to dryness to afford N-(2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)-3-fluoropropan-1-amine (5.0 mg, 8%) as a colourless oil. $^1$H NMR (500 MHz, CDCl$_3$, 27° C.): 1.16 (3H, d), 1.77-1.91 (2H, m), 2.55-2.64 (2H, m), 2.69-2.8 (3H, m), 2.88 (2H, dd), 2.92-2.98 (1H, m), 2.98-3.09 (1H, m), 3.45-3.53 (1H, m), 3.89 (2H, t), 3.92 (3H, s), 4.44 (1H, t), 4.53 (1H, t), 5.29 (1H, s), 5.86 (1H, tdd), 6.67 (1H, d), 6.78 (1H, dd), 6.89 (1H, d), 7.07-7.16 (2H, m), 7.23 (1H, ddd), 7.49-7.54 (1H, m), 7.69 (1H, s). m/z: ES+ [M+H]+ 476.

The tert-butyl (2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)(3-fluoropropyl)carbamate used as starting material was prepared as follows:

Preparation of 2,2-difluoroethyl Trifluoromethanesulfonate

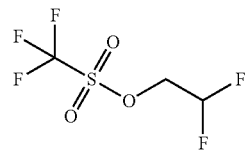 [SMILES: O=S(=O)(OCC(F)F)C(F)(F)F]

Trifluoromethanesulfonic anhydride (3.97 ml, 23.5 mmol) was added dropwise to a solution of 2,2-difluoroethan-1-ol (1.75 g, 21.3 mmol) in DCM (40 mL at) at −10° C. (salt/ice bath). Lutidine (2.98 ml, 25.6 mmol) was then added, and the reaction was stirred for 1 hour at −10° C. The reaction was then quenched with water, and the layers were separated. The organic layer was washed with water and then dried over sodium sulfate, filtered and concentrated under reduced pressure to afford 2,2-difluoroethyl trifluoromethanesulfonate (3.10 g, 67.9%) as a colorless liquid. $^1$H NMR (500 MHz, CDCl$_3$, 27° C.) 4.57 (2H, td), 6.03 (1H, tt).

Preparation of (R)—N-(2,2-difluoroethyl)-1-(1H-indol-3-yl)propan-2-amine

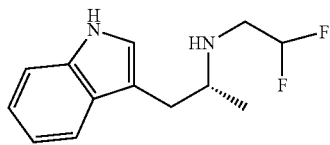 [SMILES: C[C@H](Cc1c[nH]c2ccccc12)NCC(F)F]

(R)-1-(1H-Indol-3-yl)propan-2-amine (5 g, 28.69 mmol) was added to a solution of 2,2-difluoroethyl trifluoromethanesulfonate (7.07 g, 33.00 mmol) and DIPEA (7.44 mL, 43.04 mmol) in chloroform (100 mL) and the reaction was stirred at 60° C. for 16 hours. The reaction mixture allowed to cool and concentrated in vacuo. The crude product was purified by flash silica chromatography, elution gradient 0 to 40% EtOAc in heptane to afford (R)—N-(2,2-difluoroethyl)-1-(1H-indol-3-yl)propan-2-amine (4.22 g, 62%) as a yellow oil.
$^1$H NMR (500 MHz, CDCl$_3$, 27° C.): 1.12 (3H, d), 2.73-3.17 (5H, m), 3.47 (1H, s), 5.77 (1H, tt), 7.01 (1H, d), 7.06-7.17 (1H, m), 7.17-7.23 (1H, m), 7.3-7.42 (1H, m), 7.59 (1H, d), 8.11 (1H, s). m/z: ES− [M−H]− 237.

Preparation of (1R,3R)-1-(5-bromo-2-methoxyphenyl)-2-(2,2-difluoroethyl)-3-methyl-2,3,4,9-tetrahydro-1H-pyrido[3,4-b]indole

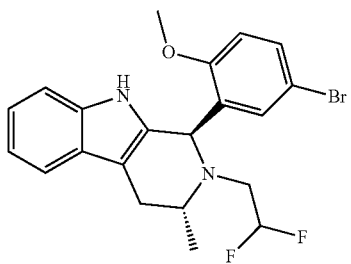 [SMILES: COc1ccc(Br)cc1[C@@H]1c2[nH]c3ccccc3c2C[C@@H](C)N1CC(F)F]

Acetic acid (1.23 mL) was added to a stirred solution of (R)—N-(2,2-difluoroethyl)-1-(1H-indol-3-yl)propan-2-amine (730 mg, 3.06 mmol) and 5-bromo-2-methoxybenzaldehyde (659 mg, 3.06 mmol) in toluene (11 mL). The resulting mixture was heated at 90° C. for 16 hours. The reaction was cooled to room temperature, concentrated under reduced pressure, redissolved in MeOH and applied to a pre-wetted (MeOH) SCX-2 cartridge. The cartridge was washed with MeOH (50 mL) and the product eluted with 1M NH$_3$ in MeOH solution (50 mL). The filtrate was concentrated under reduced pressure. The resulting residue was purified by flash silica chromatography, elution gradient 0 to 20% EtOAc in heptane. Product fractions were combined and concentrated under reduced pressure to afford (1R,3R)-1-(5-bromo-2-methoxyphenyl)-2-(2,2-difluoroethyl)-3-methyl-2,3,4,9-tetrahydro-1H-pyrido[3,4-b]indole (429 mg, 32%) as a white solid. $^1$H NMR (500 MHz, CDCl$_3$, 27° C.): 1.13 (3H, d), 2.56 (1H, ddd), 2.61-2.75 (1H, m), 2.89 (1H, ddd), 3.02 (1H, qd), 3.33-3.47 (1H, m), 3.90 (3H, s), 5.25 (1H, s), 5.88 (1H, tdd), 6.81 (1H, d), 7.05-7.15 (3H, m), 7.16-7.22 (1H, m), 7.33 (1H, dd), 7.51 (1H, dd), 7.57 (1H, s). m/z: ES− [M−H]− 433.

Preparation of tert-butyl (2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)(3-fluoropropyl)carbamate

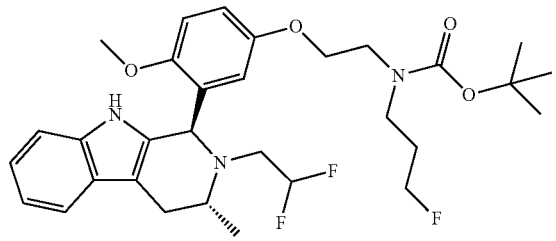 [SMILES: COc1ccc(OCCN(CCCF)C(=O)OC(C)(C)C)cc1[C@@H]1c2[nH]c3ccccc3c2C[C@@H](C)N1CC(F)F]

RockPhos Pd G3 (11.6 mg, 0.01 mmol) was added to a degassed suspension of (1R,3R)-1-(5-bromo-2-methoxyphenyl)-2-(2,2-difluoroethyl)-3-methyl-2,3,4,9-tetrahydro-1H-pyrido[3,4-b]indole (120 mg, 0.28 mmol), tert-butyl (3-fluoropropyl)(2-hydroxyethyl)carbamate (122 mg, 0.55 mmol) and cesium carbonate (225 mg, 0.69 mmol) in anhydrous toluene (2.76 mL) and the reaction was heated to 90° C. for 1 hour. The reaction mixture was cooled to room temperature and quenched with water (5 mL), diluted with EtOAc (5 mL) and the layers were separated. The aqueous layer was extracted with EtOAc (3×5 mL) and the combined organic layers were dried with MgSO$_4$, filtered and the filtrate was concentrated under reduced pressure. The resulting residue was purified by flash silica chromatography, elution gradient 0 to 50% EtOAc in heptane. Pure fractions were evaporated to dryness to afford tert-butyl (2-(3-((1R,3R)-2-(2,2-difluoroethyl)-3-methyl-2,3,4,9-tetrahydro-1H-pyrido[3,4-b]indol-1-yl)-4-methoxyphenoxy)ethyl)(3-fluoropropyl)carbamate (82 mg, 52%) as a colourless gum. $^1$H NMR (500 MHz, CDCl$_3$, 27° C.): 1.15 (3H, d), 1.38 (9H, s), 1.79-1.99 (2H, m), 2.58 (1H, dd), 2.65-2.82 (1H, m), 2.89-3.11 (2H, m), 3.32 (2H, t), 3.4-3.53 (3H, m), 3.84-3.95 (5H, m), 4.22-4.50 (2H, m), 5.27 (1H, s), 5.70-6.01 (1H, m), 6.66 (1H, d), 6.76 (1H, dd), 6.88 (1H, d), 7.09 (2H, pd), 7.20 (1H, dd), 7.50 (1H, d), 7.80 (1H, s). m/z: ES− [M−H]− 574

Example 7

3-Fluoro-N-(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine

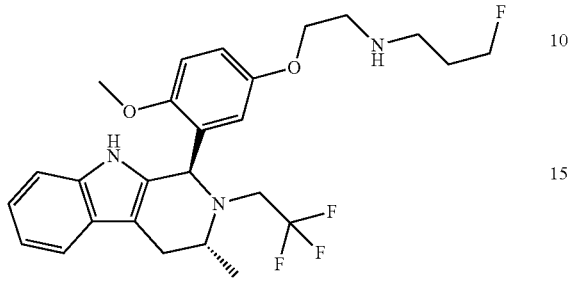

To a solution of tert-butyl (3-fluoropropyl)(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)carbamate (62 mg, 0.10 mmol) in DCM (4 mL) was added trifluoroacetic acid (0.5 mL, 0.10 mmol). The mixture was stirred at room temperature for 16 hours. The reaction was concentrated under vacuum, redissolved in MeOH and applied to a pre-wetted (MeOH) SCX-2 cartridge (5 g). The cartridge was washed with MeOH (50 mL) and the product eluted with 1M $NH_3$ in MeOH is solution (30 mL). The resulting residue was purified by preparative HPLC (Waters XSelect CSH C18 column, 5µ silica, 30 mm diameter, 100 mm length), using decreasingly polar mixtures of water (containing 1% $NH_3$) and MeCN as eluents. Fractions containing the desired compound were evaporated to dryness to afford 3-fluoro-N-(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine (17 mg, 33%) as a colourless oil. $^1$H NMR (500 MHz, $CDCl_3$, 27° C.): 1.18 (3H, d), 1.77-1.89 (2H, m), 2.60 (1H, ddd), 2.73 (2H, t), 2.86-2.9 (2H, m), 2.92-3.02 (2H, m), 3.24 (1H, dq), 3.61 (1H, td), 3.90 (6H, m), 4.48 (2H, dt), 5.36 (1H, s), 6.76-6.81 (2H, m), 6.87-6.92 (1H, m), 7.06-7.15 (2H, m), 7.22 (1H, ddd), 7.48-7.54 (1H, m), 7.83 (1H, s). m/z: ES+ [M+H]+ 494.

The tert-butyl (3-fluoropropyl)(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)carbamate used a starting material was prepared as follows:

Preparation of 2,2,2-trifluoroethyl Trifluoromethanesulfonate

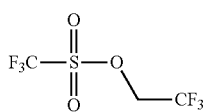

Trifluoromethanesulfonic anhydride (3.14 mL, 18.6 mmol) was added dropwise via syringe over 5 minutes to a stirred solution of 2,2,2-trifluoroethan-1-ol (1.23 mL, 16.9 mmol) and 2,6-dimethylpyridine (2.36 mL, 20.3 mmol) in DCM (50 mL) at −10° C. After 2 hours the reaction was washed successively with aqueous HCl (1N; 2×30 mL) and saturated aqueous $NaHCO_3$ (20 mL). The organic layer was then dried over $MgSO_4$, filtered, and concentrated under reduced pressure to give 2,2,2-trifluoroethyl trifluoromethanesulfonate (0.92 g, 23%) as a red oil. $^1$H NMR (300 MHz, $CDCl_3$, 27° C.): 4.69 (2H, q).

Preparation of (R)-1-(1H-indol-3-yl)-N-(2,2,2-trifluoroethyl)propan-2-amine

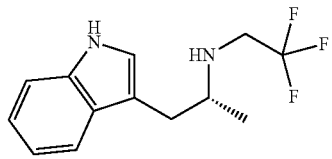 [SMILES: C[C@H](Cc1c[nH]c2ccccc12)NCC(F)(F)F]

2,2,2-Trifluoroethyl trifluoromethanesulfonate (1.91 g, 13.29 mmol) was added to a solution of (R)-1-(1H-indol-3-yl)propan-2-amine (2.32 g, 13.29 mmol) and DIPEA (3.44 ml, 19.93 mmol) in 1,4-dioxane (30 ml) and the reaction was stirred at 85° C. for 4 hours. The reaction mixture allowed to cool and concentrated in vacuo. The crude product was purified by flash silica chromatography, elution gradient 0 to 40% EtOAc in heptane. Pure fractions were evaporated to dryness to afford (R)-1-(1H-indol-3-yl)-N-(2,2,2-trifluoroethyl)propan-2-amine (2.81 g, 83%) as a colourless oil.
$^1$H NMR (500 MHz, $CDCl_3$, 27° C.): 1.14 (3H, d), 2.81-2.88 (2H, m), 3.11-3.22 (3H, m), 7.06 (1H, d), 7.12 (1H, ddd), 7.21 (1H, ddd), 7.37 (1H, dt), 7.60 (1H, ddd), 8.01 (1H, s). m/z: ES− [M−H]− 255.

Preparation of (1R,3R)-1-(5-bromo-2-methoxyphenyl)-3-methyl-2-(2,2,2-trifluoroethyl)-2,3,4,9-tetrahydro-1H-pyrido[3,4-b]indole

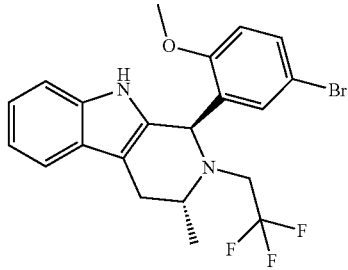 [SMILES: COc1ccc(Br)cc1[C@@H]1c2[nH]c3ccccc3c2C[C@@H](C)N1CC(F)(F)F]

Acetic acid (1.06 mL) was added to a stirred solution of (R)-1-(1H-indol-3-yl)-N-(2,2,2-trifluoroethyl)propan-2-amine (680 mg, 2.65 mmol) and 5-bromo-2-methoxybenzaldehyde (571 mg, 2.65 mmol) in toluene (9.55 mL). The resulting mixture was heated at 90° C. for 16 hours. The reaction was concentrated under vacuum, redissolved in MeOH and applied to a pre-wetted (MeOH) SCX-2 cartridge (5 g). The cartridge was washed with MeOH (50 mL) and the product eluted with 1M $NH_3$ in MeOH solution (50 mL). The filtrate was concentrated under vacuum. The resulting residue was purified by flash silica chromatography, elution gradient 0 to 20% EtOAc in heptane. Pure fractions were evaporated to dryness to afford (1R,3R)-1-(5-bromo-2-methoxyphenyl)-3-methyl-2-(2,2,2-trifluoroethyl)-2,3,4,9-tetrahydro-1H-pyrido[3,4-b]indole (681 mg, 57%) as a colourless gum. $^1$H NMR (500 MHz, $CDCl_3$, 27°

C.): 1.17 (3H, d), 2.58 (1H, ddd), 2.82-3.01 (2H, m), 3.23 (1H, dq), 3.52 (1H, td), 3.92 (3H, s), 5.36 (1H, s), 6.83 (1H, d), 7.07-7.17 (3H, m), 7.19-7.24 (1H, m), 7.34 (1H, dd), 7.49-7.55 (1H, m), 7.68 (1H, s). m/z: ES− [M+H]+ 453

Preparation of tert-butyl (3-fluoropropyl)(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)carbamate

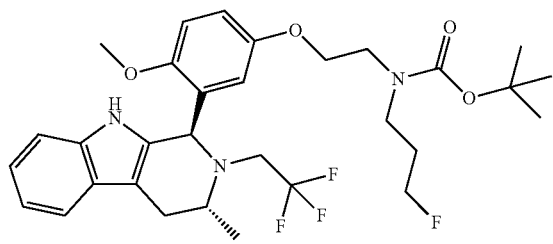 [SMILES: COc1ccc(OCCN(CCCF)C(=O)OC(C)(C)C)cc1[C@@H]1c2[nH]c3ccccc3c2C[C@@H](C)N1CC(F)(F)F]

RockPhos Pd G3 (11.57 mg, 0.01 mmol) was added to a degassed suspension of (1R,3R)-1-(5-bromo-2-methoxyphenyl)-3-methyl-2-(2,2,2-trifluoroethyl)-2,3,4,9-tetrahydro-1H-pyrido[3,4-b]indole (125 mg, 0.28 mmol), tert-butyl (3-fluoropropyl)(2-hydroxyethyl)carbamate (122 mg, 0.55 mmol) and cesium carbonate (225 mg, 0.69 mmol) in toluene (2.76 mL) and the reaction was heated to 90° C. for 1 hour. The reaction mixture was cooled to room temperature and quenched with water (5 mL), diluted with EtOAc (5 mL) and the layers were separated. The aqueous layer was extracted with EtOAc (3×5 mL) and the combined organic layers were dried over MgSO$_4$, filtered and concentrated under vacuum. The resulting residue was purified by flash silica chromatography, elution gradient 0 to 50% EtOAc in heptane. Pure fractions were evaporated to dryness to afford tert-butyl (3-fluoropropyl)(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)carbamate (69.0 mg, 42%) as a colourless oil. $^1$H NMR (500 MHz, CDCl$_3$, 27° C.): 1.19 (3H, d), 1.40 (9H, s), 1.81-1.99 (2H, m), 2.61 (1H, dd), 2.89-3.07 (2H, m), 3.24 (1H, dq), 3.32-3.39 (2H, m), 3.41-3.57 (2H, m), 3.63 (1H, h), 3.85-3.97 (5H, m), 4.39 (2H, d), 5.35 (1H, s), 6.72-6.83 (2H, m), 6.90 (1H, d), 7.04-7.16 (2H, m), 7.2-7.24 (1H, m), 7.46-7.55 (1H, m), 7.83 (1H, s). m/z: ES− [M−H]− 592.

Example 8

2,2-Difluoro-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)propan-1-ol

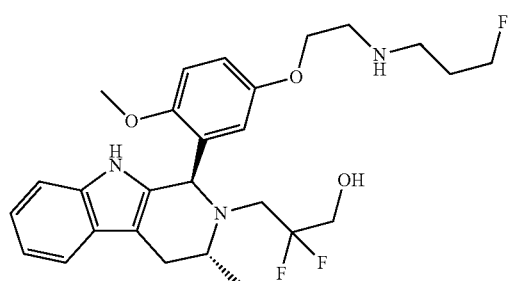

To a solution of tert-butyl (2-(3-((1R,3R)-2-(2,2-difluoro-3-hydroxypropyl)-3-methyl-2,3,4,9-tetrahydro-1H-pyrido[3,4-b]indol-1-yl)-4-methoxyphenoxy)ethyl)(3-fluoropropyl)carbamate (152 mg, 0.25 mmol) in DCM (4 mL) was added trifluoroacetic acid (0.5 mL, 0.25 mmol). The mixture was stirred at room temperature for 16 hours. The reaction was concentrated under vacuum, redissolved in MeOH and applied to a pre-wetted (MeOH) SCX-2 cartridge. The cartridge was washed with MeOH (50 mL) and the product eluted with IM NH$_3$ in MeOH solution (50 mL). The resulting residue was purified by preparative HPLC (Waters XSelect CSH C18 column, 5μ silica, 30 mm diameter, 100 mm length), using decreasingly polar mixtures of water (containing 1% NH$_3$) and MeCN as eluents. Fractions containing the desired compound were evaporated to dryness to afford 2,2-difluoro-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)propan-1-ol (62 mg, 49%) as a colourless oil. $^1$H NMR (500 MHz, CDCl$_3$, 27° C.): 1.18 (3H, d), 1.74-1.88 (2H, m), 2.58-2.67 (1H, m), 2.70 (2H, t), 2.79-3 (4H, m), 3.08-3.23 (1H, m), 3.57-3.81 (3H, m), 3.82-3.91 (6H, m), 4.04 (1H, s), 4.41 (1H, t), 4.50 (1H, t), 5.35 (1H, s), 6.60 (1H, d), 6.79 (1H, dd), 6.86 (1H, d), 7.06-7.15 (2H, m), 7.15-7.22 (1H, m), 7.45-7.58 (1H, m), 7.87 (1H, s). m/z: ES+ [M+H]+ 506.

The tert-butyl (2-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)ethyl)(3-fluoropropyl)carbamate used as starting material was prepared as follows:

Preparation of 3-((tert-butyldiphenylsilyl)oxy)-2,2-difluoropropan-1-ol

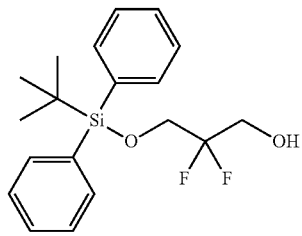 [SMILES: CC(C)(C)[Si](OCC(F)(F)CO)(c1ccccc1)c1ccccc1]

NaH in mineral oil (60 wt %; 343 mg, 8.58 mmol) was added in one portion to a stirred solution of 2,2-difluoropropane-1,3-diol (874 mg, 7.80 mmol) in THF (32 mL) at 0° C. The reaction was allowed to warm to room temperature, and was stirred at room temperature for 2 hours. The reaction mixture was again cooled to 0° C., and tert-butyldiphenylchlorosilane (2.0 mL, 7.8 mmol) was added dropwise via syringe. The reaction mixture was allowed to warm room temperature over 1 hour and was then quenched with water and extracted with EtOAc. The organic layer was dried with Na$_2$SO$_4$, filtered, and the filtrate was concentrated under reduced pressure. The resulting residue was purified by flash silica chromatography, eluting to with isocratic 5% ethyl acetate in hexanes, to afford 3-((tert-butyldiphenylsilyl)oxy)-2,2-difluoropropan-1-ol (1.94, 71%) as a colorless oil. $^1$H NMR (300 MHz, CDCl$_3$, 27° C.): 1.03-1.14 (9H, s), 3.87-3.93 (4H, m), 7.37-7.44 (6H, m), 7.64-7.66 (4H, m).

Preparation of 3-((tert-butyldiphenylsilyl)oxy)-2,2-difluoropropyl Trifluoromethanesulfonate

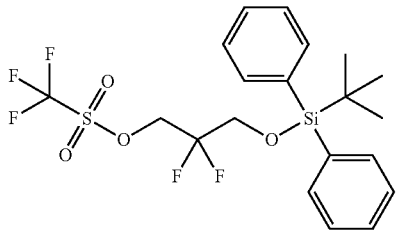 [SMILES: CC(C)(C)[Si](OCC(F)(F)COS(=O)(=O)C(F)(F)F)(c1ccccc1)c1ccccc1]

A solution of 3-((tert-butyldiphenylsilyl)oxy)-2,2-difluoropropan-1-ol (1.94 g, 5.55 mmol) and 2,6-dimethylpyridine (1.94 ml, 16.6 mmol) in DCM (18 ml) was cooled to −10° C. (salt/ice bath). Trifluoromethanesulfonic anhydride (1.88 ml, 11.1 mmol) was added slowly dropwise over 10 minutes. The reaction was maintained under these conditions for 2 hours. The reaction was then washed with water, aqueous HCl (N, 100 mL), and saturated aqueous sodium bicarbonate. The organic layer was dried over MgSO$_4$, filtered, and concentrated under reduced pressure to afford 3-((tert-butyldiphenylsilyl)oxy)-2,2-difluoropropyl trifluoromethanesulfonate (2.68 g, 100%) as a red oil. $^1$H NMR (300 MHz, CDCl$_3$, 27° C.): 1.03-1.14 (9H, s), 3.90 (2H, t), 4.76 (2H, t), 7.39-7.56 (6H, m), 7.59-7.75 (4H, m).

Preparation of (R)—N-(1-(1H-indol-3-yl)propan-2-yl)-3-((tert-butyldiphenylsilyl)oxy)-2,2-difluoropropan-1-amine

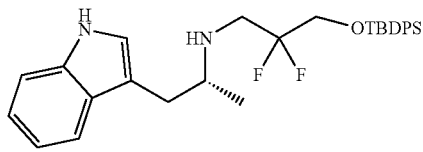

3-((Tert-butyldiphenylsilyl)oxy)-2,2-difluoropropyl trifluoromethanesulfonate (481 mg, 1.00 mmol) was added to a stirred solution of (R)-1-(1H-indol-3-yl)propan-2-amine (174 mg, 1.00 mmol) in 1,4-dioxane (3 mL), followed by DIPEA (0.244 mL, 1.40 mmol). The reaction was stirred at 85° C. for 5 hours. The reaction was poured into a mixture of DCM and saturated aqueous sodium bicarbonate. The organic layer was dried over sodium sulfate, filtered, and concentrated. The resulting residue was purified by flash silica chromatography, elution gradient 0 to 35% ethyl acetate in hexanes, to yield (R)—N-(1-(1H-indol-3-yl)propan-2-yl)-3-((tert-butyldiphenylsilyl)oxy)-2,2-difluoropropan-1-amine (465 mg, 92%). m/z: ES+ [M+H]+ 507.

Preparation of (1R,3R)-1-(5-bromo-2-methoxyphenyl)-2-(3-((tert-butyldiphenylsilyl)oxy)-2,2-difluoropropyl)-3-methyl-2,3,4,9-tetrahydro-1H-pyrido[3,4-b]indole

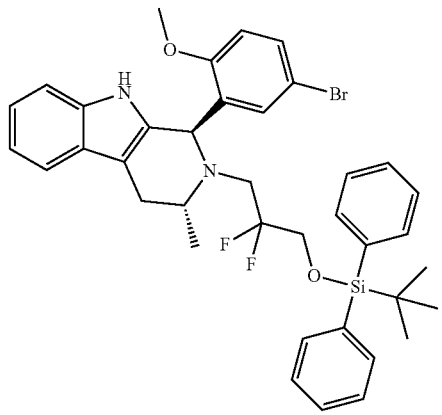 [SMILES: COc1ccc(Br)cc1[C@@H]1c2[nH]c3ccccc3c2C[C@@H](C)N1CC(F)(F)CO[Si](c1ccccc1)(c1ccccc1)C(C)(C)C]

Acetic acid (545 μL) was added to a stirred solution of (R)—N-(1-(1H-indol-3-yl)propan-2-yl)-3-((tert-butyldiphenylsilyl)oxy)-2,2-difluoropropan-1-amine (690 mg, 1.36 mmol) and 5-bromo-2-methoxybenzaldehyde (293 mg, 1.36 mmol) in toluene (4.90 mL). The reaction mixture was heated to 90° C. for 16 hours. The reaction mixture was cooled to room temperature and concentrated under vacuum, redissolved in MeOH and applied to a pre-wetted (MeOH) SCX-2 cartridge. The cartridge was washed with MeOH (50 mL) and the product eluted with 1M NH$_3$ in MeOH solution (50 mL). The filtrate was concentrated under vacuum. The resulting residue was purified by flash silica chromatography, elution gradient 0 to 40% EtOAc in heptane. Pure fractions were evaporated to dryness to afford (1R,3R)-1-(5-bromo-2-methoxyphenyl)-2-(3-((tert-butyldiphenylsilyl)oxy)-2,2-difluoropropyl)-3-methyl-2,3,4,9-tetrahydro-1H-pyrido[3,4-b]indole (395 mg, 41%) as a white solid. $^1$H NMR (500 MHz, CDCl$_3$, 27° C.): 0.96 (9H, s), 1.12 (3H, d), 2.50 (1H, ddd), 2.67-2.79 (2H, m), 3.16 (1H, ddd), 3.38-3.47 (1H, m), 3.61-3.71 (4H, m), 3.96 (1H, dt), 5.33 (1H, s), 6.66 (1H, d), 6.99-7.07 (2H, m), 7.08 (1H, d), 7.14 (1H, dt), 7.25 (5H, tt), 7.29-7.35 (2H, m), 7.4-7.46 (1H, m), 7.52-7.59 (4H, m), 7.73 (1H, s). m/z: ES+ [M+H]+ 703.

Preparation of tert-butyl (2-(3-((1R,3R)-2-(2,2-difluoro-3-hydroxypropyl)-3-methyl-2,3,4,9-tetrahydro-1H-pyrido[3,4-b]indol-1-yl)-4-methoxyphenoxy)ethyl)(3-fluoropropyl)carbamate

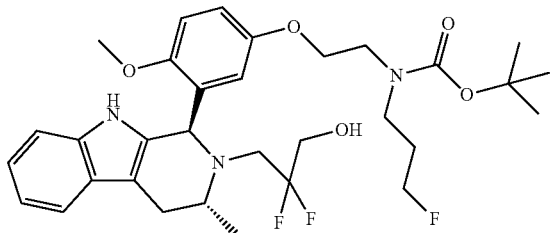

RockPhos Pd G3 (22.66 mg, 0.03 mmol) was added to a degassed suspension of (1R,3R)-1-(5-bromo-2-methoxyphenyl)-2-(3-((tert-butyldiphenylsilyl)oxy)-2,2-difluoropropyl)-3-methyl-2,3,4,9-tetrahydro-1H-pyrido[3,4-b]indole (380 mg, 0.54 mmol), tert-butyl (3-fluoropropyl)(2-hydroxyethyl)carbamate (239 mg, 1.08 mmol) and cesium carbonate (440 mg, 1.35 mmol) in toluene (5.4 mL) and the reaction was heated to 90° C. for 1 hour. The reaction mixture was cooled to room temperature and quenched with water (5 mL), diluted with EtOAc (5 mL) and the layers were separated. The aqueous layer was extracted with EtOAc (3×5 mL) and the combined organic layers were dried over MgSO$_4$, filtered and concentrated under vacuum. A solution of 1.0 M TBAF in THF (10 mL) was added and left to stir for 30 min. The reaction mixture was quenched with water (10 mL), diluted with EtOAc (10 mL) and the layers were separated. The aqueous layer was extracted with EtOAc (3×10 mL) and the combined organic layers were dried over MgSO$_4$, filtered and concentrated under vacuum. The resulting residue was purified by flash silica chromatography, elution gradient 0 to 50% EtOAc in heptane. Pure fractions were evaporated to dryness to afford tert-butyl (2-(3-((1R,3R)-2-(2,2-difluoro-3-hydroxypropyl)-3-methyl-2,3,4,9-tetrahydro-1H-pyrido[3,4-b]indol-1-yl)-4-methoxyphenoxy)ethyl)(3-fluoropropyl)carbamate (160 mg, 49%) as a colourless oil. $^1$H NMR (500 MHz, CDCl$_3$, 27° C.): 1.21 (3H, d), 1.39 (9H, s), 1.8-1.99 (2H, m), 2.65 (1H, dd), 2.86-3.03 (2H, m), 3.12-3.25 (1H, m), 3.3-3.37 (2H, m), 3.42-3.57 (2H, m), 3.62-3.83 (4H, m), 3.84-4.03 (5H, m), 4.34 (1H, s), 4.44 (1H, s), 5.35 (1H, s), 6.62 (1H, d), 6.81 (1H, dd), 6.90 (1H, d), 7.07-7.17 (2H, m), 7.21-7.25 (1H, m), 7.5-7.54 (1H, m), 7.68 (1H, s). m/z: ES+ [M+H]+ 606.

Example 9

Preparation of N-(2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine

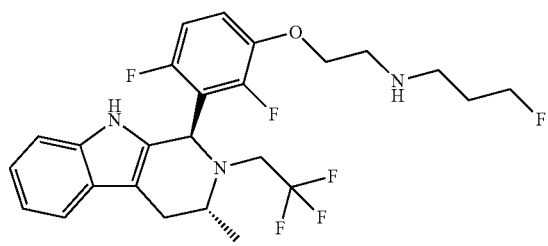 [SMILES: C[C@@H]1Cc2c([nH]c3ccccc23)[C@@H](c2c(F)ccc(OCCNCCCF)c2F)N1CC(F)(F)F]

A solution of tert-butyl (2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.30 g, 0.50 mmol) in formic acid (4 mL, 104 mmol) was stirred at room temperature for 24 hours and then concentrated under reduced pressure. The resulting residue was taken up in dichloromethane and washed with saturated aqueous sodium hydrogencarbonate, dried over anhydrous sodium sulfate, filtered and concentrated under reduced pressure. The resulting residue was purified by flash silica chromatography, elution gradient 0 to 10% methanol in dichloromethane. Product fractions were combined and concentrated under reduced pressure to afford a yellow foam solid (131 mg). The material was further purified by preparative SFC (column: CHIRALPAK IG, 5 µm, 21.2 mm diameter, 250 mm length, 5 mL/min flow rate), eluting with isocratic 20% methanol (containing 0.2% NH$_4$OH) in CO$_2$, to give N-(2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine (0.080 g, 32%) as a pale yellow solid. $^1$H NMR (300 MHz, DMSO-d$_6$, 27° C.) 1.13 (3H, d), 1.67-1.84 (3H, m), 2.57-2.70 (3H, m), 2.74-2.79 (3H, m), 2.92-3.11 (1H, m), 3.35-3.67 (2H, m), 4.03 (2H, t), 4.47 (2H, dt), 5.31 (1H, s), 6.93-7.05 (3H, m), 7.14-7.23 (2H, m), 7.42 (1H, d), 10.64 (1H, s). m/z: ES+ [M+H]+ 500.

Procedures used to prepare the starting material tert-butyl (2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate are described below.

Preparation of (1R,3R)-1-(3-bromo-2,6-difluorophenyl)-3-methyl-2-(2,2,2-trifluoroethyl)-2,3,4,9-tetrahydro-1H-pyrido[3,4-b]indole

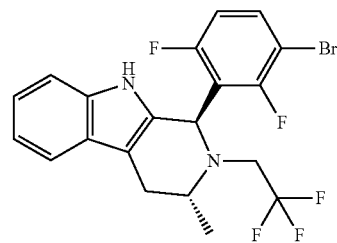 [SMILES: C[C@@H]1Cc2c([nH]c3ccccc23)[C@@H](c2c(F)ccc(Br)c2F)N1CC(F)(F)F]

A mixture of (R)-1-(1H-indol-3-yl)-N-(2,2,2-trifluoroethyl)propan-2-amine (0.50 g, 1.95 mmol) and 3-bromo-2,6-difluorobenzaldehyde (0.453 g, 2.05 mmol) in toluene (10 mL) and acetic acid (1 mL) was stirred at 100° C. for 5 hours. The reaction was then allowed to cool to room temperature and was concentrated under reduced pressure. The resulting residue was treated with saturated aqueous sodium hydrogencarbonate and extracted with ethyl acetate. The organic layer was dried over anhydrous sodium sulfate, filtered and concentrated under reduced pressure. The resulting residue was purified by flash silica chromatography, elution gradient 0 to 10% ethyl acetate in hexanes, to give (1R,3R)-1-(3-bromo-2,6-difluorophenyl)-3-methyl-2-(2,2,2-trifluoroethyl)-2,3,4,9-tetrahydro-1H-pyrido[3,4-b]indole (0.85 g, 95%) as a white foam solid. $^1$H NMR (300 MHz, DMSO-d$_6$, 27° C.) 1.13 (3H, d), 2.65 (1H, dd), 2.88 (1H, br dd), 2.93-3.12 (1H, m), 3.35-3.47 (1H, m), 3.47-3.67 (1H, m), 5.35 (1H, s), 6.92-7.15 (3H, m), 7.22 (1H, d), 7.44 (1H, d), 7.68-7.78 (1H, m), 10.66 (1H, s). m/z: ES+ [M+H]+ 459.

Preparation of tert-butyl (2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate

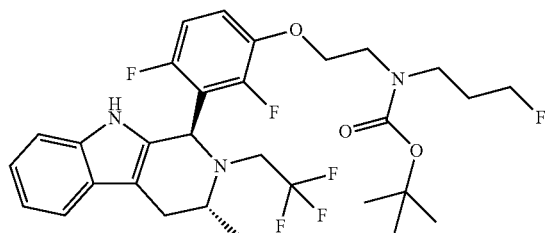

A mixture of (1R,3R)-1-(3-bromo-2,6-difluorophenyl)-3-methyl-2-(2,2,2-trifluoroethyl)-2,3,4,9-tetrahydro-1H-pyrido[3,4-b]indole (0.30 g, 0.65 mmol), tert-butyl (3-fluoropropyl)(2-hydroxyethyl)carbamate (0.289 g, 1.31 mmol), RockPhos 3$^{rd}$ Generation Precatalyst (0.027 g, 0.03 mmol) and cesium carbonate (0.532 g, 1.63 mmol) was evacuated and backfilled with nitrogen (3×). Toluene (3.5 mL) was added, and the mixture was again evacuated and backfilled with nitrogen (2×). The resulting suspension was stirred at 90° C. for 2.3 hours and was then cooled to room temperature. The mixture was filtered, and the filtrate was concentrated under reduced pressure. The resulting residue was purified by flash silica chromatography, elution gradient 0 to 30% ethyl acetate in hexanes, to give tert-butyl (2-(2,4-difluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.30 g, 77%) as a pale yellow foam. $^1$H NMR (300 MHz, DMSO-d$_6$, 27° C.) 1.03-1.19 (3H, d), 1.34-1.40 (9H, m), 1.71-1.97 (2H, m), 2.63 (1H, dd), 2.70-3.13 (2H, m), 3.36-3.63 (4H, m), 4.09 (2H, br t), 4.41 (2H, dt), 5.31 (1H, s), 6.88-7.08 (3H, m), 7.13-7.31 (2H, m), 7.42 (1H, d), 10.63 (1H, s). (Two hydrogen multiplet obscured by water peak). m/z: ES+ [M+H]+ 600.

Example 10

Preparation of 3-fluoro-N-(2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine

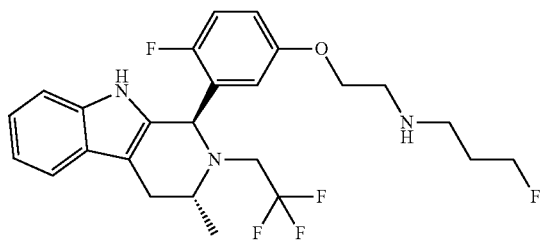 [SMILES: C[C@@H]1Cc2c([nH]c3ccccc23)[C@@H](c2cc(OCCNCCCF)ccc2F)N1CC(F)(F)F]

A solution of tert-butyl (2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.59 g, 1.01 mmol) in formic acid (4 mL, 104 mmol) was stirred at room temperature for 24 hours and was then concentrated under reduced pressure. The resulting residue was taken up in dichloromethane and washed with saturated aqueous sodium hydrogencarbonate, dried over anhydrous sodium sulfate, filtered and concentrated under reduced pressure. The resulting residue was purified by flash silica chromatography, elution gradient 0 to 10% methanol in dichloromethane. Product fractions were concentrated under reduced pressure to afford a pale yellow foam solid (425 mg). This material was further purified by preparative SFC (column: CHIRALPAK IG, 5 jam, 21.2 mm diameter, 250 mm length, 4 mL/min flow rate), eluting with isocratic 15% methanol (containing 0.2% NH$_4$OH) in CO$_2$ over, to give 3-fluoro-N-(2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine (0.35 g, 71%) as a pale yellow solid. $^1$H NMR (300 MHz, DMSO-d$_6$, 27° C.) 1.10 (3H, d), 1.53-1.83 (3H, m), 2.56-2.83 (4H, m), 2.88-3.13 (1H, m), 3.14-3.30 (1H, m), 3.44-3.61 (1H, m), 3.81 (2H, br t), 4.42 (2H, dt), 5.28 (1H, s), 6.16 (1H, dd), 6.91 (1H, dt), 6.96-7.04 (1H, m), 7.07 (1H, td), 7.17 (1H, t), 7.27 (1H, d), 7.47 (1H, d), 10.70 (1H, s). (Two hydrogen multiplet obscured by DMSO). m/z: ES+, [M+H] 482.

Procedures used to prepare the starting material tert-butyl (2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate are described below.

Preparation of (1R,3R)-1-(5-bromo-2-fluorophenyl)-3-methyl-2-(2,2,2-trifluoroethyl)-2,3,4,9-tetrahydro-1H-pyrido[3,4-b]indole

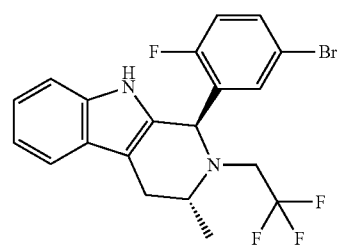 [SMILES: C[C@@H]1Cc2c([nH]c3ccccc23)[C@@H](c2cc(Br)ccc2F)N1CC(F)(F)F]

A mixture of (R)-1-(1H-indol-3-yl)-N-(2,2,2-trifluoroethyl)propan-2-amine (0.30 g, 1.17 mmol) and 5-bromo-2-fluorobenzaldehyde (0.250 g, 1.23 mmol) in toluene (6 mL) and acetic acid (0.67 mL) was stirred at 100° C. for 5 hours. The reaction was allowed to cool to room temperature and then concentrated under reduced pressure. The resulting residue was basified with saturated aqueous sodium hydrogencarbonate and extracted with ethyl acetate. The organic layer was dried over sodium sulfate, filtered and concentrated under reduced pressure. The resulting residue was purified by flash silica chromatography, elution gradient 0 to 10% ethyl acetate in hexanes, to give (1R,3R)-1-(5-bromo-2-fluorophenyl)-3-methyl-2-(2,2,2-trifluoroethyl)-2,3,4,9-tetrahydro-1H-pyrido[3,4-b]indole (0.51 g, 99%) as a white foam solid. $^1$H NMR (300 MHz, DMSO-d$_6$, 27° C.) 1.10 (3H, d), 2.60 (1H, dd), 2.77 (1H, dd), 3.97-3.08 (1H, m), 3.13-3.28 (1H, m), 3.40-3.69 (1H, m), 5.31 (1H, s), 6.73 (1H, dd), 6.97-7.04 (1H, m), 7.09 (1H, td), 7.29 (2H, d), 7.49 (1H, d), 7.57 (1H, ddd), 10.71 (1H, s). m/z: ES+ [M+H]+ 441.

Preparation of tert-butyl (2-(4-fluoro-3-((1R,3R)-3-methyl-2-(2,2,2-(2,2-trifluoroethyl)-2,3,4,9-tetrahydro-1H-pyrido[3,4-b]indol-1-yl)phenoxy)ethyl)(3-fluoropropyl)carbamate

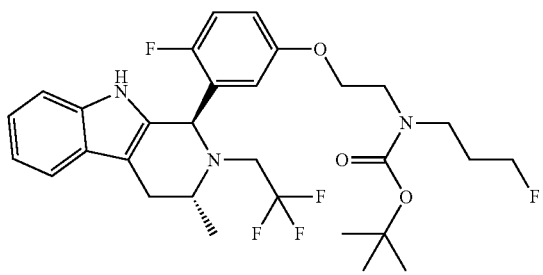 [SMILES: C[C@@H]1Cc2c([nH]c3ccccc23)[C@@H](c2cc(OCCN(CCCF)C(=O)OC(C)(C)C)ccc2F)N1CC(F)(F)F]

A flask containing a mixture of (1R,3R)-1-(5-bromo-2-fluorophenyl)-3-methyl-2-(2,2,2-trifluoroethyl)-2,3,4,9-tetrahydro-1H-pyrido[3,4-b]indole (0.510 g, 1.16 mmol), tert-butyl (3-fluoropropyl)(2-hydroxyethyl)carbamate (0.511 g, 2.31 mmol), RockPhos 3$^{rd}$ Generation Precatalyst (48 mg, 0.060 mmol) and cesium carbonate (0.941 g, 2.89 mmol) was evacuated and backfilled with nitrogen (3×). Toluene (6 mL) was added, and the reaction flask was again evacuated and backfilled with nitrogen (2×). The resulting suspension was stirred at 90° C. for 2.3 hours and then allowed to cool to room temperature. The mixture was filtered, and the filtrate was concentrated under reduced pressure. The resulting residue was purified by flash silica chromatography, elution gradient 0 to 30% ethyl acetate in hexanes, to give tert-butyl (2-(4-fluoro-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.595 g, 89%) as a pale yellow foamy solid. $^1$H NMR (300 MHz, DMSO-d$_6$, 27° C.) 1.09 (3H, d), 1.16-1.42 (9H, m), 1.60-1.90 (2H, m), 2.57-2.82 (1H, m), 3.01 (1H, br dd), 3.19 (2H, t), 3.22-3.28 (1H, m), 3.34-3.64 (3H, m), 3.87 (2H, br t), 4.32 (2H, dt), 5.28 (1H, s), 6.14 (1H, dd), 6.86-6.96 (1H, br m), 6.96-7.02 (1H, m), 7.06 (1H, td), 7.17 (1H, t), 7.26 (1H, d), 7.47 (1H, d), 10.67 (1H, s). m/z: ES+ [M+H]+ 582.

Example 11

Preparation of 3-fluoro-N-(2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine

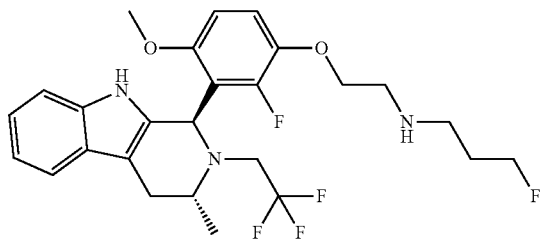 [SMILES: COc1ccc(OCCNCCCF)c(F)c1[C@@H]1c2[nH]c3ccccc3c2C[C@@H](C)N1CC(F)(F)F]

A solution of tert-butyl (2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.21 g, 0.34 mmol) in formic acid (4.0 mL, 104 mmol) was stirred at room temperature for 20 hours and then concentrated under reduced pressure. The resulting residue was taken up in dichloromethane and washed with saturated aqueous sodium hydrogencarbonate, dried over anhydrous sodium sulfate, filtered and concentrated under reduced pressure. The resulting residue was purified by flash silica chromatography, elution gradient 0 to 10% methanol in dichloromethane. Product fractions were concentrated under reduced pressure to afford a yellow foam solid (120 mg). This solid was further purified by preparative SFC ((S,S) Whelk-O1 column, 5 jam, 21.2 mm diameter, 250 mm length, 4.0 mL/min flow rate), eluting with isocratic 25% methanol (containing 0.2% NH$_4$OH) in CO$_2$, to give 3-fluoro-N-(2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine (0.10 g, 57%) as a pale yellow solid. $^1$H NMR (300 MHz, DMSO-d$_6$, 27° C.) 1.10 (3H, d), 1.61-1.81 (3H, m), 2.54-2.67 (3H, m), 2.76 (2H, br t) 2.86-3.03 (2H, m), 3.35-3.52 (2H, m), 3.79 (3H, s), 3.85-3.98 (2H, m), 4.44 (2H, dt), 5.41 (1H, s), 6.83 (1H, dd), 6.96 (2H, quind), 7.11 (1H, t), 7.15-7.20 (1H, m), 7.35-7.43 (1H, m), 10.45 (1H, s). m/z: ES+ [M+H]+ 512.

Procedures used to prepare the starting material tert-butyl (2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate are described below.

Preparation of (1R,3R)-1-(3-bromo-2-fluoro-6-methoxyphenyl)-3-methyl-2-(2,2,2-trifluoroethyl)-2,3,4,9-tetrahydro-1H-pyrido[3,4-b]indole

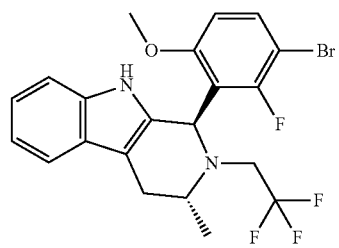 [SMILES: COc1ccc(Br)c(F)c1[C@@H]1c2[nH]c3ccccc3c2C[C@@H](C)N1CC(F)(F)F]

A mixture of (R)-1-(1H-indol-3-yl)-N-(2,2,2-trifluoroethyl)propan-2-amine (0.20 g, 0.78 mmol) and 3-bromo-2-fluoro-6-methoxybenzaldehyde (0.191 g, 0.820 mmol) in toluene (4 mL) and acetic acid (0.44 mL) was stirred at 100° C. for 5 hours. The reaction was then allowed to cool to room temperature and was concentrated under reduced pressure. The resulting residue was basified with saturated aqueous sodium hydrogencarbonate and extracted with ethyl acetate. The organic layer was dried over sodium sulfate, filtered and concentrated under reduced pressure. The resulting residue was purified by flash silica chromatography, elution gradient 0 to 10% ethyl acetate in hexanes, to give (1R,3R)-1-(3-bromo-2-fluoro-6-methoxyphenyl)-3-methyl-2-(2,2,2-trifluoroethyl)-2,3,4,9-tetrahydro-1H-pyrido[3,4-b]indole (0.32 g, 87%) as a white foam solid. $^1$H NMR (300 MHz, DMSO-d$_6$, 27° C.) 1.10 (3H, d), 2.62 (1H, dd), 2.72-2.99 (2H, m), 3.38-3.57 (2H, m), 3.86 (3H, s), 5.45 (1H, s), 6.92-7.03 (3H, m), 7.15-7.23 (1H, m), 7.37-7.44 (1H, m), 7.64 (1H, dd), 10.48 (1H, s). m/z: ES+ [M+H]+ 471.

Preparation of tert-butyl (2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate

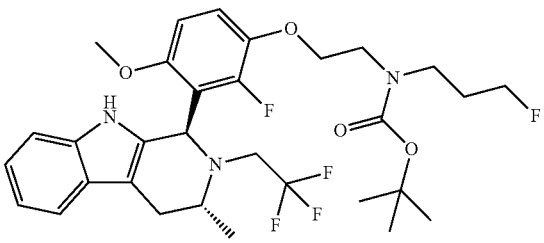 [SMILES: COc1ccc(OCCN(CCCF)C(=O)OC(C)(C)C)c(F)c1[C@@H]1c2[nH]c3ccccc3c2C[C@@H](C)N1CC(F)(F)F]

A flask containing a mixture of (1R,3R)-1-(3-bromo-2-fluoro-6-methoxyphenyl)-3-methyl-2-(2,2,2-trifluoroethyl)-2,3,4,9-tetrahydro-1H-pyrido[3,4-b]indole (0.32 g, 0.68 mmol), tert-butyl (3-fluoropropyl)(2-hydroxyethyl)carbamate (0.225 g, 1.02 mmol), RockPhos 3$^{rd}$ Generation Precatalyst (28 mg, 0.030 mmol) and cesium carbonate (0.553 g, 1.70 mmol) was evacuated and backfilled with nitrogen (3×). Toluene (3.5 mL) was added, and the flask was again evacuated and backfilled with nitrogen (2×). The resulting suspension was stirred at 90° C. for 2.3 hours and then allowed to cool to room temperature. The mixture was filtered, and the filtrate was concentrated under reduced pressure. The resulting residue was purified by flash silica chromatography, elution gradient 0 to 30% ethyl acetate in hexanes, to give tert-butyl (2-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)(3-fluoropropyl)carbamate (0.22 g, 52%) as a pale yellow foam solid. $^1$H NMR (300 MHz, DMSO-d$_6$, 27° C.) 1.10 (3H, d), 1.34 (9H, br s), 1.63-1.96 (3H, m), 2.54-2.69 (1H, m), 2.87-2.97 (1H, m), 3.18-3.28 (2H, m), 3.46-3.49 (4H, m), 3.78 (3H, s), 3.89-4.03 (2H, m), 4.35 (2H, dt), 5.41 (1H, br d), 6.82 (1H, dd), 6.96 (2H, quin), 7.12 (1H, t), 7.18 (1H, dd), 7.37-7.41 (1H, m), 10.43 (1H, s). m/z: ES+ [M+H]+ 612.

Example 12

Preparation of 3-fluoro-N-(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine

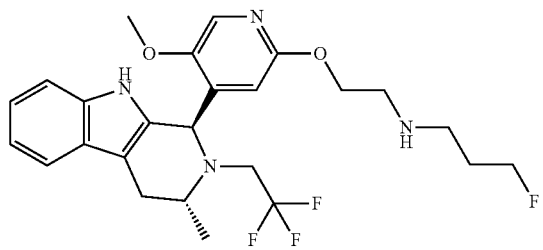 [SMILES: COc1cnc(OCCNCCCF)cc1[C@@H]1c2[nH]c3ccccc3c2C[C@@H](C)N1CC(F)(F)F]

Trifluoroacetic acid (0.96 mL, 12 mmol) was added to a solution of tert-butyl (3-fluoropropyl)(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)carbamate (370 mg, 0.62 mmol) in DCM (5.2 mL). The mixture was stirred at room temperature for 16 hours. Saturated aqueous NaHCO$_3$ (25 mL) was added cautiously, and once addition was complete, the mixture was extracted with DCM (3×50 mL). The combined organic layers were dried over sodium sulfate, filtered, and concentrated under reduced pressure. The resulting residue was purified by preparative SFC (column: (S,S) Whelk-O1, 5 μm, 21.2 mm diameter, 250 mm length, 70 mL/min flow rate), eluting with isocratic 25% methanol (containing 0.2% NH$_4$OH) in CO$_2$. Product fractions were concentrated under reduced pressure to give 3-fluoro-N-(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine (109 mg, 35%) as a yellow foamy solid. 1H NMR (300 MHz, DMSO-d$_6$, 27° C.) 1.10 (3H, d), 1.64-1.79 (3H, m), 2.52-2.64 (3H, m), 2.71-2.78 (3H, m), 2.93-3.08 (1H, m), 3.22-3.28 (1H, m), 3.44-3.60 (1H, m), 3.90 (3H, s), 4.13 (2H, br t), 4.43 (2H, dt), 5.31 (1H, s), 5.92 (1H, s), 6.96-7.03 (1H, m), 7.03-7.10 (1H, m), 7.24 (1H, d), 7.45 (1H, d), 7.92 (1H, s), 10.61 (1H, s). m/z: ES+ [M+H]+ 495.

Preparation of the starting material tert-butyl (3-fluoropropyl)(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)carbamate is described below.

Preparation of (1R,3R)-1-(2-chloro-5-methoxypyridin-4-yl)-3-methyl-2-(2,2,2-trifluoroethyl)-2,3,4,9-tetrahydro-1H-pyrido[3,4-b]indole

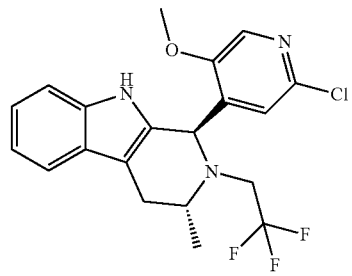 [SMILES: COc1cnc(Cl)cc1[C@@H]1c2[nH]c3ccccc3c2C[C@@H](C)N1CC(F)(F)F]

Acetic acid (1.33 mL) was added to a stirred solution of (R)-1-(1H-indol-3-yl)-N-(2,2,2-trifluoroethyl)propan-2-amine (855 mg, 3.34 mmol) and 2-chloro-5-methoxyisonicotinaldehyde (572 mg, 3.34 mmol) in toluene (11.6 mL). The resulting mixture was heated at 90° C. for 5 hours. The reaction was then concentrated under vacuum, and the resulting residue was redissolved in dichloromethane. This solution was washed with saturated aqueous sodium bicarbonate and saturated aqueous sodium chloride and then dried over sodium sulfate, filtered, and concentrated under reduced pressure. The resulting residue was purified by flash silica chromatography, eluting with 0 to 75% ethyl acetate in hexanes. Product fractions were concentrated under reduced pressure to afford (1R,3R)-1-(2-chloro-5-methoxypyridin-4-yl)-3-methyl-2-(2,2,2-trifluoroethyl)-2,3,4,9-tetrahydro-1H-pyrido[3,4-b]indole (1.28 g, 97%) as a colourless gum. 1H NMR (300 MHz, DMSO-d$_6$, 27° C.) 1.09 (3H, d), 2.60 (1H, dd), 2.80 (1H, dd), 2.90-3.08 (1H, m), 3.19-3.28 (1H, m), 3.38-3.63 (1H, m), 3.99 (3H, s), 5.33 (1H, s), 6.54 (1H, s), 6.97-7.04 (1H, m) 7.05-7.11 (1H, m), 7.24-7.29 (1H, m), 7.48 (1H, d), 8.27 (1H, s), 10.59 (1H, s). m/z: ES+ [M+H]+ 410.

Preparation of tert-butyl (3-fluoropropyl)(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)carbamate

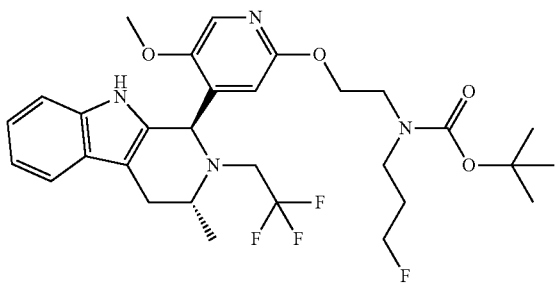 [SMILES: COc1cnc(OCCN(CCCF)C(=O)OC(C)(C)C)cc1[C@@H]1c2[nH]c3ccccc3c2C[C@@H](C)N1CC(F)(F)F]

RockPhos 3$^{rd}$ Generation Precatalyst (64.6 mg, 0.08 mmol) was added to a degassed suspension of (1R,3R)-1-(2-bromo-5-methoxypyridin-4-yl)-3-methyl-2-(2,2,2-trifluoroethyl)-2,3,4,9-tetrahydro-1H-pyrido[3,4-b]indole (350 mg, 0.77 mmol) and cesium carbonate (628 mg, 1.93 mmol) in toluene (7.7 mL) and the reaction was heated at 90° C. for 16 hours. The reaction mixture was then cooled to room temperature and quenched with water (15 mL). The mixture is was diluted with EtOAc (15 mL), and the layers were separated. The aqueous layer was extracted with EtOAc (3×15 mL), and the combined organic layers were dried over MgSO$_4$, filtered and concentrated under reduced pressure. The resulting residue was purified by flash silica chromatography, elution gradient 0 to 50% EtOAc in hexane. Product fractions were concentrated under reduced pressure to afford tert-butyl (3-fluoropropyl)(2-((5-methoxy-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)carbamate (370 mg, 81%) as a colourless oil. $^1$H NMR (300 MHz, DMSO-d$_6$, 27° C.): 1.09 (3H, d), 1.14-1.35 (9H, m), 1.67-1.85 (2H, m), 2.54-2.61 (1H, m), 2.69-2.76 (1H, m), 2.96-3.04 (1H, m), 3.17-3.29 (3H, m), 3.35-3.57 (3H, m), 3.90 (3H, s), 4.09-4.25 (2H, m), 4.33 (2H, dt), 5.31 (1H, s), 5.90 (1H, s), 6.93-7.09 (2H, m), 7.22-7.26 (1H, m), 7.46 (1H, d), 7.91 (1H, s), 10.58 (1H, s). m/z: ES+ [M+H]+ 595.

Example 13

Preparation of N-(2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)-3-fluoropropan-1-amine

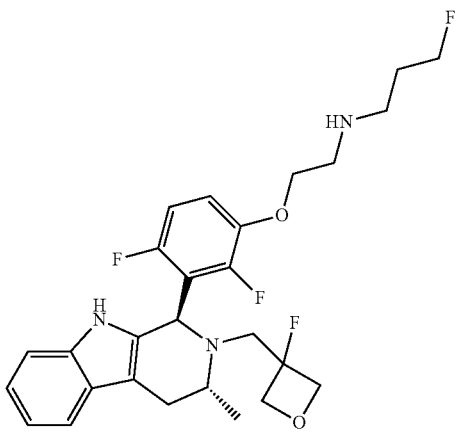 [SMILES: C[C@@H]1Cc2c([nH]c3ccccc23)[C@@H](c2c(F)ccc(OCCNCCCF)c2F)N1CC1(F)COC1]

Formic acid (5 mL) was added to tert-butyl (2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate (0.15 g, 0.25 mmol). The reaction was stirred at room temperature for 2 hours and then concentrated under reduced pressure. The resulting residue was purified via ion-exchange chromatography using an SCX-2 cartridge and eluting with ammonia in methanol (3N). Product fractions were combined and concentrated under reduced pressure. The resulting residue was further purified by flash silica chromatography, elution gradient 5 to 10% MeOH in DCM. Product fractions were concentrated under reduced pressure to afford N-(2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)-3-fluoropropan-1-amine (84 mg, 67%) as a white solid. $^1$H NMR (400 MHz, DMSO-d$_6$, 27° C.) 1.10 (3H, d), 1.65-1.83 (2H, m), 2.58-2.65 (3H, m), 2.70-2.88 (4H, m), 3.17-3.27 (1H, m), 3.33-3.42 (1H, m), 4.01 (2H, t), 4.27 (1H, dd), 4.40 (1H, t), 4.42-4.60 (4H, m), 5.27 (1H, s), 6.87-7.03 (3H, m), 7.10-7.22 (2H, m), 7.40 (1H, d), 10.60 (1H, s). m/z: ES+ [M+H]+ 506.

Procedures used to prepare the starting material tert-butyl (2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate are described below.

Preparation of (1R,3R)-1-(3-bromo-2,6-difluorophenyl)-2-((3-fluorooxetan-3-yl)methyl)-3-methyl-2,3,4,9-tetrahydro-1H-pyrido[3,4-b]indole

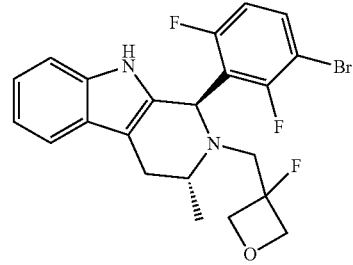 [SMILES: C[C@@H]1Cc2c([nH]c3ccccc23)[C@@H](c2c(F)ccc(Br)c2F)N1CC1(F)COC1]

3-Bromo-2,6-difluorobenzaldehyde (0.973 g, 4.40 mmol) was added to a solution of (R)—N-((3-fluorooxetan-3-yl)methyl)-1-(1H-indol-3-yl)propan-2-amine (1.1 g, 4.2 mmol) in toluene (18 mL) and acetic acid (2 mL), and the reaction was heated at 80° C. for 18 hours. The reaction was then concentrated under reduced pressure, and the resulting residue was dissolved in EtOAc and washed with saturated aqueous NaHCO$_3$. The organic layer was dried over sodium sulfate, filtered, and concentrated under reduced pressure. The resulting residue was purified by flash to silica chromatography, elution gradient 5 to 50% EtOAc in hexane. Product fractions were concentrated under reduced pressure to afford (1R,3R)-1-(3-bromo-2,6-difluorophenyl)-2-((3-fluorooxetan-3-yl)methyl)-3-methyl-2,3,4,9-tetrahydro-1H-pyrido[3,4-b]indole (1.4 g, 72%) as a white solid. $^1$H NMR (500 MHz, DMSO-d$_6$, 27° C.) 1.11 (3H, d), 2.59 (1H, dd), 2.71-2.85 (2H, m), 3.20-3.29 (1H, m), 3.32-3.39 (1H, m), 4.28 (1H, dd), 4.44-4.61 (3H, m), 5.30 (1H, s), 6.93-6.98 (1H, m), 6.99-7.04 (1H, m), 7.05-7.12 (1H, m), 7.20 (1H, d), 7.41 (1H, d), 7.74 (1H, td), 10.64 (1H, s). m/z: ES+ [M+H]+ 465.

Preparation of tert-butyl (2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate

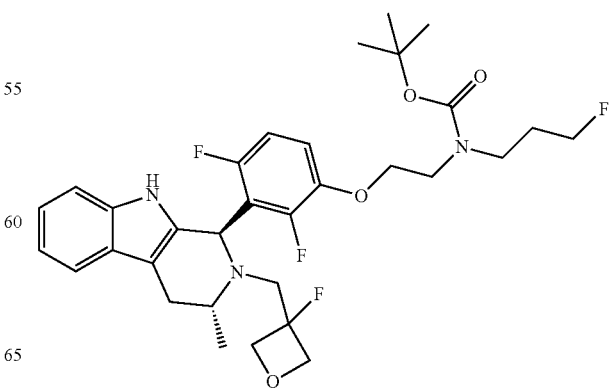

Toluene (4.5 mL) was added to a mixture of (1R,3R)-1-(3-bromo-2,6-difluorophenyl)-2-((3-fluorooxetan-3-yl)methyl)-3-methyl-2,3,4,9-tetrahydro-1H-pyrido[3,4-b]indole (0.25 g, 0.54 mmol) and tert-butyl (3-fluoropropyl)(2-hydroxyethyl)carbamate (0.238 g, 1.07 mmol). The reaction flask was evacuated and backfilled with nitrogen. Cesium carbonate (0.438 g, 1.34 mmol) and RockPhos 3$^{rd}$ Generation Precatalyst (0.046 g, 0.05 mmol) were added, and the reaction mixture was again subjected to vacuum and then backfilled with nitrogen. The reaction was heated at 100° C. for 1 hour before being cooled to room temperature and filtered through Celite using a DCM wash. The filtrate was concentrated under reduced pressure, and the resulting residue was purified by flash silica chromatography, elution gradient 2 to 10% MeOH in DCM. Product fractions were concentrated under reduced pressure to afford tert-butyl (2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)(3-fluoropropyl)carbamate (151 mg, 46%) as a solid. $^1$H NMR (500 MHz, DMSO-d$_6$, 27° C.) 1.10 (3H, d), 1.33-1.39 (9H, m), 1.78-1.89 (2H, m), 2.58 (1H, br dd), 2.72-2.84 (2H, m), 3.18-3.30 (3H, m), 3.34-3.40 (2H, m), 3.45-3.53 (2H, m), 4.07 (2H, br t), 4.28 (1H, br dd), 4.35 (1H, t), 4.42-4.58 (3H, m), 5.27 (1H, s), 6.91-6.97 (2H, m), 6.97-7.02 (1H, m), 7.13-7.21 (2H, m), 7.40 (1H, d), 10.60 (1H, s). m/z: ES+ [M+H]+ 606.

Example 14

3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol

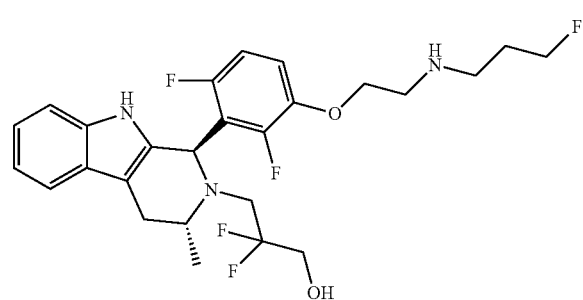 [SMILES: C[C@@H]1Cc2c([nH]c3ccccc23)[C@@H](c2c(F)ccc(OCCNCCCF)c2F)N1CC(F)(F)CO]

tert-Butyl (2-(3-((1R,3R)-2-(2,2-difluoro-3-hydroxypropyl)-3-methyl-2,3,4,9-tetrahydro-1H-pyrido[3,4-b]indol-1-yl)-2,4-difluorophenoxy)ethyl)(3-fluoropropyl)carbamate (0.55 g, 0.90 mmol) was dissolved in formic acid (5 mL). The reaction mixture was heated to 40° C. for 1 hour and the reaction mixture evaporated. The crude product was purified by flash reverse phase silica chromatography (Puriflash HP C18, 30p silica, 120 g), using decreasingly polar mixtures of water (containing 1% NH$_3$) and MeCN as eluents to afford 3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol as a foam (0.230 g, 50%). $^1$H NMR (500 MHz, CDCl$_3$, 27° C.) 1.18 (3H, d), 1.82-1.93 (2H, m), 2.68 (1H, ddd), 2.80 (2H, t), 2.83-2.93 (1H, m), 2.96-3.01 (2H, m), 3.11 (1H, ddd), 3.25 (1H, dt), 3.61-3.78 (3H, m), 4.06-4.12 (2H, m), 4.52 (2H, dt), 5.29 (1H, s), 6.84 (1H, td), 6.96 (1H, td), 7.09-7.16 (2H, m), 7.21-7.24 (1H, m), 7.45 (1H, s), 7.50-7.54 (1H, m) (2H not observed). m/z: ES− [M−H]− 510.

The tert-butyl (2-(3-((1R,3R)-2-(2,2-difluoro-3-hydroxypropyl)-3-methyl-2,3,4,9-tetrahydro-1H-pyrido[3,4-b]indol-1-yl)-2,4-difluorophenoxy)ethyl)(3-fluoropropyl)carbamate was prepared as follows:

Preparation of (1R,3R)-1-(3-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole

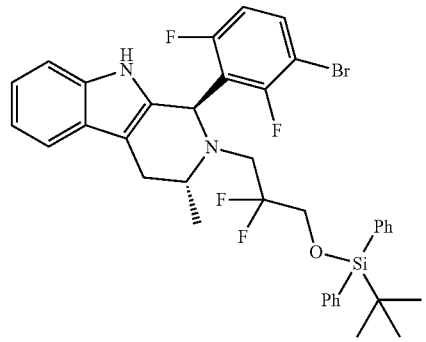 [SMILES: C[C@@H]1Cc2c([nH]c3ccccc23)[C@@H](c2c(F)ccc(Br)c2F)N1CC(F)(F)CO[Si](c1ccccc1)(c1ccccc1)C(C)(C)C]

To a solution of (R)—N-(1-(1H-indol-3-yl)propan-2-yl)-3-((tert-butyldiphenylsilyl)oxy)-2,2-difluoropropan-1-amine (1.12 g, 2.21 mmol) in toluene (15 mL) and acetic acid (1.67 mL) was added 3-bromo-2,6-difluorobenzaldehyde (0.624 g, 2.82 mmol). The solution was heated to 90° C. and stirred for 16 hours. The reaction mixture was evaporated and the residue was partitioned between DCM and 2M NaOH (50 mL each). The organic phase was evaporated and the crude product was purified by flash silica chromatography, elution gradient 0 to 25% EtOAc in heptane to afford (1R,3R)-1-(3-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole (1.070 g, 68%) as a white foam. $^1$H NMR (500 MHz, CDCl$_3$, 27° C.) 1.05 (9H, s), 1.16 (3H, d), 2.61 (1H, ddd), 2.71-2.81 (1H, m), 2.99 (1H, ddd), 3.25-3.38 (1H, m), 3.57-3.69 (2H, m), 3.91-4.01 (1H, m), 5.36 (1H, s), 6.65-6.71 (1H, m), 7.08-7.16 (2H, m), 7.21-7.25 (1H, m), 7.36-7.44 (8H, m), 7.51-7.55 (1H, m), 7.60-7.66 (4H, m).

Preparation of tert-butyl (2-(3-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-2,4-difluorophenoxy)ethyl)(3-fluoropropyl)carbamate

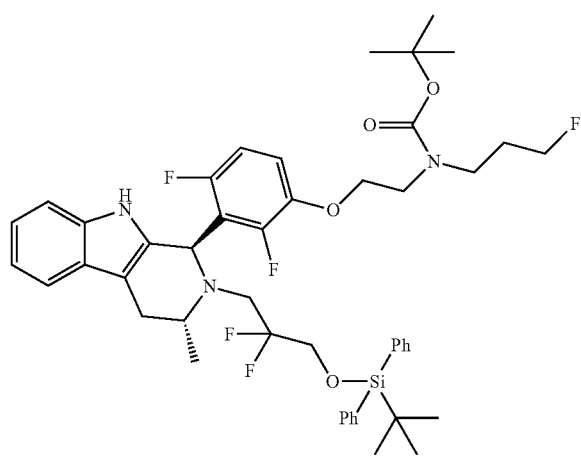 [SMILES: C[C@@H]1Cc2c([nH]c3ccccc23)[C@@H](c2c(F)ccc(OCCN(CCCF)C(=O)OC(C)(C)C)c2F)N1CC(F)(F)CO[Si](c1ccccc1)(c1ccccc1)C(C)(C)C]

RockPhos Pd G3 (0.063 g, 0.08 mmol) was added to a degassed suspension of (1R,3R)-1-(3-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole (1.07 g, 1.51 mmol), tert-butyl (3-fluoropropyl)(2-hydroxyethyl)carbamate (0.667 g, 3.02 mmol) and cesium carbonate (1.23 g, 3.77 mmol) in toluene (15 mL) and the reaction was heated to 90° C. for 5 hours. The reaction mixture was allowed to cool to room temperature and diluted with water (15 mL). DCM (30 mL) was added and the organic phase was separated and evaporated. The crude product was purified by flash silica chromatography, elution gradient 0 to 50% EtOAc in heptane to afford tert-butyl (2-(3-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-2,4-difluorophenoxy)ethyl)(3-fluoropropyl)carbamate (0.850 g, 66%) as a tan foam. $^1$H NMR (500 MHz, CDCl$_3$, 27° C.) 1.04 (9H, s), 1.15 (3H, d), 1.43 (9H, s), 1.84-1.99 (2H, m), 2.60 (1H, dd), 2.74-2.85 (1H, m), 3.00 (1H, ddd), 3.23-3.34 (1H, m), 3.35-3.41 (2H, m), 3.45-3.62 (3H, m), 3.65-3.72 (1H, m), 3.93-4.09 (3H, m), 4.33-4.49 (2H, m), 5.33 (1H, s), 6.62 (1H, s), 6.77-6.85 (1H, m), 7.07-7.14 (2H, m), 7.20-7.23 (1H, m), 7.33-7.44 (6H, m), 7.49-7.52 (1H, m), 7.56 (1H, s), 7.58-7.66 (4H, m). m/z: ES+ [M+H]+ 850.

Preparation of tert-butyl (2-(3-((1R,3R)-2-(2,2-difluoro-3-hydroxypropyl)-3-methyl-2,3,4,9-tetrahydro-H-pyrido[3,4-b]indol-1-yl)-2,4-difluorophenoxy)ethyl)(3-fluoropropyl)carbamate

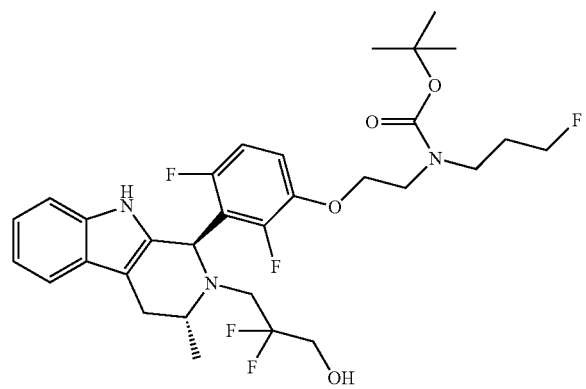 [SMILES: C[C@@H]1Cc2c([nH]c3ccccc23)[C@@H](c2c(F)ccc(OCCN(CCCF)C(=O)OC(C)(C)C)c2F)N1CC(F)(F)CO]

Tetrabutylammonium fluoride (1.0 M in THF) (1.50 mL, 1.50 mmol) was added to a solution of tert-butyl (2-(3-((1R, 3R)-2-(3-((tert-butyldiphenylsilyl)oxy)-2,2-difluoropropyl)-3-methyl-2,3,4,9-tetrahydro-1H-pyrido[3,4-b]indol-1-yl)-2,4-difluorophenoxy)ethyl)(3-fluoropropyl)carbamate (0.850 g, 1.00 mmol) in tetrahydrofuran (10 mL). The reaction was stirred at room temp for 90 minutes and then the reaction mixture was evaporated. The crude product was purified by flash silica chromatography, elution gradient 0 to 80% EtOAc in heptane. Product containing fractions were evaporated to dryness to afford tert-butyl (2-(3-((1R,3R)-2-(2,2-difluoro-3-hydroxypropyl)-3-methyl-2,3,4,9-tetrahydro-1H-pyrido[3,4-b]indol-1-yl)-2,4-difluorophenoxy)ethyl)(3-fluoropropyl)carbamate (0.550 g, 90%) as a colourless foam. $^1$H NMR (500 MHz, CDCl$_3$, 27° C.) 1.18 (3H, d), 1.44 (9H, s), 1.88-2.02 (2H, m), 2.69 (1H, ddd), 2.83-2.93 (1H, m), 3.13 (1H, dd), 3.21-3.32 (2H, m), 3.39-3.44 (2H, m), 3.47-3.79 (6H, m), 4.16 (1H, s), 4.45 (2H, dt), 5.28 (1H, s), 6.82 (1H, td), 6.96 (1H, s), 7.08-7.15 (2H, m), 7.23 (1H, d), 7.49-7.65 (2H, m). m/z: ES+ [M+H]+ 612.

Example 15

3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2,2-difluoropropan-1-ol

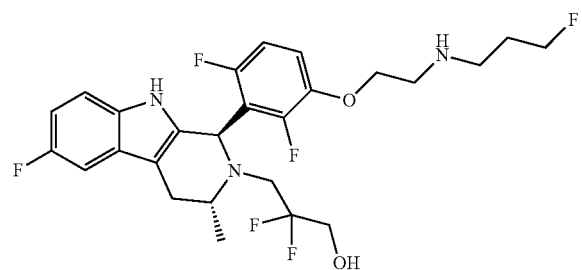

TBAF solution (IM in THF) (1.58 mL, 1.58 mmol) was added to tert-butyl (2-(3-((1R,3R)-2-(3-((tert-butyldiphenylsilyl)oxy)-2,2-difluoropropyl)-6-fluoro-3-methyl-2,3,4,9-tetrahydro-1H-pyrido[3,4-b]indol-1-yl)-2,4-difluorophenoxy)ethyl)(3-fluoropropyl)carbamate (275 mg, 0.32 mmol) and the reaction was stirred at room temperature for 1 hour. The reaction was diluted with DCM (10 mL) and washed with saturated aqueous sodium chloride (10 mL). The aqueous was extracted with DCM (10 mL), then the combined organics were dried over Na$_2$SO$_4$ and evaporated. The crude product was passed through a plug of silica gel, eluting with 1:1 EtOAc/heptane. The fractions containing product were evaporated to afford crude title compound as a pale yellow gum (~200 mg). The residue was dissolved in formic acid (2 mL) and stirred at 40° C. for 1 hour. The volatiles were evaporated, then the crude product was purified by preparative HPLC (Waters SunFire column, 5μ silica, 19 mm diameter, 100 mm length), using decreasingly polar mixtures of water (containing 1% NH$_3$) and MeCN as eluents. Fractions containing the desired compound were evaporated to dryness. The sample was is dissolved in MeOH and further purified using the SFC: Column: Phenomenex A1, 30×250 mm, 5 micron; Mobile phase: 20% MeOH+0.1% NH$_3$/80% sc CO$_2$; Flow rate: 100 ml/min; Temperature: 40° C.; BPR: 120 bar, to afford 3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2,2-difluoropropan-1-ol (72.6 mg, 77%) as a colourless solid. $^1$H NMR (500 MHz, CDCl$_3$, 27° C.) 1.18 (3H, d), 1.82-1.95 (2H, m), 2.62 (1H, dd), 2.80 (2H, t), 2.87 (1H, dd), 2.97-3.01 (2H, m), 3.07 (1H, dd), 3.19-3.28 (1H, m), 3.56-3.82 (2H, m), 4.04-4.17 (2H, m), 4.52 (3H, dt), 5.28 (1H, s), 6.82-6.91 (2H, m), 6.97 (1H, td), 7.14 (2H, td), 7.43 (1H, s); m/z: ES+ [M+H]+ 530.

The tert-butyl (2-(3-((1R,3R)-2-(3-((tert-butyldiphenylsilyl)oxy)-2,2-difluoropropyl)-6-fluoro-3-methyl-2,3,4,9-tetrahydro-1H-pyrido[3,4-b]indol-1-yl)-2,4-difluorophenoxy)ethyl)(3-fluoropropyl)carbamate used as starting material was prepared as follows:

Tert-butyl (R)-(1-(5-fluoro-1H-indol-3-yl)propan-2-yl)carbamate

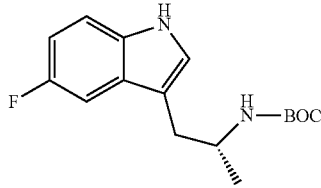 [SMILES: C[C@H](Cc1c[nH]c2ccc(F)cc12)NC(=O)OC(C)(C)C]

5-fluoro-1H-indole (9.34 g, 69.11 mmol) was dissolved in DCM (470 ml) and cooled to −78° C. Methylmagnesium bromide solution (23.50 mL, 70.50 mmol) was added dropwise over 10 min, then tert-butyl (R)-4-methyl-1,2,3-oxathiazolidine-3-carboxylate 2,2-dioxide (6.56 g, 27.65 mmol) in DCM (15 mL) was added dropwise. The reaction was stirred at −78° C. for 30 min, then allowed to warm to 0° C. over 2 hours. Ice-cold IM aqueous citric acid solution was added (80 mL) and the biphasic mixture was stirred for 10 min. The layers were separated, then the aqueous layer was extracted with DCM (2×100 mL). The combined organics were is washed with H$_2$O (50 mL), saturated aqueous sodium chloride (50 mL) then dried over MgSO$_4$, filtered and concentrated. The crude product was purified by flash silica chromatography, elution gradient 0 to 50% EtOAc in heptane. Pure fractions were evaporated to dryness to afford tert-butyl (R)-(1-(5-fluoro-1H-indol-3-yl)propan-2-yl)carbamate (5.56 g, 69%) as a brown solid.

$^1$H NMR (500 MHz, CDCl$_3$, 27° C.) 1.12 (3H, d), 1.43 (9H, s), 2.87 (2H, td), 3.93-4.08 (1H, m), 4.36-4.51 (1H, m), 6.93 (1H, td), 7.05 (1H, d), 7.23-7.29 (2H, m), 8.11 (1H, s); m/z: ES− [M+H]+ 291.

(R)-1-(5-fluoro-1H-indol-3-yl)propan-2-amine

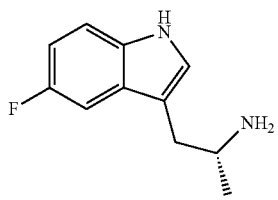

To a solution of tert-butyl (R)-(1-(5-fluoro-1H-indol-3-yl)propan-2-yl)carbamate (5.5 g, 18.81 mmol) in DCM (40 ml) was added trifluoroacetic acid (1.45 mL, 18.81 mmol) and the mixture was stirred at room temperature for 16 hours. The reaction was concentrated in vacuo, re-dissolved in methanol and applied to a pre-wetted (methanol) SCX-2 cartridge. The cartridge was washed with methanol (250 mL), the product eluted with IM NH$_3$ in methanol solution (250 mL) and concentrated in vacuo to afford (R)-1-(5-fluoro-1H-indol-3-yl)propan-2-amine (3.56 g, 98%) as a yellow solid. $^1$H NMR (500 MHz, CDCl$_3$, 27° C.) 1.16 (3H, d), 2.62 (1H, dd), 2.82 (1H, dd), 3.27 (1H, ddt), 6.9-7.01 (1H, m), 7.09 (1H, s), 7.22-7.32 (2H, m), 8.16 (1H, s); m/z: ES+ [M−H]− 191.

(R)-3-((tert-butyldiphenylsilyl)oxy)-2,2-difluoro-N-(1-(5-fluoro-1H-indol-3-yl)propan-2-yl)propan-1-amine

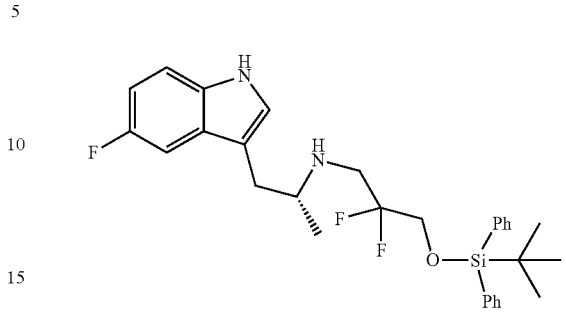

3-((tert-butyldiphenylsilyl)oxy)-2,2-difluoropropyl trifluoromethanesulfonate (1.44 g, 2.99 mmol) was added to a solution of (R)-1-(5-fluoro-1H-indol-3-yl)propan-2-amine (0.500 g, 2.6 mmol) and DIPEA (0.674 ml, 3.90 mmol) in 1,4-dioxane (9.73 ml). The reaction was heated to 80° C. for 6 hours. After cooling, the volatiles were evaporated. The residue was dissolved in DCM (25 mL) and washed with saturated aqueous sodium chloride (25 mL). The organic phase was dried over Na$_2$SO$_4$ and evaporated. The crude product was purified by flash silica chromatography, elution gradient 0 to 100% EtOAc in heptane. Pure fractions were evaporated to dryness to afford (R)-3-((tert-butyldiphenylsilyl)oxy)-2,2-difluoro-N-(1-(5-fluoro-1H-indol-3-yl)propan-2-yl)propan-1-amine (1.13 g, 83%) as a colourless gum.

$^1$H NMR (500 MHz, CDCl$_3$, 27° C.) 1.04 (9H, s), 1.11 (3H, d), 2.68-2.77 (1H, m), 2.81 (1H, dd), 3.02-3.26 (3H, m), 3.74-3.88 (2H, m), 6.93 (1H, td), 7.03 (1H, d), 7.18-7.25 (2H, m), 7.38 (4H, ddd), 7.4-7.49 (2H, m), 7.65 (4H, dq), 7.85 (1H, s); m/z: ES+ [M+H]+ 525.

(1R,3R)-1-(3-bromo-2,6-difluorophenyl)-2-(3-((tert-butyldiphenylsilyl)oxy)-2,2-difluoropropyl)-6-fluoro-3-methyl-2,3,4,9-tetrahydro-1H-pyrido[3,4-b]indole

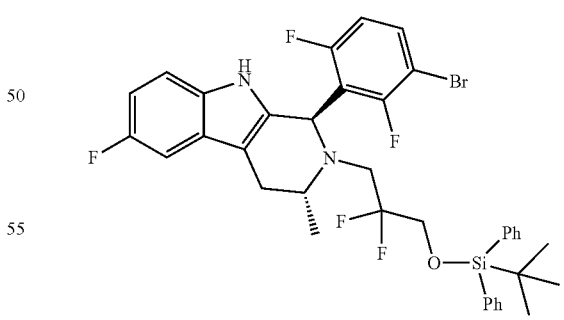

(R)-3-((tert-butyldiphenylsilyl)oxy)-2,2-difluoro-N-(1-(5-fluoro-1H-indol-3-yl)propan-2-yl)propan-1-amine (352 mg, 0.67 mmol) and 3-bromo-2,6-difluorobenzaldehyde (155 mg, 0.70 mmol) were heated in toluene (3.02 mL)/acetic acid (0.33 mL) to 80° C. for 4 hours. After cooling, the volatiles were evaporated. The residue was dissolved in DCM (25 mL) and washed with saturated NaHCO$_3$ solution (25 mL), then dried over Na₂SO₄ and evaporated. The crude product was purified by flash silica chromatography, elution gradient 0 to 25% EtOAc in heptane. Pure fractions were evaporated to dryness to afford (1R,3R)-1-(3-bromo-2,6-difluorophenyl)-2-(3-((tert-butyldiphenylsilyl)oxy)-2,2-difluoropropyl)-6-fluoro-3-methyl-2,3,4,9-tetrahydro-1H-pyrido[3,4-b]indole (483 mg, 99%) as a colourless solid. ¹H NMR (500 MHz, CDCl₃, 27° C.) 1.05 (9H, s), 1.16 (3H, d), 2.54 (1H, dd), 2.76 (1H, td), 2.89-2.98 (1H, m), 3.29 (1H, ddd), 3.56-3.69 (2H, m), 3.95 (1H, ddd), 5.35 (1H, s), 6.70 (1H, td), 6.88 (1H, td), 7.11-7.18 (2H, m), 7.34-7.47 (8H, m), 7.6-7.67 (4H, m); m/z: ES+ [M+H]+ 727.

tert-butyl (2-(3-((1R,3R)-2-(3-((tert-butyldiphenylsilyl)oxy)-2,2-difluoropropyl)-6-fluoro-3-methyl-2,3,4,9-tetrahydro-1H-pyrido[3,4-b]indol-1-yl)-2,4-difluorophenoxy)ethyl)(3-fluoropropyl)carbamate

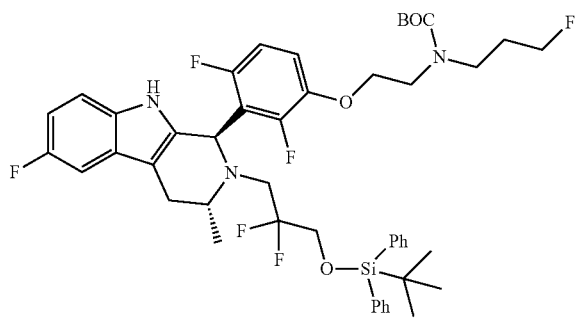 [SMILES: C[C@@H]1Cc2c([nH]c3ccc(F)cc23)[C@@H](c2c(F)ccc(OCCN(CCCF)C(=O)OC(C)(C)C)c2F)N1CC(F)(F)CO[Si](c1ccccc1)(c1ccccc1)C(C)(C)C]

Tert-butyl (3-fluoropropyl)(2-hydroxyethyl)carbamate (137 mg, 0.62 mmol) was added in toluene (2.06 mL) to a flask containing (1R,3R)-1-(3-bromo-2,6-difluorophenyl)-2-(3-((tert-butyldiphenylsilyl)oxy)-2,2-difluoropropyl)-6-fluoro-3-methyl-2,3,4,9-tetrahydro-1H-pyrido[3,4-b]indole (300 mg, 0.41 mmol), cesium carbonate (268 mg, 0.82 mmol) and Rockphos 3$^{rd}$ generation precatalyst (18.65 mg, 0.02 mmol). The reaction was degassed then heated to 90° C. for 2 hours. After cooling, the reaction was diluted with EtOAc (25 mL) and washed with saturated aqueous sodium chloride (25 mL). The organic phase was dried over Na₂SO₄ and evaporated. The crude product was purified by flash silica chromatography, elution gradient 0 to 50% EtOAc in heptane. Pure fractions were evaporated to dryness to afford tert-butyl (2-(3-((1R,3R)-2-(3-((tert-butyldiphenylsilyl)oxy)-2,2-difluoropropyl)-6-fluoro-3-methyl-2,3,4,9-tetrahydro-1H-pyrido[3,4-b]indol-1-yl)-2,4-difluorophenoxy)ethyl)(3-fluoropropyl)carbamate as a beige solid. ¹H NMR (500 MHz, CDCl₃, 27° C.) 1.04 (9H, s), 1.15 (3H, d), 1.43 (9H, s), 1.91 (2H, d), 2.53 (1H, dd), 2.79 (1H, q), 2.92-3 (1H, m), 3.21-3.35 (1H, m), 3.35-3.4 (1H, m), 3.41-3.54 (2H, m), 3.53-3.63 (2H, m), 3.63-3.74 (1H, m), 3.89-4.01 (1H, m), 4.03 (1H, s), 4.09 (1H, d), 4.37 (1H, d), 4.46 (1H, s), 5.31 (1H, s), 6.63 (1H, s), 6.76-6.89 (2H, m), 7.06-7.12 (1H, m), 7.14 (1H, dd), 7.33-7.47 (6H, m), 7.60 (3H, ddd), 7.63-7.68 (2H, m).

Example 55

(S)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic Acid

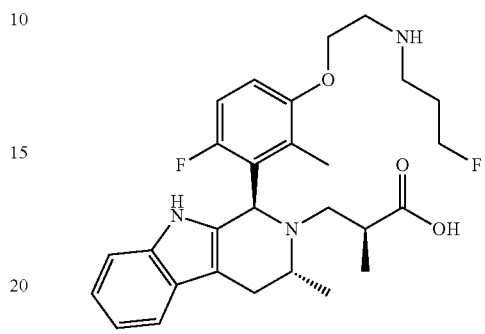

Tert-butyl (3-fluoropropyl)(2-hydroxyethyl)carbamate (235 mg, 1.06 mmol) was added in anhydrous toluene (4.25 mL) to a flask containing methyl (S)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate (402 mg, 0.85 mmol), cesium carbonate (553 mg, 1.70 mmol) and Rockphos 3$^{rd}$ generation precatalyst (38.5 mg, 0.04 mmol). The reaction was degassed, then heated to 90° C. for 4 hours. A further portion of tert-butyl (3-fluoropropyl)(2-hydroxyethyl)carbamate (235 mg, 1.06 mmol) and Rockphos 3$^{rd}$ generation precatalyst (38.5 mg, 0.04 mmol) were added and the reaction was heated to 90° C. overnight. The residue was dissolved in THF (3 mL)/MeOH (3 mL) and then 2N NaOH solution (1.5 mL) was added. The reaction was stirred for 3 hours, then diluted with EtOAc (20 mL) and water (20 mL). The pH was adjusted to ~6 by addition of 2N HCl solution and the layers were separated. The aqueous layer was extracted with EtOAc (20 mL), then the combined organics were evaporated. The residue was dissolved in formic acid (2 mL) and stirred at 40° C. for 1 hour. The volatiles were evaporated, then the residue was partitioned between DCM (20 mL) and water (20 mL). The desired product was observed solely in the aqueous phase. The aqueous phase was evaporated, then the crude product was purified by preparative HPLC (Waters SunFire column, 5μ silica, 19 mm diameter, 100 mm length), using decreasingly polar mixtures of water (containing 0.1% NH₃) and MeCN as eluents. Fractions containing the desired compound were evaporated to dryness to afford (S)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (83 mg, 20%) as a pale yellow solid. ¹H NMR (500 MHz, CDCl₃, 27° C.) 0.86 (3H, d), 1.20 (3H, d), 1.82-1.97 (5H, m), 2.68-2.80 (3H, m), 2.83 (3H, t), 2.94-3.07 (2H, m), 3.21 (1H, dd), 3.42 (2H, s), 3.54-3.65 (1H, m), 4.02 (1H, q), 4.40 (1H, t), 4.50 (1H, t), 5.47 (1H, s), 6.18 (1H, s), 6.77 (1H, dd), 6.89 (1H, t), 7.09 (2H, td), 7.14-7.22 (1H, m), 7.48-7.52 (1H, m), 7.82 (1H, s). m/z: ES+ [M+H]⁺ 500.

The methyl (S)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate used as starting material was prepared as follows:

Methyl (S)-2-methyl-3-(((trifluoromethyl)sulfonyl)oxy)propanoate

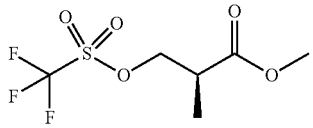

Trifluoromethanesulfonic anhydride (3.53 mL, 21.00 mmol), followed by 2,6-dimethylpyridine (2.56 mL, 22.00 mmol) were added to a solution of methyl (S)-3-hydroxy-2-methylpropanoate (2.36 g, 20.0 mmol) in DCM (74 mL) at 5° C. The reaction was stirred for 1 hour, then was washed with 2N HCl solution (50 mL). The organic phase was washed with saturated aqueous sodium chloride (50 mL), then dried over $Na_2SO_4$ and evaporated to afford is methyl (S)-2-methyl-3-(((trifluoromethyl)sulfonyl)oxy)propanoate (5.46 g, >100%) as a red oil which was used directly. $^1$H NMR (500 MHz, $CDCl_3$, 27° C.) 1.31 (3H, d), 2.96 (1H, pd), 3.75 (3H, s), 4.56 (1H, dd), 4.69 (1H, dd).

Methyl (S)-3-(((R)-1-(1H-indol-3-yl)propan-2-yl)amino)-2-methylpropanoate

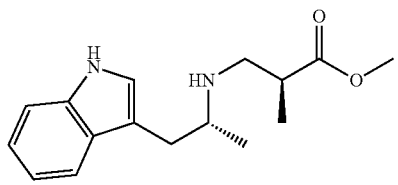 [SMILES: COC(=O)[C@@H](C)CN[C@H](C)Cc1c[nH]c2ccccc12]

Methyl (S)-2-methyl-3-(((trifluoromethyl)sulfonyl)oxy)propanoate (4.60 g, 18.40 mmol) was added to a solution of (R)-1-(1H-indol-3-yl)propan-2-amine (2.79 g, 16 mmol) and DIPEA (3.59 mL, 20.80 mmol) in 1,4-dioxane (42.1 mL) and the reaction was stirred at room temperature for 1 hour. The reaction mixture was diluted with EtOAc (100 mL) and washed with water (100 mL). The aqueous was extracted with EtOAc (50 mL), then the combined organics were dried over $Na_2SO_4$ and evaporated. The crude product was purified by flash silica chromatography, elution gradient 0 to 100% EtOAc in heptane. Pure fractions were evaporated to dryness to afford methyl (S)-3-(((R)-1-(1H-indol-3-yl)propan-2-yl)amino)-2-methylpropanoate (3.71 g, 85%) as a pale yellow gum. $^1$H NMR (500 MHz, $CDCl_3$, 27° C.) 1.11 (3H, d), 1.21-1.25 (3H, m), 2.72 (1H, ddd), 2.79 (1H, dd), 2.86 (1H, dd), 2.93 (2H, d), 3.13 (1H, q), 3.50 (3H, s), 7.08-7.15 (2H, m), 7.20 (1H, ddd), 7.38 (1H, dt), 7.49-7.69 (1H, m), 8.23 (1H, s). m/z: ES+ [M+H]+ 275.

3-Bromo-6-fluoro-2-methylbenzaldehyde

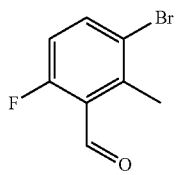

N-bromo succinimide (2.99 g, 16.80 mmol) was added to 2-fluoro-6-methylbenzaldehyde (2.21 g, 16.0 mmol) in $H_2SO_4$ (16.00 mL) and the reaction was stirred at room temperature for 30 min. The mixture was poured onto ice-water (150 mL). The precipitate was collected by filtration and dried to afford 3-bromo-6-fluoro-2-methylbenzaldehyde (3.14 g, 90%) as a beige, low-melting solid. $^1$H NMR (500 MHz, $CDCl_3$, 27° C.) 2.70 (3H, s), 6.94 (1H, ddd), 7.74 (1H, dd), 10.46 (1H, s).

Methyl (S)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate

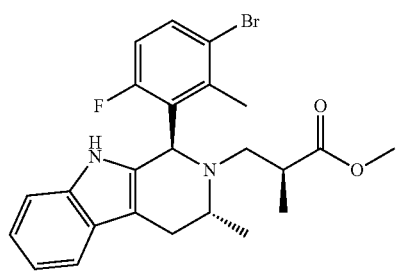 [SMILES: COC(=O)[C@@H](C)CN1[C@H](c2c(F)ccc(Br)c2C)c2[nH]c3ccccc3c2C[C@H]1C]

Methyl (S)-3-(((R)-1-(1H-indol-3-yl)propan-2-yl)amino)-2-methylpropanoate (549 mg, 2.0 mmol) and 3-bromo-6-fluoro-2-methylbenzaldehyde (456 mg, 2.10 mmol) were heated in toluene (9.0 mL)/acetic acid (1.0 mL) to 80° C. overnight. After cooling, the volatiles were evaporated. The crude product was purified by ion exchange chromatography, using an SCX column. The desired product was eluted from the column using MeOH, then 1M $NH_3$/MeOH to elute the product. The basic filtrate was evaporated, then the crude product was purified by flash silica chromatography, elution gradient 0 to 30% EtOAc in heptane. Pure fractions were evaporated to dryness to afford methyl (S)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate (421 mg, 44%) as a beige solid. $^1$H NMR (500 MHz, $CDCl_3$, 27° C.) 0.85-0.89 (3H, m), 1.11 (3H, d), 2.10 (3H, s), 2.18 (1H, p), 2.36 (1H, ddd), 2.67-2.72 (1H, m), 2.95 (1H, dd), 3.10 (1H, ddd), 3.52-3.59 (1H, m), 3.64 (3H, s), 5.39 (1H, s), 6.89 (1H, t), 7.07-7.14 (2H, m), 7.19-7.22 (1H, m), 7.22 (1H, s), 7.47-7.51 (1H, m), 7.54 (1H, dd). m/z: ES- [M-H]- 471.

Example 57

(S)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic Acid

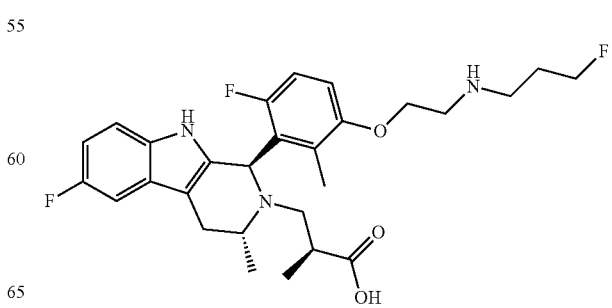

2N NaOH solution (1.19 mL, 2.37 mmol) was added to a solution of methyl (S)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (0.300 g, 0.47 mmol) in THF (2.37 mL)/MeOH (1.19 mL) and the reaction was stirred at room temperature for 4 hours. The reaction was diluted with EtOAc (20 mL) and water (20 mL), then the pH was adjusted to ~6 by addition of 2N HCl solution. The layers were separated and the aqueous was extracted with EtOAc (10 mL). The combined organics were dried over $Na_2SO_4$ and evaporated. The residue was dissolved in formic acid (2 mL) and warmed to 40° C. for 1 hour. The volatiles were evaporated, then the crude product was purified by preparative HPLC (Waters SunFire column, 5μ silica, 19 mm diameter, 100 mm length), using decreasingly polar mixtures of water (containing 1% $NH_3$) and MeCN as eluents. Fractions containing the desired compound were evaporated to dryness to afford (S)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (0.147 g, 60%) as a beige solid. $^1$H NMR (500 MHz, CDCl$_3$, 27° C.) 0.84 (3H, d), 1.17 (3H, d), 1.83-1.89 (4H, m), 1.92 (2H, dd), 2.65 (2H, dd), 2.80 (1H, dd), 2.86 (2H, t), 3-3.1 (2H, m), 3.1-3.2 (1H, m), 3.55-3.65 (1H, m), 4.03 (2H, dq), 4.38 (1H, t), 4.48 (1H, t), 5.42 (1H, s), 6.73 (1H, dd), 6.78-6.83 (1H, m), 6.83-6.89 (1H, m), 7.07 (1H, dd), 7.11 (1H, dd), 7.54 (1H, s), 8.00 (1H, s). 1 exchangeable not observed. m/z: ES+ [M+H]+ 518.

The methyl (S)-3-((1R,3R)-1-(3-(2-((tert-butoxycarbonyl)(3-fluoropropyl)amino) ethoxy)-6-fluoro-2-methylphenyl)-6-fluoro-3-methyl-1,3,4,9-tetrahydro-2H-pyrido[3,4-b]indol-2-yl)-2-methylpropanoate used as starting material was prepared as follows:

Methyl (S)-3-(((R)-1-(5-fluoro-1H-indol-3-yl)propan-2-yl)amino)-2-methylpropanoate

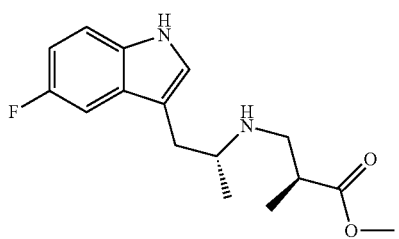 [SMILES: COC(=O)[C@@H](C)CN[C@H](C)Cc1c[nH]c2ccc(F)cc12]

To a cooled solution of (R)-1-(5-fluoro-1H-indol-3-yl)propan-2-amine (1.105 g, 5.75 mmol) and DIPEA (0.993 mL, 5.75 mmol) in dioxane (15 mL) at 0° C. was added methyl (S)-2-methyl-3-(((trifluoromethyl)sulfonyl)oxy)propanoate (1.44 g, 5.75 mmol). The reaction was allowed to warm to room temperature and stirred overnight. The reaction was diluted with EtOAc (50 mL) and washed with water (50 mL). The organic phase was dried over $Na_2SO_4$ and evaporated. The crude product was purified by flash silica chromatography, elution gradient 25 to 100% EtOAc in heptane. Pure fractions were evaporated to dryness to afford methyl (S)-3-(((R)-1-(5-fluoro-1H-indol-3-yl)propan-2-yl)amino)-2-methylpropanoate (1.520 g, 90%) as a pale yellow oil. $^1$H NMR (500 MHz, CDCl$_3$, 27° C.) 1.13 (3H, d), 1.26-1.29 (3H, m), 2.67-2.85 (2H, m), 2.86-2.98 (3H, m), 3.14 (1H, h), 3.53 (3H, s), 6.95 (1H, td), 7.17-7.23 (2H, m), 7.30 (1H, dd), 8.37 (1H, s). m/z: ES+ [M+H]+ 293.

Methyl (S)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate

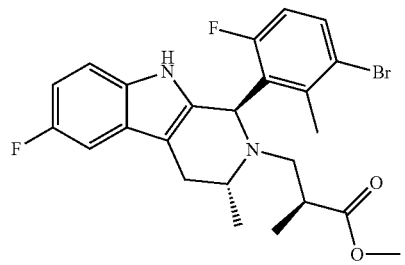 [SMILES: COC(=O)[C@@H](C)CN1[C@H](c2c(F)ccc(Br)c2C)c2[nH]c3ccc(F)cc3c2C[C@H]1C]

Methyl (S)-3-(((R)-1-(5-fluoro-1H-indol-3-yl)propan-2-yl)amino)-2-methylpropanoate (439 mg, 1.5 mmol) and 3-bromo-6-fluoro-2-methylbenzaldehyde (326 mg, 1.50 mmol) were heated in toluene (6.75 mL)/acetic acid (0.75 mL) to 110° C. overnight. The volatiles were evaporated, then the residue was dissolved in DCM (25 mL) and washed with saturated NaHCO$_3$ solution (25 mL). The organic was dried over $Na_2SO_4$ and evaporated. The crude product was purified by flash silica chromatography, elution gradient 0 to 30% EtOAc in heptane. Pure fractions were evaporated to dryness to afford methyl (S)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (204 mg, 28%) as a pale yellow solid. $^1$H NMR (500 MHz, CDCl$_3$, 27° C.) 0.87 (3H, d), 1.11 (3H, d), 2.10 (3H, s), 2.16 (1H, q), 2.35 (1H, ddd), 2.63 (1H, d), 2.95 (1H, dd), 3.07 (1H, ddd), 3.52-3.59 (1H, m), 3.64 (3H, s), 5.37 (1H, s), 6.84 (1H, td), 6.90 (1H, t), 7.08-7.15 (2H, m), 7.20 (1H, s), 7.55 (1H, dd). m/z: ES+ [M+H]+ 491.

Methyl (S)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate

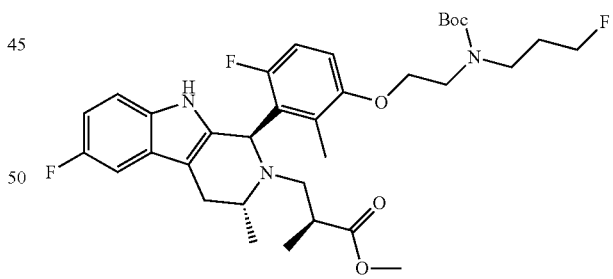

Tert-butyl (3-fluoropropyl)(2-hydroxyethyl)carbamate (342 mg, 1.55 mmol) was added in toluene (6.18 mL) to a flask containing methyl (S)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (380 mg, 0.77 mmol), cesium carbonate (628 mg, 1.93 mmol) and Rockphos 3$^{rd}$ generation precatalyst (70.0 mg, 0.08 mmol). The reaction was degassed, then heated to 105° C. for 3 hours. The reaction was diluted with DCM (25 mL) and washed with saturated aqueous sodium chloride (25 mL). The organic layer was dried over $Na_2SO_4$ and evaporated, then the crude product was purified by flash silica chromatography, elution gradient 0 to 60% EtOAc in heptane. Pure fractions were evaporated to dryness to afford methyl (S)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (321 mg, 66%) as a beige solid. m/z: ES+ [M+H]+ 632.

Example 117

(R)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic Acid

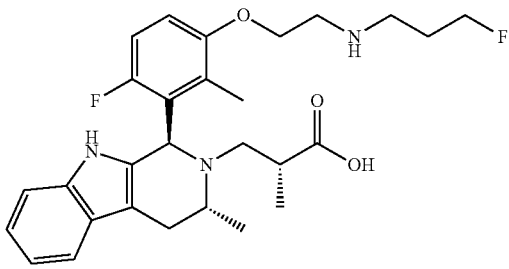

(R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoic acid (200 mg, 0.33 mmol) was stirred in formic acid (2.0 mL) at 40° C. for 1 hour. The volatiles were evaporated, then the crude product was purified by preparative HPLC (Waters XSelect CSH C18 column, 5μ silica, 19 mm diameter, 100 mm length), using decreasingly polar mixtures of water (containing 1% NH$_3$) and MeCN as eluents. Fractions containing the desired compound were evaporated to dryness to afford (R)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (120 mg, 72%) as a colourless solid. $^1$H NMR (500 MHz, CDCl$_3$, 27° C.) 1.10 (3H, d), 1.22 (3H, d), 1.80 (3H, s), 1.88 (2H, dq), 2.56 (1H, t), 2.71-2.90 (5H, m), 2.95 (1H, s), 2.99-3.07 (1H, m), 3.22-3.32 (1H, m), 3.85 (1H, p), 4.06 (2H, t), 4.45 (1H, t), 4.55 (1H, t), 5.35 (1H, s), 6.84 (1H, dd), 6.93 (1H, d), 7.08-7.17 (2H, m), 7.19-7.23 (1H, m), 7.38 (1H, s), 7.51 (1H, dd). (2× exchangeables not observed.); m/z: ES+ [M+H]+ 500.

The (R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoic acid used as starting material was prepared as follows:

Methyl (R)-2-methyl-3-(((trifluoromethyl)sulfonyl)oxy)propanoate

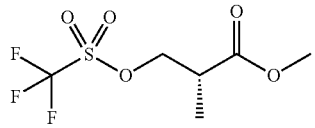

Trifluoromethanesulfonic anhydride (7.48 mL, 44.44 mmol) was added to a solution of methyl (R)-3-hydroxy-2-methylpropanoate (5.00 g, 42.3 mmol) in DCM (128 mL) at 5° C., followed by addition of 2,6-dimethylpyridine (5.42 mL, 46.6 mmol). The reaction was stirred for 1 hour, then was washed with 2N HCl solution (100 mL), dried over MgSO$_4$ and evaporated to afford methyl (R)-2-methyl-3-(((trifluoromethyl)sulfonyl)oxy)propanoate (11.64 g, ≥100%) as a red oil which was used without further purification. $^1$H NMR (500 MHz, CDCl$_3$, 27° C.) 1.31 (3H, d), 2.91-3.03 (1H, m), 3.75 (3H, s), 4.56 (1H, dd), 4.69 (1H, dd).

Methyl (R)-3-(((R)-1-(1H-indol-3-yl)propan-2-yl)amino)-2-methylpropanoate

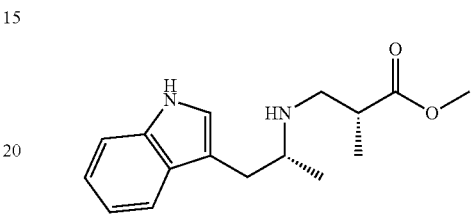

Methyl (R)-2-methyl-3-(((trifluoromethyl)sulfonyl)oxy)propanoate (10.46 g, 41.80 mmol) was added in DCM (20 mL) to a solution of (R)-1-(1H-indol-3-yl)propan-2-amine (6.62 g, 38.0 mmol) and DIPEA (8.21 mL, 47.5 mmol) in DCM (107 mL) at 5° C. The reaction was warmed to room temperature and stirred overnight. The reaction was washed with saturated aqueous sodium chloride (50 mL), then dried over Na$_2$SO$_4$ and evaporated. The crude product was purified by flash silica chromatography, elution gradient 25 to 100% EtOAc in heptane. Pure fractions were evaporated to dryness to afford methyl (R)-3-(((R)-1-(1H-indol-3-yl)propan-2-yl)amino)-2-methylpropanoate (8.45 g, 81%) as an orange liquid. $^1$H NMR (500 MHz, CDCl$_3$, 27° C.) 1.10 (3H, d), 1.12 (3H, d), 2.53-2.71 (2H, m), 2.74-2.89 (2H, m), 2.94 (1H, dd), 3.05 (1H, h), 3.48 (3H, s), 7.04 (1H, d), 7.11 (1H, ddd), 7.18 (1H, ddd), 7.35 (1H, dt), 7.53-7.64 (1H, m), 8.12 (1H, s). (1× exchangeable not observed); m/z: ES+ [M+H]+ 275.

Methyl (R)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate

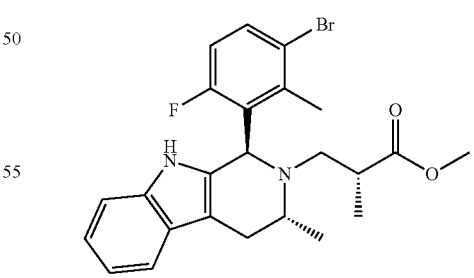

Methyl (R)-3-(((R)-1-(1H-indol-3-yl)propan-2-yl)amino)-2-methylpropanoate (686 mg, 2.50 mmol) and 3-bromo-6-fluoro-2-methylbenzaldehyde (570 mg, 2.63 mmol) were heated in toluene (9.0 mL)/acetic acid (1.0 mL) to 90° C. for 6 hours. After cooling, the reaction mixture was evaporated. The residue was dissolved in DCM (25 mL) and washed with saturated aqueous NaHCO$_3$ (25 mL). The aqueous was extracted with DCM (25 mL), then the combined organics were dried over Na$_2$SO$_4$ and evaporated. The crude product was purified by flash silica chromatography, elution gradient 0 to 30% EtOAc in heptane. Product containing fractions were evaporated to dryness to afford methyl (R)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate (795 mg, 67%) as a beige solid. $^1$H NMR (500 MHz, CDCl$_3$, 27° C.) 1.01-1.05 (3H, m), 1.09 (3H, d), 2.03 (3H, s), 2.57-2.64 (3H, m), 2.69-2.75 (1H, m), 3.08-3.14 (1H, m), 3.52 (3H, s), 3.66-3.74 (1H, m), 5.31 (1H, s), 6.90 (1H, t), 7.05-7.14 (2H, m), 7.18-7.22 (2H, m), 7.49 (1H, dd), 7.54 (1H, dd); m/z: ES+ [M+H]+ 473.

Methyl (R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoate

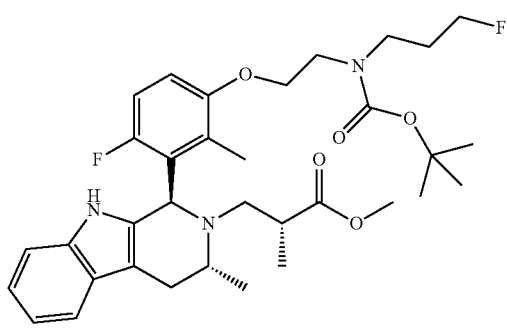 [SMILES: COC(=O)[C@H](C)CN1[C@H](c2c(F)ccc(OCCN(CCCF)C(=O)OC(C)(C)C)c2C)c2[nH]c3ccccc3c2C[C@H]1C]

Tert-butyl (3-fluoropropyl)(2-hydroxyethyl)carbamate (351 mg, 1.58 mmol) was added in toluene (5.0 mL) to a flask containing methyl (R)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate (500 mg, 1.06 mmol), cesium carbonate (858 mg, 2.64 mmol) and rockphos 3$^{rd}$ generation precatalyst (45.1 mg, 0.05 mmol) under nitrogen. The reaction was degassed, then heated to 90° C. for 4 hours. After cooling, the reaction was diluted with DCM (25 mL) and washed with saturated aqueous sodium chloride (25 mL). The aqueous layer was extracted with DCM (25 mL), then the combined organics were dried over Na$_2$SO$_4$ and evaporated. The crude product was purified by flash silica chromatography, elution gradient 0 to 40% EtOAc in heptane. Product containing fractions were evaporated to dryness to afford methyl (R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoate (425 mg, 66%) as a beige solid. $^1$H NMR (500 MHz, CDCl$_3$, 27° C.) 1.03 (3H, d), 1.09 (3H, d), 1.43 (9H, s), 1.82 (3H, s), 1.85-1.97 (2H, m), 2.53-2.61 (1H, m), 2.61-2.68 (1H, m), 2.70 (1H, d), 3.12 (1H, ddd), 3.39 (2H, t), 3.49 (3H, s), 3.52-3.59 (3H, m), 3.64-3.73 (1H, m), 4.01 (2H, d), 4.36 (1H, s), 4.45 (1H, s), 5.27 (1H, s), 6.79 (1H, dd), 6.91 (1H, t), 7.01-7.12 (2H, m), 7.16-7.21 (1H, m), 7.23-7.26 (1H, m), 7.47-7.52 (1H, m). m/z: ES+ [M+H]+ 614.

(R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoic Acid

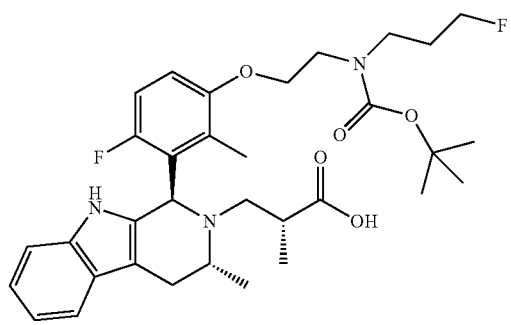 [SMILES: Cc1c(OCCN(CCCF)C(=O)OC(C)(C)C)ccc(F)c1[C@@H]1c2[nH]c3ccccc3c2C[C@@H](C)N1C[C@@H](C)C(=O)O]

2N NaOH solution (2.00 mL, 4.00 mmol) was added to a solution of methyl (R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoate (400 mg, 0.65 mmol) in THF (2.5 mL)/MeOH (2.5 mL) and the reaction was stirred at room temperature for 2 hours. The reaction was diluted with EtOAc (25 mL) and water (25 mL) then the pH was is adjusted to ~5 by addition of 2N HCl solution. The layers were separated and the aqueous layer was extracted with EtOAc (25 mL). The combined organics were dried over Na$_2$SO$_4$ and evaporated. The crude product was purified by preparative HPLC (Waters XSelect CSH C18 column, 5µ silica, 30 mm diameter, 100 mm length), using decreasingly polar mixtures of water (containing 1% NH$_3$) and MeCN as eluents. Fractions containing the desired compound were evaporated to dryness to afford (R)-3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)-2-methylpropanoic acid (225 mg, 58%) as a colourless solid. $^1$H NMR (500 MHz, CDCl$_3$, 27° C.) 1.13 (3H, d), 1.24 (3H, d), 1.41-1.47 (9H, m), 1.76 (3H, s), 1.88 (2H, d), 2.57 (1H, t), 2.75 (1H, s), 2.87 (2H, d), 3.29 (1H, d), 3.39 (2H, s), 3.58 (2H, s), 3.82-3.96 (1H, m), 4.10 (2H, d), 4.38 (1H, s), 4.47 (1H, s), 5.39 (1H, s), 6.84 (1H, s), 6.95 (1H, s), 7.08-7.19 (2H, m), 7.23 (1H, d), 7.40 (1H, d), 7.50-7.57 (1H, m). (1× exchangeable not observed.); m/z: ES+ [M+H]+ 600.

Example 121

(R)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic Acid

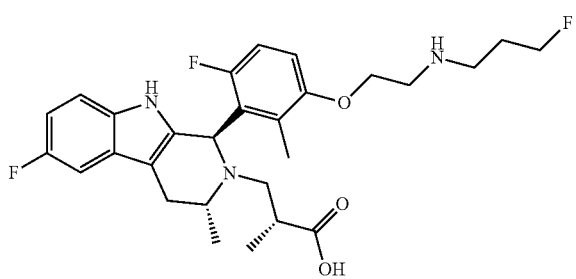 [SMILES: Cc1c(OCCNCCCF)ccc(F)c1[C@@H]1c2[nH]c3ccc(F)cc3c2C[C@@H](C)N1C[C@@H](C)C(=O)O]

Aqueous sodium hydroxide (2N, 0.45 mL, 0.90 mmol) was added to a solution of methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (0.11 g, 0.18 mmol) in THF (0.54 mL) and MeOH (0.27 mL) and the reaction was stirred at room temperature for 21 hours. The reaction was then diluted with water, acidified to pH 6 by addition of aqueous HCl (2N), and extracted with ethyl acetate (2×). The combined organic layers were dried over Na$_2$SO$_4$, filtered and concentrated under reduced pressure to afford (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoic acid (0.095 g, 85%) as an orange gum. This gum was dissolved in formic acid (1 mL) and stirred at room temperature for 3 hours. The reaction was then concentrated under reduced pressure, and the resulting residue was purified by preparative SFC (Chiralpak IC, 5 µm, 21.2 mm diameter, 250 mm length, 75 mL/min flow rate), eluting with isocratic (25% MeOH containing 0.2% NH$_4$OH) in CO$_2$, to afford (R)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (0.034 g, 42%) as a colorless solid. $^1$H NMR (300 MHz, DMSO-d$_6$, 27° C.) 0.88 (3H, d), 0.99 (3H, d), 1.63-1.95 (6H, m), 2.52-2.65 (4H, m), 2.77-2.85 (2H, m), 2.95 (1H, br dd), 3.84-4.00 (2H, m), 4.44 (2H, dt), 5.17 (1H, s), 6.77 (1H, td), 6.87-6.93 (1H, m), 6.93-7.01 (1H, m), 7.08-7.15 (2H, m), 10.29 (1H, s). Two hydrogen multiplet obscured by water; another two hydrogens not observed. m/z: ES+ [M+H]+ 518.

Also isolated was (R)-3-((1S,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (0.015 g, 19%) as a white solid. $^1$H NMR (300 MHz, DMSO-d$_6$, 27° C.) 0.88 (3H, d), 0.99 (3H, d), 1.63-1.95 (6H, m), 2.52-2.65 (4H, m), 2.77-2.85 (2H, m), 2.95 (1H, br dd), 3.84-4.00 (2H, m), 4.44 (2H, dt), 5.17 (1H, s), 6.77 (1H, td), 6.87-6.93 (1H, m), 6.93-7.01 (1H, m), 7.08-7.15 (2H, m), 10.29 (1H, s). Two hydrogen multiplet obscured by water; another two hydrogens not observed. m/z: ES+ [M+H]+ 518.

Procedures used to prepare the starting material methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate are described below.

Methyl (R)-3-(((R)-1-(5-fluoro-1H-indol-3-yl)propan-2-yl)amino)-2-methylpropanoate

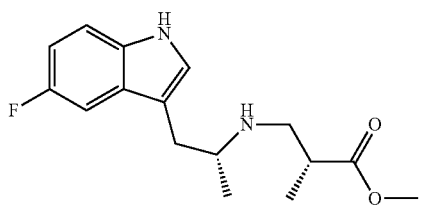 [SMILES: COC(=O)[C@H](C)CN[C@H](C)Cc1c[nH]c2ccc(F)cc12]

A solution of crude methyl (R)-2-methyl-3-(((trifluoromethyl)sulfonyl)oxy)propanoate (0.456 g, 1.82 mmol) in DCM (1 mL) was added to a solution of (R)-1-(5-fluoro-1H-indol-3-yl)propan-2-amine (0.35 g, 1.8 mmol) and DIPEA (0.32 mL, 1.8 mmol) in 1,4-dioxane (7.0 mL) at 0° C. The reaction was allowed to warm to room temperature and stirred under these conditions for 18 hours. The reaction was diluted with ethyl acetate and washed with water. The organic layer was dried over Na$_2$SO$_4$, filtered, and concentrated under reduced pressure. The resulting residue was purified by flash silica chromatography, elution gradient 25 to 100% EtOAc in hexane. Product fractions were concentrated under reduced pressure to afford methyl (R)-3-(((R)-1-(5-fluoro-1H-indol-3-yl)propan-2-yl)amino)-2-methylpropanoate (0.33 g, 62%) as a pale yellow oil. $^1$H NMR (300 MHz, DMSO-d$_6$, 27° C.) 0.96 (3H, d), 1.05 (3H, d), 2.53-3.03 (6H, m), 3.52 (3H, s), 6.88 (1H, td), 7.21 (1H, d), 7.24 (1H, dd), 7.31 (1H, dd), 10.92 (1H, br s). m/z: ES+ [M+H]+ 292.

Methyl (R)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate

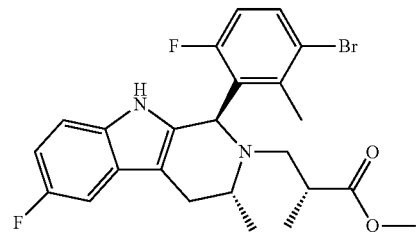 [SMILES: COC(=O)[C@H](C)CN1[C@H](c2c(F)ccc(Br)c2C)c2[nH]c3ccc(F)cc3c2C[C@H]1C]

A solution of methyl (R)-3-(((R)-1-(5-fluoro-1H-indol-3-yl)propan-2-yl)amino)-2-methylpropanoate (0.332 g, 1.14 mmol) and 3-bromo-6-fluoro-2-methylbenzaldehyde (0.259 g, 1.19 mmol) in toluene (6.5 mL) and acetic acid (0.72 mL) was heated at 80° C. for 24 hours. The reaction temperature was increased to 90° C., and the reaction was maintained under these conditions for 24 hours. The reaction temperature was then increased to 100° C., and the reaction was maintained under these conditions for 24 hours. The reaction was then cooled, concentrated under reduced pressure, and the resulting residue was dissolved in DCM and washed with saturated aqueous NaHCO$_3$. The organic layer was dried over Na$_2$SO$_4$, filtered, and concentrated is under reduced pressure. The resulting residue was purified by flash silica chromatography, elution gradient 0 to 30% EtOAc in hexane. Product fractions were concentrated under reduced pressure to afford methyl (R)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (0.170 g, 30%) as a pale yellow solid. m/z: ES+ [M+H]+ 491.

Methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate

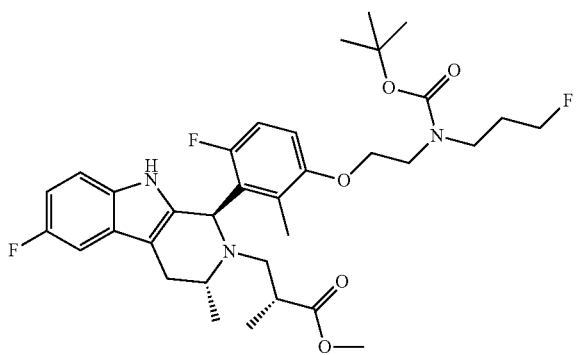 [SMILES: COC(=O)[C@H](C)CN1[C@H](c2c(F)ccc(OCCN(CCCF)C(=O)OC(C)(C)C)c2C)c2[nH]c3ccc(F)cc3c2C[C@H]1C]

A solution of tert-butyl (3-fluoropropyl)(2-hydroxyethyl)carbamate (0.15 g, 0.69 mmol) in toluene (2.77 mL) was added to a flask containing methyl (R)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (0.17 g, 0.35 mmol), cesium carbonate (0.28 g, 0.87 mmol) and RockPhos 3$^{rd}$ Generation Precatalyst (0.03 g, 0.03 mmol). The resulting mixture was degassed and then heated at 100° C. for 3 hours. Additional RockPhos 3$^{rd}$ Generation Precatalyst (64 mg) was added, and the reaction was maintained under these conditions for another hour. The reaction was then allowed to cool to room temperature, diluted with DCM and washed with saturated to aqueous sodium chloride. The organic layer was dried over Na$_2$SO$_4$, filtered, and concentrated under reduced pressure. The resulting residue was purified by flash silica chromatography, elution gradient 0 to 60% EtOAc in hexane. Product fractions were concentrated under reduced pressure to afford methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2 methylpropanoate (0.11 g, 52%) as a beige solid. m/z: ES+ [M+H]+ 632.

Example 124

(S)-3-((1R,3R)-1-(3-(2-((3,3-Difluoropropyl)amino)ethoxy)-6-fluoro-2-methylphenyl)-3-methyl-1,3,4,9-tetrahydro-2H-pyrido[3,4-b]indol-2-yl)-2-methylpropanoic Acid

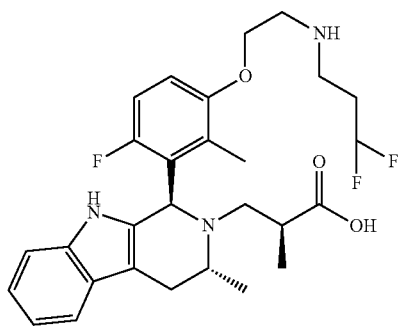 [SMILES: Cc1c(OCCNCCC(F)F)ccc(F)c1[C@@H]1c2[nH]c3ccccc3c2C[C@@H](C)N1C[C@H](C)C(=O)O]

2M Sodium hydroxide (0.020 mL, 0.04 mmol) was added to a solution of methyl (S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoate (0.007 g, 0.01 mmol) in methanol (0.2 mL). The reaction mixture was stirred at room temperature overnight and then evaporated. The crude product was purified by preparative HPLC (Waters CSH C18 OBD column, 5μ silica, 30 mm diameter, 100 mm length), using decreasingly polar mixtures of water (containing 1% NH$_3$) and MeCN as eluents to afford (S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid (3.0 mg, 44%) as a dry film. $^1$H NMR (500 MHz, CDCl$_3$, 27° C.) 0.91 (3H, d), 1.26 (3H, d), 1.53-2.07 (6H, m), 2.71-2.87 (4H, m), 2.89-3.04 (3H, m), 3.29 (1H, d), 3.57-3.67 (1H, m), 3.95-4.05 (2H, m), 5.54 (1H, s), 5.91 (1H, tt), 6.83 (1H, dd), 6.96 (1H, t), 7.10-7.17 (2H, m), 7.21-7.24 (1H, m), 7.40 (1H, s), 7.49-7.54 (1H, m). (2 exchangeables not seen). m/z: ES+ [M+H]+ 518.

The methyl (S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoate used as starting material was prepared as follows:

Methyl (S)-3-((1R,3R)-1-(3-(2-((tert-butyldimethylsilyl)oxy)ethoxy)-6-fluoro-2-methylphenyl)-3-methyl-1,3,4,9-tetrahydro-2H-pyrido[3,4-b]indol-2-yl)-2-methylpropanoate

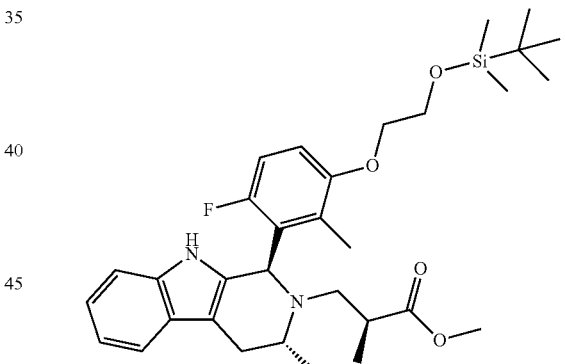

RockPhos 3$^{rd}$ generation precatalyst (0.018 g, 0.02 mmol) was added to a degassed suspension of methyl (S)-3-((1R,3R)-1-(3-bromo-6-fluoro-2-methylphenyl)-3-methyl-1,3,4,9-tetrahydro-2H-pyrido[3,4-b]indol-2-yl)-2-methylpropanoate (0.200 g, 0.42 mmol), 2-((tert-butyldimethylsilyl)oxy)ethan-1-ol (0.089 g, 0.51 mmol) and cesium carbonate (0.344 g, 1.06 mmol) in toluene (3 mL). The reaction was heated to 90° C. overnight and the reaction mixture was allowed to cool. The reaction mixture was diluted with water (20 mL) and DCM (50 mL). The organic phase was separated and evaporated. The crude product was purified by flash silica chromatography, elution gradient 0 to 100% EtOAc in heptane to give impure to methyl (S)-3-((1R,3R)-1-(3-(2-((tert-butyldimethylsilyl)oxy)ethoxy)-6-fluoro-2-methylphenyl)-3-methyl-1,3,4,9-tetrahydro-2H-pyrido[3,4-b]indol-2-yl)-2-methylpropanoate (0.038 g, 17%). m/z: ES+ [M+H]+ 569.

Methyl (S)-3-((1R,3R)-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate

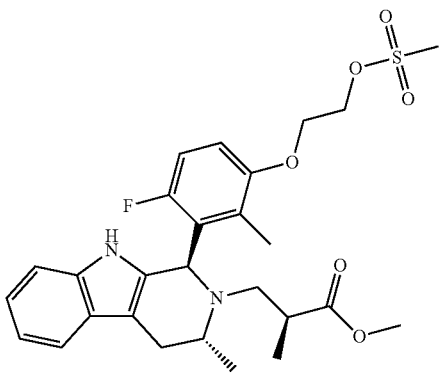 [SMILES: COC(=O)[C@@H](C)CN1[C@H](c2c(F)ccc(OCCOS(C)(=O)=O)c2C)c2[nH]c3ccccc3c2C[C@H]1C]

To a solution of methyl (S)-3-((1R,3R)-1-(3-(2-((tert-butyldimethylsilyl)oxy)ethoxy)-6-fluoro-2-methylphenyl)-3-methyl-1,3,4,9-tetrahydro-2H-pyrido[3,4-b]indol-2-yl)-2-methylpropanoate (0.038 g, 0.07 mmol) in tetrahydrofuran (1 mL) was added tetrabutylammonium fluoride (1.0 M in THF, 0.134 mL, 0.13 mmol). The reaction mixture was stirred at room temperature for 2 hours and then evaporated to a gum which was dissolved in dichloromethane (2 mL) and to which DIPEA (0.035 mL, 0.20 mmol) was added. Methanesulfonyl chloride (8.0 µl, 0.10 mmol) was added to this solution and the reaction mixture was stirred at room temperature for 1 hour. The reaction mixture was diluted with DCM (5 mL), washed with water and the organic phase evaporated to give methyl (S)-3-((1R,3R)-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate (0.028 g, 0.05 mmol). m/z: ES+ [M+H]+ 569.

Methyl (S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoate

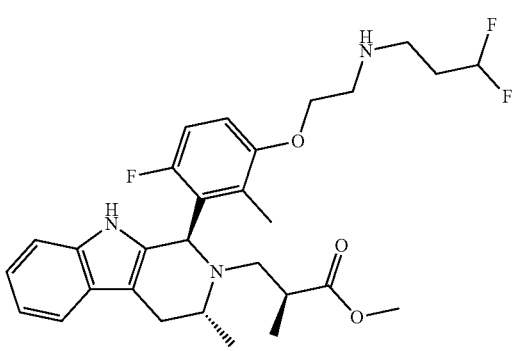 [SMILES: COC(=O)[C@@H](C)CN1[C@H](c2c(F)ccc(OCCNCCC(F)F)c2C)c2[nH]c3ccccc3c2C[C@H]1C]

3,3-Difluoro-1-aminopropane hydrochloride (8 mg, 0.06 mmol), methyl (S)-3-((1R,3R)-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate (0.028 g, 0.05 mmol), potassium carbonate (0.036 g, 0.26 mmol) and sodium iodide (0.016 g, 0.11 mmol) in acetonitrile (0.5 mL) were heated to 85° C. under microwave irradiation for 4 hours. The reaction mixture was partitioned between water (5 mL) and DCM (5 mL) and the organic phase was evaporated. The crude product was purified by flash silica chromatography, elution gradient 0 to 100% EtOAc in heptane to afford methyl (S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoate (7.0 mg, 25%) as a solid. $^1$H NMR (500 MHz, CDCl$_3$, 27° C.) 0.87 (3H, d), 1.11 (3H, d), 1.88 (3H, s), 1.93-2.04 (2H, m), 2.21 (1H, h), 2.40 (1H, dd), 2.68 (1H, d), 2.82 (2H, t), 2.91-3.03 (3H, m), 3.10 (1H, ddd), 3.50-3.58 (1H, m), 3.63 (3H, s), 3.90-4.00 (2H, m), 5.34 (1H, s), 5.90 (1H, tt), 6.80 (1H, dd), 6.91 (1H, t), 7.03-7.13 (2H, m), 7.15-7.22 (1H, m), 7.42-7.54 (1H, m). (2 exchangables not seen). m/z: ES+ [M+H]+ 532.

Example 126

(S)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic Acid

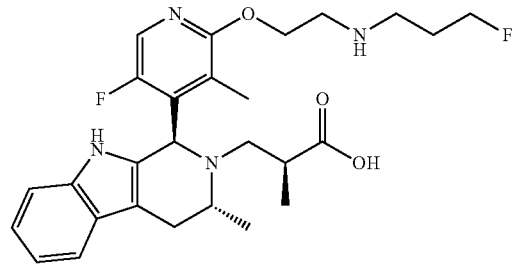 [SMILES: Cc1c(OCCNCCCF)ncc(F)c1[C@@H]1c2[nH]c3ccccc3c2C[C@@H](C)N1C[C@H](C)C(=O)O]

Tert-butyl (3-fluoropropyl)(2-hydroxyethyl)carbamate (212 mg, 0.96 mmol) was added in toluene (3.20 mL) to a flask containing methyl (S)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate (275 mg, 0.64 mmol), cesium carbonate (416 mg, 1.28 mmol) and rockphos 3$^{rd}$ generation precatalyst (29.0 mg, 0.03 mmol). The reaction was degassed, then heated to 90° C. for 4 hours. After cooling, the reaction was diluted with DCM (20 mL) and saturated is aqueous sodium chloride (20 mL). The layers were separated and the aqueous layer was extracted with DCM (20 mL). The combined organics were evaporated. The crude product was dissolved in THF (2.5 mL) and MeOH (2.5 mL), then 2N NaOH solution (2.5 mL) was added and the reaction was stirred at room temperature for a further 2 hours. The reaction was diluted with EtOAc (20 mL) and water (20 mL) and the pH was adjusted to ~5 by addition of 2N HCl solution. The layers were separated, then the aqueous layer was extracted with EtOAc (2×15 mL). The combined organics were dried over Na$_2$SO$_4$ and evaporated. The crude product was purified by flash silica chromatography, elution gradient 25 to 100% EtOAc in heptane. Product containing fractions were evaporated to dryness to afford (S)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoic acid (350 mg), which was impure.

The residue was dissolved in formic acid (2 mL) and warmed to 40° C. for 1 hour. The volatiles were evaporated, then the crude product was purified by preparative HPLC (Waters SunFire column, 5p silica, 19 mm diameter, 100 mm length), using decreasingly polar mixtures of water (containing 1% NH₃) and MeCN as eluents. Fractions containing the desired compound were evaporated to dryness to afford (S)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid (65.0 mg, 20%) as a beige solid. ¹H NMR (500 MHz, CDCl₃, 27° C.) 0.96 (3H, d), 1.19 (3H, d), 1.87 (3H, s), 1.90-2.05 (3H, m), 2.68-2.79 (2H, m), 2.88 (1H, dd), 3.04 (2H, t), 3.19 (1H, d), 3.24 (2H, s), 3.61 (1H, d), 4.44 (2H, dt), 4.52 (1H, t), 4.57-4.69 (1H, m), 5.40 (1H, s), 7.07-7.17 (2H, m), 7.21 (1H, d), 7.44-7.55 (1H, m), 7.84 (1H, s), 8.25 (1H, s), 8.34 (1H, s). (1× exchangeable not observed.) m/z: ES+ [M+H]+ 501.

The methyl (S)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate used as starting material was prepared as follows:

2-chloro-5-fluoro-3-methylisonicotinaldehyde

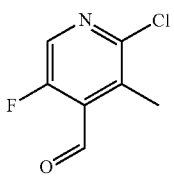

LDA solution (2M, 3.85 mL, 7.70 mmol) was added to a cooled solution of 2-chloro-5-fluoro-3-methylpyridine (1.02 g, 7.00 mmol) in THF (22.9 mL) at −78° C. The reaction was stirred for 30 min, then methyl formate (1.30 mL, 21.0 mmol) was added and the reaction was stirred for a further 30 minutes. The reaction was quenched by addition of 1N HCl solution (20 mL) and extracted with EtOAc (40 mL). The organic phase was washed with saturated aqueous sodium chloride, dried over Na₂SO₄ and evaporated. The crude product was purified by flash silica chromatography, elution gradient 0 to 20% EtOAc in heptane. Product containing fractions were evaporated to dryness to afford 2-chloro-5-fluoro-3-methylisonicotinaldehyde (754 mg, 62%) as a straw coloured liquid. ¹H NMR (500 MHz, CDCl₃, 27° C.) 2.65 (3H, s), 8.33 (1H, s), 10.51 (1H, s).

Methyl (S)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate

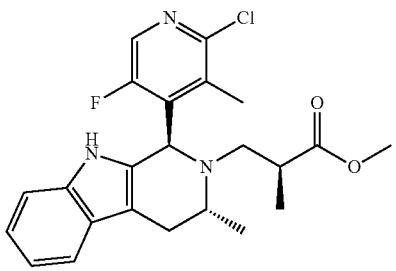 [SMILES: COC(=O)[C@@H](C)CN1[C@H](c2c(F)cnc(Cl)c2C)c2[nH]c3ccccc3c2C[C@H]1C]

Methyl (S)-3-(((R)-1-(1H-indol-3-yl)propan-2-yl)amino)-2-methylpropanoate (439 mg, 1.60 mmol) and 2-chloro-5-fluoro-3-methylisonicotinaldehyde (292 mg, 1.68 mmol) were heated in toluene (7.20 mL)/acetic acid (0.80 mL) to 90° C. for 5 hours. After cooling, the volatiles were evaporated. The residue was dissolved in DCM (20 mL) and washed with saturated aqueous NaHCO₃ (20 mL). The layers were separated, then the organic phase was dried over Na₂SO₄ and evaporated. The crude product was purified by flash silica chromatography, elution gradient 0 to 30% EtOAc in heptane. Product containing fractions were evaporated to dryness to afford methyl (S)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate (283 mg, 41%) as a beige solid. ¹H NMR (500 MHz, CDCl₃, 27° C.) 0.91 (3H, d), 1.11 (3H, d), 2.10 (3H, s), 2.27 (2H, ddd), 2.72 (1H, d), 3.02 (1H, dd), 3.11 (1H, ddd), 3.53-3.60 (1H, m), 3.65 (3H, s), 5.37 (1H, s), 7.09-7.17 (2H, m), 7.24 (1H, dd), 7.30 (1H, s), 7.51 (1H, d), 8.20 (1H, s). m/z: ES+ [M+H]+ 430.

Example 127

(R)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic Acid

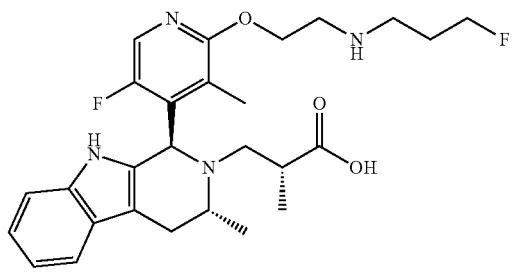 [SMILES: Cc1c(OCCNCCCF)ncc(F)c1[C@@H]1c2[nH]c3ccccc3c2C[C@@H](C)N1C[C@@H](C)C(=O)O]

(R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoic acid (450 mg, 0.75 mmol) was stirred in formic acid (4.0 mL) at 40° C. for 1 hour. The volatiles were evaporated, then the crude product was purified by preparative HPLC (Waters XSelect CSH C18 column, 5μ silica, 19 mm diameter, 100 mm length), using decreasingly polar mixtures of water (containing 1% NH₃) and MeCN as eluents. Fractions containing the desired compound were evaporated to dryness to afford (R)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid (302 mg, 81%) as a colourless solid. ¹H NMR (500 MHz, CDCl₃, 27° C.) 1.01 (3H, d), 1.12 (3H, d), 1.85 (3H, s), 1.87-1.98 (2H, m), 2.45-2.52 (1H, m), 2.57 (1H, ddd), 2.63 (1H, dd), 2.75 (1H, d), 2.81 (2H, t), 2.89 (1H, ddd), 3.12 (1H, ddd), 3.17 (1H, ddd), 3.73 (1H, q), 4.23 (1H, ddd), 4.40 (1H, t), 4.50 (1H, t), 4.69 (1H, ddd), 5.25 (1H, s), 7.01-7.16 (2H, m), 7.20 (1H, dd), 7.41 (1H, s), 7.50 (1H, dd), 7.86 (1H, s). (2× exchangeables not observed); m/z: ES+ [M+H]+ 501.

The (R)-3-((1R,3R)-1-(2-(2-((tert-butoxycarbonyl)(3-fluoropropyl)amino)ethoxy)-5-fluoro-3-methylpyridin-4- yl)-3-methyl-1,3,4,9-tetrahydro-2H-pyrido[3,4-b]indol-2-yl)-2-methylpropanoic acid used as starting material was prepared as follows:

Methyl (R)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate

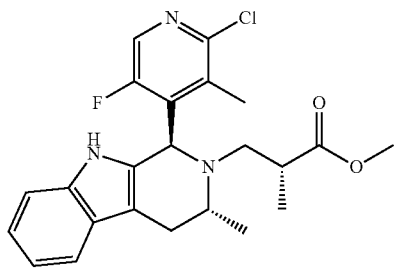 [SMILES: COC(=O)[C@H](C)CN1[C@H](c2c(F)cnc(Cl)c2C)c2[nH]c3ccccc3c2C[C@H]1C]

Methyl (R)-3-(((R)-1-(1H-indol-3-yl)propan-2-yl)amino)-2-methylpropanoate (741 mg, 2.7 mmol) and 2-chloro-5-fluoro-3-methylisonicotinaldehyde (492 mg, 2.84 mmol) were heated in toluene (9.72 mL)/acetic acid (1.08 mL) to 90° C. for 6 hours. After cooling, the reaction mixture was evaporated. The residue was dissolved in DCM (25 mL) and washed with saturated aqueous NaHCO$_3$ (25 mL). The aqueous layer was extracted with DCM (25 mL), then the combined organics were dried over Na$_2$SO$_4$ and evaporated. The crude product was purified by flash silica chromatography, elution gradient 0 to 30% EtOAc in heptane. Product containing fractions were evaporated to dryness to afford methyl (R)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate (950 mg, 82%) as a beige solid. $^1$H NMR (500 MHz, CDCl$_3$, 27° C.) 1.04 (3H, d), 1.09 (3H, d), 2.01 (3H, s), 2.46-2.57 (1H, m), 2.62-2.70 (2H, m), 2.75 (1H, d), 3.11 (1H, ddd), 3.53 (3H, s), 3.68-3.78 (1H, m), 5.30 (1H, s), 7.08-7.18 (2H, m), 7.21-7.26 (1H, m), 7.46-7.52 (1H, m), 7.53 (1H, s), 8.15 (1H, s); m/z: ES+ [M+H]+ 430.

Methyl (R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoate

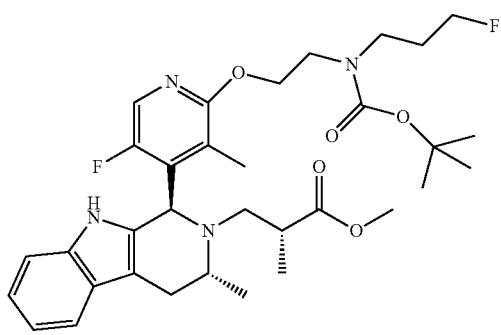 [SMILES: COC(=O)[C@H](C)CN1[C@H](c2c(F)cnc(OCCN(CCCF)C(=O)OC(C)(C)C)c2C)c2[nH]c3ccccc3c2C[C@H]1C]

Tert-butyl (3-fluoropropyl)(2-hydroxyethyl)carbamate (581 mg, 2.63 mmol) was added to a suspension of methyl (R)-3-((1R,3R)-1-(2-chloro-5-fluoro-3-methylpyridin-4-yl)-3-methyl-1,3,4,9-tetrahydro-2H-pyrido[3,4-b]indol-2-yl)-2-methylpropanoate (752 mg, 1.75 mmol), cesium carbonate (1.42 g, 4.38 mmol) and rockphos 3$^{rd}$ generation precatalyst (74.7 mg, 0.09 mmol) in degassed toluene (8.75 mL). The reaction was heated to 90° C. and stirred for 4 hours. After cooling, the reaction was diluted with DCM (25 mL) and washed with saturated aqueous sodium chloride (25 mL). The aqueous layer was extracted with DCM (25 mL), then the combined organics were dried over Na$_2$SO$_4$ and evaporated. The crude product was purified by flash silica chromatography, elution gradient 0 to 40% EtOAc in heptane. Product containing to fractions were evaporated to dryness to afford methyl (R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoate (571 mg, 53%) as a beige solid. $^1$H NMR (500 MHz, CDCl$_3$, 27° C.) 1.04 (3H, d), 1.08 (3H, d), 1.42 (9H, d), 1.82 (3H, s), 1.84-2.00 (2H, m), 2.50-2.60 (1H, m), 2.60-2.77 (3H, m), 3.10 (1H, ddd), 3.30-3.41 (2H, m), 3.51 (3H, s), 3.53-3.61 (2H, m), 3.65-3.73 (1H, m), 4.31-4.44 (3H, m), 4.46 (1H, t), 5.22 (1H, s), 7.10 (2H, dqt), 7.20 (1H, dd), 7.27-7.40 (1H, m), 7.49 (1H, dd), 7.88 (1H, s); m/z: ES+ [M+H]+ 615.

(R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoic Acid

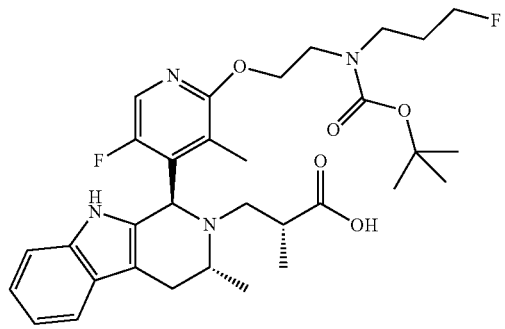 [SMILES: Cc1c(OCCN(CCCF)C(=O)OC(C)(C)C)ncc(F)c1[C@@H]1c2[nH]c3ccccc3c2C[C@@H](C)N1C[C@@H](C)C(=O)O]

2N NaOH solution (2.68 mL, 5.37 mmol) was added to a solution of methyl (R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoate (550 mg, 0.89 mmol) in THF (3.1 mL)/MeOH (3.1 mL). The reaction was stirred at room temperature for 2 hours, then was diluted with EtOAc (25 mL) and water (25 mL). The pH was adjusted to ~5 by addition of 2N HCl solution and the layers were separated. The aqueous layer was extracted with EtOAc (25 mL), then the combined organics were dried over Na$_2$SO$_4$ and evaporated. The crude product was passed through a plug of silica gel, eluting with EtOAc. The filtrate was evaporated to afford (R)-3-((1R,3R)-1-(2-(2-((tert-butoxycarbonyl)(3-fluoropropyl)amino)ethoxy)-5-fluoro-3-methylpyridin-4-yl)-3-methyl-1,3,4,9-tetrahydro-2H-pyrido[3,4-b]indol-2-yl)-2-methylpropanoic acid (492 mg, 92%) as a beige solid. m/z: ES+ [M+H]+ 601.

Example 143

(S)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic Acid

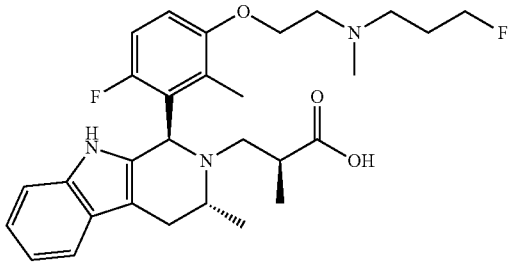 [SMILES: Cc1c(OCCN(C)CCCF)ccc(F)c1[C@@H]1c2[nH]c3ccccc3c2C[C@@H](C)N1C[C@H](C)C(=O)O]

Iodomethane (6.85 al, 0.11 mmol) was added to a solution of (S)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid (50 mg, 0.10 mmol) and DIPEA (51.9 al, 0.30 mmol) in acetonitrile (0.95 mL). The reaction was stirred at room temperature for 3 hours. The volatiles were evaporated, then the crude product was purified by preparative HPLC (Waters XSelect CSH C18 column, 5μ silica, 19 mm diameter, 100 mm length), using decreasingly polar mixtures of water (containing 1% NH₃) and MeCN as eluents. Fractions containing the desired compound were evaporated to dryness to afford (S)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid (14.4 mg, 28%) as a colourless solid. ¹H NMR (500 MHz, CDCl₃, 27° C.) 0.90 (3H, d), 1.27 (3H, d), 1.70-1.90 (5H, m), 2.32 (3H, s), 2.57 (2H, t), 2.67-2.77 (1H, m), 2.77-2.82 (4H, m), 2.96 (1H, dd), 3.29 (1H, d), 3.55-3.68 (1H, m), 4.00 (2H, t), 4.42 (1H, t), 4.51 (1H, t), 5.55 (1H, s), 6.83 (1H, dd), 6.95 (1H, t), 7.13 (2H, dtd), 7.22 (1H, dd), 7.46 (1H, s), 7.48-7.58 (1H, m). (1× exchangeable not observed). m/z: ES+ [M+H]+ 514.

Example 145

(S)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic Acid

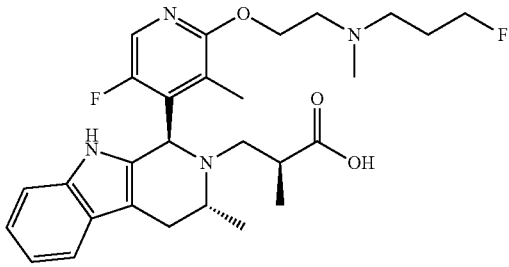 [SMILES: Cc1c(OCCN(C)CCCF)ncc(F)c1[C@@H]1c2[nH]c3ccccc3c2C[C@@H](C)N1C[C@H](C)C(=O)O]

Methyl (S)-3-(((R)-1-(1H-indol-3-yl)propan-2-yl)amino)-2-methylpropanoate (151 mg, 0.55 mmol) and 5-fluoro-2-(2-((3-fluoropropyl)(methyl)amino)ethoxy)-3-methylisonicotinaldehyde (300 mg, 50% wt, 0.55 mmol) were heated in toluene (2.50 mL)/acetic acid (0.278 mL) to 90° C. for 4 hours. After cooling, the volatiles were evaporated. The residue was dissolved in DCM (20 mL) and washed with saturated aqueous NaHCO₃ solution (20 mL). The aqueous layer was extracted with DCM (20 mL), then the combined organics were dried over Na₂SO₄ and evaporated. The crude product was purified by flash silica chromatography, elution gradient 100% EtOAc. Fractions containing the product were evaporated to dryness to afford a yellow gum (300 mg). The residue was dissolved in THF (2 mL) and methanol (2 mL), then 2N NaOH solution (2 mL) was added. The mixture was stirred at room temperature for 2 hours. The reaction was diluted with EtOAc (20 mL) and water (20 mL). The pH was adjusted to ~5 by addition of 2N HCl solution, then the layers were separated. The aqueous layer was extracted with EtOAc (20 mL), then the combined organic layers were dried over Na₂SO₄ and evaporated to dryness. The crude product was purified by preparative HPLC (Waters XSelect CSH C18 column, 5μ silica, 19 mm diameter, 100 mm length), using decreasingly polar mixtures of water (containing 1% NH₃) and MeCN as eluents. Fractions containing the desired compound were evaporated to dryness to afford (S)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid (98 mg, 35%) as a colourless solid. ¹H NMR (500 MHz, CDCl₃, 27° C.) 0.99 (3H, d), 1.23 (3H, d), 1.77-1.86 (2H, m), 1.87 (3H, d), 2.32 (3H, s), 2.59 (2H, t), 2.72-2.90 (6H, m), 3.21 (1H, d), 3.54-3.64 (1H, m), 4.36 (1H, ddd), 4.40 (1H, t), 4.43-4.48 (1H, m), 4.50 (1H, t), 5.43 (1H, s), 7.14 (2H, dtd), 7.24 (1H, d), 7.52 (2H, d), 7.90 (1H, s). (1× exchangeable not observed.) m/z: ES+ [M+H]+ 515.

The 5-fluoro-2-(2-((3-fluoropropyl)(methyl)amino)ethoxy)-3-methylisonicotinaldehyde used as starting material was prepared as follows:

2-((3-fluoropropyl)(methyl)amino)ethan-1-ol

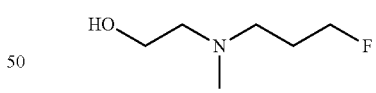

1-Fluoro-3-iodopropane (5.64 g, 30.0 mmol) was added to a suspension of 2-(methylamino)ethan-1-ol (2.65 mL, 33.0 mmol) and potassium carbonate (8.28 g, 60.0 mmol) in acetonitrile (88 mL). The reaction was heated to 50° C. for 2 hours, then cooled and stirred at room temperature overnight. The volatiles were evaporated, then the residue was partitioned between EtOAc (80 mL) and water (80 mL). The layers were separated and the aqueous layer was extracted with EtOAc (4×50 mL). The combined organics were dried over Na₂SO₄, filtered and evaporated to afford 2-((3-fluoropropyl)(methyl)amino)ethan-1-ol (3.95 g, 97%) as a colourless oil. ¹H NMR (500 MHz, CDCl₃, 27° C.) 1.88 (2H, ddd), 2.27 (3H, s), 2.51-2.62 (4H, m), 3.55-3.65 (2H, m), 4.47 (1H, t), 4.56 (1H, t).

N-(2-((3-chloro-5-fluoropyridin-2-yl)oxy)ethyl)-3-fluoro-N-methylpropan-1-amine

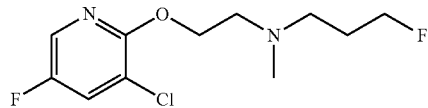 [SMILES: CN(CCCF)CCOc1ncc(F)cc1Cl]

Sodium hydride (0.308 g, 7.69 mmol) was added to a solution of 2-((3-fluoropropyl)(methyl)amino)ethan-1-ol (1.040 g, 7.69 mmol) in THF (26.8 mL). After stirring for 10 minutes, 3-chloro-2,5-difluoropyridine (1.00 g, 6.69 mmol) was added and stirring was continued for 1 hour. The reaction was quenched by addition of water (50 mL) and extracted with EtOAc (2×50 mL). The combined organics were dried over MgSO$_4$, filtered and evaporated. The crude product was purified by flash silica chromatography, elution gradient 0 to 100% EtOAc in heptane. Product containing fractions were evaporated to dryness to afford N-(2-((3-chloro-5-fluoropyridin-2-yl)oxy)ethyl)-3-fluoro-N-methylpropan-1-amine (1.630 g, 92%) as a colourless liquid. $^1$H NMR (500 MHz, CDCl$_3$, 27° C.) 1.81-1.95 (2H, m), 2.36 (3H, s), 2.57-2.64 (2H, m), 2.83 (2H, t), 4.44 (2H, t), 4.47 (1H, t), 4.57 (1H, t), 7.46 (1H, dd), 7.90 (1H, d). m/z: ES+ [M+H]+ 265.

3-fluoro-N-(2-((5-fluoro-3-methylpyridin-2-yl)oxy)ethyl)-N-methylpropan-1-amine

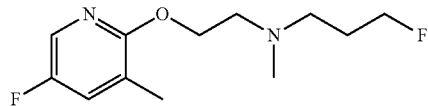 [SMILES: Cc1cc(F)cnc1OCCN(C)CCCF]

XPhos 2$^{nd}$ generation precatalyst (0.122 g, 0.16 mmol) and potassium carbonate (1.720 g, 12.47 mmol) were added to a solution of N-(2-((3-chloro-5-fluoropyridin-2-yl)oxy)ethyl)-3-fluoro-N-methylpropan-1-amine (1.65 g, 6.23 mmol) and 2,4,6-trimethyl-1,3,5,2,4,6-trioxatriborinane (0.436 mL, 3.12 mmol) in 1,4-dioxane (25.6 mL)/water (5.1 mL). The reaction was degassed and heated to 90° C. for 6 hours. After cooling, the reaction was diluted with EtOAc (50 mL) and water (50 mL). The layers were separated and the aqueous was extracted with EtOAc (25 mL). The combined organics were dried over Na$_2$SO$_4$ and evaporated. The crude product was purified by flash silica chromatography, elution gradient 20 to 100% EtOAc in heptane. Product containing fractions were evaporated to dryness to afford 3-fluoro-N-(2-((5-fluoro-3-methylpyridin-2-yl)oxy)ethyl)-N-methylpropan-1-amine (1.50 g, 99%) as a light brown liquid. $^1$H NMR (500 MHz, CDCl$_3$, 27° C.) 1.82-1.94 (2H, m), 2.19 (3H, t), 2.35 (3H, s), 2.58-2.63 (2H, m), 2.81 (2H, t), 4.38 (2H, t), 4.47 (1H, t), 4.56 (1H, t), 7.15-7.19 (1H, m), 7.78-7.82 (1H, m). m/z: ES+ [M+H]+ 245.

5-fluoro-2-(2-((3-fluoropropyl)(methyl)amino)ethoxy)-3-methylisonicotinaldehyde

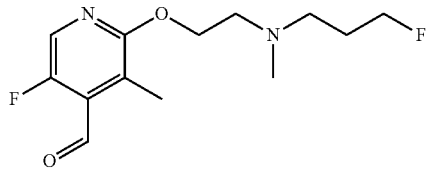 [SMILES: Cc1c(OCCN(C)CCCF)ncc(F)c1C=O]

LDA solution (2M, 3.84 mL, 7.68 mmol) was added to an oven-dried flask containing 3-fluoro-N-(2-((5-fluoro-3-methylpyridin-2-yl)oxy)ethyl)-N-methylpropan-1-amine (1.5 g, 6.14 mmol) in THF (20.0 mL). The reaction was stirred for 30 minutes, then methyl formate (0.946 mL, 15.4 mmol) was then added and the reaction was stirred for a further 30 minutes. The reaction was quenched by addition of water (25 mL) and extracted with EtOAc (2×40 mL). The to combined organics were dried over MgSO$_4$ and evaporated. The crude product was purified by flash silica chromatography, elution gradient 25 to 100% EtOAc in heptane. Product containing fractions were evaporated to dryness to afford 5-fluoro-2-(2-((3-fluoropropyl)(methyl)amino)ethoxy)-3-methylisonicotinaldehyde as a pale yellow liquid, which was contaminated with unreacted starting material in a 1:1 ratio. m/z: ES+ [M+H]+ 273.

Example 152

(R)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic Acid

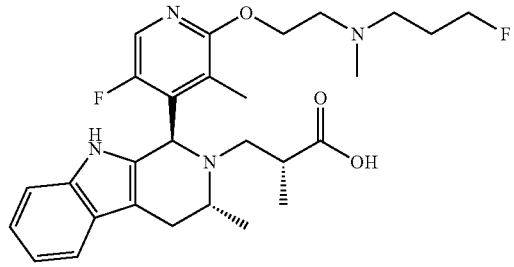 [SMILES: Cc1c(OCCN(C)CCCF)ncc(F)c1[C@@H]1c2[nH]c3ccccc3c2C[C@@H](C)N1C[C@@H](C)C(=O)O]

Formaldehyde solution (37% vol, 0.021 mL, 0.29 mmol) was added to a solution of (R)-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid (90 mg, 0.18 mmol) in DCM (1.5 mL). After stirring for 5 minutes, sodium triacetoxyhydroborate (61.0 mg, 0.29 mmol) was added and the reaction was stirred at room temperature for 1 hour. The reaction was diluted with DCM (10 mL) and washed with saturated aqueous sodium chloride (10 mL). The layers were separated and the aqueous was extracted with DCM (2×10 mL). The combined organics were dried over Na$_2$SO$_4$ and evaporated. The crude product was purified by preparative HPLC (Waters XSelect CSH C18 column, 5µ silica, 19 mm diameter, 100 mm length), using decreasingly polar mixtures of water (containing 1% NH$_3$) and MeCN as eluents. Fractions containing the desired compound were evaporated to dryness to afford (R)-3-((1R,3R)-1-(5-fluoro-2-(2-((3-fluoropropyl)(methyl)amino) ethoxy)-3-methylpyridin-4-yl)-3-methyl-1,3,4,9-tetrahydro-2H-pyrido[3,4-b]indol-2-yl)-2-methylpropanoic acid (63.0 mg, 68%) as a colourless solid.
$^1$H NMR (500 MHz, CDCl$_3$, 27° C.) 1.03 (3H, d), 1.13 (3H, d), 1.70-1.96 (5H, m), 2.32 (3H, s), 2.46-2.55 (1H, m), 2.55-2.60 (1H, m), 2.60-2.65 (2H, m), 2.68 (2H, dt), 2.77 (1H, d), 2.96 (1H, ddd), 3.12-3.24 (1H, m), 3.64-3.79 (1H, m), 4.25 (1H, ddd), 4.37 (1H, t), 4.47 (1H, t), 4.64 (1H, dt), 5.25 (1H, s), 7.02-7.17 (2H, m), 7.19 (1H, dd), 7.50 (1H, dd), 7.58 (1H, s), 7.86 (1H, s), 9.62 (1H, s); m/z: ES+ [M+H]+ 515.

Example 155

(2R)-3-[(1R,3R)-6-fluoro-1-[5-fluoro-2-[2-[3-fluoropropyl(methyl)amino]ethoxy]-3-methyl-4-pyridyl]-3-methyl-1,3,4,9-tetrahydropyrido[3,4-b]indol-2-yl]-2-methyl-propanoic Acid

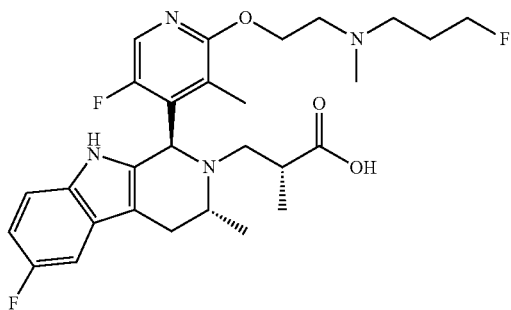 [SMILES: Cc1c(OCCN(C)CCCF)ncc(F)c1[C@@H]1c2[nH]c3ccc(F)cc3c2C[C@@H](C)N1C[C@@H](C)C(=O)O]

2M sodium hydroxide solution (1.17 mL, 2.34 mmol) was added to a stirred solution of methyl (R)-3-((1R,3R)-6-fluoro-1-(5-fluoro-2-(2-((3-fluoropropyl)(methyl)amino) ethoxy)-3-methylpyridin-4-yl)-3-methyl-1,3,4,9-tetrahydro-2H-pyrido[3,4-b]indol-2-yl)-2-methylpropanoate (426 mg, 0.47 mmol) in THF (4 mL) and MeOH (2 mL) at 21° C. The resulting mixture was stirred at 21° C. for 16 hours. The mixture was concentrated under reduced pressure. Water (5 mL) and AcOH (1 mL) were added and the resulting mixture was extracted with DCM (3×15 mL). The combined organics were dried (phase separation cartridge) and concentrated under reduced pressure to give the crude product which was purified successively by preparative HPLC (Puriflash C18, 15µ silica, 35 g), using decreasingly polar mixtures of water (containing 0.1% formic acid) and MeCN as eluents followed by preparative HPLC (Waters CSH C18 OBD column, 5µ silica, 30 mm diameter, 100 mm length), using decreasingly polar mixtures of water (containing 1% NH$_3$) and MeCN as eluents. Fractions containing the desired compound were evaporated to dryness to afford (2R)-3-((1R,3R)-6-fluoro-1-(5-fluoro-2-(2-((3-fluoropropyl) (methyl)amino)ethoxy)-3-methylpyridin-4-yl)-3-methyl-1,3,4,9-tetrahydro-2H-pyrido[3,4-b]indol-2-yl)-2-methylpropanoic acid (45.0 mg, 18%) as an off-white solid.
$^1$H NMR (500 MHz, DMSO, 27° C.) 0.94 (3H, d), 1.01 (3H, d), 1.69-1.86 (5H, m), 2.22 (3H, s), 2.40-2.49 (4H, m), 2.56-2.71 (5H, m), 2.95 (1H, dd), 3.59-3.70 (1H, m), 4.25-4.31 (2H, m), 4.43 (2H, dt), 5.13 (1H, s), 6.83 (1H, td), 7.12-7.20 (2H, m), 8.00 (1H, s), 10.49 (1H, s); m/z: ES+ [M+H]+ 533.

Procedures used to prepare the starting material methyl (R)-3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate are described below.

Methyl (R)-3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate

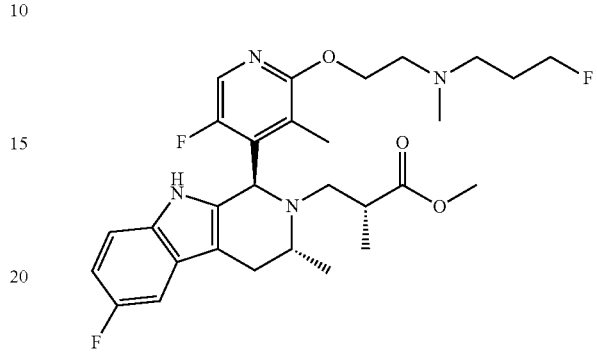

A solution of methyl (R)-3-(((R)-1-(5-fluoro-1H-indol-3-yl)propan-2-yl)amino)-2-methylpropanoate (200 mg, 0.68 mmol) and 5-fluoro-2-(2-((3-fluoropropyl)(methyl)amino) ethoxy)-3-methylisonicotinaldehyde (484 mg, 0.89 mmol) in toluene (3 mL) and acetic acid (0.33 mL) was heated at 95° C. for 16 hours. The resulting mixture was concentrated under reduced pressure and the residue was dissolved in EtOAc (50 mL) and washed with saturated aqueous NaHCO$_3$ (25 mL). The aqueous phase was extracted with EtOAc (50 mL) and the combined organics were dried over Na$_2$SO$_4$ and concentrated under reduced pressure. The crude product was partially purified by flash silica chromatography, eluting with EtOAc. Fractions containing the desired product were evaporated to dryness to afford methyl (R)-3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate (426 mg, ≥100%) as a yellow gum. Taken onto the next step without further purification.

Example 156

Preparation of 3-((1R,3R)-6-fluoro-1-(5-fluoro-2-(2-((3-fluoropropyl)(methyl)amino)ethoxy)-3-methylpyridin-4-)-3-methyl-1,3,4,9-tetrahydro-2H-pyrido[3,4-b]indol-2-yl)propanoic Acid

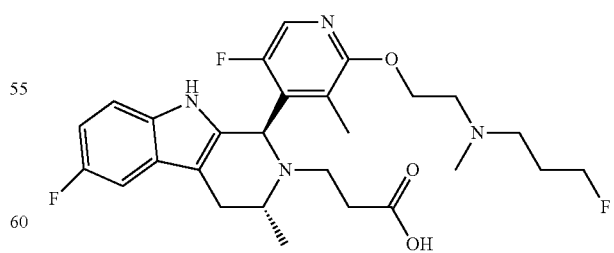

2N NaOH solution (0.563 mL, 1.13 mmol) was added to a solution of methyl 3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate (120 mg, 0.23 mmol) in THF (1.0 mL)/MeOH (1.0 mL). The reaction was stirred at room temperature for 2 hours, then was diluted with EtOAc (20 mL) and water (20 mL). The pH was adjusted to ~5 by addition of 2N HCl solution and the layers were separated. The aqueous layer was extracted with EtOAc (2×10 mL), then the combined organics were dried over Na$_2$SO$_4$ and evaporated. The crude product was purified by flash silica chromatography, elution gradient 0 to 20% MeOH in DCM. Product containing fractions were evaporated to dryness to afford 3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid (82 mg, 70%) as a beige solid. $^1$H NMR (500 MHz, CDCl$_3$, 27° C.) 1.10 (3H, d), 1.88 (3H, s), 1.89-1.93 (2H, m), 2.10-2.38 (2H, m), 2.43 (3H, s), 2.66 (2H, d), 2.76 (2H, s), 2.81-2.93 (2H, m), 2.98-3.07 (1H, m), 3.11 (1H, d), 3.63 (1H, s), 4.22-4.36 (1H, m), 4.36-4.41 (1H, m), 4.47 (1H, s), 4.57-4.69 (1H, m), 5.29 (1H, s), 6.83 (1H, t), 7.11 (2H, t), 7.81 (1H, s), 11.71 (1H, s). (1× exchangeable not observed.) m/z: ES+ [M+H]+ 519.

Procedures used to prepare the starting material methyl 3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate are described below.

Methyl (R)-3-((1-(5-fluoro-1H-indol-3-yl)propan-2-yl)amino)propanoate

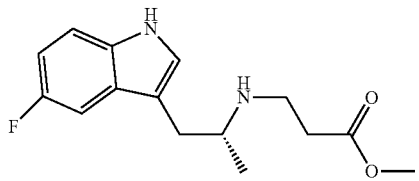 [SMILES: COC(=O)CCN[C@H](C)Cc1c[nH]c2ccc(F)cc12]

Methyl acrylate (95 al, 1.05 mmol) was added to a solution of (R)-1-(5-fluoro-1H-indol-3-yl)propan-2-amine (192 mg, 1.0 mmol) in MeOH (0.40 mL). The reaction was stirred at room temperature for 2 hours. The volatiles were evaporated, then the crude product was purified by flash silica chromatography, elution gradient 0 to 10% MeOH in DCM. Product containing fractions were evaporated to dryness to afford methyl (R)-3-((1-(5-fluoro-1H-indol-3-yl)propan-2-yl)amino)propanoate (270 mg, 97%) as a pale yellow liquid. $^1$H NMR (500 MHz, CDCl$_3$, 27° C.) 1.10 (3H, d), 2.36-2.53 (2H, m), 2.70-2.80 (2H, m), 2.80-2.90 (1H, m), 2.91-3.06 (2H, m), 3.57 (3H, s), 6.93 (1H, td), 7.09 (1H, d), 7.23 (1H, dd), 7.25-7.30 (1H, m), 8.04 (1H, s). (x exchangeable not observed.) m/z: ES+ [M+H]+ 279.

Methyl 3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate

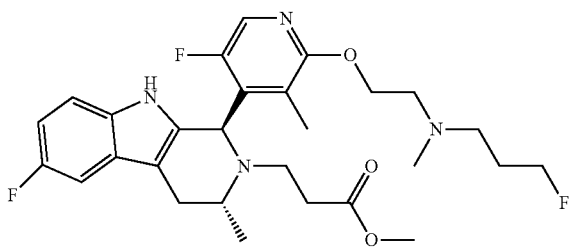 [SMILES: COC(=O)CCN1[C@H](c2c(F)cnc(OCCN(C)CCCF)c2C)c2[nH]c3ccc(F)cc3c2C[C@H]1C]

Methyl (R)-3-((1-(5-fluoro-1H-indol-3-yl)propan-2-yl)amino)propanoate (139 mg, 0.50 mmol) and 5-fluoro-2-(2-((3-fluoropropyl)(methyl)amino)ethoxy)-3-methylisonicotinaldehyde (65% weight, 209 mg, 0.50 mmol) were heated to 90° C. in toluene (2.25 mL)/acetic acid (0.25 mL) overnight. After cooling, the volatiles were evaporated. The residue was dissolved in DCM (20 mL) and washed with saturated aqueous NaHCO$_3$ (20 mL). The aqueous layer was extracted with DCM (20 mL), then the combined organics were dried over Na$_2$SO$_4$ and evaporated. The to crude product was purified by preparative HPLC (Waters XSelect CSH C18 column, 5µ silica, 19 mm diameter, 100 mm length), using decreasingly polar mixtures of water (containing 1% NH$_3$) and MeCN as eluents. Fractions containing the desired compound were evaporated to dryness to afford methyl 3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate (134 mg, 50%) as a pale yellow gum. $^1$H NMR (500 MHz, CDCl$_3$, 27° C.) 1.09 (3H, d), 1.74-1.87 (2H, m), 1.88 (3H, s), 2.30 (3H, s), 2.30-2.40 (2H, m), 2.53 (2H, t), 2.64 (1H, d), 2.67-2.73 (1H, m), 2.73-2.77 (2H, m), 2.91 (1H, dt), 3.08 (1H, ddd), 3.56 (3H, s), 3.59-3.67 (1H, m), 4.33 (2H, t), 4.39 (1H, t), 4.49 (1H, t), 5.27 (1H, s), 6.84 (1H, td), 7.09 (1H, dd), 7.12 (1H, dd), 7.51 (1H, s), 7.85 (1H, s). m/z: ES+ [M+H]+ 533.

Example 157

Preparation of 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic Acid

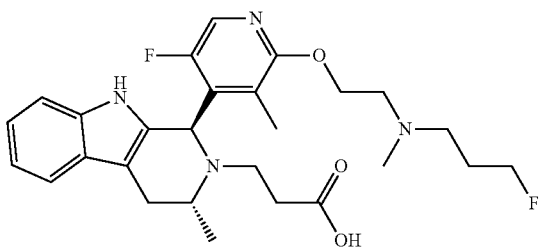 [SMILES: Cc1c(OCCN(C)CCCF)ncc(F)c1[C@@H]1c2[nH]c3ccccc3c2C[C@@H](C)N1CCC(=O)O]

2N NaOH solution (0.729 mL, 1.46 mmol) was added to a solution of methyl 3-((1R,3R)-1-(5-fluoro-2-(2-((3-fluoropropyl)(methyl)amino) ethoxy)-3-methylpyridin-4-yl)-3-methyl-1,3,4,9-tetrahydro-2H-pyrido[3,4-b]indol-2-yl)propanoate (150 mg, 0.29 mmol) in THF (1.0 mL)/MeOH (1.0 mL). The reaction was stirred at room temperature for 2 hours, then was diluted with EtOAc (20 mL) and water (20 mL). The pH was adjusted to ~5 by addition of 2N HCl solution and the layers were separated. The aqueous layer was extracted with EtOAc (2×10 mL), then the combined organics were dried over Na$_2$SO$_4$ and evaporated. The crude product was purified by flash silica chromatography, elution gradient 0 to 20% MeOH in DCM. Product to containing fractions were evaporated to dryness to afford 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid (128 mg, 88%) as a beige solid. $^1$H NMR (500 MHz, CDCl$_3$, 27° C.) 1.14 (3H, d), 1.81-1.95 (5H, m), 2.18 (1H, dt), 2.35 (3H, s), 2.43 (1H, ddd), 2.63-2.74 (4H, m), 2.77 (1H, d), 2.87 (1H, dt), 3.00

(1H, ddd), 3.19 (1H, ddd), 3.65 (1H, p), 4.26 (1H, ddd), 4.40 (1H, t), 4.49 (1H, t), 4.75 (1H, dt), 5.31 (1H, s), 7.09-7.16 (2H, m), 7.23 (1H, dd), 7.43 (1H, s), 7.49-7.53 (1H, m), 7.89 (1H, s). (2× exchangeables not observed.) m/z: ES+ [M+H]+ 501.

Procedures used to prepare the starting material methyl 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate are described below.

Methyl (R)-3-((1-(1H-indol-3-yl)propan-2-yl)amino)propanoate

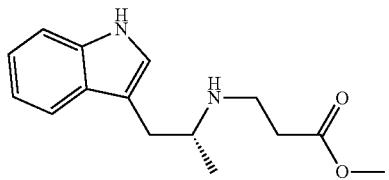 [SMILES: COC(=O)CCN[C@H](C)Cc1c[nH]c2ccccc12]

Methyl acrylate (0.284 mL, 3.15 mmol) was added to a solution of (R)-1-(1H-indol-3-yl)propan-2-amine (523 mg, 3.00 mmol) in MeOH (0.92 mL). The reaction was stirred at room temperature for 2 hours. The volatiles were evaporated, then the crude product was purified by flash silica chromatography, elution gradient 0 to 10% MeOH in DCM. Product containing fractions were evaporated to dryness to afford methyl (R)-3-((1-(1H-indol-3-yl)propan-2-yl)amino)propanoate (755 mg, 97%) as a pale yellow liquid. $^1$H NMR (500 MHz, CDCl$_3$, 27° C.) 1.12 (3H, d), 2.34-2.53 (2H, m), 2.68-2.91 (3H, m), 2.96 (1H, dt), 3.04 (1H, h), 3.55 (3H, s), 7.05 (1H, d), 7.11 (1H, ddd), 7.36 (1H, dt), 7.59-7.66 (1H, m), 8.02 (1H, s). (1× exchangeable not observed.) m/z: ES+ [M+H]+ 261.

Methyl 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate

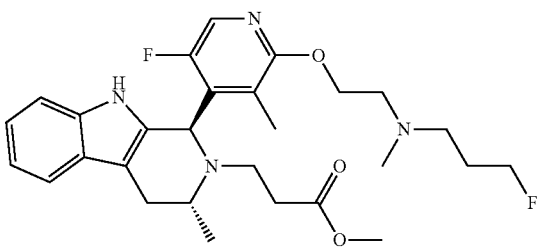 [SMILES: COC(=O)CCN1[C@H](c2c(F)cnc(OCCN(C)CCCF)c2C)c2[nH]c3ccccc3c2C[C@H]1C]

Methyl (R)-3-((1-(1H-indol-3-yl)propan-2-yl)amino)propanoate (156 mg, 0.60 mmol) and 5-fluoro-2-(2-((3-fluoropropyl)(methyl)amino)ethoxy)-3-methylisonicotinaldehyde (65% weight, 251 mg, 0.60 mmol) were heated in toluene (4.50 mL)/acetic acid (0.50 mL) to 90° C. overnight. After cooling, the volatiles were evaporated. The residue was dissolved in DCM (20 mL) and washed with saturated aqueous NaHCO$_3$ solution (20 mL). The aqueous layer was extracted with DCM (20 mL), then the combined organics were dried over Na$_2$SO$_4$ and evaporated. The crude product was purified by preparative HPLC (Waters XSelect CSH C18 column, 5μ silica, 19 mm diameter, 100 mm length), using decreasingly polar mixtures of water (containing 1% NH$_3$) and MeCN as eluents. Fractions containing the desired compound were evaporated to dryness to afford methyl 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoate (164 mg, 53%) as a beige gum. $^1$H NMR (500 MHz, CDCl$_3$, 27° C.) 1.09 (3H, d), 1.72-1.86 (2H, m), 1.88 (3H, s), 2.29 (3H, s), 2.30-2.40 (2H, m), 2.53 (2H, t), 2.63-2.73 (2H, m), 2.74 (2H, td), 2.92 (1H, dt), 3.11 (1H, ddd), 3.56 (3H, s), 3.59-3.67 (1H, m), 4.32 (2H, t), 4.39 (1H, t), 4.48 (1H, t), 5.28 (1H, s), 7.00-7.15 (2H, m), 7.15-7.21 (1H, m), 7.49 (1H, dd), 7.55 (1H, s), 7.84 (1H, s); m/z: ES+ [M+H]+ 514.

Example 158 & 159

Preparation of 3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)butanoic Acid

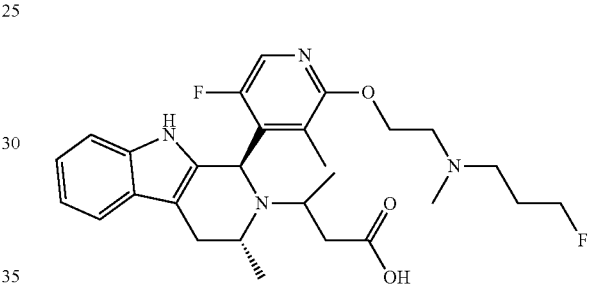

Ethyl 3-(((R)-1-(1H-indol-3-yl)propan-2-yl)amino)butanoate (216 mg, 0.75 mmol) and 5-fluoro-2-(2-((3-fluoropropyl)(methyl)amino)ethoxy)-3-methylisonicotinaldehyde (314 mg, 0.75 mmol) were heated in toluene (3.375 mL)/acetic acid (0.375 mL) to 100° C. overnight. After cooling, the volatiles were evaporated. The residue was dissolved in DCM (20 mL) and washed with saturated aqueous NaHCO$_3$ (20 mL). The aqueous layer was extracted with DCM (20 mL), then the combined organics were dried over Na$_2$SO$_4$ and evaporated. The crude product was purified by flash silica chromatography, elution gradient 0 to 10% MeOH in EtOAc. Pure fractions were evaporated to dryness to afford a pale yellow oil (~250 mg) which was contaminated with unreacted starting material. The residue was dissolved in THF (1 mL) and MeOH (1 mL), then 2N NaOH solution (1 mL) was added. The reaction was stirred at room temperature overnight, then was diluted with EtOAc (10 mL) and water (10 mL). The aqueous was adjusted to pH 5 by addition of 2N HCl and the layers were separated. The aqueous layer was extracted with EtOAc (2×10 mL), then the combined organics were dried over Na$_2$SO$_4$ and evaporated. The crude product was purified by preparative HPLC (Waters XSelect CSH C18 column, 5μ silica, 19 mm diameter, 100 mm length), using decreasingly polar mixtures of water (containing 1% NH$_3$) and MeCN as eluents. Fractions containing the desired compound were evaporated to dryness to afford the two isomers, (3R)-3-((1R,3R)-1-(5-fluoro-2-(2-((3-fluoropropyl)(methyl)amino) ethoxy)-3-methyl pyridin-4-yl)-3-methyl-1,3,4,9-tetrahydro-2H-pyrido[3,4-b]indol-2-yl)butanoic acid and (3S)-3-((1R,3R)-1-(5-fluoro-2-

(2-((3-fluoropropyl)(methyl)amino) ethoxy)-3-methyl pyridin-4-yl)-3-methyl-1,3,4,9-tetrahydro-2H-pyrido[3,4-b]indol-2-yl)butanoic acid:

Example 158; Isomer 1

15.0 mg, 4% (as a colourless solid). ¹H NMR (500 MHz, CDCl₃, 27° C.) 1.21 (3H, d), 1.25 (3H, d), 1.82 (3H, s), 1.85-1.93 (2H, m), 2.26 (1H, dd), 2.33 (3H, s), 2.57-2.63 (2H, m), 2.67 (1H, d), 2.73-2.82 (2H, m), 2.86 (1H, ddd), 3.12-3.19 (2H, m), 3.84-3.92 (1H, m), 4.27-4.36 (1H, m), 4.39 (1H, t), 4.43-4.54 (2H, m), 5.73 (1H, s), 7.01-7.16 (2H, m), 7.16-7.25 (1H, m), 7.42-7.55 (1H, m), 7.65 (1H, s), 7.88 (1H, s). (1× exchangeable not observed.) m/z: ES+ [M+H]+ 515.

Example 159; Isomer 2

35.0 mg, 9% (as a colourless solid). ¹H NMR (500 MHz, CDCl₃, 27° C.) 1.17 (3H, d), 1.19 (3H, d), 1.79-1.91 (2H, m), 1.92 (3H, s), 2.12 (1H, dd), 2.37 (3H, s), 2.63-2.79 (4H, m), 2.81-2.91 (2H, m), 3.05-3.14 (1H, m), 3.26 (1H, d), 3.83 (1H, dq), 4.32-4.41 (3H, m), 4.47 (1H, q), 5.68 (1H, s), 7.10 (2H, tdt), 7.20 (1H, dd), 7.48 (1H, dd), 7.73 (1H, s), 7.86 (1H, s). (1× exchangeable not observed.) m/z: ES+ [M+H]+ 515.

Procedures used to prepare the starting material ethyl 3-(((R)-1-(1H-indol-3-yl)propan-2-yl)amino)butanoate are described below.

Ethyl 3-(((R)-1-(1H-indol-3-yl)propan-2-yl)amino) butanoate

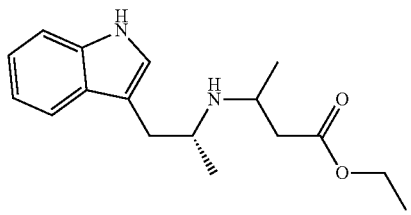 [SMILES: CCOC(=O)CC(C)N[C@H](C)Cc1c[nH]c2ccccc12]

(R)-1-(1H-indol-3-yl)propan-2-amine (0.871 g, 5 mmol) and ethyl (E)-but-2-enoate (0.777 mL, 6.25 mmol) were stirred in MeOH (2.50 mL) at 50° C. for 1 hour, then further heated to reflux and stirring was continued overnight. After cooling the volatiles were evaporated. The crude product was purified by flash silica chromatography, elution gradient 25 to 100% EtOAc in heptane. Product containing fractions were evaporated to dryness to afford ethyl 3-(((R)-1-(1H-indol-3-yl)propan-2-yl)amino)butanoate (1.310 g, 91%) as a pale yellow gum, as a 1:1 mixture of diastereoisomers. ¹H NMR (500 MHz, CDCl₃, 27° C.) 0.99-1.27 (9H, m), 2.18 (0.5H, dd), 2.30 (0.5H, dd), 2.41 (1H, ddd), 2.75 (1H, dddd), 2.81-2.94 (1H, m), 3.12 (1H, hd), 3.25 (1H, dq), 4.11 (2H, p), 7.04 (1H, dd), 7.11 (1H, ddt), 7.18 (1H, tt), 7.35 (1H, d), 7.52-7.70 (1H, m), 8.02 (1H, s). (1× exchangeable not observed.) m/z: ES+ [M+H]+ 289.

Example 160

(R)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic Acid

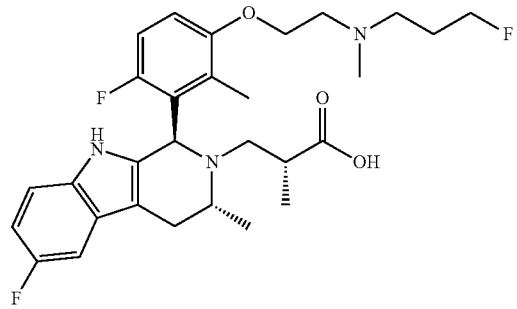 [SMILES: Cc1c(OCCN(C)CCCF)ccc(F)c1[C@@H]1c2[nH]c3ccc(F)cc3c2C[C@@H](C)N1C[C@@H](C)C(=O)O]

2M Sodium hydroxide (1 mL, 2.00 mmol) was added to a stirred solution of methyl (R)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoate (87 mg, 0.16 mmol) in THF (2 mL) and MeOH (1 mL). The resulting mixture was stirred at 21° C. for 16 hours. The mixture was concentrated under reduced pressure then water (5 mL) and AcOH (1 mL) were added and the aqueous mixture was extracted with DCM (4×15 mL). The combined organics were dried (phase separation cartridge) and concentrated under reduced pressure to give the crude product as a yellow gum which was purified by preparative HPLC (Waters CSH C18 OBD column, 5μ silica, 30 mm diameter, 100 mm length), using decreasingly polar mixtures of water (containing 0.1% formic acid) and MeCN as eluents. Fractions containing the desired compound were evaporated under reduced pressure, redissolved in IM ammonia in MeOH (1 mL) and concentrated under reduced pressure to give (R)-3-((1R,3R)-6-fluoro-1-(6-fluoro-3-(2-((3-fluoropropyl)(methyl)amino) ethoxy)-2-methylphenyl)-3-methyl-1,3,4,9-tetrahydro-2H-pyrido[3,4-b]indol-2-yl)-2-methylpropanoic acid (32.0 mg, 38%) as a pale yellow solid. ¹H NMR (500 MHz, DMSO, 27° C.) 0.99 (3H, d), 1.07 (3H, d), 1.72-1.95 (5H, m), 2.27 (3H, s), 2.30-2.38 (1H, m), 2.51 (2H, t), 2.64-2.72 (1H, m), 2.73 (2H, t), 3.02 (1H, dd), 3.23 (3H, s), 3.64-3.73 (1H, m), 4.03 (2H, ddt), 4.49 (2H, dt), 5.24 (1H, s), 6.86 (1H, td), 6.97-7.14 (2H, m), 7.14-7.25 (2H, m), 10.40 (1H, s); m/z: ES+ [M+H]+ 532.

Procedures used to prepare the starting material methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate are described below.

Methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate

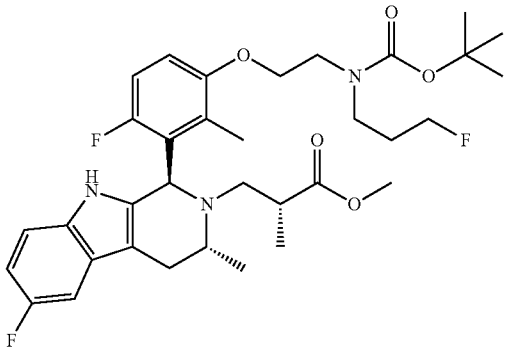 [SMILES: COC(=O)[C@H](C)CN1[C@H](c2c(F)ccc(OCCN(CCCF)C(=O)OC(C)(C)C)c2C)c2[nH]c3ccc(F)cc3c2C[C@H]1C]

RockPhos 3<sup>rd</sup> generation catalyst (31.2 mg, 0.04 mmol) was added to a degassed mixture of methyl (R)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (181 mg, 0.37 mmol), tert-butyl (3-fluoropropyl)(2-hydroxyethyl)carbamate (163 mg, 0.74 mmol) and cesium carbonate (360 mg, 1.11 mmol) in toluene (2 mL) at 21° C. The resulting mixture was heated at 90° C. for 6 hours. The mixture was allowed to cool to room temperature and diluted with EtOAc (25 mL) and water (25 mL). The layers were separated and the aqueous layer was extracted with EtOAc (2×25 mL). The combined organics were dried (phase separation cartridge) and concentrated to give the crude product as a brown gum which was purified by flash silica chromatography, elution gradient 0 to 60% EtOAc in heptane. Product containing fractions were evaporated to dryness to afford methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (108 mg, 46%) as a pale yellow foam. $^1$H NMR (500 MHz, CDCl$_3$, 27° C.) 1.02 (3H, d), 1.09 (3H, d), 1.40-1.48 (9H, m), 1.81 (3H, s), 1.84-1.94 (2H, m), 2.52-2.67 (4H, m), 3.04-3.12 (1H, m), 3.35-3.46 (2H, m), 3.50 (3H, s), 3.52-3.59 (2H, m), 3.64-3.72 (1H, m), 4.03 (2H, s), 4.41 (2H, d), 5.26 (1H, s), 6.73-6.86 (2H, m), 6.91 (1H, t), 7.04-7.13 (2H, m), 7.23 (1H, s); ES+ [M+H]+ 632.

Methyl (R)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoate

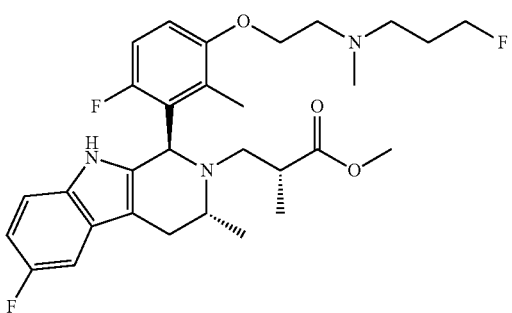 [SMILES: COC(=O)[C@H](C)CN1[C@H](c2c(F)ccc(OCCN(C)CCCF)c2C)c2[nH]c3ccc(F)cc3c2C[C@H]1C]

A solution of methyl (R)-3-((1R,3R)-1-(3-(2-((tert-butoxycarbonyl)(3-fluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (100 mg, 0.16 mmol) in formic acid (610 µL) was stirred at 40° C. for 1 hour. The mixture was concentrated under reduced pressure and the is resulting residue was dissolved in DCM (25 mL) and washed with saturated aqueous NaHCO$_3$ (25 mL). The aqueous layer was extracted with DCM (25 mL) and the combined organics were evaporated to ~10 mL in volume. To this solution was added 37% w/w aqueous formaldehyde solution (23.55 µL, 0.24 mmol) followed by sodium triacetoxyborohydride (51.8 mg, 0.24 mmol). The resulting mixture was stirred at 21° C. for 1 hour. The reaction mixture was diluted with DCM (10 mL) and washed with saturated aqueous NaHCO$_3$ (20 mL). The aqueous layer was extracted with DCM (20 mL) and the combined organics were dried over Na$_2$SO$_4$ and concentrated under reduced pressure. The crude product was taken immediately on to the next step.

Example 161

Preparation of (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic Acid

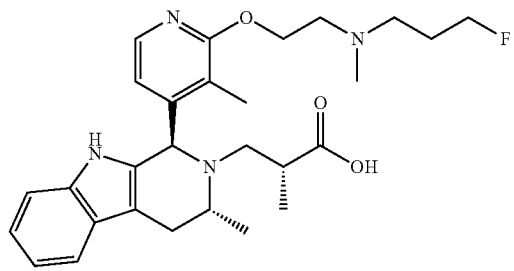 [SMILES: Cc1c([C@@H]2c3[nH]c4ccccc4c3C[C@@H](C)N2C[C@@H](C)C(=O)O)ccnc1OCCN(C)CCCF]

Lithium hydroxide monohydrate (9.0 mg, 0.22 mmol) was added to a solution of methyl (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate (0.011 g, 0.020 mmol) in tetrahydrofuran (0.2 mL), methanol (0.2 mL) and water (0.2 mL). The resulting mixture was stirred at room temperature for 5 hours and then neutralized with aqueous hydrochloric acid (1N; 0.21 mL, 0.21 mmol). The mixture was extracted with ethyl acetate, and the extract was dried over anhydrous sodium sulfate, filtered and concentrated under reduced pressure. The resulting residue was purified by flash silica chromatography, elution gradient 0 to 70% MeOH in DCM, to give (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid (7.6 mg, 71%) as a pale yellow solid. $^1$H NMR (500 MHz, DMSO-d$_6$, 27° C.) 1.03 (3H, d), 1.05 (3H, d), 1.72-1.88 (2H, m), 2.14-2.33 (6H, m), 2.55-2.63 (5H, m), 2.75 (2H, br t), 2.83 (1H, br dd), 4.29-4.40 (2H, m), 4.49 (2H, dt), 4.98 (1H, br s), 6.40 (1H, br d), 6.94-6.99 (1H, m), 7.00-7.05 (1H, m), 7.22 (1H, d), 7.43 (1H, d), 7.82 (1H, br d), 10.39 (1H, br s), 11.93-12.45 (1H, br s). (Two hydrogens not observed.) m/z: ES+ [M+H]+ 497.

Procedures used to prepare the starting material methyl (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate are described below.

Preparation of Methyl (R)-3-((1R,3R)-1-(2-chloro-3-methylpyridin-4-yl)-3-methyl-1,3,4,9-tetrahydro-2H-pyrido[3,4-b]indol-2-yl)-2-methylpropanoate

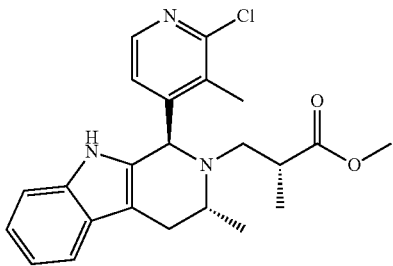 [SMILES: COC(=O)[C@H](C)CN1[C@H](c2ccnc(Cl)c2C)c2[nH]c3ccccc3c2C[C@H]1C]

A mixture of methyl (R)-3-(((R)-1-(1H-indol-3-yl)propan-2-yl)amino)-2-methylpropanoate (0.85 g, 3.1 mmol), 2-chloro-3-methylisonicotinaldehyde (0.50 g, 3.2 mmol) in toluene (10 mL) and acetic acid (1.0 mL) was stirred at 90° C. for 8 hours. The reaction was allowed to cool to room temperature and was then concentrated under reduced pressure. The resulting residue was purified by flash silica chromatography, elution gradient 0 to 40% ethyl acetate in hexanes, to give methyl (R)-3-((1R,3R)-1-(2-chloro-3-methylpyridin-4-yl)-3-methyl-1,3,4,9-tetrahydro-2H-pyrido[3,4-b]indol-2-yl)-2-methylpropanoate (0.75 g, 59%) as a pale yellow foam. $^1$H NMR (300 MHz, DMSO-$d_6$, 27° C.) 1.03 (6H, d), 2.33 (3H, br s), 2.40-2.48 (1H, m), 2.56-2.80 (3H, m), 2.81-2.93 (1H, m), 3.35-3.48 (1H, m), 3.52 (3H, s), 4.98 (1H, s), 6.82-7.09 (3H, m), 7.13-7.30 (1H, m), 7.44 (1H, d), 8.15 (1H, d), 10.34 (1H, s). m/z: ES+ [M+H]+ 412.

Preparation of methyl (R)-3-((1R,3R)-1-(2-(2-((tert-butoxycarbonyl)(3-fluoropropyl)amino)ethoxy)-3-methylpyridin-4-yl)-3-methyl-1,3,4,9-tetrahydro-2H-pyrido[3,4-b]indol-2-yl)-2-methylpropanoate

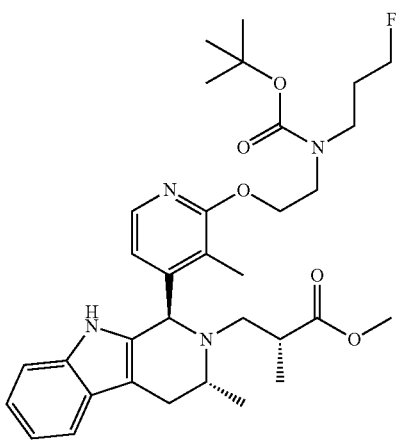 [SMILES: COC(=O)[C@H](C)CN1[C@H](c2ccnc(OCCN(CCCF)C(=O)OC(C)(C)C)c2C)c2[nH]c3ccccc3c2C[C@H]1C]

A mixture of methyl (R)-3-((1R,3R)-1-(2-chloro-3-methylpyridin-4-yl)-3-methyl-1,3,4,9-tetrahydro-2H-pyrido[3,4-b]indol-2-yl)-2-methylpropanoate (0.30 g, 0.73 mmol), tert-butyl (3-fluoropropyl)(2-hydroxyethyl)carbamate (0.209 g, 0.95 mmol), RockPhos 3$^{rd}$ Generation Precatalyst (0.031 g, 0.04 mmol) and cesium carbonate (0.593 g, 1.82 mmol) was evacuated and back-filled with nitrogen (3×). Toluene (3.5 mL) was added, and the mixture was again evacuated and back-filled with nitrogen (2×). The resulting suspension was stirred at 90° C. for 24 hours, allowed to cool to room temperature, and filtered. The filtrate was concentrated under reduced pressure. The resulting residue was purified by flash silica chromatography, elution gradient 0 to 40% ethyl acetate in hexanes, to give crude product which was further purified by SFC (Chiralpak IB column, 250 mm length, 21.2 mm diameter, 5 μm, 75 mL/min flow rate), eluting with 10% (0.2% NH$_4$OH methanol) in CO$_2$ over 10 min, to give methyl (R)-3-((1R,3R)-1-(2-(2-((tert-butoxycarbonyl)(3-fluoropropyl)amino)ethoxy)-3-methylpyridin-4-yl)-3-methyl-1,3,4,9-tetrahydro-2H-pyrido[3,4-b]indol-2-yl)-2-methylpropanoate (0.041 g, 9%) as a pale amber foam. $^1$H NMR (500 MHz, DMSO-$d_6$, 27° C.) 0.97-1.10 (6H, m), 1.30-1.47 (9H, m), 1.81-1.97 (2H, m), 2.19 (3H, br s), 2.54-2.66 (3H, m), 2.68-2.79 (1H, br m), 2.84 (1H, br d), 3.35-3.44 (3H, m), 3.45-3.75 (2H, m), 3.51 (3H, s), 4.24-4.34 (1H, m), 4.34-4.47 (1H, m), 4.46 (2H, dt), 4.93 (1H, br s), 6.45 (1H, br s), 6.93-6.99 (1H, m), 6.99-7.04 (1H, m), 7.21 (1H, d), 7.43 (1H, d), 7.84 (1H, br d), 10.33 (1H, br s). m/z: ES+ [M+H]+ 597.

Preparation of methyl (R)-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoate

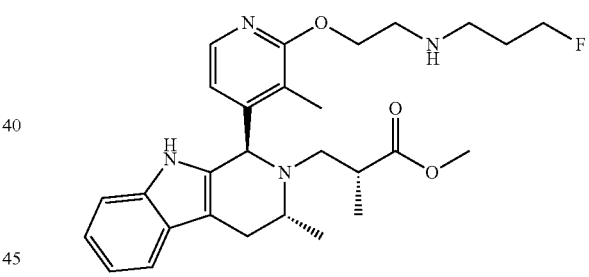

A solution of methyl (R)-3-((1R,3R)-1-(2-(2-((tert-butoxycarbonyl)(3-fluoropropyl)amino)ethoxy)-3-methylpyridin-4-yl)-3-methyl-1,3,4,9-tetrahydro-2H-pyrido[3,4-b]indol-2-yl)-2-methylpropanoate (0.04 g, 0.07 mmol) in formic acid (1 mL, 26.07 mmol) was allowed to stand at room temperature for 18 hours and was then concentrated under reduced pressure. The residue was basified with saturated aqueous sodium hydrogen carbonate, and extracted with ethyl acetate. The organic layer was dried over anhydrous sodium sulfate, filtered and concentrated under reduced pressure. The resulting residue was purified by flash silica chromatography, elution gradient 0 to 10% MeOH in DCM, to give methyl (R)-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoate (0.030 g, 90%) as a clear film. $^1$H NMR (500 MHz, DMSO-$d_6$, 27° C.) 0.97-1.10 (6H, m), 1.74-1.86 (2H, m), 2.08-2.29 (3H, m), 2.57-2.64 (2H, m), 2.69 (2H, t), 2.71-2.78 (1H, m), 2.85 (1H, br dd), 2.90 (2H, t), 3.39-3.47 (1H, m), 3.51 (3H, s), 4.25-4.34 (2H, m), 4.50 (2H, dt), 4.91 (1H, s), 6.37-6.52 (1H, m), 6.93-6.98 (1H, m), 6.99-7.05 (1H, m), 7.21 (1H, d), 7.42 (1H, d), 7.84 (1H, br d), 10.34 (1H, s). (Two hydrogens not observed.); m/z: ES+ [M+H]+ 497.

Preparation of methyl (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate

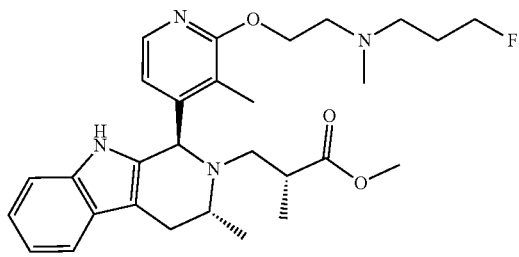 [SMILES: COC(=O)[C@H](C)CN1[C@H](c2ccnc(OCCN(C)CCCF)c2C)c2[nH]c3ccccc3c2C[C@H]1C]

A solution of formaldehyde in water (37 wt %; 7.8 µL, 0.10 mmol) was added to a stirring solution of methyl (R)-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoate (26 mg, 0.05 mmol) in dichloromethane (1 mL). Sodium triacetoxyborohydride (22 mg, 0.10 mmol) was then added and the resulting mixture was stirred at room temperature for 2 hours and then treated with saturated aqueous sodium hydrogencarbonate and extracted with dichloromethane. The organic layer was dried over anhydrous sodium sulfate, filtered and concentrated under reduced pressure. The resulting residue was purified by flash silica chromatography, elution gradient 0 to 10% MeOH in DCM, to give methyl (R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoate (14 mg, 52%) as a white solid. $^1$H NMR (500 MHz, DMSO-$d_6$, 27° C.) 0.98-1.07 (6H, m), 1.74-1.88 (2H, m), 2.18 (3H, br s), 2.28 (3H, s), 2.56-2.68 (3H, m), 2.68-2.78 (3H, m), 2.85 (1H, br dd), 3.39-3.47 (1H, m), 3.51 (3H, s), 4.29-4.40 (2H, m), 4.49 (2H, dt), 4.92 (1H, br s), 6.45 (1H, br d), 6.93-6.98 (1H, m), 6.99-7.04 (1H, m), 7.21 (1H, d), 7.42 (1H, d), 7.84 (1H, br d), 10.32 (1H, s). (Two hydrogens not observed.); m/z: ES+ [M+H]+ 511.

Example 162

Preparation of (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoic Acid

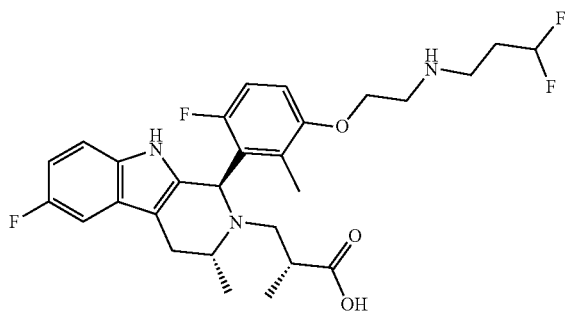 [SMILES: Cc1c(OCCNCCC(F)F)ccc(F)c1[C@@H]1c2[nH]c3ccc(F)cc3c2C[C@@H](C)N1C[C@@H](C)C(=O)O]

Methyl (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (115 mg, 0.21 mmol) was dissolved in THF (0.8 mL)/MeOH (0.8 mL) and treated with a solution of lithium hydroxide monohydrate (88 mg, 2.1 mmol) in water (0.8 mL). The reaction was stirred at room temperature for 4.5 hours and then concentrated under reduced pressure. The resulting residue was neutralized carefully with aqueous HCl (1N) to pH 7, and the resulting mixture was extracted with EtOAc (2×). The combined extracts were dried over sodium sulfate, filtered, and concentrated under reduced pressure. The resulting residue was purified by preparative SFC (Chiralpak IC column, 5 µm, 21 mm diameter, 250 mm length, 75 mL/min flow rate), eluting with 20% (0.2% NH$_4$OH in MeOH) in CO$_2$, to afford (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoic acid (41 mg, 37%) as a beige dry film. $^1$H NMR (500 MHz, DMSO-$d_6$, 27° C.) 0.91 (3H, d), 0.99 (3H, d), 1.63-2.04 (5H, m), 2.17-2.33 (1H, m), 2.51-2.57 (2H, m), 2.62 (br 1H, d), 2.67 (2H, t), 2.72-2.89 (2H, m), 2.92-3.00 (1H, m), 3.53-3.70 (1H, m), 3.78-3.93 (1H, m), 3.93-4.04 (1H, m), 5.16 (1H, s), 6.07 (1H, tt), 6.78 (1H, td), 6.87-6.98 (1H, m), 6.99-7.07 (1H, m), 7.07-7.23 (2H, m), 10.34 (1H, s). (Two hydrogens not observed.); m/z: ES+ [M+H]+ 536.

Procedures used to prepare the starting material methyl (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate are described below.

Preparation of methyl (R)-3-((1R,3R)-6-fluoro-1-(6-fluoro-3-(2-hydroxyethoxy)-2-methylphenyl)-3-methyl-1,3,4,9-tetrahydro-2H-pyrido[3,4-b]indol-2-yl)-2-methylpropanoate

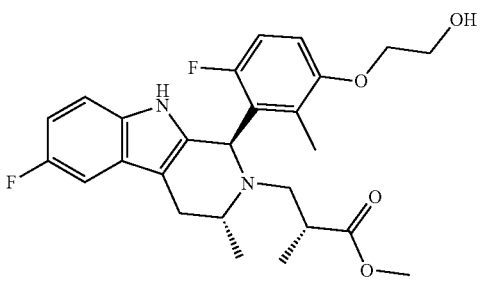 [SMILES: COC(=O)[C@H](C)CN1[C@H](c2c(F)ccc(OCCO)c2C)c2[nH]c3ccc(F)cc3c2C[C@H]1C]

Methyl (R)-3-((1R,3R)-1-(3-bromo-6-fluoro-2-methylphenyl)-6-fluoro-3-methyl-1,3,4,9-tetrahydro-2H-pyrido[3,4-b]indol-2-yl)-2-methylpropanoate (330 mg, 0.67 mmol), cesium carbonate (547 mg, 1.68 mmol), and 2-((tert-butyldimethylsilyl)oxy)ethan-1-ol (178 mg, 1.01 mmol) were suspended in toluene (3.5 mL). The reaction flask was then evacuated and back-filled with nitrogen (3×) before the addition of RockPhos 3$^{rd}$ Generation Precatalyst (30 mg, 0.03 mmol). The reaction flask was again evacuated and back-filled with nitrogen (3×) before being heated at 90° C. for 2 hrs. The reaction was cooled to room temperature, diluted with DCM (25 mL), and washed with saturated aqueous sodium chloride (25 mL). The aqueous layer was extracted with DCM (25 mL), and the combined organic layers were dried over sodium sulfate, filtered, and concentrated under reduced pressure. The resulting residue was dissolved in THF (3.5 mL) and treated with TBAF (1.0 M in THF; 2 mL). After 30 minutes, the reaction was diluted with EtOAc (25 mL), washed with saturated aqueous sodium chloride (25 mL), and the organic layer was dried over sodium sulfate, filtered and concentrated under reduced pressure. The resulting residue was purified by flash silica chromatography, elution gradient 0 to 80% EtOAc in hexanes. Product fractions were concentrated under reduced pressure to afford methyl (R)-3-((1R,3R)-6-fluoro-1-(6-fluoro-3-(2-hydroxyethoxy)-2-methylphenyl)-3-methyl-1,3,4,9-tetrahydro-2H-pyrido[3,4-b]indol-2-yl)-2-methylpropanoate (130 mg, 39%) as a brown solid. ¹H NMR (500 MHz, DMSO-d₆, 27° C.) 0.91 (3H, d), 0.98 (3H, d), 1.55-1.91 (3H, m), 2.42-2.65 (4H, m), 2.85-2.98 (1H, m), 3.41 (3H, s), 3.57-3.71 (3H, m), 3.77-3.99 (2H, m), 4.76 (1H, t), 5.11 (1H, s), 6.72-6.83 (1H, m), 6.89-7.06 (2H, m), 7.07-7.19 (2H, m), 10.33 (1H, s). m/z: ES+ [M+H]+ 473.

Preparation of methyl (R)-3-((1R,3R)-6-fluoro-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate

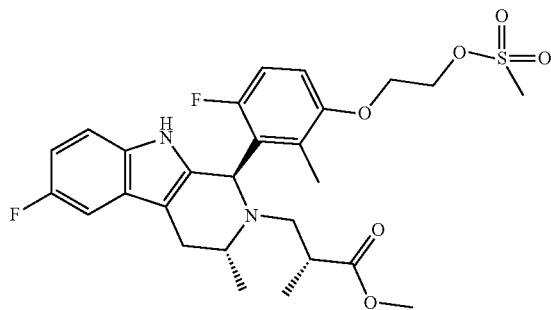 [SMILES: COC(=O)[C@H](C)CN1[C@H](c2c(F)ccc(OCCOS(C)(=O)=O)c2C)c2[nH]c3ccc(F)cc3c2C[C@H]1C]

Methanesulfonyl chloride (0.022 mL, 0.28 mmol) was added to a solution of methyl (R)-3-((1R,3R)-6-fluoro-1-(6-fluoro-3-(2-hydroxyethoxy)-2-methylphenyl)-3-methyl-1,3,4,9-tetrahydro-2H-pyrido[3,4-b]indol-2-yl)-2-methylpropanoate (121 mg, 0.26 mmol), DIPEA (0.056 mL, 0.32 mmol), and DCM (2.5 mL). The reaction was stirred at room temperature for 20 minutes and then diluted with DCM (10 mL) and washed with saturated aqueous sodium chloride. The organic layer was dried over sodium sulfate, filtered, and concentrated under reduced pressure to afford crude methyl (R)-3-((1R,3R)-6-fluoro-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate (141 mg, 100%) as a yellow foam. m/z: ES+ [M+H]+ 551.

Preparation of methyl (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate

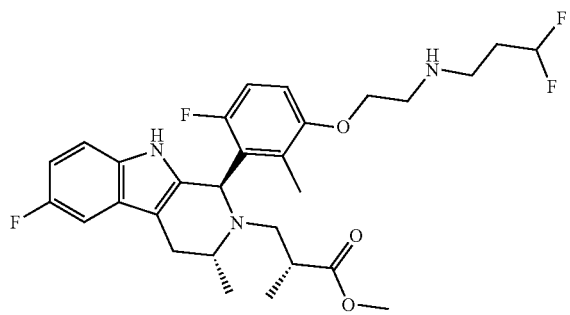 [SMILES: COC(=O)[C@H](C)CN1[C@H](c2c(F)ccc(OCCNCCC(F)F)c2C)c2[nH]c3ccc(F)cc3c2C[C@H]1C]

Methyl (R)-3-((1R,3R)-6-fluoro-1-(6-fluoro-2-methyl-3-(2-((methylsulfonyl)oxy)ethoxy)phenyl)-3-methyl-1,3,4,9-tetrahydro-2H-pyrido[3,4-b]indol-2-yl)-2-methylpropanoate (141 mg, 0.26 mmol), 3,3-difluoropropan-1-amine hydrochloride (67 mg, 0.51 mmol), potassium carbonate (106 mg, 0.77 mmol), and potassium iodide (42.5 mg, 0.26 mmol) were suspended in acetonitrile (2.5 mL) and heated at 80° C. for 17 hours. The reaction was cooled to room temperature, diluted with EtOAc, and washed with saturated aqueous sodium chloride. The aqueous layer was extracted with EtOAc, and the combined organic layers were dried over sodium sulfate, filtered, and concentrated under reduced pressure. The resulting residue was purified by flash silica chromatography, elution gradient 0 to 20% MeOH in DCM. Product fractions were concentrated under reduced pressure to afford methyl (R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoate (119 mg, 85%) as a beige foam. m/z: ES+ [M+H]+ 550.

Example 163

Preparation of 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoic Acid

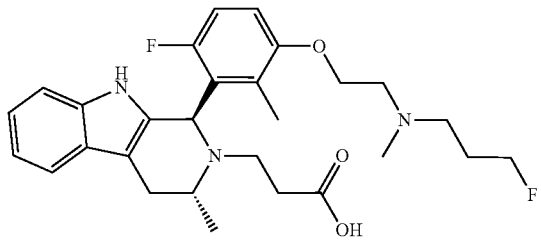 [SMILES: Cc1c(OCCN(C)CCCF)ccc(F)c1[C@@H]1c2[nH]c3ccccc3c2C[C@@H](C)N1CCC(=O)O]

NaOH solution (0.82 mL, 1.65 mmol) was added to a solution of methyl 3-((1R,3R)-1-(6-fluoro-3-(2-((3-fluoropropyl)(methyl)amino) ethoxy)-2-methylphenyl)-3-methyl-1,3,4,9-tetrahydro-2H-pyrido[3,4-b]indol-2-yl)propanoate (170 mg, 0.33 mmol) in THF (1.24 mL)/MeOH (1.24 mL). The reaction was stirred at room temperature for 2 hours, then was neutralised by addition of 2N HCl solution. The volatiles were evaporated, then the crude product was purified by preparative HPLC (Waters XSelect CSH C18 ODB column, 5µ silica, 30 mm diameter, 100 mm length), using decreasingly polar mixtures of water (containing 1% NH₃) and MeCN as eluents. Fractions containing the desired compound were evaporated to dryness to afford 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoic acid (145 mg, 88%) as a colourless solid. ¹H NMR (500 MHz, CDCl₃, 27° C.) 1.23 (3H, d), 1.85 (2H, ddt), 1.87 (3H, s), 2.16 (1H, d), 2.32 (3H, s), 2.48-2.56 (1H, m), 2.58 (2H, t), 2.66-2.88 (3H, m), 2.89-2.96 (2H, m), 3.27 (1H, ddd), 3.76 (1H, p), 4.03 (2H, dp), 4.42 (1H, t), 4.52 (1H, t), 5.40 (1H, s), 6.83 (1H, dd), 6.94 (1H, t), 7.09-7.19 (2H, m), 7.22 (1H, dd), 7.38 (1H, s), 7.51 (1H, dd). (1× exchangeable not observed.); m/z: ES+ [M+H]+ 500.

Procedures used to prepare the starting material methyl 3-((1R,3R)-1-(6-fluoro-3-(2-((3-fluoropropyl)(methyl)

amino)ethoxy)-2-methylphenyl)-3-methyl-1,3,4,9-tetra-hydro-2H-pyrido[3,4-b]indol-2-yl)propanoate are described below.

2-(3-Bromo-6-fluoro-2-methylphenyl)-1,3-dioxolane

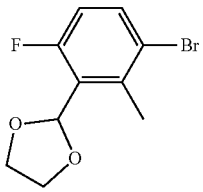

3-Bromo-6-fluoro-2-methylbenzaldehyde (4.8 g, 22.12 mmol) was added to ethane-1,2-diol (4.12 g, 66.35 mmol) and 4-methylbenzenesulfonic acid (0.381 g, 2.21 mmol) in toluene (100 mL). The resulting mixture was stirred at 100° C. for 16 hours. The reaction mixture was poured into saturated NaHCO₃ solution (50 mL), extracted with EtOAc (2×50 mL), then the organic layer was dried over Na₂SO₄, filtered and evaporated to afford a yellow gum which was purified by flash silica chromatography, elution gradient 0 to 20% EtOAc in petroleum ether. Pure fractions were evaporated to dryness to afford 2-(3-bromo-6-fluoro-2-methylphenyl)-1,3-dioxolane (5.00 g, 87%) as a colourless oil. $^1$H NMR (300 MHz, CDCl₃, 27° C.) 2.50 (3H, s), 3.94-4.14 (2H, m), 4.10-4.30 (2H, m), 6.16 (1H, s), 6.74-6.87 (1H, m), 7.47-7.58 (1H, m).

Tert-butyl (2-(3-(1,3-dioxolan-2-yl)-4-fluoro-2-methylphenoxy)ethyl)(3-fluoropropyl)carbamate

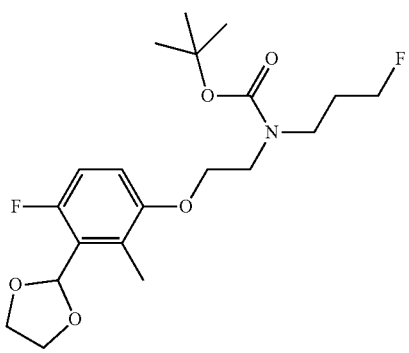 [SMILES: Cc1c(OCCN(CCCF)C(=O)OC(C)(C)C)ccc(F)c1C1OCCO1]

Tert-butyl (3-fluoropropyl)(2-hydroxyethyl)carbamate (5.08 g, 23.0 mmol) was added to 2-(3-bromo-6-fluoro-2-methylphenyl)-1,3-dioxolane (5.00 g, 19.2 mmol), Cs₂CO₃ (18.72 g, 57.45 mmol) and rockphos 3$^{rd}$ generation precatalyst (0.801 g, 0.96 mmol) in toluene (12 mL) under nitrogen. The resulting mixture was stirred at 80° C. for 16 hours. The solvent was removed under reduced pressure then the reaction mixture was diluted with EtOAc (50 mL), and washed sequentially with saturated aqueous NaHCO₃ (2×20 mL), water (20 mL), and saturated aqueous sodium chloride (20 mL). The organic layer was dried over Na₂SO₄, filtered and evaporated. The crude product was purified by flash C18-flash chromatography, elution gradient 0 to 80% MeCN in water. Pure fractions were evaporated to dryness to afford tert-butyl (2-(3-(1,3-dioxolan-2-yl)-4-fluoro-2-methylphenoxy)ethyl)(3-fluoropropyl)carbamate (4.80 g, 62%) as a yellow gum. $^1$H NMR (300 MHz, CDCl₃, 27° C.) 1.45 (9H, s), 1.85-2.11 (2H, m), 2.29 (3H, s), 3.46 (2H, t), 3.57-3.64 (2H, m), 3.94-4.09 (4H, m), 4.17-4.29 (2H, m), 4.40 (1H, t), 4.55 (1H, t), 6.15 (1H, s), 6.70-6.90 (2H, m). m/z (ES+), [M−tBu]+=346.

Tert-butyl (2-(4-fluoro-3-formyl-2-methylphenoxy)ethyl)(3-fluoropropyl)carbamate

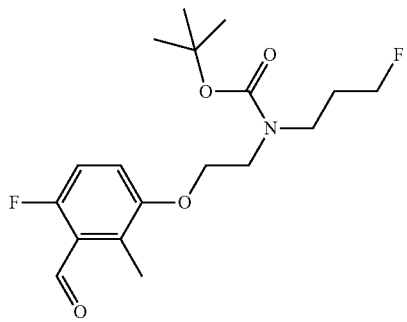 [SMILES: Cc1c(OCCN(CCCF)C(=O)OC(C)(C)C)ccc(F)c1C=O]

4-Methylbenzenesulfonic acid (0.244 g, 1.42 mmol) was added to tert-butyl (2-(3-(1,3-dioxolan-2-yl)-4-fluoro-2-methylphenoxy)ethyl)(3-fluoropropyl)carbamate (5.70 g, 14.2 mmol) in acetone (80 mL). The resulting mixture was stirred at room temperature for 16 hours. The reaction mixture was poured into saturated aqeuous NaHCO₃ (50 mL), extracted with EtOAc (2×50 mL), then the organic layer was dried over Na₂SO₄, filtered and is evaporated to afford a yellow gum which was purified by flash silica chromatography, elution gradient 0 to 20% EtOAc in petroleum ether. Product containing fractions were evaporated to dryness to afford tert-butyl (2-(4-fluoro-3-formyl-2-methylphenoxy)ethyl)(3-fluoropropyl)carbamate (3.40 g, 67%) as a yellow gum, which solidified on standing. $^1$H NMR (400 MHz, CDCl₃, 27° C.) 1.47 (9H, s), 1.86-2.10 (2H, m), 2.50 (3H, s), 3.48 (2H, t), 3.60-3.74 (2H, m), 3.99-4.15 (2H, m), 4.44 (1H, t), 4.55 (1H, t), 6.81-7.16 (2H, m), 10.51 (1H, s). m/z (ES+), [M−Boc]=258.

Methyl 3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)propanoate

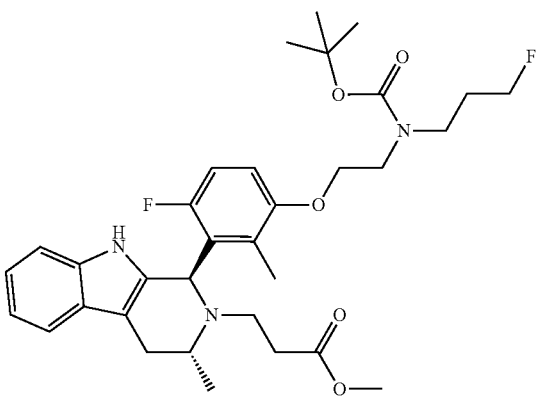 [SMILES: COC(=O)CCN1[C@H](c2c(F)ccc(OCCN(CCCF)C(=O)OC(C)(C)C)c2C)c2[nH]c3ccccc3c2C[C@H]1C]

Methyl (R)-3-((1-(1H-indol-3-yl)propan-2-yl)amino)propanoate (260 mg, 1.0 mmol) and tert-butyl (2-(4-fluoro-3-formyl-2-methylphenoxy)ethyl)(3-fluoropropyl)carbamate (357 mg, 1.00 mmol) were heated in toluene (3.60 mL)/acetic acid (0.40 mL) to 100° C. for 6 hours. After cooling, the volatiles were evaporated and the residue was dissolved in DCM (20 mL) and washed with saturated aqueous NaHCO$_3$ (20 mL). The aqueous layer was extracted with DCM (20 mL), then the combined organics were dried over Na$_2$SO$_4$ and evaporated. The crude product was purified by flash silica chromatography, elution gradient 0 to 40% EtOAc in heptane. Product containing fractions were evaporated to dryness to afford methyl 3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)propanoate (301 mg, 50%) as a beige solid. m/z: ES+ [M+H]+ 600.

Methyl 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoate

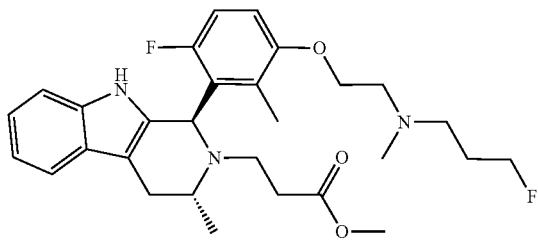 [SMILES: COC(=O)CCN1[C@H](c2c(F)ccc(OCCN(C)CCCF)c2C)c2[nH]c3ccccc3c2C[C@H]1C]

Methyl 3-((1R,3R)-1-(3-(2-((tert-butoxycarbonyl)(3-fluoropropyl)amino)ethoxy)-6-fluoro-2-methylphenyl)-3-methyl-1,3,4,9-tetrahydro-2H-pyrido[3,4-b]indol-2-yl)propanoate (280 mg, 0.47 mmol) was stirred in formic acid (2.33 mL) at 40° C. for 1 hour. The volatiles were evaporated, then the residue was dissolved in DCM (20 mL) and washed with saturated aqueous NaHCO$_3$ (20 mL). The aqueous layer was extracted with DCM (10 mL), then the combined organics were dried over Na$_2$SO$_4$ and evaporated to a volume of ~10 mL. To this solution was added 37% formaldehyde solution (71.9 mg, 0.70 mmol), followed by sodium triacetoxyborohydride (97 mg, 0.70 mmol). The reaction was stirred at room temperature for 1 hour, then was diluted with DCM (10 mL) and washed with saturated aqueous NaHCO$_3$ solution (20 mL). The aqueous layer was extracted with DCM (20 mL), then the combined organics were dried over Na$_2$SO$_4$ and evaporated. The crude product was purified by preparative HPLC (Waters XSelect CSH C18 ODB column, 5p silica, 30 mm diameter, 100 mm length), using decreasingly polar mixtures of water (containing 1% NH$_3$) and MeCN as eluents. Fractions containing the desired compound were evaporated to dryness to afford methyl 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoate (180 mg, 75%) as a beige solid. $^1$H NMR (500 MHz, CDCl$_3$, 27° C.) 1.00 (3H, d), 1.72 (2H, ddd), 1.78 (3H, s), 2.11-2.19 (2H, m), 2.19 (3H, s), 2.44 (2H, t), 2.59 (1H, d), 2.61-2.68 (3H, m), 2.79 (1H, dt), 3.02 (1H, ddd), 3.44 (3H, s), 3.49-3.56 (1H, m), 3.87 (2H, tt), 4.30 (1H, t), 4.39 (1H, t), 5.24 (1H, s), 6.68 (1H, dd), 6.80 (1H, t), 6.91-7.00 (2H, m), 7.00-7.07 (1H, m), 7.23 (1H, s), 7.38 (1H, dd). m/z: ES+ [M+H]+ 514.

Examples 16-56, 58-116, 118-120, 122-123, 125, 128-142, 144, 146-151 and 153-154 (Table G below) were prepared using methods analogous to those described above.

TABLE G

| Example | Structure | Name | 1H NMR | LCMS [M + H]+ |
|---|---|---|---|---|
| 16 | 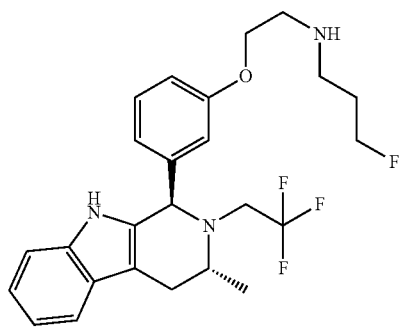 [SMILES: C[C@@H]1Cc2c([nH]c3ccccc23)[C@@H](c2cccc(OCCNCCCF)c2)N1CC(F)(F)F] | 3-fluoro-N-(2-(3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | $^1$H NMR (300 MHz, DMSO-d$_6$, 27° C.) 1.11 (3H, d), 1.59-1.92 (3H, m), 2.54-2.71 (4H, m), 2.82 (2H, br t), 2.91-3.05 (1H, m), 3.07-3.20 (1H, m), 3.57 (1H, dq), 3.94 (2H, br t), 4.47 (2H, dt), 4.97 (1H, s), 6.74 (1H, br s), 6.79-6.89 (2H, m), 6.95-7.02 (1H, m), 7.04-7.11 (1H, m), 7.25 (1H, t), 7.30 (1H, d), 7.45 (1H, d), 10.83 (1H, s). | 464 |

TABLE G-continued

| Example | Structure | Name | 1H NMR | LCMS [M + H]+ |
|---|---|---|---|---|
| 17 | 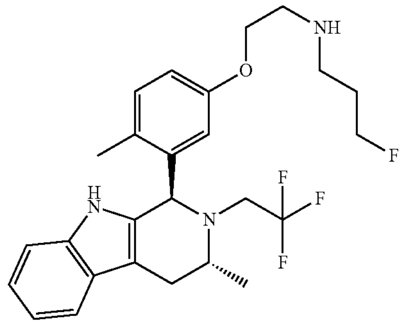 [SMILES: Cc1ccc(OCCNCCCF)cc1[C@@H]1c2[nH]c3ccccc3c2C[C@@H](C)N1CC(F)(F)F] | 3-fluoro-N-(2-(4-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.07 (3H, d), 1.52-1.83 (3H, m), 2.34 (3H, s), 2.52-2.59 (2H, m), 2.63 (1H, br dd), 2.69-2.83 (3H, m), 2.99 (1H, dq), 3.28-3.37 (1H, m), 3.47 (1H, dq), 3.82 (2H, t), 4.43 (2H, dt), 5.09 (1H, s), 6.22 (1H, br s), 6.78 (1H, dd), 6.95-7.02 (1H, m), 7.02-7.08 (1H, m), 7.12 (1H, d), 7.22-7.29 (1H, m), 7.45 (1H, d), 10.57 (1H, s). | 478 |
| 18 | 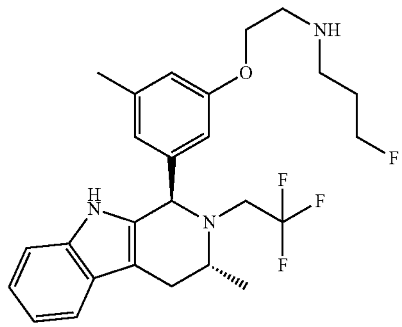 [SMILES: Cc1cc(OCCNCCCF)cc([C@@H]2c3[nH]c4ccccc4c3C[C@@H](C)N2CC(F)(F)F)c1] | 3-fluoro-N-(2-(3-methyl-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.11 (3H, d), 1.64-1.88 (3H, m), 2.23 (3H, s), 2.53-2.70 (4H, m), 2.81 (2H, t), 2.89-3.06 (1H, m), 3.07-3.23 (1H, m), 3.55 (1H, dq), 3.92 (2H, t), 4.47 (2H, dt), 4.92 (1H, s), 6.54-6.60 (1H, m), 6.60-6.64 (1H, m), 6.66-6.71 (1H, m), 6.95-7.02 (1H, m), 7.03-7.11 (1H, m), 7.27-7.33 (1H, m), 7.44 (1H, d), 10.80 (1H, s). | 478 |
| 19 | 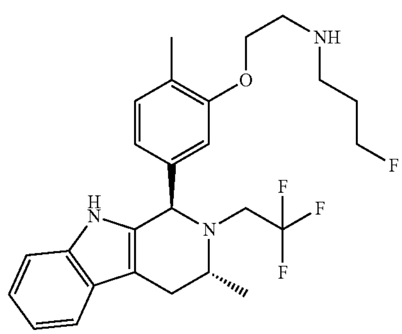 [SMILES: Cc1ccc([C@@H]2c3[nH]c4ccccc4c3C[C@@H](C)N2CC(F)(F)F)cc1OCCNCCCF] | 3-fluoro-N-(2-(2-methyl-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.11 (3H, d), 1.61-1.90 (3H, m), 2.13 (3H, s), 2.55-2.72 (4H, m), 2.86 (2H, t), 2.92-3.07 (1H, m), 3.09-3.24 (1H, m), 3.54 (1H, dq), 3.90 (2H, t), 4.49 (2H, dt), 4.95 (1H, s), 6.63 (1H, d), 6.91 (1H, s), 6.94-7.01 (1H, m), 7.02-7.10 (2H, m), 7.29 (1H, d), 7.44 (1H, d), 10.77 (1H, s). | 478 |
| 20 | 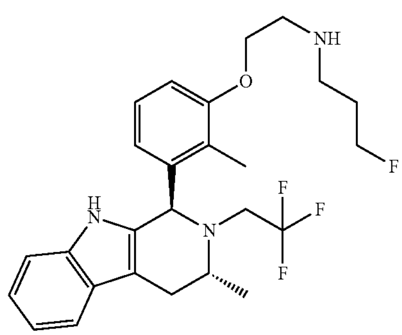 [SMILES: Cc1c(OCCNCCCF)cccc1[C@@H]1c2[nH]c3ccccc3c2C[C@@H](C)N1CC(F)(F)F] | 3-fluoro-N-(2-(2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.07 (3H, d), 1.65-1.96 (3H, m), 2.29 (3H, s), 2.56-2.86 (4H, m), 2.91 (2H, t), 2.90-3.10 (1H, m), 3.28-3.37 (1H, m), 3.37-3.57 (1H, m), 4.00 (2H, t), 4.52 (2H, dt), 5.15 (1H, s), 6.29 (1H, br d), 6.90 (1H, d), 6.94-7.09 (3H, m), 7.20-7.28 (1H, m), 7.44 (1H, d), 10.53 (1H, s). | 478 |

TABLE G-continued

| Example | Structure | Name | 1H NMR | LCMS [M + H]+ |
|---|---|---|---|---|
| 21 | 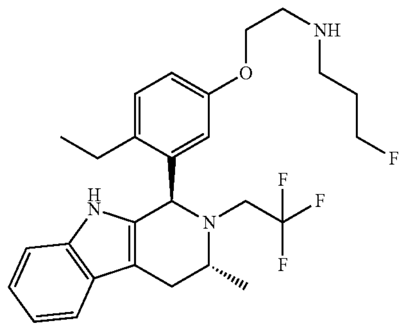 [SMILES: CCc1ccc(OCCNCCCF)cc1[C@@H]1c2[nH]c3ccccc3c2C[C@@H](C)N1CC(F)(F)F] | N-(2-(4-ethyl-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | $^1$H NMR (300 MHz, DMSO-d$_6$, 27° C.) 1.07 (3H, d), 1.15 (3H, t), 1.61-1.78 (3H, m), 2.52-2.56 (2H, m), 2.63-2.85 (6H, m), 2.90-3.10 (1H, m), 2.90-3.10 (1H, m), 3.39-3.58 (1H, m), 3.81 (2H, t), 4.42 (2H, dt), 5.16 (1H, s), 6.14 (1H, br s), 6.84 (1H, dd), 6.96-7.02 (1H, m), 7.02-7.08 (1H, m), 7.17 (1H, d), 7.24-7.28 (1H, m), 7.46 (1H, d), 10.61 (1H, s). | 492 |
| 22 | 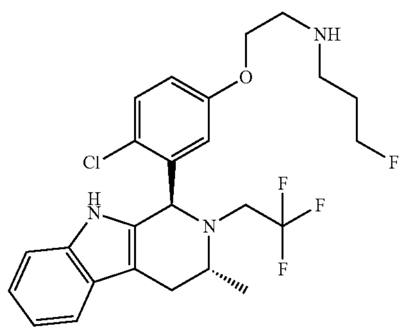 [SMILES: C[C@@H]1Cc2c([nH]c3ccccc23)[C@@H](c2cc(OCCNCCCF)ccc2Cl)N1CC(F)(F)F] | N-(2-(4-chloro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | $^1$H NMR (300 MHz, DMSO-d$_6$, 27° C.) 1.10 (3H, d), 1.60-1.77 (3H, m), 2.58-2.77 (3H, m), 2.83 (1H, dd), 2.92-3.10 (1H, m), 3.31-3.41 (1H, m), 3.51 (1H, br dq), 3.83 (2H, t), 4.41 (2H, dt), 5.32 (1H, s), 6.30 (1H, d), 6.94 (1H, dd), 6.96-7.03 (1H, m), 7.03-7.09 (1H, m), 7.21-7.29 (1H, m), 7.42 (1H, d), 7.47 (1H, d), 10.62 (1H, s). (Two hydrogen multiplet obscured by DMSO). | 498 |
| 23 | 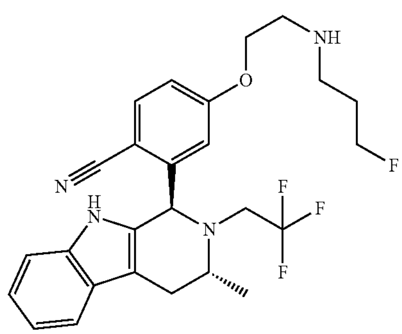 [SMILES: C[C@@H]1Cc2c([nH]c3ccccc23)[C@@H](c2cc(OCCNCCCF)ccc2C#N)N1CC(F)(F)F] | 4-(2-((3-fluoropropyl)amino)ethoxy)-2-((1R,3R)-3-methyl-2-(2,2,2-trifluoroethyl)-2,3,4,9-tetrahydro-1H-pyrido[3,4-b]indol-1-yl)benzonitrile | $^1$H NMR (300 MHz, Methanol-d4, 27° C.) 1.08 (3H, d), 1.59-1.91 (2H, m), 2.51-2.70 (3H, m), 2.81 (2H, t), 2.80-2.96 (1H, m), 3.04 (1H, dd), 3.27-3.38 (1H, obsc m), 3.40-3.52 (1H, m), 3.95 (2H, t), 4.35 (2H, dt), 5.11 (1H, s), 6.79 (1H, d), 6.85-7.00 (3H, m), 7.08-7.16 (1H, m), 7.27-7.42 (1H, m), 7.60 (1H, d). (2 exchangeables not observed). | 489 |
| 24 | 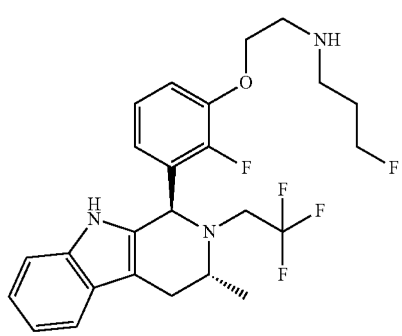 | 3-fluoro-N-(2-(2-fluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | $^1$H NMR (300 MHz, DMSO-d$_6$, 27° C.) 1.09 (3H, d), 1.66-1.95 (3H, m), 2.55-2.80 (4H, m), 2.92 (2H, t), 2.91-3.01 (1H, m), 3.17-3.32 (1H, m), 3.53 (1H, dq), 4.09 (2H, t), 4.52 (2H, dt), 5.32 (1H, s), 6.18-6.26 (1H, m), 6.89-7.17 (4H, m), 7.20-7.30 (1H, m), 7.46 (1H, d), 10.69 (1H, s). | 482 |

TABLE G-continued

| Example | Structure | Name | 1H NMR | LCMS [M + H]+ |
|---|---|---|---|---|
| 25 | 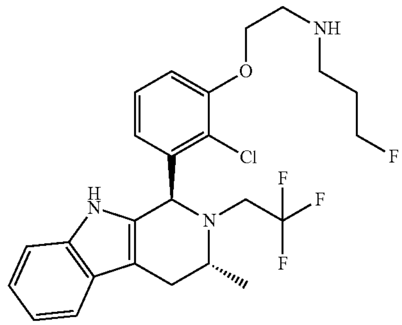 [SMILES: C[C@@H]1Cc2c([nH]c3ccccc23)[C@@H](c2cccc(OCCNCCCF)c2Cl)N1CC(F)(F)F] | N-(2-(2-chloro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | ¹H NMR (300 MHz, DMSO-d₆, 27° C.) 1.09 (3H, d), 1.67-1.96 (3H, m), 2.64 (1H, d), 2.72 (2H, t), 2.83 (1H, br dd), 2.90-3.08 (3H, m), 3.33-3.42 (1H, m), 3.51 (1H, dq), 4.02-4.19 (2H, m), 4.53 (2H, dt), 5.41 (1H, s), 6.40 (1H, dd), 6.94-7.17 (4H, m), 7.20-7.26 (1H, m), 7.46 (1H, d), 10.59 (1H, s). | 498 |
| 26 | 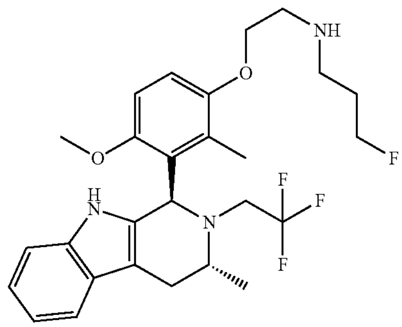 [SMILES: COc1ccc(OCCNCCCF)c(C)c1[C@@H]1c2[nH]c3ccccc3c2C[C@@H](C)N1CC(F)(F)F] | 3-fluoro-N-(2-(4-methoxy-2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (500 MHz, CDCl₃, 27° C.) 1.17 (3H, d), 1.78-1.84 (1H, m), 1.86-1.89 (4H, m), 2.70 (1H, d), 2.76 (2H, t), 2.84-2.99 (3H, m), 3.12 (1H, dt), 3.24 (1H, ddd), 3.66-3.74 (1H, m), 3.84 (3H, s), 3.92-4.01 (2H, m), 4.44 (1H, t), 4.53 (1H, t), 5.73 (1H, s), 6.76 (1H, d), 6.85 (1H, d), 7.05-7.11 (2H, m), 7.15-7.19 (1H, m), 7.24 (1H, s), 7.48 (1H, dt). (1 exchangeable not observed). | 508 |
| 27 | 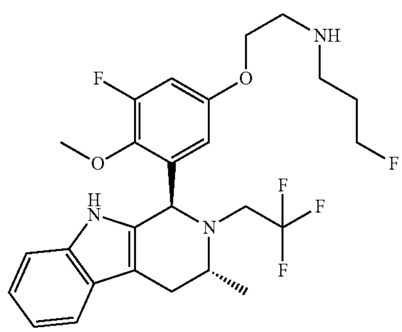 [SMILES: COc1c(F)cc(OCCNCCCF)cc1[C@@H]1c2[nH]c3ccccc3c2C[C@@H](C)N1CC(F)(F)F] | 3-fluoro-N-(2-(3-fluoro-4-methoxy-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.11 (3H, d), 1.55-1.81 (3H, m), 2.56-2.82 (4H, m), 2.86-3.08 (1H, m), 3.35-3.25 (1H, m), 3.51 (1H, dq), 3.80 (2H, t), 3.87 (3H, s), 4.41 (2H, dt), 5.32 (1H, s), 5.90 (1H, dd), 6.91 (1H, dd), 6.96-7.03 (1H, m), 7.03-7.10 (1H, m), 7.23-7.29 (1H, m), 7.46 (1H, d), 10.64 (1H, s). (Two hydrogen multiplet obscured by DMSO). | 512 |
| 28 | 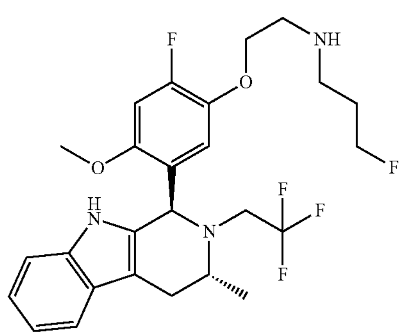 [SMILES: COc1cc(F)c(OCCNCCCF)cc1[C@@H]1c2[nH]c3ccccc3c2C[C@@H](C)N1CC(F)(F)F] | 3-fluoro-N-(2-(2-fluoro-4-methoxy-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (300 MHz, DMSO-d₆, 27° C.) 1.09 (3H, d), 1.51-1.78 (3H, m), 2.41-2.48 (2H, m), 2.54-2.69 (3H, m), 2.77-3.05 (2H, m), 3.33-3.55 (2H, m), 3.63-3.81 (2H, m), 3.84 (3H, s), 4.39 (2H, dt), 5.32 (1H, s), 6.44 (1H, d), 6.92-7.00 (1H, m), 7.00-7.06 (1H, m), 7.07 (1H, d), 7.19-7.26 (1H, m), 7.44 (1H, d), 10.47 (1H, s). | 512 |

TABLE G-continued

| Example | Structure | Name | 1H NMR | LCMS [M + H]+ |
|---|---|---|---|---|
| 29 | 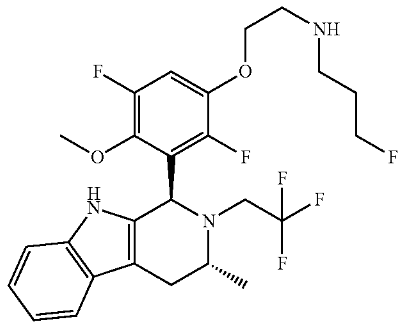 [SMILES: COc1c(F)cc(OCCNCCCF)c(F)c1[C@@H]1c2[nH]c3ccccc3c2C[C@@H](C)N1CC(F)(F)F] | N-(2-(2,5-difluoro-4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | ¹H NMR (500 MHz, CDCl₃, 27° C.) 1.18 (3H, d), 1.84 (2H, dddd), 2.64 (1H, ddd), 2.76 (2H, t), 2.95 (2H, dd), 2.97-3.05 (1H, m), 3.11 (1H, ddd), 3.25 (1H, dq), 3.60-3.68 (1H, m), 3.69 (3H, d), 4.01 (2H, td), 4.44 (1H, t), 4.54 (1H, t), 5.40 (1H, s), 6.76 (1H, dd), 7.05-7.14 (2H, m), 7.18-7.22 (1H, m), 7.49-7.52 (1H, m), 7.63 (1H, s). (1 exchangeable not observed) | 530 |
| 30 | 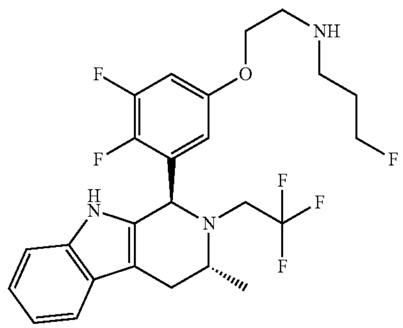 [SMILES: C[C@@H]1Cc2c([nH]c3ccccc23)[C@@H](c2cc(OCCNCCCF)cc(F)c2F)N1CC(F)(F)F] | N-(2-(3,4-difluoro-5-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | ¹H NMR (500 MHz, CDCl₃, 27° C.) 1.17 (3H, d), 1.82 (2H, dddd), 2.58 (1H, ddd), 2.72 (2H, t), 2.87 (2H, t), 2.88-3.01 (2H, m), 3.25 (1H, dd), 3.42-3.53 (1H, m), 3.83 (2H, t), 4.41 (1H, t), 4.51 (1H, t), 5.29 (1H, s), 6.30 (1H, dt), 6.64 (1H, ddd), 7.12 (1H, td), 7.14-7.21 (1H, m), 7.25 (1H, dd), 7.49-7.58 (1H, m), 7.87 (1H, s). (1 exchangeable not observed) | 500 |
| 31 | 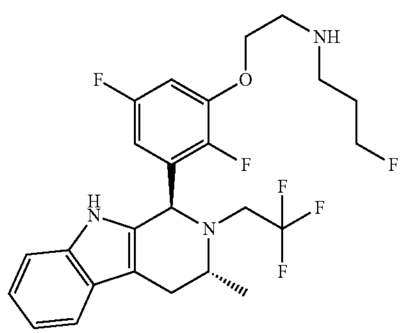 [SMILES: C[C@@H]1Cc2c([nH]c3ccccc23)[C@@H](c2cc(F)cc(OCCNCCCF)c2F)N1CC(F)(F)F] | N-(2-(2,5-difluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | ¹H NMR (500 MHz, CDCl₃, 27° C.) 1.19 (3H, d), 1.92 (2H, dddd), 2.59 (1H, ddd), 2.85 (2H, t), 2.91 (1H, dd), 2.96 (1H, dd), 3.06 (2H, td), 3.27 (1H, dq), 3.47-3.52 (1H, m), 4.11 (2H, td), 4.51 (1H, t), 4.60 (1H, t), 5.31 (1H, s), 6.32 (1H, ddd), 6.62 (1H, dd), 7.12 (1H, td), 7.15-7.20 (1H, m), 7.25-7.30 (1H, m), 7.53 (1H, d), 7.88 (1H, s). (1 exchangeable not observed) | 500 |
| 32 | 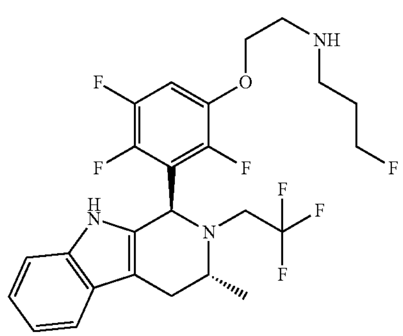 [SMILES: C[C@@H]1Cc2c([nH]c3ccccc23)[C@@H](c2c(F)c(F)cc(OCCNCCCF)c2F)N1CC(F)(F)F] | 3-fluoro-N-(2-(2,4,5-trifluoro-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (500 MHz, CDCl₃, 27° C.) 1.18 (3H, d), 1.86 (2H, dddd), 2.65 (1H, ddd), 2.79 (2H, t), 2.86-3.02 (3H, m), 3.08 (1H, ddd), 3.29 (1H, dq), 3.59 (1H, d), 4.01-4.11 (2H, m), 4.47 (1H, t), 4.56 (1H, t), 5.38 (1H, s), 6.83 (1H, dt), 7.11 (1H, td), 7.13-7.19 (1H, m), 7.21-7.25 (1H, m), 7.49-7.54 | 518 |

TABLE G-continued

| Example | Structure | Name | 1H NMR | LCMS [M + H]+ |
|---|---|---|---|---|
| | | | (1H, m), 7.55 (1H, s). (1 exchangeable not observed) | |
| 33 | 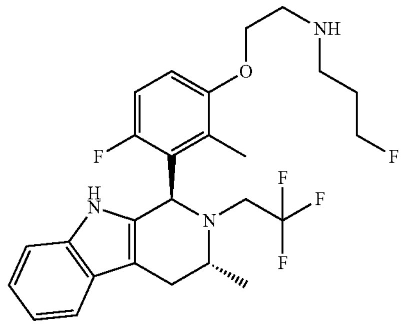 [SMILES: Cc1c(OCCNCCCF)ccc(F)c1[C@@H]1c2[nH]c3ccccc3c2C[C@@H](C)N1CC(F)(F)F] | 3-fluoro-N-(2-(4-fluoro-2-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | $^1$H NMR (500 MHz, CDCl$_3$, 27° C.) 1.17 (3H, d), 1.74-1.96 (5H, m), 2.66-2.81 (3H, m), 2.85-3.04 (3H, m), 3.13-3.31 (2H, m), 3.66-3.77 (1H, m), 3.98 (2H, ddt), 4.43 (1H, t), 4.52 (1H, t), 5.46 (1H, s), 6.82 (1H, dd), 6.92 (1H, t), 7.06-7.15 (2H, m), 7.16-7.23 (1H, m), 7.38 (1H, s), 7.46-7.56 (1H, m). (1 exchangeable not observed). | 496 |
| 34 | 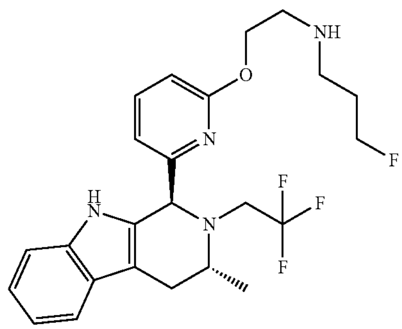 [SMILES: C[C@@H]1Cc2c([nH]c3ccccc23)[C@@H](c2cccc(OCCNCCCF)n2)N1CC(F)(F)F] | 3-fluoro-N-(2-((6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | $^1$H NMR (500 MHz, DMSO-d$_6$, 27° C.) 1.19 (3H, d), 1.62-1.78 (2H, m), 2.52-2.62 (3H, m), 2.63-2.67 (1H, m), 2.72-2.83 (2H, m), 3.00-3.13 (1H, m), 3.25-3.35 (2H, m), 3.54-3.69 (1H, m), 4.21-4.32 (2H, m), 4.46 (2H, dt), 4.96 (1H, s), 6.67 (1H, d), 6.92-6.96 (1H, m), 7.00 (1H, d), 7.03-7.08 (1H, m), 7.30 (1H, d), 7.41 (1H, d), 7.67 (1H, t), 10.67 (1H, s) | 465 |
| 35 | 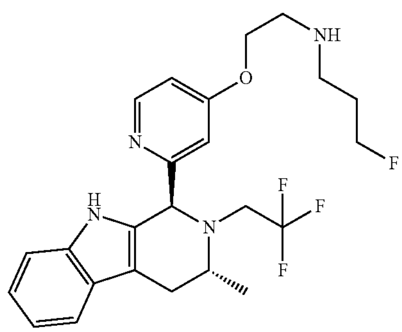 [SMILES: C[C@@H]1Cc2c([nH]c3ccccc23)[C@@H](c2cc(OCCNCCCF)ccn2)N1CC(F)(F)F] | 3-fluoro-N-(2-((2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)propan-1-amine | $^1$H NMR (500 MHz, DMSO-d$_6$, 27° C.) 1.18 (3H, d), 1.69-1.81 (2H, m), 1.86 (1H, br s), 2.54-2.66 (4H, m), 2.86 (2H, t), 2.99-3.11 (1H, m), 3.23-3.30 (1H, m), 3.57-3.67 (1H, m), 4.05 (2H, br t), 4.47 (2H, dt), 4.99 (1H, s), 6.90 (1H, dd), 6.92-6.96 (1H, m), 6.98 (1H, br d), 7.00-7.04 (1H, m), 7.30 (1H, d), 7.40 (1H, d), 8.33 (1H, d), 10.67 (1H, s) | 465 |
| 36 | 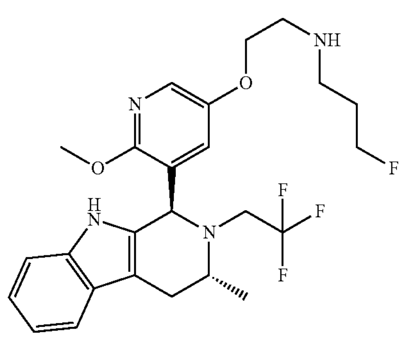 [SMILES: COc1ncc(OCCNCCCF)cc1[C@@H]1c2[nH]c3ccccc3c2C[C@@H](C)N1CC(F)(F)F] | 3-fluoro-N-(2-((6-methoxy-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine | $^1$H NMR (300 MHz, DMSO-d$_6$, 27° C.) 1.09 (3H, d), 1.62-1.77 (3H, m), 2.52-2.64 (3H, m), 2.70-2.80 (3H, m), 2.99 (1H, br dq) 3.14-3.28 (1H, m) 3.51 (1H, dq), 3.87 (2H, t), 3.91 (3H, s), 4.41 (2H, dt), 5.26 (1H, s), 6.52 (1H, d), 6.94-7.02 (1H, m), 7.02-7.09 (1H, m), 7.21-7.26 (1H, m), 7.46 | 495 |

TABLE G-continued

| Example | Structure | Name | 1H NMR | LCMS [M + H]+ |
|---|---|---|---|---|
| | | | (1H, d), 7.81 (1H, d), 10.59 (1H, s). | |
| 37 | 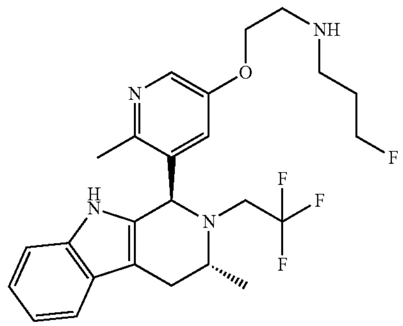 [SMILES: Cc1ncc(OCCNCCCF)cc1[C@@H]1c2[nH]c3ccccc3c2C[C@@H](C)N1CC(F)(F)F] | 3-fluoro-N-(2-((6-methyl-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine | ¹H NMR (500 MHz, CDCl₃, 27° C.) 1.15 (3H, d), 1.74-1.91 (2H, m), 2.60-2.69 (4H, m), 2.73 (2H, t), 2.85-3.00 (4H, m), 3.23 (1H, dq), 3.37-3.44 (1H, m), 3.89 (2H, tt), 4.43 (1H, t), 4.52 (1H, t), 5.06 (1H, s), 6.70 (1H, d), 7.11-7.21 (2H, m), 7.29 (1H, d), 7.55 (1H, d), 7.92 (1H, d), 8.57 (1H, s). (1 exchangeable not observed). | 479 |
| 38 | 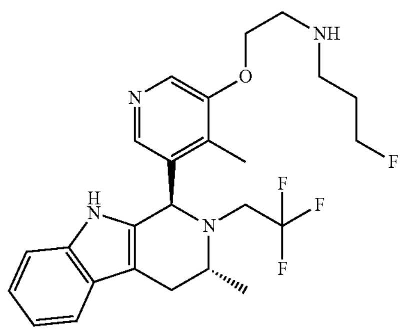 [SMILES: Cc1c(OCCNCCCF)cncc1[C@@H]1c2[nH]c3ccccc3c2C[C@@H](C)N1CC(F)(F)F] | 3-fluoro-N-(2-((4-methyl-5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine | ¹H NMR (500 MHz, CDCl₃, 27° C.) 1.16 (3H, d), 1.87 (1H, ddd), 1.92 (1H, ddd), 2.19 (3H, s), 2.63-2.71 (1H, m), 2.84 (2H, t), 2.95-3.08 (4H, m), 3.20 (1H, dt), 3.48-3.57 (1H, m), 4.10-4.22 (2H, m), 4.49 (1H, t), 4.58 (1H, t), 5.05 (1H, s), 7.10-7.19 (2H, m), 7.23-7.25 (1H, m), 7.53 (2H, d), 7.84 (1H, s), 8.17 (1H, s). (1 exchangeable not observed). | 479 |
| 39 | 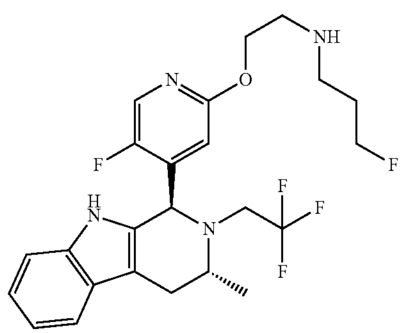 [SMILES: C[C@@H]1Cc2c([nH]c3ccccc23)[C@@H](c2cc(OCCNCCCF)ncc2F)N1CC(F)(F)F] | 3-fluoro-N-(2-((5-fluoro-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | ¹H NMR (500 MHz, CDCl₃, 27° C.) 1.20 (3H, d), 1.83 (2H, dddd), 2.54 (1H, ddd), 2.66-2.80 (3H, m), 2.83-2.99 (3H, m), 3.19-3.36 (2H, m), 4.27 (2H, td), 4.42 (1H, t), 4.52 (1H, t), 5.25 (1H, s), 6.25 (1H, d), 7.14 (1H, ddd), 7.19 (1H, ddd), 7.28 (1H, dt), 7.54 (1H, d), 7.98 (1H, d), 8.13 (1H, s). (1 exchangeable not observed) | 483 |
| 40 | 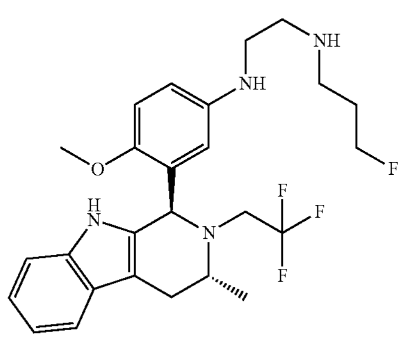 [SMILES: COc1ccc(NCCNCCCF)cc1[C@@H]1c2[nH]c3ccccc3c2C[C@@H](C)N1CC(F)(F)F] | N1-(3-fluoropropyl)-N2-(4-methoxy-3-((1R,3R)-3-methyl-2-(2,2,2-trifluoroethyl)-2,3,4,9-tetrahydro-1H-pyrido[3,4-b]indol-1-yl)phenyl)ethane-1,2-diamine | ¹H NMR (300 MHz, DMSO-d₆, 27° C.) 1.09 (3H, d), 1.61-1.74 (3H, m), 2.44-2.49 (m, 2 H), 2.53-2.64 (2H, m), 2.71-3.01 (4H, m), 3.34-3.44 (2H, m), 3.76 (3H, s), 4.42 (2H, dt), 4.96 (1H, t), 5.34 (1H, s), 6.03 (1H, d) 6.45 (1H, dd), 6.86 (1H, d), 6.93-6.99 (1H, m), 6.99-7.06 (1H, m), 7.18-7.26 (1H, m), 7.43 (1H, d), 10.52 (1H, d). (One hydrogen not | 493 |

| Example | Structure | Name | 1H NMR | LCMS [M + H]+ |
|---|---|---|---|---|
| | | | observed, obscured by DMSO) | |
| 41 | 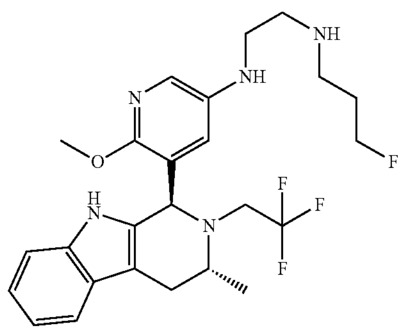 [SMILES: COc1ncc(NCCNCCCF)cc1[C@@H]1c2[nH]c3ccccc3c2C[C@@H](C)N1CC(F)(F)F] | N1-(3-fluoropropyl)-N2-(6-methoxy-5-((1R,3R)-3-methyl-2-(2,2,2-trifluoroethyl)-2,3,4,9-tetrahydro-1H-pyrido[3,4-b]indol-1-yl)pyridin-3-yl)ethane-1,2-diamine | ¹H NMR (300 MHz, DMSO-d₆, 27° C.) 1.09 (3H, d), 1.58-1.78 (3H, m), 2.54-2.64 (3H, m), 2.70-2.78 (1H, m), 2.85-3.04 (3H, m), 3.24-3.35 (1H, obsc m), 3.41-3.57 (1H, m), 3.84 (3H, s), 4.43 (2H, dt), 5.10 (1H, t), 5.24 (1H, s), 6.43 (1H, d), 6.91-6.99 (1H, m), 6.99-7.06 (1H, m), 7.18-7.27 (1H, m), 7.38 (1H, d), 7.45 (1H, d), 10.58 (1H, s). (Two hydrogen not observed, obscured by DMSO) | 494 |
| 42 | 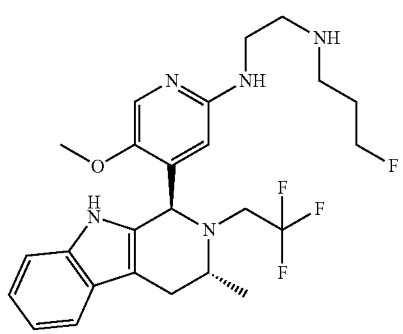 [SMILES: COc1cnc(NCCNCCCF)cc1[C@@H]1c2[nH]c3ccccc3c2C[C@@H](C)N1CC(F)(F)F] | N1-(3-fluoropropyl)-N2-(5-methoxy-4-((1R,3R)-3-methyl-2-(2,2,2-trifluoroethyl)-2,3,4,9-tetrahydro-1H-pyrido[3,4-b]indol-1-yl)pyridin-2-yl)ethane-1,2-diamine | ¹H NMR (300 MHz, DMSO-d₆, 27° C.) 1.11 (3H, d), 1.58 (1H, br d), 1.60-1.82 (2H, m), 2.52-2.74 (6H, m), 2.84-3.05 (1H, m), 3.07-3.21 (2H, m), 3.26-3.39 (1H, obsc m), 3.49 (1H, dq), 3.81 (3H, s), 4.44 (2H, dt), 5.25 (1H, s), 5.83 (1H, s), 6.00 (1H, t), 6.95-7.01 (1H, m), 7.01-7.09 (1H, m), 7.22-7.28 (1H, m), 7.45 (1H, d), 7.79 (1H, s), 10.61 (s, 1 H). | 494 |
| 43 | 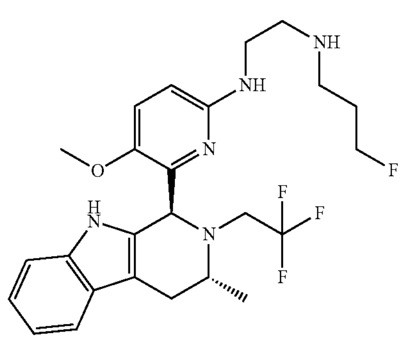 | N1-(3-fluoropropyl)-N2-(5-methoxy-6-((1S,3R)-3-methyl-2-(2,2,2-trifluoroethyl)-2,3,4,9-tetrahydro-1H-pyrido[3,4-b]indol-1-yl)pyridin-2-yl)ethane-1,2-diamine | ¹H NMR (300 MHz, DMSO-d₆, 27° C.) 1.15 (3H, d), 1.23-1.42 (1H, m), 1.55-1.68 (2H, m), 2.35-2.44 (4H, m), 2.52-2.58 (1H, m), 2.65 (1H, dd), 2.89-3.07 (3H, m), 3.48 (1H, dq), 3.77 (3H, s), 4.08-4.20 (1H, m), 4.40 (2H, dt), 5.40 (1H, s), 5.86 (1H, t), 6.40 (1H, d), 6.92-7.03 (2H, m), 7.18-7.25 (1H, m), 7.30 (1H, d), 7.39 (1H, d), 10.32 (1H, s). | 494 |

TABLE G-continued

| Example | Structure | Name | 1H NMR | LCMS [M + H]+ |
|---|---|---|---|---|
| 44 | 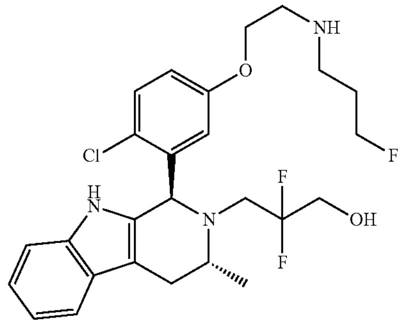 [SMILES: C[C@@H]1Cc2c([nH]c3ccccc23)[C@@H](c2cc(OCCNCCCF)ccc2Cl)N1CC(F)(F)CO] | 3-((1R,3R)-1-(2-chloro-5-(2-((3-fluoropropyl)amino)ethoxy)phenyl)-3-methyl-1,3,4,9-tetrahydro-2H-pyrido[3,4-b]indol-2-yl)-2,2-difluoropropan-1-ol | 1H NMR (500 MHz, CDCl3, 27° C.) 1.18 (3H, d), 1.78-1.89 (2H, m), 2.69 (1H, ddd), 2.74 (2H, t), 2.78-2.87 (1H, m), 2.89 (2H, ddd), 3.12-3.26 (2H, m), 3.60 (1H, ddd), 3.66-3.74 (1H, m), 3.74-3.81 (1H, m), 3.88-3.98 (2H, m), 4.44 (1H, t), 4.53 (1H, t), 5.34 (1H, s), 6.79-6.87 (2H, m), 7.09-7.17 (2H, m), 7.22 (1H, dt), 7.35 (1H, d), 7.42 (1H, s), 7.51-7.57 (1H, m). (2 exchangeables not observed). | 510 |
| 45 | 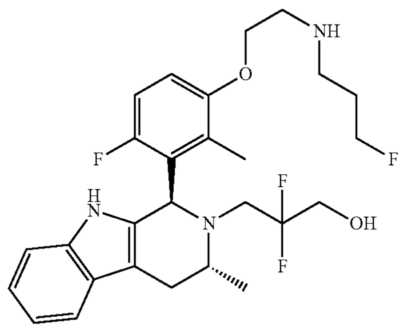 [SMILES: Cc1c(OCCNCCCF)ccc(F)c1[C@@H]1c2[nH]c3ccccc3c2C[C@@H](C)N1CC(F)(F)CO] | 2,2-difluoro-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propan-1-ol | $^1$H NMR (500 MHz, CDCl$_3$, 27° C.) 1.18 (3H, d), 1.78-2.00 (5H, m), 2.70-2.89 (4H, m), 2.98 (2H, tq), 3.13-3.24 (2H, m), 3.53-3.64 (2H, m), 3.75-3.85 (1H, m), 4.02 (2H, t), 4.46 (1H, t), 4.55 (1H, t), 5.34 (1H, s), 6.84 (1H, dd), 6.94 (1H, t), 7.07-7.15 (2H, m), 7.17-7.23 (1H, m), 7.29 (1H, s), 7.50 (1H, dd). (2 exchangeables not observed). | 508 |
| 46 | 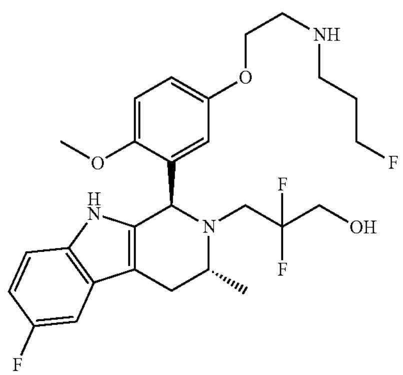 [SMILES: COc1ccc(OCCNCCCF)cc1[C@@H]1c2[nH]c3ccc(F)cc3c2C[C@@H](C)N1CC(F)(F)CO] | 2,2-difluoro-3-((1R,3R)-6-fluoro-1-(5-(2-((3-fluoropropyl)amino)ethoxy)-2-methoxyphenyl)-3-methyl-1,3,4,9-tetrahydro-2H-pyrido[3,4-b]indol-2-yl)propan-1-ol | $^1$H NMR (500 MHz, CDCl$_3$, 27° C.) 1.20 (3H, d), 1.79-1.91 (2H, m), 2.59 (1H, ddd), 2.75 (2H, t), 2.84-3.01 (4H, m), 3.12-3.23 (1H, m), 3.63-3.73 (2H, m), 3.78 (1H, q), 3.86-3.97 (5H, m), 4.44 (1H, t), 4.54 (1H, t), 5.34 (1H, s), 6.64 (1H, d), 6.81-6.92 (3H, m), 7.10-7.17 (2H, m), 7.67 (1H, s). (2 exchangeables not observed). | 524 |
| 47 | 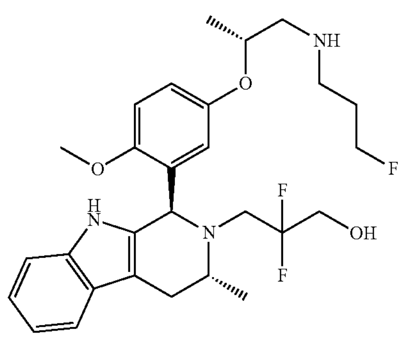 [SMILES: COc1ccc(O[C@H](C)CNCCCF)cc1[C@@H]1c2[nH]c3ccccc3c2C[C@@H](C)N1CC(F)(F)CO] | 2,2-difluoro-3-((1R,3R)-1-(5-(((R)-1-((3-fluoropropyl)amino)propan-2-yl)oxy)-2-methoxyphenyl)-3-methyl-1,3,4,9-tetrahydro-2H-pyrido[3,4-b]indol-2-yl)propan-1-ol | $^1$H NMR (DMSO-d6, 300 MHz) 1.00-1.13 (6H, m), 1.52-1.70 (2H, m), 2.38-2.46 (4H, m), 2.53-2.79 (4H, m), 2.98-3.17 (1H, m), 3.65-3.82 (5H, m), 4.06-4.19 (1H, m), 4.31 (1H, t), 4.47 (1H, t), 5.21 (1H, br s), 5.35 (1H, s), 6.11 (1H, d), 6.86 (1H, dd), 6.91-7.08 (3H, m), 7.21 (1H, d), 7.44 (1H, d), 10.56 (1H, s). (NH not observed) | 520 |

TABLE G-continued

| Example | Structure | Name | 1H NMR | LCMS [M + H]+ |
|---|---|---|---|---|
| 48 | 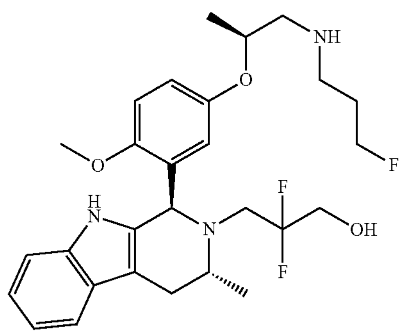 [SMILES: COc1ccc(O[C@@H](C)CNCCCF)cc1[C@@H]1c2[nH]c3ccccc3c2C[C@@H](C)N1CC(F)(F)CO] | 2,2-difluoro-3-((1R,3R)-1-(5-(((S)-1-((3-fluoropropyl)amino)propan-2-yl)oxy)-2-methoxyphenyl)-3-methyl-1,3,4,9-tetrahydro-2H-pyrido[3,4-b]indol-2-yl)propan-1-ol | $^1$H NMR (DMSO-d6, 400 MHz) 1.05-1.08 (6H, m), 1.59-1.69 (2H, m), 2.42-2.51 (4H, m), 2.52-2.77 (4H, m), 3.03-3.20 (1H,m), 3.68-3.91 (5H, m), 4.11-4.24 (1H, m), 4.34 (1H, t), 4.46 (1H, t), 5.23 (1H, t), 5.36 (1H, s), 6.12 (1H, d), 6.86 (1H, dd), 6.93-7.08 (3H, m), 7.22 (1H, d), 7.45 (1H, d), 10.58 (1H, s). (NH not observed) | 520 |
| 49 | 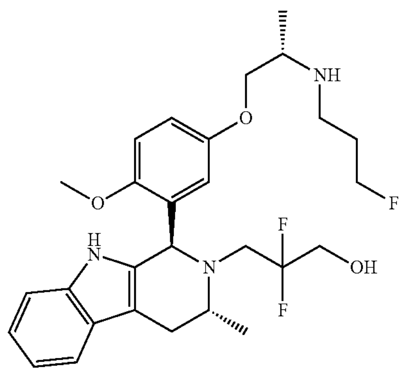 [SMILES: COc1ccc(OC[C@H](C)NCCCF)cc1[C@@H]1c2[nH]c3ccccc3c2C[C@@H](C)N1CC(F)(F)CO] | 2,2-difluoro-3-((1R,3R)-1-(5-((S)-2-((3-fluoropropyl)amino)propoxy)-2-methoxyphenyl)-3-methyl-1,3,4,9-tetrahydro-2H-pyrido[3,4-b]indol-2-yl)propan-1-ol | 1H NMR (Methanol-d4, 300 MHz) 1.16 (3H, d), 1.31 (3H, d), 1.83-2.08 (2H, m), 2.63 (1H, dd), 2.73-2.91 (2H, m), 2.94-3.31 (3H, m), 3.40-3.58 (2H, m), 3.69-3.98 (6H, m), 4.04 (1H, dd), 4.39 (1H, t), 4.55 (1H, t), 5.49 (1H, s), 6.47 (1H, d), 6.93 (1H, dd), 6.98-7.12 (3H, m), 7.24 (1H, d), 7.47 (1H, d), 8.54 (1H, s). (NH and OH not observed) | 520 |
| 50 | 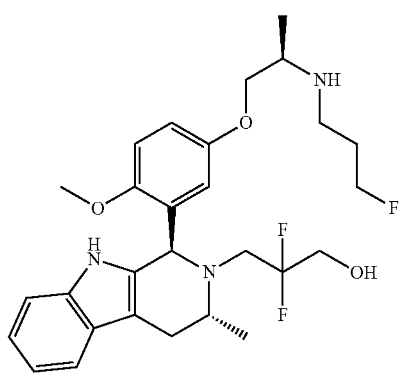 [SMILES: COc1ccc(OC[C@@H](C)NCCCF)cc1[C@@H]1c2[nH]c3ccccc3c2C[C@@H](C)N1CC(F)(F)CO] | 2,2-difluoro-3-((1R,3R)-1-(5-((R)-2-((3-fluoropropyl)amino)propoxy)-2-methoxyphenyl)-3-methyl-1,3,4,9-tetrahydro-2H-pyrido[3,4-b]indol-2-yl)propan-1-ol | 1H NMR (Methanol-d4, 300 MHz) 1.16 (3H, d), 1.31 (3H, d), 1.86-2.10 (2H, m), 2.63 (1H, dd), 2.68-2.91 (2H, m), 2.97-3.32 (3H, m), 3.39-3.57 (2H, m), 3.70-3.96 (6H, m), 4.05 (1H, dd), 4.39 (1H, t), 4.55 (1H, t), 5.49 (1H, s), 6.47 (1H, d), 6.93 (1H, dd), 6.99-7.12 (3H, m), 7.25 (1H, d), 7.47 (1H, d), 8.53 (1H, s). (NH and OH not observed) | 520 |
| 51 | 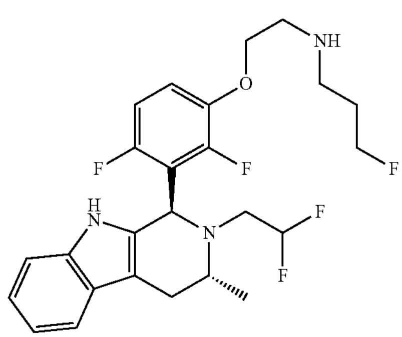 [SMILES: C[C@@H]1Cc2c([nH]c3ccccc23)[C@@H](c2c(F)ccc(OCCNCCCF)c2F)N1CC(F)F] | N-(2-(3-((1R,3R)-2-(2,2-difluoroethyl)-3-methyl-2,3,4,9-tetrahydro-1H-pyrido[3,4-b]indol-1-yl)-2,4-difluorophenoxy)ethyl)-3-fluoropropan-1-amine | $^1$H NMR (500 MHz, CDCl$_3$, 27° C.) 1.17 (3H, d), 1.82-1.94 (2H, m), 2.64 (1H, ddd), 2.72-2.83 (3H, m), 2.97-3.00 (2H, m), 3.02-3.12 (2H, m), 3.48-3.56 (1H, m), 4.06-4.11 (2H, m), 4.52 (2H, dt), 5.30 (1H, s), 5.67 (1H, tdd), 6.80 (1H, td), 6.92 (1H, td), 7.08-7.15 (2H, m), 7.22-7.25 (1H, m), 7.50-7.54 (2H, m). (1 exchangeable not observed). | 482 |

TABLE G-continued

| Example | Structure | Name | 1H NMR | LCMS [M + H]+ |
|---|---|---|---|---|
| 52 | 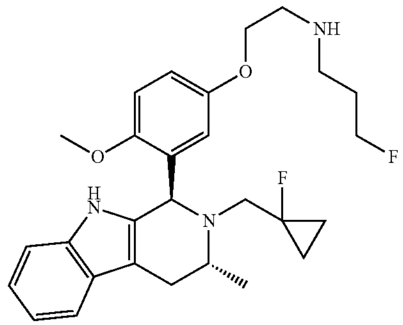 [SMILES: COc1ccc(OCCNCCCF)cc1[C@@H]1c2[nH]c3ccccc3c2C[C@@H](C)N1CC1(F)CC1] | 3-fluoro-N-(2-(3-((1R,3R)-2-((1-fluorocyclopropyl)methyl)-3-methyl-2,3,4,9-tetrahydro-1H-pyrido[3,4-b]indol-1-yl)-4-methoxyphenoxy)ethyl)propan-1-amine | ¹H NMR (300 MHz, DMSO-d₆, 27° C.) 0.55-0.68 (2H, m), 0.90-1.02 (2H, m), 1.05 (3H, dd), 1.56-1.76 (2H, m), 1.84 (1H, br s), 2.52-2.64 (4H, m), 2.67-2.78 (2H, m), 2.85 (1H, dd), 3.06 (1H, dd), 3.47-3.60 (1H, m), 3.78-3.81 (2H, m), 3.85 (3H, s), 4.42 (2H, dt), 5.35 (1H, s), 6.38 (1H, d), 6.83 (1H, dd), 6.88-7.08 (3H, m), 7.21 (1H, dd), 7.42 (1H, d), 10.27 (1H, s). | 484 |
| 53 | 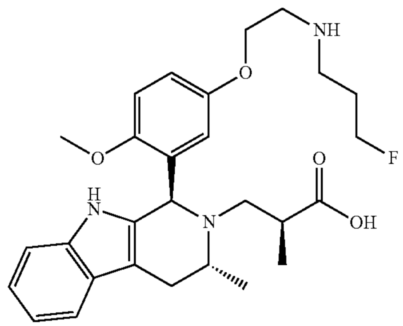 [SMILES: COc1ccc(OCCNCCCF)cc1[C@@H]1c2[nH]c3ccccc3c2C[C@@H](C)N1C[C@H](C)C(=O)O] | (S)-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)-2-methylpropanoic acid | ¹H NMR (500 MHz, CDCl₃, 27° C.) 1.13 (3H, d), 1.25 (3H, d), 1.72-1.89 (2H, m), 2.57-2.69 (2H, m), 2.71 (2H, t), 2.80-2.88 (4H, m), 2.97 (1H, s), 3.56 (1H, ddd), 3.80 (3H, s), 3.87 (2H, t), 4.42 (1H, t), 4.51 (1H, t), 5.59 (1H, s), 6.35 (1H, s), 6.82 (1H, dd), 6.85 (1H, d), 7.17 (1H, td), 7.19-7.24 (1H, m), 7.27-7.36 (1H, m), 7.56 (1H, d), 7.89 (1H, s). (2 exchangeables not observed) | 498 |
| 54 | 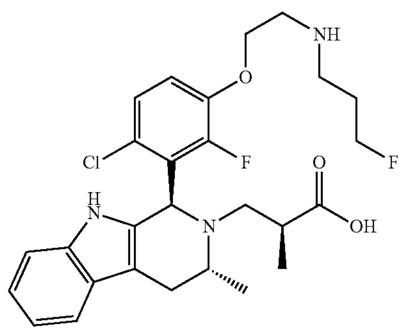 | (S)-3-((1R,3R)-1-(6-chloro-2-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid | ¹H NMR (500 MHz, CDCl₃, 27° C.) 1.01 (3H, d), 1.28 (3H, d), 1.85 (2H, dq), 2.14 (1H, br s), 2.69-2.86 (4H, m), 2.88-3.03 (3H, m), 3.15 (1H, d), 3.66 (1H, q), 4.01-4.09 (2H, m), 4.43 (1H, t), 4.52 (1H, t), 5.62 (1H, s), 6.93 (1H, t), 7.10-7.18 (3H, m), 7.24 (1H, d), 7.50-7.56 (1H, m), 7.73 (1H, s). (2 exchangeables not observed) | 520 |
| 55 | 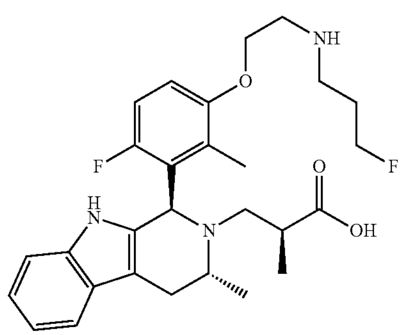 [SMILES: Cc1c(OCCNCCCF)ccc(F)c1[C@@H]1c2[nH]c3ccccc3c2C[C@@H](C)N1C[C@H](C)C(=O)O] | (S)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid | ¹H NMR (500 MHz, CDCl₃, 27° C.) 0.86 (3H, d), 1.20 (3H, d), 1.82-1.97 (5H, m), 2.68-2.80 (3H, m), 2.83 (3H, t), 2.94-3.07 (2H, m), 3.21 (1H, dd), 3.42 (2H, s), 3.54-3.65 (1H, m), 4.02 (1H, q), 4.40 (1H, t), 4.50 (1H, t), 5.47 (1H, s), 6.18 (1H, s), 6.77 (1H, dd), 6.89 (1H, t), 7.09 (2H, td), 7.14-7.22 (1H, m), 7.48-7.52 (1H, m), 7.82 | 500 |

TABLE G-continued

| Example | Structure | Name | 1H NMR | LCMS [M + H]+ |
|---|---|---|---|---|
| | | | (1H, s). | |
| 56 | 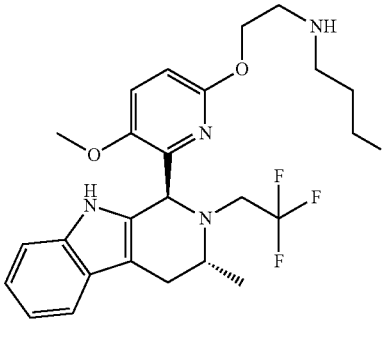 | 3-fluoro-N-(2-((5-methoxy-6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | $^1$H NMR (300 MHz, DMSO-$d_6$, 27° C.) 1.15 (3H, d), 1.55-1.68 (2H, m), 2.38 (2H, t), 2.54-2.61 (3H, m), 2.64-2.73 (1H, m), 2.98-3.11 (1H, m), 3.43-3.56 (1H, m), 3.85 (3H, s), 3.88 (2H, dt), 3.92-4.00 (1H, m), 4.39 (2H, dt), 5.45 (1H, s), 6.72 (1H, d), 6.92-7.00 (2H, m), 7.18-7.25 (1H, m), 7.38-7.44 (1H, d), 7.55 (1H, d), 10.37 (1H, s). (1 exchangeable not observed.) | 495 |
| 58 | 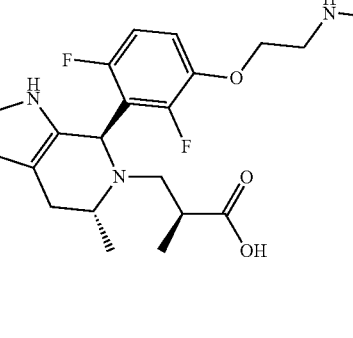 | (S)-3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 1.06 (3H, d), 1.28 (3H, d), 1.76-1.89 (2H, m), 2.51 (1H, s), 2.65-2.79 (4H, m), 2.85 (1H, t), 2.91-3.02 (3H, m), 3.59-3.68 (1H, m), 4.04 (2H, t), 4.47 (2H, dt), 5.45 (1H, s), 6.76 (1H, t), 6.87-6.94 (1H, m), 7.13 (2H, dtd), 7.26 (1H, d), 7.52 (1H, d), 8.26 (1H, s). (2 exchangeables not observed.) | 504 |
| 59 | 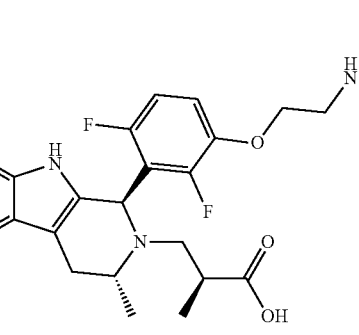 | (S)-3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid | $^1$H NMR (500 MHz, CDCl$_3$, 27° C.) 1.06 (3H, d), 1.29 (3H, d), 1.77-1.91 (2H, m), 2.65 (1H, dd), 2.71-3.01 (8H, m), 3.58-3.67 (1H, m), 4.04 (2H, t), 4.47 (2H, dt), 5.44 (1H, s), 6.72-6.79 (1H, m), 6.86-6.95 (2H, m), 7.13-7.2 (2H, m), 8.45 (1H, s). (2 exchangeables not observed.) | 522 |
| 60 | 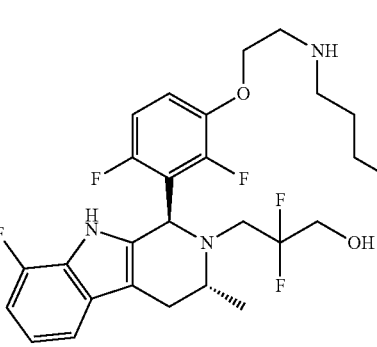 | 3-((1R,3R)-1-(2,6-difluoro-3-(2-((3-fluoropropyl)amino)ethoxy)phenyl)-8-fluoro-3-methyl-1,3,4,9-tetrahydro-2H-pyrido[3,4-b]indol-2-yl)-2,2-difluoropropan-1-ol | $^1$H NMR (300 MHz, DMSO-$d_6$, 27° C.) 1.10 (3H, d), 1.67-1.85 (3H, m), 2.55-2.71 (4H, m), 2.79-2.89 (3H, m), 3.17 (1H, q), 3.34-3.53 (2H, m), 3.56-3.76 (1H, m), 4.02 (2H, t), 4.47 (2H, dt), 5.24-5.32 (2H, m), 6.81-6.98 (3H, m), 7.16 (1H, br td), 7.25 (1H, d), 11.13 (1H, s). | 530 |

TABLE G-continued

| Example | Structure | Name | 1H NMR | LCMS [M + H]+ |
|---|---|---|---|---|
| 61 | 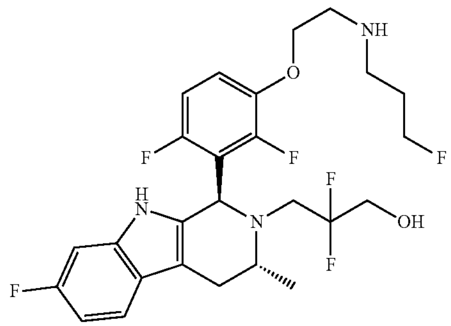 [SMILES: C[C@@H]1Cc2c([nH]c3cc(F)ccc23)[C@@H](c2c(F)ccc(OCCNCCCF)c2F)N1CC(F)(F)CO] | 3-((1R,3R)-1-(2,6-difluoro-3-(2-((3-fluoropropyl)amino)ethoxy)phenyl)-7-fluoro-3-methyl-1,3,4,9-tetrahydro-2H-pyrido[3,4-b]indol-2-yl)-2,2-difluoropropan-1-ol | ¹H NMR (300 MHz, DMSO-d₆, 27° C.) 1.08 (3H, d), 1.67-1.88 (3H, m), 2.53-2.68 (4H, m), 2.80-2.89 (3H, m), 3.16 (1H, q), 3.37-3.51 (2H, m), 3.55-3.74 (1H, m), 4.02 (2H, t), 4.48 (2H, dt), 5.23 (1H, s), 5.26 (1H, t), 6.81 (1H, ddd), 6.91-7.00 (2H, m), 7.17 (1H, td), 7.39 (1H, dd), 10.71 (1H, s). | 530 |
| 62 | 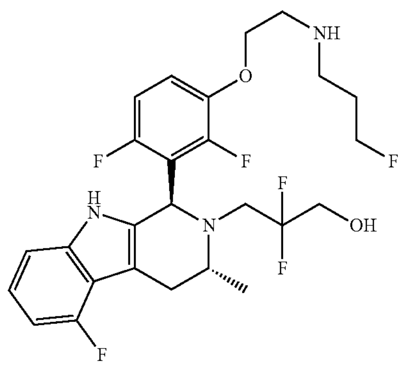 [SMILES: C[C@@H]1Cc2c([nH]c3cccc(F)c23)[C@@H](c2c(F)ccc(OCCNCCCF)c2F)N1CC(F)(F)CO] | 3-((1R,3R)-1-(2,6-difluoro-3-(2-((3-fluoropropyl)amino)ethoxy)phenyl)-5-fluoro-3-methyl-1,3,4,9-tetrahydro-2H-pyrido[3,4-b]indol-2-yl)-2,2-difluoropropan-1-ol | ¹H NMR (300 MHz, DMSO-d₆, 27° C.) 1.09 (3H, d), 1.64-1.84 (2H, m), 1.79 (1H, s), 2.55-2.77 (4H, m), 2.83 (2H, t), 2.99 (1H, dd), 3.16 (1H, q), 3.33-3.51 (2H, m), 3.64 (1H, br dd), 4.01 (2H, t), 4.46 (2H, dt), 5.21-5.28 (2H, m), 6.68 (1H, ddd), 6.90-7.04 (3H, m), 7.16 (1H, td), 10.91 (1H, d). | 530 |
| 63 | 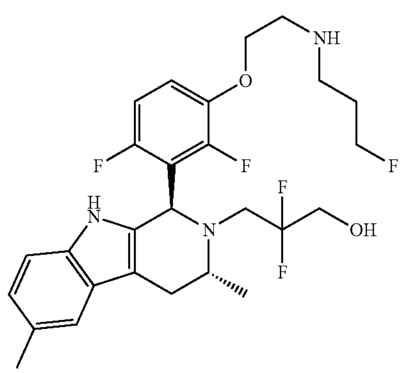 [SMILES: Cc1ccc2[nH]c3c(c2c1)C[C@@H](C)N(CC(F)(F)CO)[C@@H]3c1c(F)ccc(OCCNCCCF)c1F] | 3-((1R,3R)-1-(2,6-difluoro-3-(2-((3-fluoropropyl)amino)ethoxy)phenyl)-3,6-dimethyl-1,3,4,9-tetrahydro-2H-pyrido[3,4-b]indol-2-yl)-2,2-difluoropropan-1-ol | ¹H NMR (300 MHz, DMSO-d₆, 27° C.) 1.08 (3H, d), 1.66-1.86 (3H, m), 2.36 (3H, s), 2.54-2.68 (4H, m), 2.79-2.88 (3H, m), 3.06-3.24 (1H, m), 3.36-3.51 (2H, m), 3.56-3.74 (1H, m), 4.02 (2H, t), 4.47 (2H, dt), 5.22 (1H, br s), 5.26 (1H, t), 6.83 (1H, dd), 6.90-6.97 (1H, m), 7.07 (1H, d), 7.11-7.21 (2H, m), 10.43 (1H, s). | 526 |
| 64 | 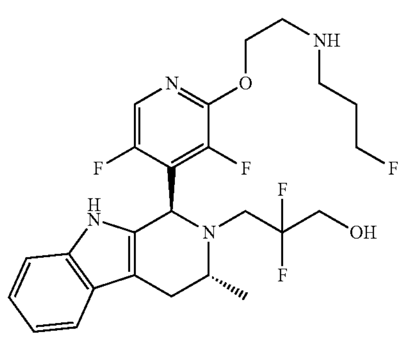 [SMILES: C[C@@H]1Cc2c([nH]c3ccccc23)[C@@H](c2c(F)cnc(OCCNCCCF)c2F)N1CC(F)(F)CO] | 3-((1R,3R)-1-(3,5-difluoro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol | ¹H NMR (500 MHz, CDCl₃, 27° C.) 1.19 (3H, d), 1.80-1.94 (2H, m), 2.67 (1H, ddd), 2.80 (2H, t), 2.82-2.90 (1H, m), 2.96-3.09 (3H, m), 3.17-3.29 (1H, m), 3.64 (1H, h), 3.70-3.87 (2H, m), 4.41 (1H, ddd), 4.44-4.53 (2H, m), 4.56 (1H, t), 5.34 (1H, s), 7.12 (1H, td), 7.16 (1H, td), 7.24 (1H, dd), 7.52 (1H, d), 7.63 (1H, s), 7.79 (1H, s). (2 exchangeables not observed.) | 513 |

TABLE G-continued

| Example | Structure | Name | 1H NMR | LCMS [M + H]+ |
|---|---|---|---|---|
| 65 | 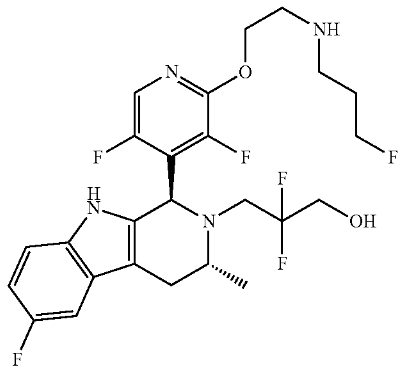 [SMILES: C[C@@H]1Cc2c([nH]c3ccc(F)cc23)[C@@H](c2c(F)cnc(OCCNCCCF)c2F)N1CC(F)(F)CO] | 3-((1R,3R)-1-(3,5-difluoro-2-(2-((3-fluoropropyl)amino)ethoxy)pyridin-4-yl)-6-fluoro-3-methyl-1,3,4,9-tetrahydro-2H-pyrido[3,4-b]indol-2-yl)-2,2-difluoropropan-1-ol | ¹H NMR (500 MHz, CDCl₃, 27° C.) 1.19 (3H, d), 1.82-1.94 (2H, m), 2.62 (1H, dd), 2.78-2.90 (3H, m), 2.96-3.05 (3H, m), 3.18-3.30 (1H, m), 3.63 (1H, q), 3.71-3.85 (2H, m), 4.42 (1H, ddd), 4.45-4.60 (3H, m), 5.33 (1H, s), 6.90 (1H, td), 7.16 (2H, dd), 7.57 (1H, s), 7.80 (1H, s). (2 exchangeables not observed.) | 531 |
| 66 | 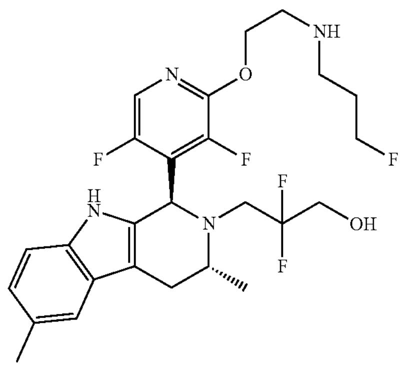 [SMILES: Cc1ccc2[nH]c3c(c2c1)C[C@@H](C)N(CC(F)(F)CO)[C@@H]3c1c(F)cnc(OCCNCCCF)c1F] | 3-((1R,3R)-1-(3,5-difluoro-2-(2-((3-fluoropropyl)amino)ethoxy)pyridin-4-yl)-3,6-dimethyl-1,3,4,9-tetrahydro-2H-pyrido[3,4-b]indol-2-yl)-2,2-difluoropropan-1-ol | ¹H NMR (300 MHz, DMSO-d₆, 27° C.) 1.08 (3H, d), 1.70-1.89 (2H, m), 2.35 (3H, s), 2.52-2.68 (2H, m), 2.74 (2H, br s), 2.91-3.06 (2H, m), 3.09-3.24 (1H, m), 3.34-3.67 (5H, m), 4.31-4.39 (2H, m), 4.50 (2H, dt), 5.22-5.33 (2H, m), 6.84 (1H, dd), 7.08 (1H, d), 7.20 (1H, s), 7.93 (1H, s), 10.48 (1H, s). | 527 |
| 67 | 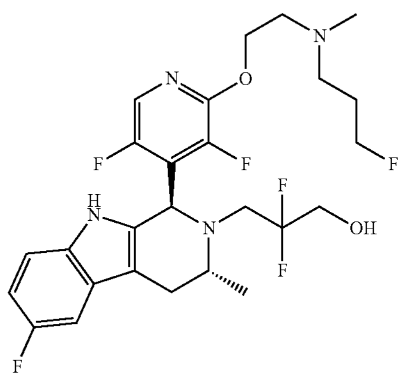 [SMILES: C[C@@H]1Cc2c([nH]c3ccc(F)cc23)[C@@H](c2c(F)cnc(OCCN(C)CCCF)c2F)N1CC(F)(F)CO] | 3-((1R,3R)-1-(3,5-difluoro-2-(2-((3-fluoropropyl)(methyl)amino)ethoxy)pyridin-4-yl)-6-fluoro-3-methyl-1,3,4,9-tetrahydro-2H-pyrido[3,4-b]indol-2-yl)-2,2-difluoropropan-1-ol | ¹H NMR (300 MHz, DMSO-d₆, 27° C.) 1.08 (3H, d), 1.61-1.87 (2H, m), 2.21 (3H, s), 2.41-2.46 (2H, m), 2.53-2.64 (2H, m), 2.70 (2H, t), 2.84 (1H, dd), 3.04-3.26 (1H, m), 3.33-3.71 (3H, m), 4.29-4.45 (4H, m), 5.27 (2H, s), 6.85 (1H, td), 7.05-7.31 (2H, m), 7.94 (1H, s), 10.75 (1H, s). | 545 |
| 68 | 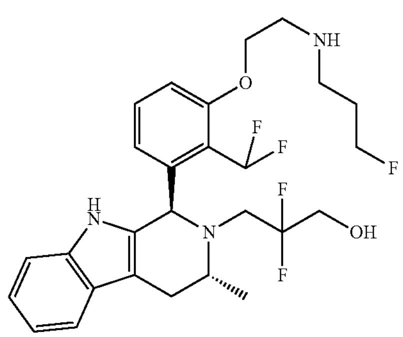 [SMILES: C[C@@H]1Cc2c([nH]c3ccccc23)[C@@H](c2cccc(OCCNCCCF)c2C(F)F)N1CC(F)(F)CO] | 3-((1R,3R)-1-(2-(difluoromethyl)-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol | ¹H NMR (400 MHz, DMSO-d6) 1.04 (3H, d), 1.03 (1H, d) 1.74-1.84 (2H, m), 2.53-2.64 (1H, m), 2.64-2.74 (3H, m), 2.82-2.90 (3H, m), 3.14 (1H, q), 3.38-3.55 (1H, m), 3.55-3.76 (2H, m), 4.08- (2H, t), 4.45 (1H, t), 4.57 (1H, t), 5.21 (1H, s), 5.36 (1H, t), 6.51 (1H, s), 6.95-7.10 (2H, m), 7.24-7.31 (2H, m), 7.42 (1H, d), 7.44-7.80 (1H, m), 10.41 (1H, s) (1 exchangeable proton not observed.) | 526 |

TABLE G-continued

| Example | Structure | Name | 1H NMR | LCMS [M + H]+ |
|---|---|---|---|---|
| 69 | 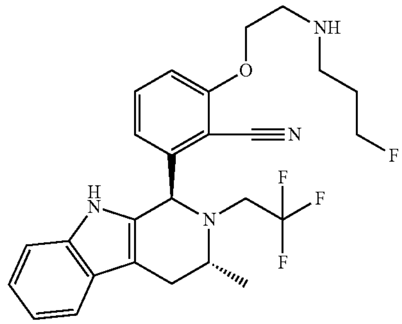 [SMILES: C[C@@H]1Cc2c([nH]c3ccccc23)[C@@H](c2cccc(OCCNCCCF)c2C#N)N1CC(F)(F)F] | 2-(2-((3-fluoropropyl)amino)ethoxy)-6-((1R,3R)-3-methyl-2-(2,2,2-trifluoroethyl)-2,3,4,9-tetrahydro-1H-pyrido[3,4-b]indol-1-yl)benzonitrile | ¹H NMR (300 MHz, DMSO-d₆, 27° C.) 1.10 (3H, d), 1.69-1.91 (3H, m), 2.61-2.72 (3H, m), 2.89-3.06 (4H, m), 3.39-3.61 (2H, m), 4.18 (2H, t), 4.51 (2H, dt), 5.17 (1H, s), 6.76 (1H, d), 6.94-7.08 (2H, m), 7.18-7.24 (2H, m), 7.45 (1H, d), 7.52 (1H, t), 10.52 (1H, s). | 489 |
| 70 | 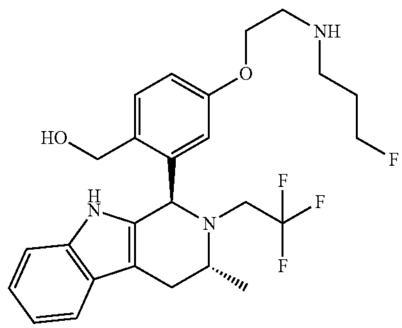 [SMILES: C[C@@H]1Cc2c([nH]c3ccccc23)[C@@H](c2cc(OCCNCCCF)ccc2CO)N1CC(F)(F)F] | (4-(2-((3-fluoropropyl)amino)ethoxy)-2-((1R,3R)-3-methyl-2-(2,2,2-trifluoroethyl)-2,3,4,9-tetrahydro-1H-pyrido[3,4-b]indol-1-yl)phenyl)methanol | 1H NMR (400 MHz MeOH-d4, 27° C.) 1.15 (3H, d), 1.77-1.95 (2H, m), 2.74 (2H, t), 2.82-2.95 (3H, m), 2.99-3.18 (2H, m), 3.23 (2H, q), 3.94-4.07 (2H, m), 4.40 (1H, t), 4.52 (1H, t), 5.11 (1H, dd), 5.29 (1H, dd), 6.49 (1H, d), 6.61 (1H, d), 6.94-7.07 (2H, m), 7.05-7.14 (1H, m), 7.23-7.33 (2H, m), 7.58 (1H, ddd) (3 exchangeable proton not observed.) | 494 |
| 71 | 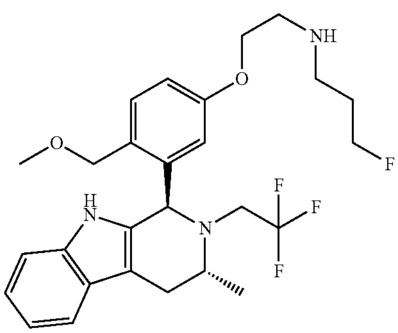 [SMILES: COCc1ccc(OCCNCCCF)cc1[C@@H]1c2[nH]c3ccccc3c2C[C@@H](C)N1CC(F)(F)F] | 3-fluoro-N-(2-(4-(methoxymethyl)-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (DMSO-d₆, 400 MHz, 27° C.) 1.07 (3H, d), 1.62-1.80 (2H, m), 2.55 (2H, t), 2.64 (1H, dd), 2.75 (2H, t), 2.85 (1H, dd), 2.94-3.11 (1H, m), 3.33 (3H, s), 3.35-3.51 (2H, m), 3.85 (2H, t), 4.38 (1H, t), 4.45-4.56 (2H, m), 4.70 (1H, d), 5.17 (1H, s), 6.34 (1H, s), 6.88 (1H, dd), 6.94-7.09 (2H, m), 7.22-7.29 (1H, m), 7.36 (1H, d), 7.45 (1H, d), 10.51 (1H, s) (1 exchangeable proton not observed.) | 508 |
| 72 | 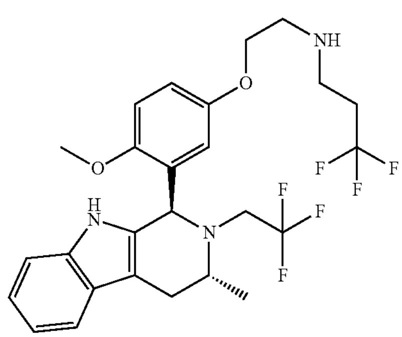 [SMILES: COc1ccc(OCCNCCC(F)(F)F)cc1[C@@H]1c2[nH]c3ccccc3c2C[C@@H](C)N1CC(F)(F)F] | 3,3,3-trifluoro-N-(2-(4-methoxy-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (DMSO-d₆, 400 MHz, 27° C.) 1.08 (3H, d), 2.23-2.40 (2H, m), 2.53-2.61 (2H, m), 2.62-2.69 (2H, m), 2.69-2.81 (3H, m), 2.87-3.03 (1H, m), 3.38-3.53 (1H, m), 3.78 (2H, t), 3.82 (3H, s), 5.36 (1H, s), 6.15 (1H, d), 6.82-6.90 (1H, m), 6.93-7.08 (3H, m), 7.22 (1H, d), 7.44 (1H, d), 10.57 (1H, s) (1 exchangeable proton not observed.) | 530 |

TABLE G-continued

| Example | Structure | Name | 1H NMR | LCMS [M + H]+ |
|---|---|---|---|---|
| 73 | 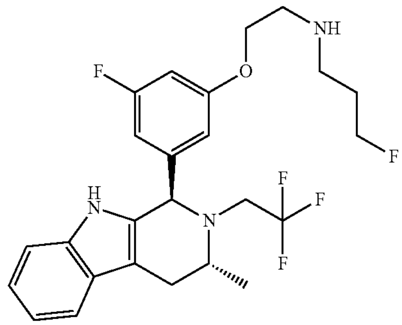 | 3-fluoro-N-(2-(3-fluoro-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (500 MHz, CDCl₃, 27° C.) 1.16 (3H, d), 1.84-1.87 (2H, m), 2.50-2.56 (1H, m), 2.73-2.85 (3H, m), 2.89-3.04 (3H, m), 3.13-3.35 (2H, m), 3.98 (2H, t), 4.47 (1H, t), 4.56 (1H, t), 4.90 (1H, s), 6.52 (1H, ddd), 6.63-6.69 (2H, m), 7.11-7.16 (1H, m), 7.19 (1H, dd), 7.28-7.33 (1H, m), 7.53 (1H, d), 7.86 (1H, d). (1 exchangeable proton not observed.) | 482 |
| 74 | 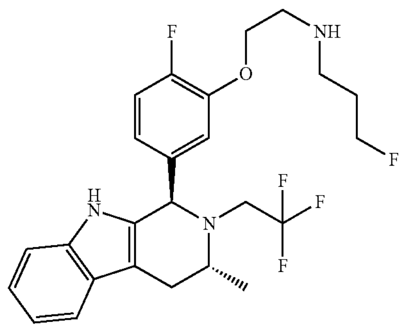 [SMILES: C[C@@H]1Cc2c([nH]c3ccccc23)[C@@H](c2ccc(F)c(OCCNCCCF)c2)N1CC(F)(F)F] | 3-fluoro-N-(2-(2-fluoro-5-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (500 MHz, CDCl₃, 27° C.) 1.15 (3H, d), 1.86-1.89 (2H, m), 2.54-2.58 (1H, m), 2.80 (2H, t), 2.85 (1H, dd), 2.91-2.97 (1H, m), 2.97-3.01 (2H, m), 3.18-3.27 (1H, m), 3.30-3.36 (1H, m), 4.07 (2H, t), 4.48 (1H, t), 4.57 (1H, t), 4.90 (1H, s), 6.74 (1H, ddd), 6.97 (1H, dd), 7.04 (1H, dd), 7.13 (1H, ddd), 7.19 (1H, ddd), 7.27-7.32 (1H, m), 7.53 (1H, d), 7.66 (1H, s). (1 exchangeable proton not observed.) | 482 |
| 75 | 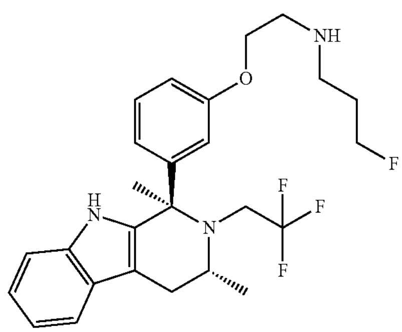 [SMILES: C[C@@H]1Cc2c([nH]c3ccccc23)[C@@](C)(c2cccc(OCCNCCCF)c2)N1CC(F)(F)F] | N-(2-(3-((1R,3R)-1,3-dimethyl-2-(2,2,2-trifluoroethyl)-2,3,4,9-tetrahydro-1H-pyrido[3,4-b]indol-1-yl)phenoxy)ethyl)-3-fluoropropan-1-amine | ¹H NMR (500 MHz, CDCl₃, 27° C.) 1.15 (3H, d), 1.74 (3H, s), 1.80-1.97 (2H, m), 2.48-2.67 (2H, m), 2.80 (2H, t), 2.97 (2H, dd), 3.06-3.25 (2H, m), 3.27-3.35 (1H, m), 4.01 (2H, t), 4.53 (2H, dt), 6.72-6.76 (1H, m), 6.91 (2H, br s), 7.12-7.18 (2H, m), 7.22 (1H, ddd), 7.39 (1H, dt), 7.49-7.53 (1H, m), 7.98 (1H, s). (1 exchangeable not observed.) | 478 |
| 76 | 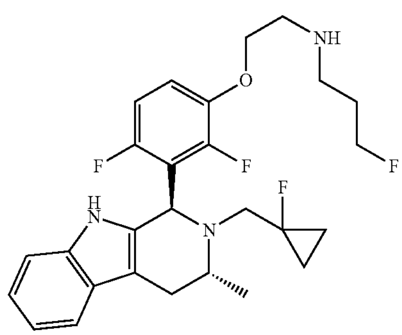 [SMILES: C[C@@H]1Cc2c([nH]c3ccccc23)[C@@H](c2c(F)ccc(OCCNCCCF)c2F)N1CC1(F)CC1] | N-(2-(2,4-difluoro-3-((1R,3R)-2-((1-fluorocyclopropyl)methyl)-3-methyl-2,3,4,9-tetrahydro-1H-pyrido[3,4-b]indol-1-yl)phenoxy)ethyl)-3-fluoropropan-1-amine | ¹H NMR (500 MHz, CDCl₃, 27° C.) 0.43-0.55 (2H, m), 0.92-1.04 (2H, m), 1.15 (3H, d), 1.81-1.94 (2H, m), 2.65 (1H, ddd), 2.72 (1H, dd), 2.79 (2H, t), 2.98 (2H, dd), 3.09 (1H, ddd), 3.17 (1H, dd), 3.71-3.79 (1H, m), 4.03-4.09 (2H, m), 4.52 (2H, dt), 5.35 (1H, s), 6.77 (1H, td), 6.89 (1H, td), 7.07-7.14 (2H, m), | 490 |

TABLE G-continued

| Example | Structure | Name | 1H NMR | LCMS [M + H]+ |
|---|---|---|---|---|
| | | | 7.20-7.23 (1H, m), 7.45 (1H, s), 7.48-7.55 (1H, m). (1 exchangeable not observed.) | |
| 77 | 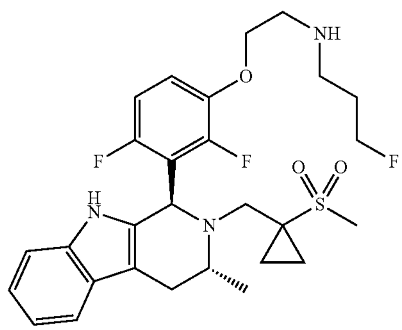 [SMILES: C[C@@H]1Cc2c([nH]c3ccccc23)[C@@H](c2c(F)ccc(OCCNCCCF)c2F)N1CC1(S(C)(=O)=O)CC1] | N-(2-(2,4-difluoro-3-((1R,3R)-3-methyl-2-((1-(methylsulfonyl)cyclopropyl)methyl)-2,3,4,9-tetrahydro-1H-pyrido[3,4-b]indol-1-yl)phenoxy)ethyl)-3-fluoropropan-1-amine | $^1$H NMR (500 MHz, CDCl$_3$, 27° C.) 0.56-0.66 (1H, m), 0.87-0.93 (1H, m), 1.11 (3H, d), 1.39-1.48 (2H, m), 1.80-1.94 (2H, m), 2.67-2.84 (4H, m), 2.98 (2H, s), 3.08-3.17 (4H, m), 3.18-3.28 (1H, m), 3.81-3.90 (1H, m), 4.09 (2H, d), 4.51 (2H, dt), 5.14 (1H, s), 6.82 (1H, t), 6.92-6.99 (1H, m), 7.07-7.15 (2H, m), 7.19-7.23 (1H, m), 7.47-7.53 (1H, m), 7.58 (1H, s). (1 exchangeable not observed.) | 550 |
| 78 | 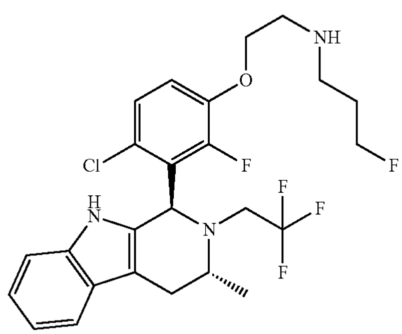 [SMILES: C[C@@H]1Cc2c([nH]c3ccccc23)[C@@H](c2c(Cl)ccc(OCCNCCCF)c2F)N1CC(F)(F)F] | N-(2-(4-chloro-2-fluoro-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | $^1$H NMR (500 MHz, DMSO-d$_6$, 27° C.) 1.12 (3H, d), 1.67-1.84 (3H, m), 2.62 (2H, br t), 2.64-2.70 (1H, m), 2.80-2.87 (2H, m), 2.87-2.98 (1H, m), 2.99-3.06 (1H, m), 3.49-3.60 (1H, m), 4.00-4.07 (2H, m), 4.46 (2H, dt), 5.45 (1H, s), 6.93-6.98 (1H, m), 6.99-7.03 (1H, m), 7.19 (1H, d), 7.21-7.30 (2H, m), 7.41 (1H, d), 10.54 (1H, s). | 516 |
| 79 | 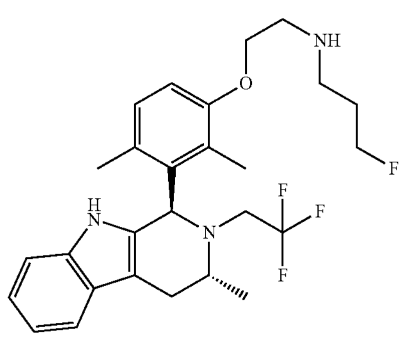 [SMILES: Cc1ccc(OCCNCCCF)c(C)c1[C@@H]1c2[nH]c3ccccc3c2C[C@@H](C)N1CC(F)(F)F] | N-(2-(2,4-dimethyl-3-((1R,3R)-3-methyl-2-(2,2,2-trifluoroethyl)-2,3,4,9-tetrahydro-1H-pyrido[3,4-b]indol-1-yl)phenoxy)ethyl)-3-fluoropropan-1-amine | $^1$H NMR (500 MHz, DMSO, 27° C.) 1.12 (3H, d), 1.63-1.87 (6H, m), 2.36-2.45 (3H, m), 2.59 (1H, t), 2.64-2.82 (4H, m), 2.93 (1H, t), 3.02-3.11 (1H, m), 3.32-3.43 (1H, m), 3.55-3.65 (1H, m), 3.83-4.07 (2H, m), 4.36-4.59 (2H, m), 5.24-5.40 (1H, m), 6.83 (1H, s), 6.84-7.09 (3H, m), 7.16 (1H, t), 7.37 (1H, d), 10.05-10.2 (1H, m). (1 exchangeable not observed). | 492 |

TABLE G-continued

| Example | Structure | Name | 1H NMR | LCMS [M + H]+ |
|---|---|---|---|---|
| 80 | 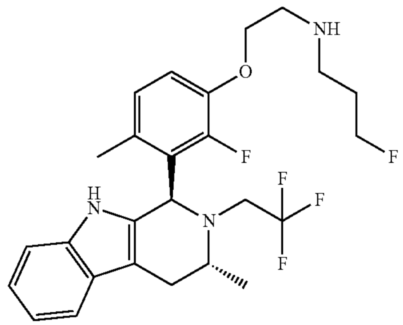 [SMILES: Cc1ccc(OCCNCCCF)c(F)c1[C@@H]1c2[nH]c3ccccc3c2C[C@@H](C)N1CC(F)(F)F] | 3-fluoro-N-(2-(2-fluoro-4-methyl-3-((1R,3R)-3-methyl-2-(2,2,2-trifluoroethyl)-2,3,4,9-tetrahydro-1H-pyrido[3,4-b]indol-1-yl)phenoxy)ethyl)propan-1-amine | ¹H NMR (600 MHz, DMSO-d₆, 27° C.) 1.13 (3H, d), 1.75-1.91 (6H, m), 2.70 (3H, dd), 2.83 (1H, qd), 2.91 (2H, br t), 3.05 (1H, qdd), 3.48 (1H, br qd), 3.56-3.65 (1H, m), 4.01-4.13 (2H, m), 4.52 (2H, td), 5.37 (1H, s), 6.84 (1H, br d), 6.95 (1H, ddd), 7.00 (1H, ddd), 7.04 (1H, dd), 7.19 (1H, d), 7.41 (1H, d), 10.43 (1H, s) | 496 |
| 81 | 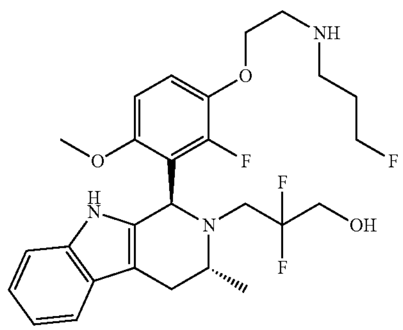 [SMILES: COc1ccc(OCCNCCCF)c(F)c1[C@@H]1c2[nH]c3ccccc3c2C[C@@H](C)N1CC(F)(F)CO] | 2,2-difluoro-3-((1R,3R)-1-(2-fluoro-3-(2-((3-fluoropropyl)amino)ethoxy)-6-methoxyphenyl)-3-methyl-1,3,4,9-tetrahydro-2H-pyrido[3,4-b]indol-2-yl)propan-1-ol | ¹H NMR (300 MHz, DMSO-d₆, 27° C.) 1.06 (3H, d), 1.59-1.82 (3H, m), 2.53-2.68 (4H, m), 2.76 (2H, br t), 2.85-2.96 (1H, m), 3.00-3.14 (1H, m), 3.22-3.39 (1H, m), 3.51 (1H, sxt), 3.56-3.74 (1H, m), 3.78 (3H, s), 3.85-3.99 (2H, m), 4.44 (2H, dt), 5.17 (1H, t), 5.35 (1H, s), 6.81 (1H, dd), 6.95 (2H, quind), 7.10 (1H, t), 7.15-7.20 (1H, m), 7.38 (1H, d), 10.40 (1H, s) | 524 |
| 82 | 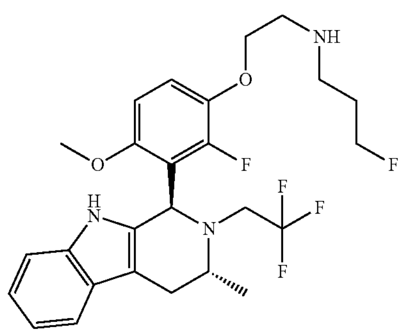 | N-(2-(3-((1R,3R)-2-(2,2-difluoroethyl)-3-methyl-2,3,4,9-tetrahydro-1H-pyrido[3,4-b]indol-1-yl)-2-fluoro-4-methoxyphenoxy)ethyl)-3-fluoropropan-1-amine | ¹H NMR (300 MHz, DMSO-d₆, 27° C.) 1.09 (3H, d), 1.61-1.83 (3H, m), 2.54-2.73 (4H, m), 2.76 (2H, t), 2.84 (1H, dd), 3.04 (1H, qd), 3.34-3.43 (1H, m), 3.81 (3H, s), 3.85-3.98 (2H, m), 4.43 (2H, dt), 5.33 (1H, s), 5.64-6.10 (1H, m), 6.83 (1H, dd), 6.90-7.03 (2H, m), 7.10 (1H, t), 7.16-7.22 (1H, m), 7.36-7.42 (1H, m), 10.49 (1H, s). | 494 |
| 83 | 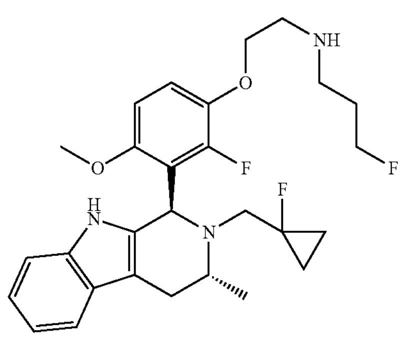 [SMILES: COc1ccc(OCCNCCCF)c(F)c1[C@@H]1c2[nH]c3ccccc3c2C[C@@H](C)N1CC1(F)CC1] | 3-fluoro-N-(2-(2-fluoro-3-((1R,3R)-2-((1-fluorocyclopropyl)methyl)-3-methyl-2,3,4,9-tetrahydro-1H-pyrido[3,4-b]indol-1-yl)-4-methoxyphenoxy)ethyl)propan-1-amine | ¹H NMR (300 MHz, DMSO-d₆, 27° C.) 0.36-0.52 (2H, m), 0.78-0.95 (2H, m), 1.05 (3H, d), 1.62-1.83 (3H, m), 2.54-2.71 (4H, m), 2.77 (2H, t), 2.92 (1H, br ddd), 3.06 (1H, dd), 3.54-3.67 (1H, m), 3.78 (3H, s), 3.84-4.01 (2H, m), 4.44 (2H, dt), 5.35 (1H, s), 6.81 (1H, dd), 6.89-6.99 (2H, m), 7.09 (1H, t), 7.15-7.18 (1H, m), 7.35-7.40 (1H, m), 10.34 (1H, s) | 502 |

TABLE G-continued

| Example | Name | 1H NMR | LCMS [M + H]+ |
|---|---|---|---|
| 84 | 3-fluoro-N-(2-(2-fluoro-3-((1R,3R)-2-((3-fluorooxetan-3-yl)methyl)-3-methyl-2,3,4,9-tetrahydro-1H-pyrido[3,4-b]indol-1-yl)-4-methoxyphenoxy)ethyl)propan-1-amine | ¹H NMR (300 MHz, DMSO-d₆, 27° C.) 1.07 (3H, d), 1.60-1.81 (3H, m), 2.53-2.62 (3H, m), 2.71-2.90 (4H, m), 3.08-3.29 (1H, m), 3.37-3.49 (1H, m), 3.78 (3H, s), 3.86-3.99 (2H, m), 4.20 (1H, dd), 4.33-4.56 (5H, m), 5.36 (1H, s), 6.83 (1H, dd) 6.95 (2H, quind), 7.10 (1H, t), 7.15-7.20 (1H, m), 7.36-7.42 (1H, m), 10.42 (1H, s). | 518 |
| 85 | 3-((1R,3R)-1-(2-chloro-6-fluoro-3-(2-((3-fluoropropyl)amino)ethoxy)phenyl)-3-methyl-1,3,4,9-tetrahydro-2H-pyrido[3,4-b]indol-2-yl)-2,2-difluoropropan-1-ol | ¹H NMR (500 MHz, CDCl₃, 27° C.) 1.16 (3H, d), 1.85-1.97 (2H, m), 2.70 (1H, d), 2.74-2.84 (1H, m), 2.86 (2H, t), 2.98-3.07 (2H, m), 3.17 (1H, ddd), 3.26 (1H, dt), 3.55-3.66 (2H, m), 3.76-3.86 (1H, m), 4.09 (2H, tt), 4.47 (1H, t), 4.56 (1H, t), 5.50 (1H, s), 6.85 (1H, dd), 6.91 (1H, t), 7.02-7.13 (1H, m), 7.14-7.20 (1H, m), 7.20-7.27 (1H, m), 7.48-7.52 (1H, m), 7.69 (1H, s). (2 exchangeables not observed). | 528 |
| 86 | 2,2-difluoro-3-((1R,3R)-6-fluoro-1-(2-fluoro-3-(2-((3-fluoropropyl)amino)ethoxy)-6-methoxyphenyl)-3-methyl-1,3,4,9-tetrahydro-2H-pyrido[3,4-b]indol-2-yl)propan-1-ol | ¹H NMR (500 MHz, CDCl₃, 27° C.) 1.16 (3H, d), 1.80-1.92 (2H, m), 2.58-2.65 (1H, m), 2.78 (2H, t), 2.81-2.92 (1H, m), 2.95 (2H, t), 3.09 (1H, ddd), 3.18-3.27 (1H, m), 3.35-3.55 (2H, m), 3.61-3.81 (6H, m), 4.06 (2H, t), 4.50 (2H, dt), 5.33 (1H, s), 6.64 (1H, dd), 6.83 (1H, td), 6.97 (1H, t), 7.08 (1H, dd), 7.13 (1H, dd), 7.49 (1H, s). | 542 |
| 87 | 3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanenitrile | ¹H NMR (DMSO-d₆, 300 MHz, 27° C.) 1.04 (3H, d), 1.88-1.95 (5H, m), 2.32-2.46 (1H, m), 2.52-2.65 (2H, m), 2.65-2.83 (2H, m), 2.83-2.92 (2H, m), 3.05-3.15 (3H, m), 3.63 (1H, s), 3.97-4.14 (2H, m), 4.41 (1H, t), 4.56 (1H, t), 5.26 (1H, s), 6.89-7.05 (3H, m), 7.06-7.23 (2H, m), 7.42 (1H, | 467 |

TABLE G-continued

| Example | Structure | Name | 1H NMR | LCMS [M + H]+ |
|---|---|---|---|---|
| | | | d), 10.34 (1H, s). (1 exchangeable proton not observed.) | |
| 88 | 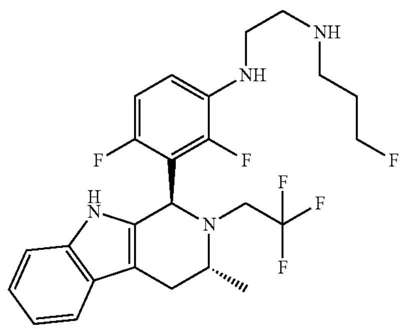 [SMILES: C[C@@H]1Cc2c([nH]c3ccccc23)[C@@H](c2c(F)ccc(NCCNCCCF)c2F)N1CC(F)(F)F] | N1-(2,4-difluoro-3-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine | $^1$H NMR (500 MHz, CDCl$_3$, 27° C.) 1.18 (3H, d), 1.80-1.85 (2H, m), 2.62-2.65 (1H, m), 2.72-2.77 (2H, m), 2.87 (2H, t), 2.95-3.04 (1H, m), 3.08-3.21 (3H, m), 3.22-3.27 (1H, m), 3.58-3.67 (1H, m), 4.46 (1H, t), 4.56 (1H, t), 5.35 (1H, s), 6.61-6.64 (1H, m), 6.73-6.81 (1H, m), 7.07-7.15 (2H, m), 7.23 (2H, d), 7.44-7.54 (2H, m). (1 exchangeable proton not observed.) | 499 |
| 89 | 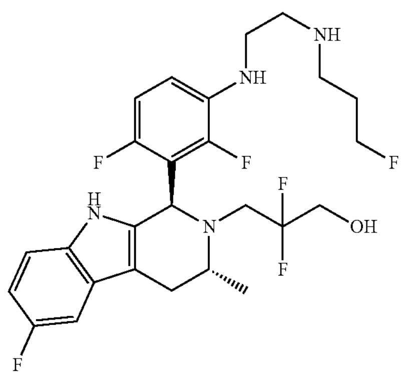 [SMILES: C[C@@H]1Cc2c([nH]c3ccc(F)cc23)[C@@H](c2c(F)ccc(NCCNCCCF)c2F)N1CC(F)(F)CO] | 3-((1R,3R)-1-(2,6-difluoro-3-((2-((3-fluoropropyl)amino)ethyl)amino)phenyl)-6-fluoro-3-methyl-1,3,4,9-tetrahydro-2H-pyrido[3,4-b]indol-2-yl)-2,2-difluoropropan-1-ol | $^1$H NMR (500 MHz, CDCl$_3$, 27° C.) 1.16 (3H, d), 1.92-2.03 (2H, m), 2.55-2.64 (1H, m), 2.81-2.94 (5H, m), 3.05 (1H, dd), 3.15-3.38 (4H, m), 3.54-3.64 (1H, m), 3.68-3.78 (2H, m), 4.38-4.55 (3H, m), 5.23 (1H, s), 6.60 (1H, td), 6.74-6.85 (2H, m), 7.08-7.16 (2H, m), 7.93 (1H, s). (1 exchangeable not observed.) | 529 |
| 90 | 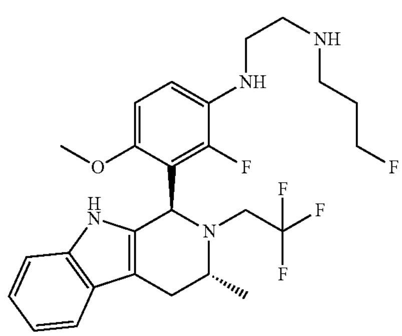 [SMILES: COc1ccc(NCCNCCCF)c(F)c1[C@@H]1c2[nH]c3ccccc3c2C[C@@H](C)N1CC(F)(F)F] | N1-(2-fluoro-4-methoxy-3-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine | $^1$H NMR (300 MHz, DMSO-d$_6$, 27° C.) 1.10 (3H, d), 1.62-1.80 (3H, m), 2.53-2.67 (5H, m), 2.87-3.05 (4H, m), 3.36-3.52 (2H, m), 3.73 (3H, s), 4.44 (2H, dt), 4.67-4.73 (1H, m), 5.40 (1H, s), 6.67 (1H, t), 6.76 (1H, d), 6.95 (2H, quint), 7.16-7.20 (1H, m), 7.36-7.40 (1H, m), 10.44 (1H, s). | 511 |
| 91 | 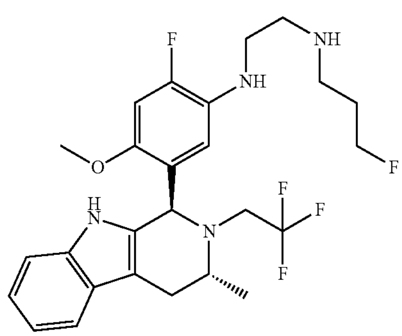 [SMILES: COc1cc(F)c(NCCNCCCF)cc1[C@@H]1c2[nH]c3ccccc3c2C[C@@H](C)N1CC(F)(F)F] | N1-(2-fluoro-4-methoxy-5-((1R,3R)-3-methyl-2-(2,2,2-trifluoroethyl)-2,3,4,9-tetrahydro-1H-pyrido[3,4-b]indol-1-yl)phenyl)-N2-(3-fluoropropyl)ethane-1,2-diamine | $^1$H NMR (300 MHz, DMSO-d$_6$, 27° C.) 1.09 (3H, d), 1.49-1.70 (3H, m), 2.37 (2H, t), 2.42-2.47 (2H, m), 2.54-3.02 (5H, m), 3.36-3.49 (2H, m), 3.78 (3H, s), 4.39 (2H, dt), 4.69-4.75 (1H, m), 5.31 (1H, s), 6.14 (1H, d), 6.91-7.05 (3H, m), 7.20-7.24 (1H, m), 7.43 (1H, d), 10.44 (1H, s). | 511 |

TABLE G-continued

| Example | Structure | Name | 1H NMR | LCMS [M + H]+ |
|---|---|---|---|---|
| 92 | 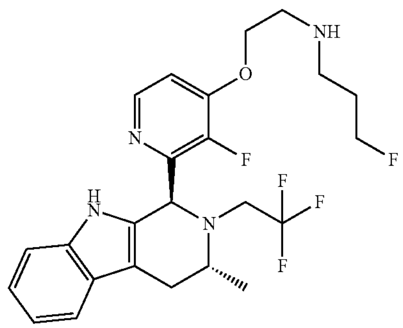 [SMILES: C[C@@H]1Cc2c([nH]c3ccccc23)[C@@H](c2nccc(OCCNCCCF)c2F)N1CC(F)(F)F] | 3-fluoro-N-(2-((3-fluoro-2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)propan-1-amine | $^1$H NMR (300 MHz, DMSO-d$_6$, 27° C.) 1.10 (3H, d), 1.70-1.88 (2H, m), 1.88-2.05 (1H, m), 2.53-2.72 (4H, m), 2.94 (2H, t), 2.97-3.15 (1H, m), 3.47-3.71 (2H, m), 4.19 (2H, quin), 4.51 (2H, dt), 5.37 (1H, s), 6.93-7.00 (1H, m), 7.00-7.06 (1H, m), 7.17-7.26 (2H, m), 7.43 (1H, d), 8.07 (1H, d), 10.58 (1H, s). | 483 |
| 93 | 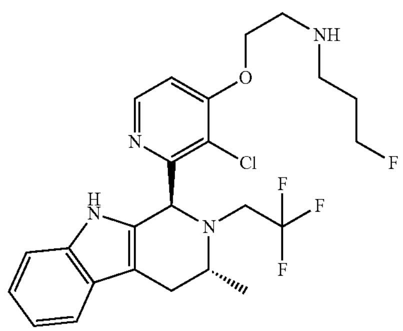 [SMILES: C[C@@H]1Cc2c([nH]c3ccccc23)[C@@H](c2nccc(OCCNCCCF)c2Cl)N1CC(F)(F)F] | N-(2-((3-chloro-2-((1S,3R)-3-methyl-2-(2,2,2-trifluoroethyl)-2,3,4,9-tetrahydro-1H-pyrido[3,4-b]indol-1-yl)pyridin-4-yl)oxy)ethyl)-3-fluoropropan-1-amine | $^1$H NMR (300 MHz, DMSO-d$_6$, 27° C.) 1.11 (3H, d), 1.68-1.96 (3H, m), 2.60-2.74 (3H, m), 2.80-3.08 (4H, m), 3.33-3.39 (1H, m), 3.56 (1H, br dd), 4.29-4.64 (4H, m), 5.38 (1H, s), 6.42 (1H, d), 6.96-7.02 (1H, m), 7.03-7.10 (1H, m), 7.21-7.26 (1H, m), 7.47 (1H, d), 7.93 (1H, d), 10.61 (1H, s). | 517 |
| 94 | 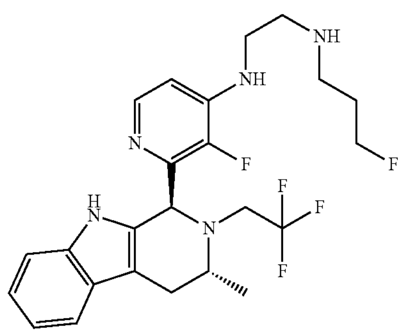 | N1-(3-fluoro-2-((1S,3R)-3-methyl-2-(2,2,2-trifluoroethyl)-2,3,4,9-tetrahydro-1H-pyrido[3,4-b]indol-1-yl)pyridin-4-yl)-N2-(3-fluoropropyl)ethane-1,2-diamine | $^1$H NMR (300 MHz, DMSO-d$_6$, 27° C.) 1.10 (3H, d), 1.68-1.94 (3H, m), 2.54-2.76 (6H, m), 2.93-3.15 (1H, m), 3.21 (2H, q), 3.45-3.63 (1H, m), 3.67-3.79 (1H, m), 4.51 (2H, dt), 5.29 (1H, s), 6.43 (1H, br td), 6.66 (1H, dd), 6.92-6.98 (1H, m), 6.98-7.05 (1H, m), 7.18-7.24 (1H, m), 7.39-7.45 (1H, m), 7.77 (1H, d), 10.57 (1H, s). | 482 |
| 95 | 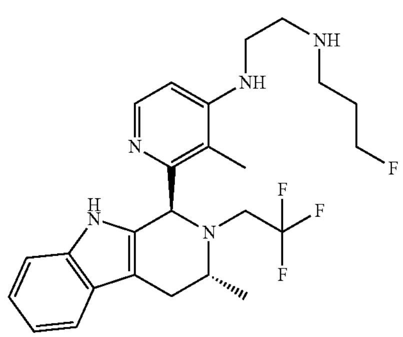 [SMILES: Cc1c(NCCNCCCF)ccnc1[C@@H]1c2[nH]c3ccccc3c2C[C@@H](C)N1CC(F)(F)F] | N1-(3-fluoropropyl)-N2-(3-methyl-2-((1S,3R)-3-methyl-2-(2,2,2-trifluoroethyl)-2,3,4,9-tetrahydro-1H-pyrido[3,4-b]indol-1-yl)pyridin-4-yl)ethane-1,2-diamine | $^1$H NMR (300 MHz, DMSO-d$_6$, 27° C.) 1.08 (3H, d), 1.67-1.85 (2H, m), 1.93 (3H, s), 2.57-2.76 (5H, m), 2.85 (1H, dd), 2.95-3.12 (1H, m), 3.19 (2H, q), 3.35-3.51 (1H, m), 3.59-3.69 (1H, m), 4.49 (2H, dt), 5.14 (1H, s), 5.61 (1H, br t), 6.50 (1H, d), 6.96 (2H, quind), 7.17-7.22 (1H, m), 7.38-7.43 (1H, m), 7.93 (1H, d), 10.32 (1H, s). (Dialkyl NH not observed.) | 478 |

TABLE G-continued

| Example | Structure | Name | 1H NMR | LCMS [M + H]+ |
|---|---|---|---|---|
| 96 | 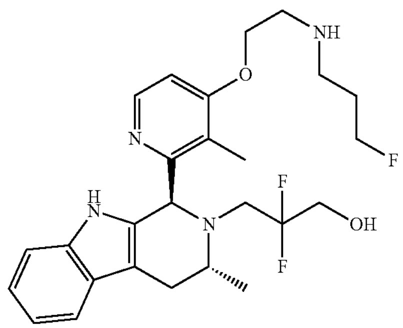 [SMILES: Cc1c(OCCNCCCF)ccnc1[C@@H]1c2[nH]c3ccccc3c2C[C@@H](C)N1CC(F)(F)CO] | 2,2-difluoro-3-((1S,3R)-1-(4-(2-((3-fluoropropyl)amino)ethoxy)-3-methylpyridin-2-yl)-3-methyl-1,3,4,9-tetrahydro-2H-pyrido[3,4-b]indol-2-yl)propan-1-ol | $^1$H NMR (500 MHz, CDCl$_3$, 27° C.) 1.18 (3H, d), 1.85-1.96 (2H, m), 2.22 (3H, s), 2.68 (1H, d), 2.76-2.89 (3H, m), 3.08 (2H, t), 3.11-3.25 (2H, m), 3.58 (1H, q), 3.75-3.85 (2H, m), 4.14 (2H, t), 4.55 (2H, dt), 5.23 (1H, s), 6.74 (1H, d), 7.06-7.12 (2H, m), 7.19 (1H, dd), 7.45-7.55 (2H, m), 8.29 (1H, d). (2 exchangeables not observed.) | 491 |
| 97 | 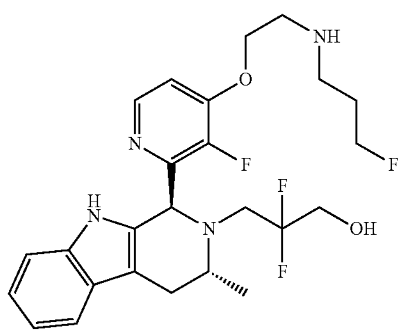 | 2,2-difluoro-3-((1S,3R)-1-(3-fluoro-4-(2-((3-fluoropropyl)amino)ethoxy)pyridin-2-yl)-3-methyl-1,3,4,9-tetrahydro-2H-pyrido[3,4-b]indol-2-yl)propan-1-ol | $^1$H NMR (300 MHz, DMSO-d$_6$, 27° C.) 1.07 (3H, d), 1.70-1.96 (2H, m), 2.52-2.72 (3H, m), 2.75 (2H, t), 3.02 (2H, br t), 3.08-3.23 (1H, m), 3.51-3.80 (3H, m), 4.22 (2H, br t), 4.51 (2H, dt), 5.33 (1H, t), 5.38 (1H, s), 6.91-6.98 (1H, m), 6.98-7.04 (1H, m), 7.15-7.23 (2H, m), 7.41 (1H, d), 8.07 (1H, d), 10.55 (1H, s). (Amine NH not observed.) | 495 |
| 98 | 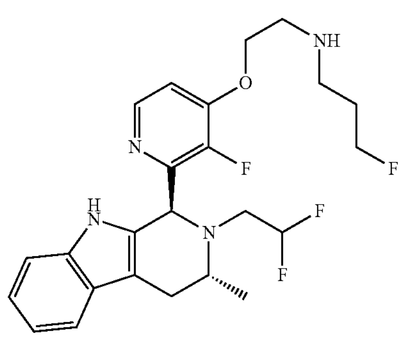 [SMILES: C[C@@H]1Cc2c([nH]c3ccccc23)[C@@H](c2nccc(OCCNCCCF)c2F)N1CC(F)F] | N-(2-((2-((1S,3R)-2-(2,2-difluoroethyl)-3-methyl-2,3,4,9-tetrahydro-1H-pyrido[3,4-b]indol-1-yl)-3-fluoropyridin-4-yl)oxy)ethyl)-3-fluoropropan-1-amine | $^1$H NMR (300 MHz, DMSO-d$_6$, 27° C.) 1.09 (3H, d), 1.70-1.94 (3H, m), 2.53-2.78 (5H, m), 2.94 (2H, t), 3.06-3.25 (1H, m), 3.41-3.59 (1H, m), 4.19 (2H, t), 4.51 (2H, dt), 5.37 (1H, s), 6.05 (1H, tt), 6.92-6.99 (1H, m), 6.99-7.07 (1H, m), 7.17-7.25 (2H, m), 7.42 (1H, d), 8.07 (1H, d), 10.55 (1H, s). | 465 |
| 99 | 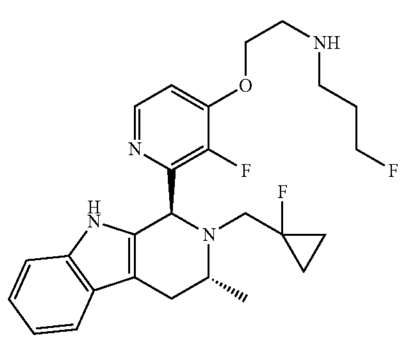 [SMILES: C[C@@H]1Cc2c([nH]c3ccccc23)[C@@H](c2nccc(OCCNCCCF)c2F)N1CC1(F)CC1] | 3-fluoro-N-(2-((3-fluoro-2-((1S,3R)-2-((1-fluorocyclopropyl)methyl)-3-methyl-2,3,4,9-tetrahydro-1H-pyrido[3,4-b]indol-1-yl)pyridin-4-yl)oxy)ethyl)propan-1-amine | $^1$H NMR (300 MHz, DMSO-d$_6$, 27° C.) 0.55-0.78 (2H, m), 0.83-1.05 (2H, m), 1.08 (3H, d), 1.70-1.89 (2H, m), 1.90-2.07 (1H, m), 2.52-2.75 (5H, m), 2.94 (2H, t), 3.08-3.22 (1H, m), 3.58-3.70 (1H, m), 4.19 (2H, t), 4.51 (2H, dt), 5.49 (1H, s), 6.90-7.04 (2H, m), 7.16-7.22 (2H, m), 7.41 (1H, d), 8.07 (1H, d), 10.50 (1H, s). | 473 |

TABLE G-continued

| Example | Name | 1H NMR | LCMS [M + H]+ |
|---|---|---|---|
| 100 | 3-fluoro-N-(2-((3-fluoro-2-((1S,3R)-2-((3-fluorooxetan-3-yl)methyl)-3-methyl-2,3,4,9-tetrahydro-1H-pyrido[3,4-b]indol-1-yl)pyridin-4-yl)oxy)ethyl)propan-1-amine | $^1$H NMR (300 MHz, DMSO-$d_6$, 27° C.) 1.13 (3H, d), 1.71-1.94 (3H, m), 2.53-2.72 (4H, m), 2.83 (1H, dd), 2.93 (2H, t), 3.20-3.37 (1H, m), 3.44-3.59 (1H, m), 4.18 (2H, t), 4.41-4.70 (6H, m), 5.43 (1H, s), 6.92-6.99 (1H, m), 6.99-7.05 (1H, m), 7.16-7.23 (2H, m), 7.39-7.45 (1H, m), 8.05 (1H, d), 10.54 (1H, s). | 489 |
| 101 | 3-fluoro-N-(2-((5-((1R,3R)-3-methyl-2-(2,2,2-trifluoroethyl)-2,3,4,9-tetrahydro-1H-pyrido[3,4-b]indol-1-yl)pyridin-3-yl)oxy)ethyl)propan-1-amine | $^1$H NMR (500 MHz, CDCl$_3$, 27° C.) 1.17 (3H, d), 1.79-1.97 (2H, m), 2.54 (1H, dd), 2.75-2.88 (3H, m), 2.95-3.03 (3H, m), 3.20-3.36 (2H, m), 4.00-4.11 (2H, m), 4.48 (1H, t), 4.57 (1H, t), 4.99 (1H, s), 7.12-7.17 (2H, m), 7.20 (1H, ddd), 7.30-7.34 (1H, m), 7.54 (1H, d), 7.92 (1H, s), 8.14 (1H, d), 8.22 (1H, d). (1 exchangeable proton not observed.) | 465 |
| 102 | 3-fluoro-N-(2-((4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | $^1$H NMR (500 MHz, CDCl$_3$, 27° C.) 1.18 (3H, d), 1.81-1.94 (2H, m), 2.54 (1H, dd), 2.71-2.82 (3H, m), 2.91-3.02 (3H, m), 3.16-3.23 (1H, m), 3.24-3.30 (1H, m), 4.33-4.42 (2H, m), 4.47 (1H, t), 4.56 (1H, t), 4.93 (1H, s), 6.48-6.62 (1H, m), 7.00 (1H, dd), 7.15 (1H, ddd), 7.20-7.25 (1H, m), 7.32-7.36 (1H, m), 7.54 (1H, d), 7.81 (1H, s), 8.09 (1H, dd). (1 exchangeable proton not observed.) | 465 |
| 103 | 2,2-difluoro-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)propan-1-ol | $^1$H NMR (500 MHz, CDCl$_3$, 27° C.) 1.17 (3H, d), 1.85-1.97 (2H, m), 2.30 (3H, s), 2.67 (1H, dd), 2.75-2.88 (3H, m), 2.98-3.08 (3H, m), 3.12-3.24 (1H, m), 3.57-3.66 (1H, m), 3.72 (2H, t), 4.44 (2H, td), 4.55 (2H, dt), 5.08 (1H, s), 6.49 (1H, d), 7.11-7.19 (2H, m), 7.21-7.25 (1H, m), 7.54 (1H, d), 7.66 (1H, s), 7.82 (1H, d). (2 exchangeables not observed.) | 491 |

TABLE G-continued

| Example | Structure | Name | 1H NMR | LCMS [M + H]+ |
|---|---|---|---|---|
| 104 | 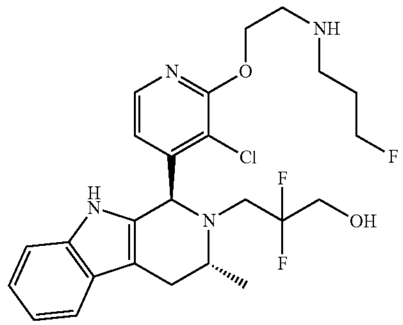 [SMILES: C[C@@H]1Cc2c([nH]c3ccccc23)[C@@H](c2ccnc(OCCNCCCF)c2Cl)N1CC(F)(F)CO] | 3-((1R,3R)-1-(3-chloro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol | $^1$H NMR (300 MHz, DMSO-d$_6$, 27° C.) 1.00 (3H, d), 1.64-1.82 (3H, m), 2.48-2.67 (4H, m), 2.78-2.90 (3H, m), 3.03-3.17 (1H, m), 3.28-3.37 (1H, m), 3.38-3.71 (2H, m), 4.31 (2H, td), 4.44 (2H, dt), 5.14-5.24 (1H, m), 5.27 (1H, s), 6.39 (1H, d), 6.88-6.94 (1H, m), 6.94-7.01 (1H, m), 7.14 (1H, d), 7.39 (1H, d), 7.84 (1H, d), 10.47 (1H, s). | 511 |
| 105 | 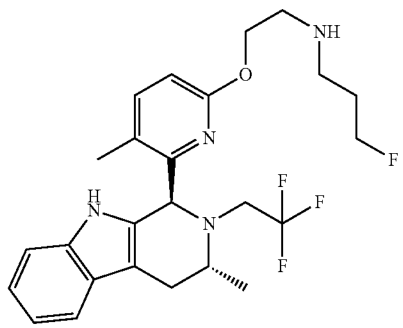 [SMILES: Cc1ccc(OCCNCCCF)nc1[C@@H]1c2[nH]c3ccccc3c2C[C@@H](C)N1CC(F)(F)F] | 3-fluoro-N-(2-((5-methyl-6-((1S,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | $^1$H NMR (500 MHz, CDCl$_3$, 27° C.) 1.19 (3H, d), 1.79-1.91 (2H, m), 2.13 (3H, s), 2.64 (1H, ddd), 2.75 (2H, t), 2.86-2.91 (2H, m), 2.95-3.05 (1H, m), 3.10 (1H, ddd), 3.15-3.25 (1H, m), 3.54-3.66 (1H, m), 4.17-4.24 (1H, m), 4.26-4.32 (1H, m), 4.51 (2H, dt), 5.13 (1H, s), 6.63 (1H, d), 7.07-7.15 (2H, m), 7.24 (1H, dt), 7.36 (1H, d), 7.49-7.53 (1H, m), 7.87 (1H, s). (1 exchangeable not observed.) | 479 |
| 106 | 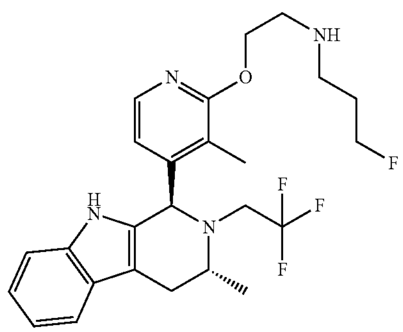 [SMILES: Cc1c([C@@H]2c3[nH]c4ccccc4c3C[C@@H](C)N2CC(F)(F)F)ccnc1OCCNCCCF] | 3-fluoro-N-(2-((3-methyl-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)propan-1-amine | $^1$H NMR (500 MHz, CDCl$_3$, 27° C.) 1.14 (3H, d), 1.82-1.96 (2H, m), 2.28 (3H, s), 2.55-2.67 (1H, m), 2.84 (2H, t), 2.93 (2H, ddt), 2.99-3.05 (2H, m), 3.13-3.28 (1H, m), 3.37-3.43 (2H, m), 4.34-4.45 (2H, m), 4.47 (1H, t), 4.57 (1H, t), 5.08 (1H, s), 6.38 (1H, d), 7.11 (1H, td), 7.15 (1H, td), 7.21-7.29 (1H, m), 7.53 (1H, d), 7.70 (1H, d), 8.44 (1H, s). | 479 |
| 107 | 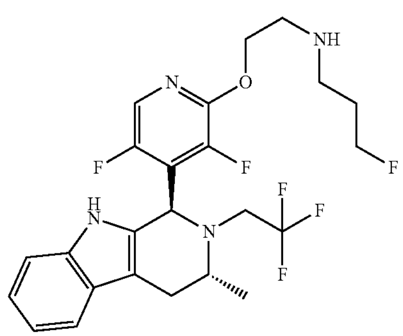 [SMILES: C[C@@H]1Cc2c([nH]c3ccccc23)[C@@H](c2c(F)cnc(OCCNCCCF)c2F)N1CC(F)(F)F] | N-(2-((3,5-difluoro-4-((1R,3R)-3-methyl-2-(2,2,2-trifluoroethyl)-2,3,4,9-tetrahydro-1H-pyrido[3,4-b]indol-1-yl)pyridin-2-yl)oxy)ethyl)-3-fluoropropan-1-amine | $^1$H NMR (500 MHz, CDCl$_3$, 27° C.) 1.20 (3H, d), 1.87 (2H, dddd), 2.65 (1H, ddd), 2.80 (2H, t), 2.95 (1H, dt), 2.99-3.09 (3H, m), 3.31 (1H, dq), 3.55 (1H, h), 4.43 (2H, ddd), 4.47 (1H, t), 4.56 (1H, t), 5.37 (1H, s), 7.12 (1H, ddd), 7.14-7.19 (1H, m), 7.24-7.28 (1H, m), 7.50-7.55 (1H, m), 7.67 | 501 |

TABLE G-continued

| Example | Structure | Name | 1H NMR | LCMS [M + H]+ |
|---|---|---|---|---|
| | | | (1H, s), 7.77 (1H, s). (1 exchangeable not observed). | |
| 108 | 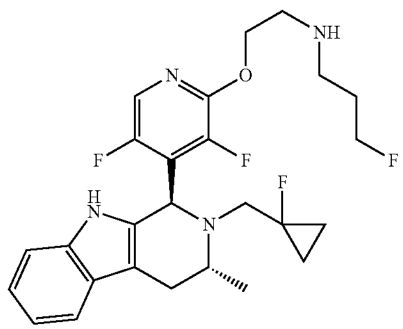 [SMILES: C[C@@H]1Cc2c([nH]c3ccccc23)[C@@H](c2c(F)cnc(OCCNCCCF)c2F)N1CC1(F)CC1] | N-(2-((3,5-difluoro-4-((1R,3R)-2-((1-fluorocyclopropyl)methyl)-3-methyl-2,3,4,9-tetrahydro-1H-pyrido[3,4-b]indol-1-yl)pyridin-2-yl)oxy)ethyl)-3-fluoropropan-1-amine | ¹H NMR (300 MHz, DMSO-d₆, 27° C.) 0.45-0.59 (2H, m), 0.79-0.96 (2H, m), 1.01 (3H, d), 1.60-1.78 (3H, m), 2.45-2.69 (4H, m), 2.75-2.85 (3H, m), 3.03 (1H, dd), 3.42-3.53 (1H, m), 4.26 (2H, t), 4.40 (2H, dt), 5.26 (1H, s), 6.85-6.92 (1H, m), 6.92-6.99 (1H, m), 7.11-7.16 (1H, m), 7.36 (1H, d), 7.88 (1H, s), 10.56 (1H, s). | 491 |
| 109 | 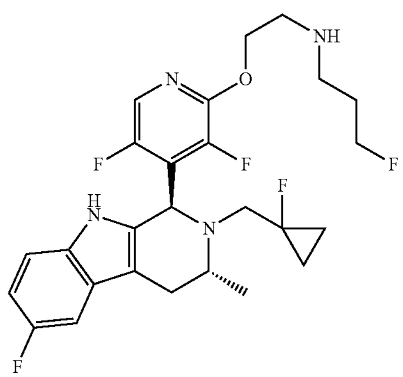 [SMILES: C[C@@H]1Cc2c([nH]c3ccc(F)cc23)[C@@H](c2c(F)cnc(OCCNCCCF)c2F)N1CC1(F)CC1] | N-(2-((3,5-difluoro-4-((1R,3R)-6-fluoro-2-((1-fluorocyclopropyl)methyl)-3-methyl-2,3,4,9-tetrahydro-1H-pyrido[3,4-b]indol-1-yl)pyridin-2-yl)oxy)ethyl)-3-fluoropropan-1-amine | ¹H NMR (300 MHz, DMSO-d₆, 27° C.) 0.44-0.60 (2H, m), 0.78-0.95 (2H, m), 1.00 (3H, d), 1.69 (3H, dsxt), 2.45-2.69 (4H, m), 2.73-2.84 (3H, m), 3.02 (1H, dd), 3.39-3.53 (1H, m), 4.26 (2H, t), 4.40 (2H, dt), 5.26 (1H, s), 6.78 (1H, td), 7.08-7.16 (2H, m), 7.89 (1H, s), 10.68 (1H, s). | 509 |
| 110 | 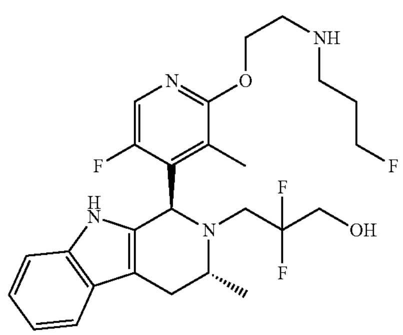 [SMILES: Cc1c(OCCNCCCF)ncc(F)c1[C@@H]1c2[nH]c3ccccc3c2C[C@@H](C)N1CC(F)(F)CO] | 2,2-difluoro-3-((1R,3R)-1-(5-fluoro-2-(2-((3-fluoropropyl)amino)ethoxy)-3-methylpyridin-4-yl)-3-methyl-1,3,4,9-tetrahydro-2H-pyrido[3,4-b]indol-2-yl)propan-1-ol | ¹H NMR (500 MHz, CDCl₃, 27° C.) 1.17 (3H, d), 1.84 (2H, dddd), 1.93 (3H, s), 2.66-2.76 (2H, m), 2.77 (2H, t), 2.96 (2H, qdd), 3.11-3.24 (2H, m), 3.51-3.69 (2H, m), 3.72-3.82 (1H, m), 4.32 (1H, ddd), 4.38-4.48 (2H, m), 4.54 (1H, t), 5.33 (1H, s), 7.07-7.16 (2H, m), 7.18-7.24 (1H, m), 7.43 (1H, s), 7.48-7.54 (1H, m), 7.88 (1H, s). (2 exchangeables not observed). | 509 |
| 111 | 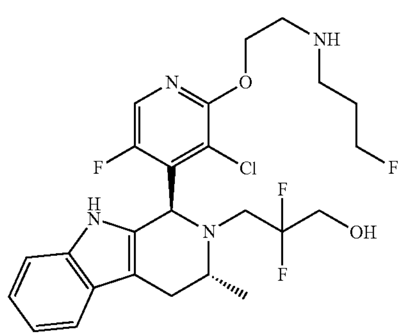 [SMILES: C[C@@H]1Cc2c([nH]c3ccccc23)[C@@H](c2c(F)cnc(OCCNCCCF)c2Cl)N1CC(F)(F)CO] | 3-((1R,3R)-1-(3-chloro-5-fluoro-2-(2-((3-fluoropropyl)amino)ethoxy)pyridin-4-yl)-3-methyl-1,3,4,9-tetrahydro-2H-pyrido[3,4-b]indol-2-yl)-2,2-difluoropropan-1-ol | ¹H NMR (500 MHz, CDCl₃, 27° C.) 1.14 (3H, d), 1.78-1.95 (2H, m), 2.54 (1H, d), 2.66-2.73 (1H, m), 2.72-2.79 (1H, m), 2.81 (2H, t), 2.92 (1H, s), 3.01 (2H, t), 3.16 (1H, ddd), 3.25 (1H, dt), 3.61-3.70 (1H, m), 3.71-3.80 (1H, m), 4.34-4.50 (3H, m), 4.55 (1H, t), 5.49 (1H, s), 7.10 (2H, tdd), 7.18 (1H, | 529 |

TABLE G-continued

| Example | Structure | Name | 1H NMR | LCMS [M + H]+ |
|---|---|---|---|---|
| | | | dd), 7.51 (1H, dd), 7.76-7.83 (1H, m), 7.95 (1H, s). (1 exchangeable not observed) | |
| 112 | 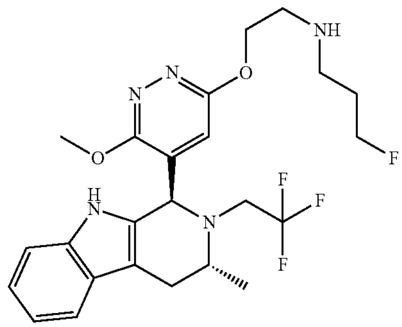 [SMILES: COc1nnc(OCCNCCCF)cc1[C@@H]1c2[nH]c3ccccc3c2C[C@@H](C)N1CC(F)(F)F] | 3-fluoro-N-(2-((6-methoxy-5-((1R,3R)-3-methyl-2-(2,2,2-trifluoroethyl)-2,3,4,9-tetrahydro-1H-pyrido[3,4-b]indol-1-yl)pyridazin-3-yl)oxy)ethyl)propan-1-amine | 1H NMR (500 MHz, CDCl$_3$, 27° C.) 1.23 (3H, d), 1.76-1.92 (2H, m), 2.56 (1H, dd), 2.67-2.84 (3H, m), 2.95 (3H, pt), 3.15-3.40 (2H, m), 4.20 (3H, s), 4.31-4.49 (3H, m), 4.52 (1H, t), 5.18 (1H, s), 6.49 (1H, s), 7.13 (1H, td), 7.19 (1H, td), 7.30-7.35 (1H, m), 7.52 (1H, d), 8.59 (1H, s). (1 exchangeable not observed). | 496 |
| 113 | 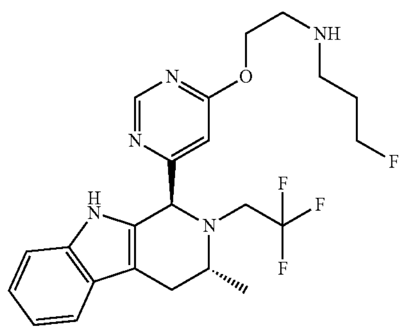 [SMILES: C[C@@H]1Cc2c([nH]c3ccccc23)[C@@H](c2cc(OCCNCCCF)ncn2)N1CC(F)(F)F] | 3-fluoro-N-(2-((6-((1S,3R)-3-methyl-2-(2,2,2-trifluoroethyl)-2,3,4,9-tetrahydro-1H-pyrido[3,4-b]indol-1-yl)pyrimidin-4-yl)oxy)ethyl)propan-1-amine | $^1$H NMR (400 MHz, DMSO-d$_6$, 27° C.) 1.24 (3H, d), 1.68-1.86 (2H, m), 1.95 (1H, s), 2.52-2.67 (4H, m), 2.87 (2H, t), 3.02-3.27 (2H, m), 3.59-3.75 (1H, m), 4.30-4.47 (3H, m), 4.54 (1H, t), 5.02 (1H, s), 6.88 (1H, s), 6.92-7.01 (1H, m), 7.02-7.11 (1H, m), 7.35 (1H, d), 7.42 (1H, d), 8.76 (1H, d), 10.77 (1H, s). | 466 |
| 114 | 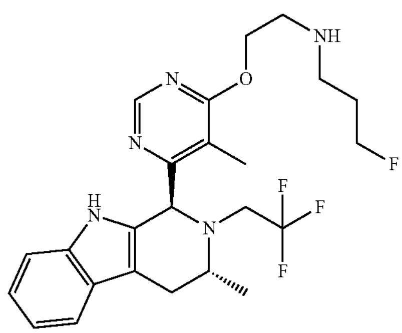 [SMILES: Cc1c(OCCNCCCF)ncnc1[C@@H]1c2[nH]c3ccccc3c2C[C@@H](C)N1CC(F)(F)F] | 3-fluoro-N-(2-((5-methyl-6-((1S,3R)-3-methyl-2-(2,2,2-trifluoroethyl)-2,3,4,9-tetrahydro-1H-pyrido[3,4-b]indol-1-yl)pyrimidin-4-yl)oxy)ethyl)propan-1-amine | $^1$H NMR (400 MHz, DMSO-d$_6$, 27° C.) 1.11 (3H, d), 1.69-1.87 (2H, m), 1.92-2.15 (4H, m), 2.59-2.71 (3H, m), 2.75-2.85 (1H, m), 2.90 (2H, t), 3.00-3.16 (1H, m), 3.47-3.69 (2H, m), 4.33-4.48 (3H, m), 4.56 (1H, t), 5.21 (1H, s), 6.92-7.07 (2H, m), 7.18-7.26 (1H, m), 7.40-7.47 (1H, m), 8.51 (1H, s), 10.50 (1H, s) | 480 |
| 115 | 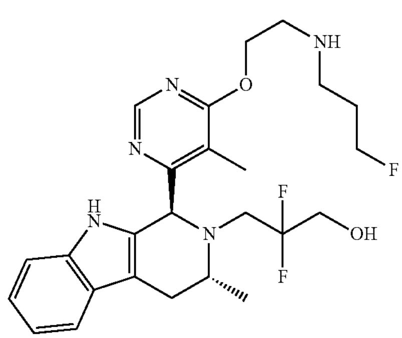 [SMILES: Cc1c(OCCNCCCF)ncnc1[C@@H]1c2[nH]c3ccccc3c2C[C@@H](C)N1CC(F)(F)CO] | 2,2-difluoro-3-((1S,3R)-1-(6-(2-((3-fluoropropyl)amino)ethoxy)-5-methylpyrimidin-4-yl)-3-methyl-1,3,4,9-tetrahydro-2H-pyrido[3,4-b]indol-2-yl)propan-1-ol | $^1$H NMR (400 MHz, DMSO-d$_6$, 27° C.) 1.10 (3H, d), 1.69-1.87 (2H, m), 2.09 (3H, s), 2.55-2.86 (5H, m), 2.90 (2H, t), 3.10-3.23 (1H, m), 3.46-3.71 (3H, m), 4.37 (2H, t), 4.44 (1H, t), 4.55 (1H, t), 5.12 (1H, s), 5.37 (1H, t), 6.92-7.06 (2H, m), 7.21 (1H, d), 7.43 (1H, d), 8.51 (1H, s), 10.46 (1H, s). (1 exchangeable proton not observed.) | 492 |

TABLE G-continued

| Example | Structure | Name | 1H NMR | LCMS [M + H]+ |
|---|---|---|---|---|
| 116 | 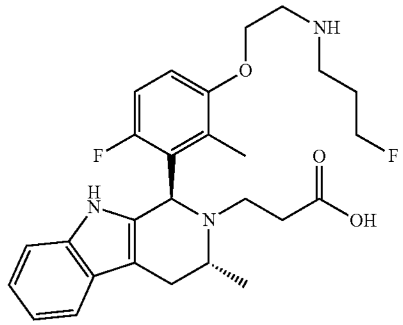 [SMILES: Cc1c(OCCNCCCF)ccc(F)c1[C@@H]1c2[nH]c3ccccc3c2C[C@@H](C)N1CCC(=O)O] | 3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid | 1H NMR (300 MHz, DMSO-d$_6$, 27° C.) 1.02 (3 H, d), 1.66-1.89 (5H, m), 1.96-2.17 (1H, m), 2.18-2.32 (1H, m), 2.53-2.70 (4H, m), 2.71-2.93 (3H, m), 2.94-3.05 (1H, m), 3.55-3.66 (1H, m), 3.86-4.06 (2H, m), 4.38 (1H, t), 4.54 (1H, t), 5.22 (1H, s), 6.87-7.11 (4H, m), 7.13-7.25 (1H, m), 7.34-7.44 (1H, m), 10.26 (1H, s). (2 exchangeable protons not observed.) | 486 |
| 118 | 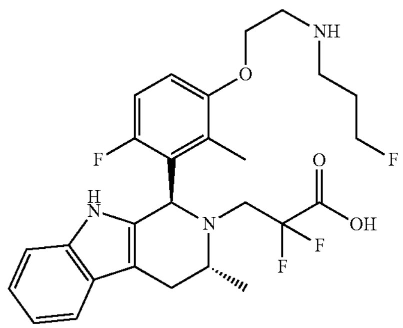 | 2,2-difluoro-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid | $^1$H NMR (300 MHz, DMSO-d$_6$, 27° C.) 1.04 (3H, d), 1.78 (3H, s), 1.90-2.10 (2H, m), 2.63 (1H, br d), 2.77-3.05 (6H, m), 3.65-3.76 (1H, m), 4.24-4.36 (1H, m), 4.37-4.58 (3H, m), 5.22 (1H, s), 6.89-7.04 (4H, m), 7.15-7.21 (1H, m), 7.35-7.43 (1H, m), 10.32 (1H, s). (Three hydrogens not observed, at least one multiplet obscured by water peak.) | 522 |
| 119 | 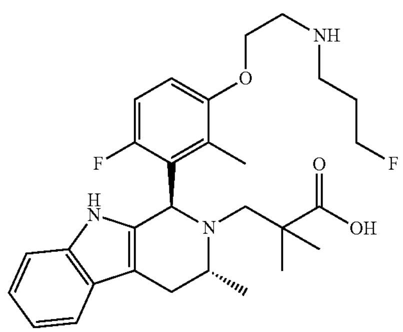 [SMILES: Cc1c(OCCNCCCF)ccc(F)c1[C@@H]1c2[nH]c3ccccc3c2C[C@@H](C)N1CC(C)(C)C(=O)O] | 3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2,2-dimethylpropanoic acid | $^1$H NMR (500 MHz, CDCl$_3$, 27° C.) 0.87 (3H, s), 1.19 (3H, d), 1.23 (3H, s), 1.82-2.03 (3H, m), 2.67-2.81 (5H, m), 2.85 (2H, t), 2.98 (1H, d), 3.13 (1H, s), 3.25 (1H, d), 3.61 (1H, s), 4.12 (1H, ddd), 4.28 (1H, s), 4.45 (1H, t), 4.55 (1H, t), 5.38 (1H, s), 6.82 (1H, dd), 6.95 (1H, t), 7.07-7.15 (2H, m), 7.16-7.21 (1H, m), 7.30 (1H, s), 7.48-7.53 (1H, m). (2 exchangeables not observed) | 514 |
| 120 | 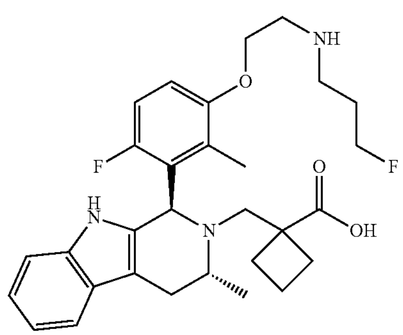 [SMILES: Cc1c(OCCNCCCF)ccc(F)c1[C@@H]1c2[nH]c3ccccc3c2C[C@@H](C)N1CC1(C(=O)O)CCC1] | 1-(((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)methyl)cyclobutane-1-carboxylic acid | 1H NMR (500 MHz, CDCl3) 1.25 (d, 3H), 1.70 (m, 2H), 1.76 (s, 3H), 1.86 (m, 2H), 1.93-2.05 (m, 2H), 2.10-2.30 (m, 2H), 2.57 (m, 1H), 2.72 (d, 1H), 2.76 (d, 1H), 3.01 (m, 1H), 3.06 (d, 1H), 3.16 (m, 2H), 3.21 (m, 1H), 3.63 (m, 1H), 4.15 (dt, 2H), 4.49 (dt, 2H), 5.36 (s, 1H), 6.79 (dd, 1H), 6.93 | 526 |

TABLE G-continued

| Example | Structure | Name | 1H NMR | LCMS [M + H]+ |
|---|---|---|---|---|
| | | | (m, 1H), 7.11 (m, 2H), 7.19 (d, 1H), 7.49 (d, 1H), 7.63 (s, 1H), 8.26 (s, 1H). (1 exchangeable not observed). | |
| 122 | 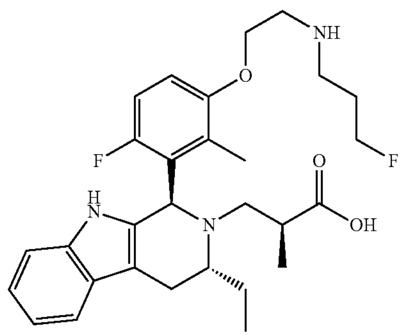 [SMILES: CC[C@@H]1Cc2c([nH]c3ccccc23)[C@@H](c2c(F)ccc(OCCNCCCF)c2C)N1C[C@H](C)C(=O)O] | (S)-3-((1R,3R)-3-ethyl-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid | $^1$H NMR (300 MHz, DMSO-d$_6$, 27° C.) 0.77 (3H, d), 0.90 (3H, t), 1.19-1.34 (1H, m), 1.65-1.93 (6H, m), 2.14-2.31 (2H, m), 2.69-3.09 (8H, m), 3.16 (1H, br d), 3.95-4.09 (2H, m), 4.47 (2H, dt), 5.27 (1H, s), 6.90-7.08 (4H, m), 7.14-7.43 (1H, m), 8.45 7.19 (1H, m), 7.38-(1H, br s), 10.29 (1H, s). | 514 |
| 123 | 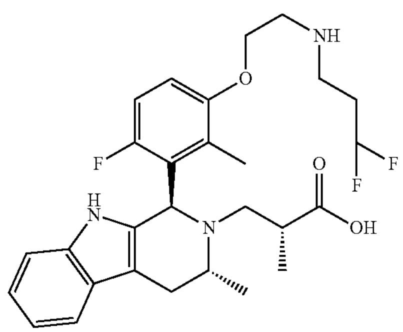 [SMILES: Cc1c(OCCNCCC(F)F)ccc(F)c1[C@@H]1c2[nH]c3ccccc3c2C[C@@H](C)N1C[C@@H](C)C(=O)O] | (R)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 1.06 (3H, d), 1.20 (3H, d), 1.80 (3H, s), 2.06 (2H, ddt), 2.49-2.63 (1H, m), 2.62-2.74 (1H, m), 2.77-2.86 (2H, m), 2.89 (2H, t), 3.03 (2H, t), 3.17-3.29 (1H, m), 3.84 (1H, p), 4.06 (2H, s), 5.35 (1H, s), 5.88 (1H, t), 6.79 (1H, dd), 6.90 (1H, d), 7.05-7.14 (2H, m), 7.18 (1H, tt), 7.50 (1H, dd), 7.62 (1H, s). (2 exchangeables not observed). | 518 |
| 125 | 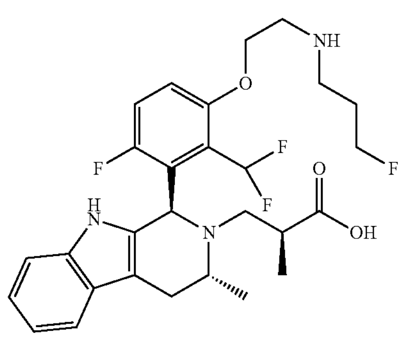 [SMILES: C[C@@H]1Cc2c([nH]c3ccccc23)[C@@H](c2c(F)ccc(OCCNCCCF)c2C(F)F)N1C[C@H](C)C(=O)O] | (S)-3-((1R,3R)-1-(2-(difluoromethyl)-6-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid | 1H NMR (500 MHz, CDCl$_3$, 27° C.) 0.94 (3H, d), 1.18 (3H, d), 1.92 (2H, ddt), 2.79 (2H, dd), 2.86 (3H, t), 3.00-3.12 (3H, m), 3.31 (1H, d), 3.62 (1H, q), 4.14 (2H, ddt), 4.50 (1H, t), 4.60 (1H, t), 5.53 (1H, s), 6.95 (1H, dd), 7.05-7.25 (4H, m), 7.20 (1H, dd), 7.41 (1H, t), 7.51 (1H, s). (2 exchangeables not observed). | 536 |

TABLE G-continued

| Example | Structure | Name | 1H NMR | LCMS [M + H]+ |
|---|---|---|---|---|
| 128 | Isomer 1, isolated as a tri-formic acid salt (structure shown) | (S)-3-((1R,3R)-1-(2,6-dichloro-3-(2-((3-fluoropropyl)amino)ethoxy)phenyl)-3-methyl-1,3,4,9-tetrahydro-2H-pyrido[3,4-b]indol-2-yl)-2-methylpropanoic acid | ¹H NMR (300 MHz, MeOH-d₄, 27° C.) 0.82-0.94 (3H, m), 1.12-1.24 (3H, m), 1.83-2.34 (3H, m), 2.40-2.64 (1H, m), 2.73 (1H, br d), 2.91-3.10 (3H, m), 3.11-3.28 (3H, m), 3.65-3.79 (1H, m), 4.11-4.31 (2H, m), 4.39 (1H, dt), 4.56 (1H, dt), 5.82 (0.5H, s), 5.89 (0.5H, s), 6.92-7.02 (2H, m), 7.06-7.19 (2H, m), 7.20-7.26 (0.5H, m), 7.37-7.42 (1H, m), 7.47 (0.5H, d). (One hydrogen not observed.) | 536 |
| 129 | Isomer 1, isolated as a tri-formic acid salt (structure shown) | 3-(((1R,3R)-1-(2,6-dichloro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid | ¹H NMR (600 MHz, MeOH-d₄, 27° C.) 0.99-1.09 (3H, m), 1.17-1.28 (3H, m), 1.94-2.16 (2H, m), 2.34-2.59 (1H, m), 2.60-2.63 (0.4H, m), 2.66-2.81 (1.6H, m), 2.82-3.28 (5H, m), 3.32-3.47 (1H, m), 3.85-3.95 (1H, m), 4.24-4.63 (4H, m), 5.80-5.85 (0.6H, m), 5.94-5.99 (0.4H, m), 6.73-6.79 (1H, m), 7.06 (1H, br d), 7.10-7.21 (2H, m), 7.23-7.28 (0.4H, m), 7.46-7.52 (0.6H, m), 8.53 (3H, br s). (Three hydrogens and formic acid OH signals not observed.) | 554 |
| 130 | Isomer 2, isolated as a tri-formic acid salt (structure shown) | 3-((1R,3R)-1-(2,6-dichloro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid | ¹H NMR (600 MHz, MeOH-d₄, 27° C.) 0.81-0.94 (3H, m), 1.12-1.19 (3H, m), 1.90-2.34 (3H, m), 2.37-2.46 (0.4H, m), 2.47-2.57 (0.6H, m), 2.65-2.72 (1H, m), 3.03 (1H, td), 3.08-3.17 (2H, m), 3.22-3.28 (1H, m), 3.32-3.39 (2H, m), 3.40-3.51 (1H, m), 3.65-3.76 (1H, m), 4.22-4.32 (1H, m), 4.37 (1H, br s), 4.40-4.46 (0.6H, m), 4.47-4.52 (0.6H, m), 4.53-4.56 (0.4H, m), 4.61-4.64 (0.4H, m), 5.80 (0.6H, br s), 5.86 (0.4H, s), 6.74 (1H, br t), 7.02-7.06 (2H, m), 7.08-7.19 (2H, m), 7.22-7.25 (0.4H, m), 7.43-7.52 (0.6H, m), 8.52 (2H, br s). (Three | 554 |

TABLE G-continued

| Example | Structure | Name | 1H NMR | LCMS [M + H]+ |
|---|---|---|---|---|
| | | | hydrogens and formic acid OH signals not observed.) | |
| 131 | 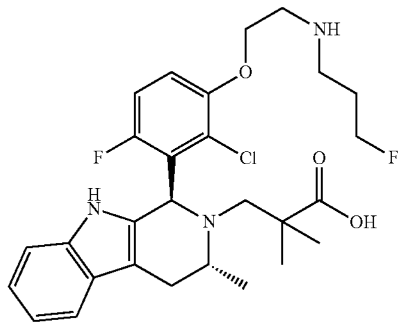 [SMILES: C[C@@H]1Cc2c([nH]c3ccccc23)[C@@H](c2c(F)ccc(OCCNCCCF)c2Cl)N1CC(C)(C)C(=O)O] | 3-((1R,3R)-1-(2-chloro-6-fluoro-3-(2-((3-fluoropropyl)amino)ethoxy)phenyl)-3-methyl-1,3,4,9-tetrahydro-2H-pyrido[3,4-b]indol-2-yl)-2,2-dimethylpropanoic acid | 1H NMR (500 MHz, DMSO, 27° C.) 0.83 (3H, s), 0.88 (3H, s), 1.06 (3H, d), 1.85 (2H, d), 2.24 (1H, d), 2.75 (2H, s), 2.87-3.07 (5H, m), 3.12 (2H, d), 4.06-4.23 (3H, m), 4.49-4.55 (1H, m), 4.56-4.63 (1H, m), 5.40 (1H, s), 6.95-7.05 (2H, m), 7.12 (1H, s), 7.19-7.24 (2H, m), 7.44 (1H, d), 10.43 (1H, s). | 534 |
| 132 | 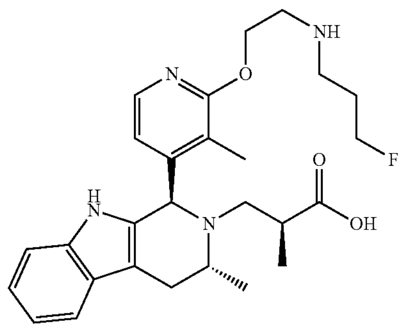 [SMILES: Cc1c([C@@H]2c3[nH]c4ccccc4c3C[C@@H](C)N2C[C@H](C)C(=O)O)ccnc1OCCNCCCF] | (S)-3-((1R,3R)-1-(2-2-((3-(fluoropropyl)amino)ethoxy)-3-methylpyridin-4-yl)-3-methyl-1,3,4,9-tetrahydro-2H-pyrido[3,4-b]indol-2-yl)-2-methylpropanoic acid | ¹H NMR (500 MHz, CDCl₃, 27° C.) 1.04 (3H, d), 1.16 (3H, d), 1.92 (2H, ddt), 2.24 (3H, s), 2.44-2.63 (2H, m), 2.67 (1H, dd), 2.85-2.92 (3H, m), 3.00 (1H, d), 3.05 (2H, s), 3.52 (1H, q), 4.38-4.47 (3H, m), 4.55 (1H, t), 5.15 (1H, s), 6.49 (1H, s), 7.09-7.18 (2H, m), 7.24 (1H, d), 7.53 (1H, d), 7.72 (1H, d), 8.40 (1H, s). (2 exchangeables not observed) | 483 |
| 133 | 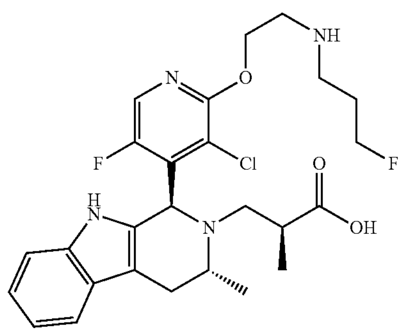 [SMILES: C[C@@H]1Cc2c([nH]c3ccccc23)[C@@H](c2c(F)cnc(OCCNCCCF)c2Cl)N1C[C@H](C)C(=O)O] | (S)-3-((1R,3R)-1-(3-chloro-5-fluoro-2-(2-((3-fluoropropyl)amino)ethoxy)pyridin-4-yl)-3-methyl-1,3,4,9-tetrahydro-2H-pyrido[3,4-b]indol-2-yl)-2-methylpropanoic acid | ¹H NMR (500 MHz, CDCl₃, 27° C.) 1.03 (3H, d), 1.23 (3H, d), 1.83-1.98 (2H, m), 2.40 (1H, s), 2.66-2.76 (2H, m), 2.87 (2H, t), 2.89-2.96 (1H, m), 3.02-3.16 (3H, m), 3.56-3.66 (2H, m), 4.43-4.54 (3H, m), 4.58 (1H, t), 5.58 (1H, s), 7.13 (1H, dd), 7.16 (1H, td), 7.24 (1H, d), 7.53 (1H, d), 7.82 (1H, s), 7.85 (1H, s). (1 exchangeable not observed). | 521 |
| 134 | 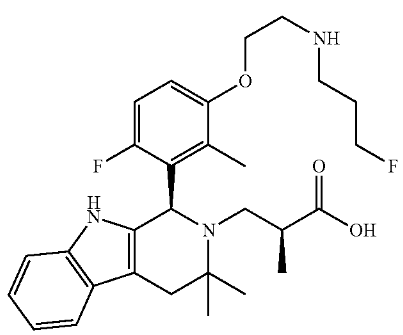 [SMILES: Cc1c(OCCNCCCF)ccc(F)c1[C@@H]1c2[nH]c3ccccc3c2CC(C)(C)N1C[C@H](C)C(=O)O] | (S)-3-((R)-1-(6-fluoro-3-(2-((3-fluoropropyl)amino)ethoxy)-2-methylphenyl)-3,3-dimethyl-1,3,4,9-tetrahydro-2H-pyrido[3,4-b]indol-2-yl)-2-methylpropanoic acid | ¹H NMR (500 MHz, CDCl₃, 27° C.) 0.87 (3H, d), 1.19-1.28 (4H, m), 1.31-1.41 (1H, m), 1.50 (3H, s), 1.77 (3H, s), 1.79-1.90 (2H, m), 2.78 (3H, q), 2.85 (1H, d), 2.87-2.97 (1H, m), 3.01 (1H, ddd), 3.05-3.14 (2H, m), 3.95-4.05 (2H, m), 4.49 (2H, dt), 5.56 (1H, s), 6.85 (1H, dd), 7.00 (1H, t), 7.10-7.18 (2H, m), 7.23 | 514 |

TABLE G-continued

| Example | Structure | Name | 1H NMR | LCMS [M + H]+ |
|---|---|---|---|---|
| | | | (1H, dd), 7.33 (1H, s), 7.47-7.52 (1H, m). (1 exchangeable not observed.) | |
| 135 | 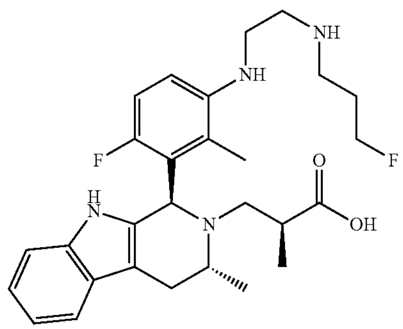 [SMILES: Cc1c(NCCNCCCF)ccc(F)c1[C@@H]1c2[nH]c3ccccc3c2C[C@@H](C)N1C[C@H](C)C(=O)O] | (S)-3-((1R,3R)-1-(6-fluoro-3-((2-((3-fluoropropyl)amino)ethyl)amino)-2-methylphenyl)-3-methyl-1,3,4,9-tetrahydro-2H-pyrido[3,4-b]indol-2-yl)-2-methylpropanoic acid | $^1$H NMR (300 MHz, MeOH-d$_4$, 27° C.) 0.91 (3H, d), 1.38 (3H, br d), 1.69-2.02 (3H, m), 2.04-2.25 (2H, m), 2.83-3.14 (3H, m), 3.16-3.25 (2H, m), 3.26-3.39 (4H, m, obsc), 3.53 (2H, t), 3.80-4.06 (1H, m), 4.56 (2H, dt), 5.82 (1H, br s), 6.85 (1H, dd), 6.97-7.12 (3H, m), 7.44 (1H, d), 7.46 (1H, d). Four hydrogens not observed. | 499 |
| 136 | 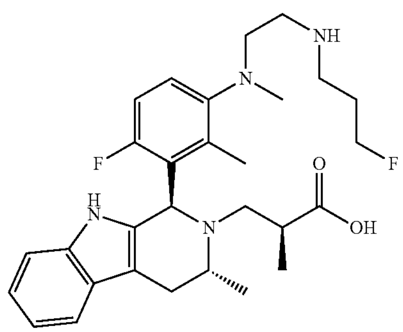 [SMILES: Cc1c(N(C)CCNCCCF)ccc(F)c1[C@@H]1c2[nH]c3ccccc3c2C[C@@H](C)N1C[C@H](C)C(=O)O] | (S)-3-((1R,3R)-1-(6-fluoro-3-((2-((3-fluoropropyl)amino)ethyl)(methyl)amino)-2-methylphenyl)-3-methyl-1,3,4,9-tetrahydro-2H-pyrido[3,4-b]indol-2-yl)-2-methylpropanoic acid | $^1$H NMR (300 MHz, MeOH-d$_4$, 27° C.) 0.81 (3H, d), 1.15 (3H, d), 1.83-2.01 (3H, m), 2.05 (3H, s), 2.45 (1H, br dd), 2.55 (3H, s), 2.62-2.74 (1H, m), 2.87-3.26 (8H, m), 3.74 (1H, br qdd), 4.44 (2H, dt), 5.45 (1H, s), 6.92-7.06 (3H, m), 7.13-7.28 (2H, m), 7.37-7.45 (1H, m). (Three hydrogens not observed.) | 513 |
| 137 | 0.5 equivalent formic acid salt | (S)-3-((1R,3S)-3-(difluoromethyl)-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid | $^1$H NMR (300 MHz, DMSO-d$_6$, 27° C.) 0.72 (3H, d), 1.63-1.93 (5H, m), 2.00-2.14 (1H, m), 2.41-2.46 (1H, m), 2.63 (2H, t), 2.80-2.97 (5H, m), 3.60-3.72 (2H, m), 3.86-4.05 (3H, m), 4.44 (2H, dt), 5.64 (1H, s), 6.24 (1H, td), 6.90-7.02 (4H, m), 7.14-7.20 (1H, m), 7.38-7.44 (1H, m), 8.18 (0.5H, s), 10.41 (1H, s). (Formic acid OH not observed.) | 536 |

TABLE G-continued

| Example | Structure | Name | 1H NMR | LCMS [M + H]+ |
|---|---|---|---|---|
| 138 | 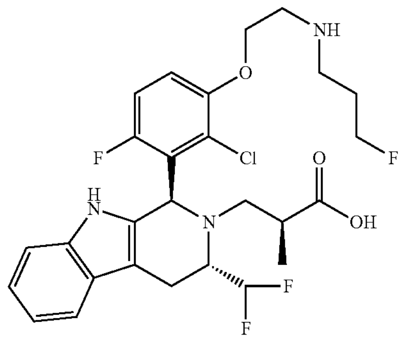 [SMILES: C[C@@H](CN1[C@H](c2c(F)ccc(OCCNCCCF)c2Cl)c2[nH]c3ccccc3c2C[C@H]1C(F)F)C(=O)O] | (S)-3-((1R,3S)-1-(2-chloro-6-fluoro-3-(2-((3-fluoropropyl)amino)ethoxy)phenyl)-3-(difluoromethyl)-1,3,4,9-tetrahydro-2H-pyrido[3,4-b]indol-2-yl)-2-methylpropanoic acid | $^1$H NMR (300 MHz, DMSO-d$_6$, 27° C.) 0.80 (3H, d), 1.76-1.93 (2H, m), 2.33-2.48 (2H, m), 2.80 (2H, br t), 2.90-2.96 (2H, m), 2.98-3.06 (2H, m), 3.56-3.72 (1H, m), 4.09-4.18 (2H, m), 4.51 (2H, dt), 5.75 (1H, s), 6.20 (1H, br td), 6.90-7.25 (6H, m), 7.41-7.46 (1H, m), 10.57 (1H, s). (Two hydrogens not observed.) | 556 |
| 139 | 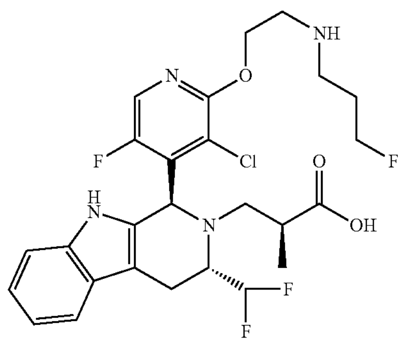 [SMILES: C[C@@H](CN1[C@H](c2c(F)cnc(OCCNCCCF)c2Cl)c2[nH]c3ccccc3c2C[C@H]1C(F)F)C(=O)O] | (S)-3-((1R,3S)-1-(3-chloro-5-fluoro-2-(2-((3-fluoropropyl)amino)ethoxy)pyridin-4-yl)-3-(difluoromethyl)-1,3,4,9-tetrahydro-2H-pyrido[3,4-b]indol-2-yl)-2-methylpropanoic acid | $^1$H NMR (300 MHz, DMSO-d$_6$, 27° C.) 0.83 (3H, d), 1.66-1.88 (2H, m), 2.35-2.48 (3H, m), 2.68 (2H, t), 2.85-3.00 (4H, m), 3.58-3.71 (1H, m), 4.36 (2H, t), 4.50 (2H, dt), 5.74 (1H, s), 6.24 (1H, td), 6.93-7.07 (2H, m), 7.17-7.21 (1H, m), 7.46 (1H, d), 8.07 (1H, s), 10.68 (1H, s). (Two hydrogens not observed.) | 557 |
| 140 | 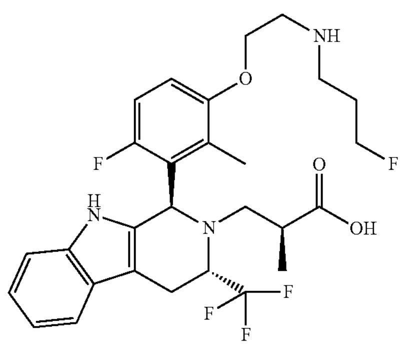 [SMILES: Cc1c(OCCNCCCF)ccc(F)c1[C@@H]1c2[nH]c3ccccc3c2C[C@@H](C(F)(F)F)N1C[C@H](C)C(=O)O] | (S)-3-((1R,3S)-1-(6-fluoro-3-(2-((3-fluoropropyl)amino)ethoxy)-2-methylphenyl)-3-(trifluoromethyl)-1,3,4,9-tetrahydro-2H-pyrido[3,4-b]indol-2-yl)-2-methylpropanoic acid | $^1$H NMR (500 MHz, CDCl$_3$, 27° C.) 0.67 (3H, d), 1.86 (3H, s), 1.89-2.02 (2H, m), 2.74 (1H, dd), 2.93 (2H, t), 3.12 (4H, dd), 3.27-3.40 (1H, m), 3.96-4.12 (2H, m), 4.12-4.25 (2H, m), 4.39 (1H, t), 4.48 (1H, t), 5.74 (1H, s), 6.73 (1H, dd), 6.88 (1H, t), 7.02-7.11 (2H, m), 7.12-7.20 (1H, m), 7.40 (1H, s), 7.45 (2H, dd). (1 exchangeable not observed). | 554 |
| 141 | 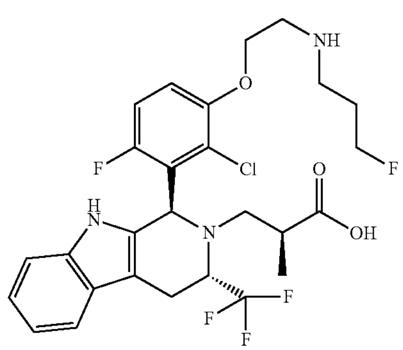 | (S)-3-((1R,3S)-1-(2-chloro-6-fluoro-3-(2-((3-fluoropropyl)amino)ethoxy)phenyl)-3-(trifluoromethyl)-1,3,4,9-tetrahydro-2H-pyrido[3,4-b]indol-2-yl)-2-methylpropanoic acid | $^1$H NMR (500 MHz, CDCl$_3$, 27° C.) 0.80-0.93 (6H, m), 1.88-2.02 (2H, m), 2.69 (1H, s), 2.86-2.99 (2H, m), 3.03-3.26 (5H, m), 3.27-3.37 (1H, m), 4.05 (1H, s), 4.13 (2H, s), 4.38-4.51 (1H, m), 4.51-4.60 (1H, m), 4.70 (2H, s), 5.87 (1H, s), 6.72-6.80 (2H, m), 7.10 (2H, td), 7.17 (1H, dd), 7.45-7.54 (1H, m), 7.70 (1H, s). | 574 |

TABLE G-continued

| Example | Structure | Name | 1H NMR | LCMS [M + H]+ |
|---|---|---|---|---|
| 142 | 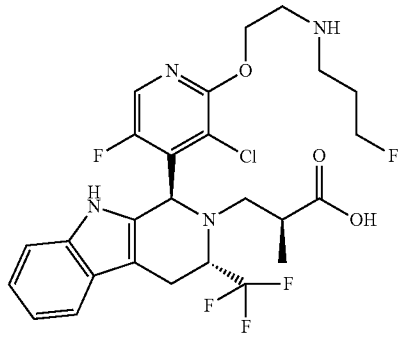 [SMILES: C[C@@H](CN1[C@H](c2c(F)cnc(OCCNCCCF)c2Cl)c2[nH]c3ccccc3c2C[C@H]1C(F)(F)F)C(=O)O] | (S)-3-((1R,3S)-1-(3-chloro-5-fluoro-2-(2-((3-fluoropropyl)amino)ethoxy)pyridin-4-yl)-3-(trifluoromethyl)-1,3,4,9-tetrahydro-2H-pyrido[3,4-b]indol-2-yl)-2-methylpropanoic acid | $^1$H NMR (500 MHz, CDCl$_3$, 27° C.) 0.92 (3H, d), 1.96 12H, d), 2.34 (1H, d), 2.59 (1H, s), 2.95 (2H, s), 3.16 (4H, d), 3.45 (1H, s), 4.01 (1H, s), 4.41 (2H, s), 4.50 (1H, s), 4.58 (1H, s), 5.82 (1H, s), 6.55-6.66 (2H, m), 7.10 (2H, dq), 7.18 (1H, d), 7.49 (1H, d), 7.61 (1H, s), 7.98 (1H, s). | 575 |
| 144 | 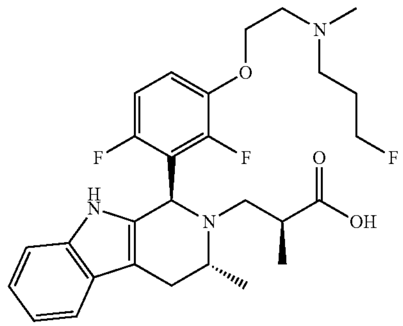 [SMILES: C[C@@H]1Cc2c([nH]c3ccccc23)[C@@H](c2c(F)ccc(OCCN(C)CCCF)c2F)N1C[C@H](C)C(=O)O] | (S)-3-((1R,3R)-1-(2,6-difluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid | $^1$H NMR (300 MHz, DMSO-d$_6$, 27° C.) 0.83 (3H, d), 1.00-1.06 (3H, m), 1.65-1.84 (2H, m), 2.15-2.28 (4H, m), 2.44 (2H, t), 2.57 (1H, br dd), 2.68 (2H, t), 2.77-2.97 (2H, m), 4.05 (2H, t), 4.44 (2H, dt), 5.15 (1H, s), 6.90-7.02 (3H, m), 7.11-7.22 (2H, m), 7.35-7.43 (1H, m), 10.56 (1H, s). (One hydrogen obscured by water, two hydrogens not observed.) | 518 |
| 146 | 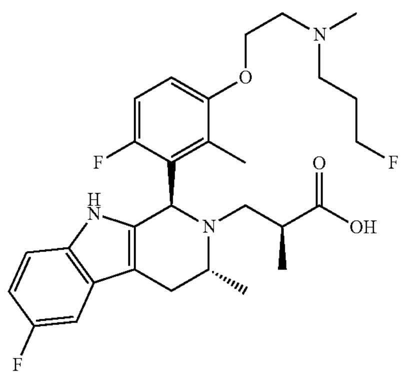 [SMILES: Cc1c(OCCN(C)CCCF)ccc(F)c1[C@@H]1c2[nH]c3ccc(F)cc3c2C[C@@H](C)N1C[C@H](C)C(=O)O] | (S)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 0.89 (3H, d), 1.25 (3H, d), 1.82 (2H, dd), 1.86-1.93 (3H, m), 2.32 (3H, s), 2.54-2.62 (2H, m), 2.63-2.86 (5H, m), 2.89 (1H, dd), 3.23 (1H, d), 3.54-3.65 (1H, m), 4.01 (2H, t), 4.41 (1H, t), 4.51 (1H, t), 5.51 (1H, s), 6.76-6.91 (2H, m), 6.94 (1H, t), 7.07-7.19 (2H, m), 7.52 (1H, s). | 532 |
| 147 | 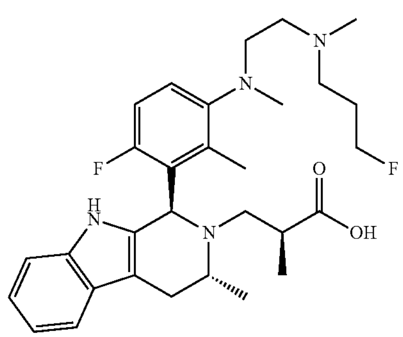 [SMILES: Cc1c(N(C)CCN(C)CCCF)ccc(F)c1[C@@H]1c2[nH]c3ccccc3c2C[C@@H](C)N1C[C@H](C)C(=O)O] | (S)-3-((1R,3R)-1-(6-fluoro-3-((2-((3-fluoropropyl)(methyl)amino)ethyl)(methyl)amino)-2-methylphenyl)-3-methyl-1,3,4,9-tetrahydro-2H-pyrido[3,4-b]indol-2-yl)-2-methylpropanoic acid | $^1$H NMR (300 MHz, MeOH-d$_4$, 27° C.) 0.84 (3H, d), 1.15-1.25 (3H, m), 1.75-2.08 (6H, m), 2.40 (3H, s), 2.54-2.58 (3H, m), 2.58-2.66 (1H, m), 2.66-2.80 (5H, m), 2.95-3.23 (4H, m), 3.68-3.81 (1H, m), 4.40 (2H, dt), 5.06 (1H, s), 5.53 (1H, br s), 6.94-7.06 (3H, m), 7.13-7.28 (2H, m), 7.33-7.51 (1H, m). (Indole NH not observed.) | 527 |

| Example | Structure | Name | 1H NMR | LCMS [M + H]+ |
|---|---|---|---|---|
| 148 | 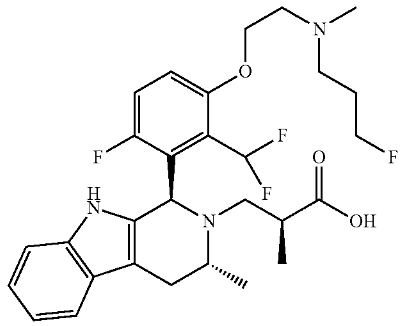 [SMILES: C[C@@H]1Cc2c([nH]c3ccccc23)[C@@H](c2c(F)ccc(OCCN(C)CCCF)c2C(F)F)N1C[C@H](C)C(=O)O] | (S)-3-((1R,3R)-1-(2-(difluoromethyl)-6-fluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 0.93 (3H, d), 1.21 (3H, d), 1.85-1.98 (2H, m), 2.37 (3H, s), 2.63 (2H, s), 2.73-2.81 (3H, m), 2.88 (2H, s), 3.17 (1H, s), 3.33-3.41 (1H, m), 3.58-3.67 (1H, m), 4.17 (2H, s), 4.54 (2H, dt), 5.60 (1H, s), 6.93-7.01 (1H, m), 7.06-7.15 (4H, m), 7.18-7.22 (1H, m), 7.39 (1H, s), 7.50-7.53 (1H, m). (1 exchangeable not observed) | 550 |
| 149 | 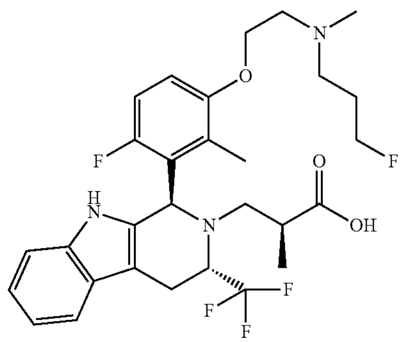 [SMILES: Cc1c(OCCN(C)CCCF)ccc(F)c1[C@@H]1c2[nH]c3ccccc3c2C[C@@H](C(F)(F)F)N1C[C@H](C)C(=O)O] | (S)-3-((1R,3S)-1-(6-fluoro-3-(2-((3-fluoropropyl)(methyl)amino)ethoxy)-2-methylphenyl)-3-(trifluoromethyl)-1,3,4,9-tetrahydro-2H-pyrido[3,4-b]indol-2-yl)-2-methylpropanoic acid | $^1$H NMR (500 MHz, CDCl$_3$, 27° C.) 0.79 (3H, d), 1.88-1.95 (2H, m), 1.98-2.06 (1H, m), 2.34-2.41 (4H, m), 2.64-2.69 (2H, m), 2.80-2.89 (4H, m), 3.13 (1H, d), 3.22 (1H, dd), 3.29-3.4 (2H, m), 4.00-4.16 (3H, m), 4.45 (2H, dt), 5.78 (1H, s), 6.81 (1H, dd), 6.93 (1H, t), 7.07-7.13 (2H, m), 7.17-7.19 (1H, m), 7.33 (1H, s), 7.45-7.49 (1H, m). (1 exchangeable not observed) | 568 |
| 150 | 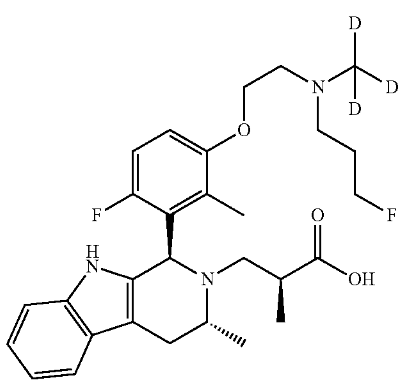 [SMILES: [2H]C([2H])([2H])N(CCCF)CCOc1ccc(F)c([C@@H]2c3[nH]c4ccccc4c3C[C@@H](C)N2C[C@H](C)C(=O)O)c1C] | (S)-3-((1R,3R)-1-(6-fluoro-3-(2-((3-fluoropropyl)(methyl-d3)amino)ethoxy)-2-methylphenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 0.90 (3H, d), 1.25 (3H, d), 1.70-1.96 (5H, m), 2.56 (2H, t), 2.70-2.82 (5H, m), 2.90 (1H, dd), 3.20-3.32 (1H, m), 3.56-3.67 (1H, m), 3.99 (2H, t), 4.42 (1H, t), 4.52 (1H, t), 5.53 (1H, s), 6.83 (1H, dd), 6.94 (1H, t), 7.06-7.18 (2H, m), 7.22 (1H, dd), 7.46 (1H, s), 7.51 (1H, dd). | 517 |
| 151 | 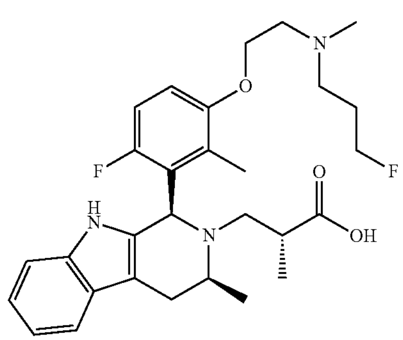 [SMILES: Cc1c(OCCN(C)CCCF)ccc(F)c1[C@@H]1c2[nH]c3ccccc3c2C[C@H](C)N1C[C@@H](C)C(=O)O] | (R)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid | $^1$H NMR (500 MHz, CDCl$_3$, 27° C.) 1.09 (3H, d), 1.21 (3H, d), 1.75-1.90 (5H, m), 2.32 (3H, s), 2.53-2.61 (3H, m), 2.68 (1H, s), 2.81 (4H, td), 3.20-3.31 (1H, m), 3.84 (1H, p), 4.02 (2H, ddq), 4.41 (1H, t), 4.51 (1H, t), 5.34 (1H, s), 6.82 (1H, dd), 6.92 (1H, t), 7.07-7.16 (2H, m), 7.17-7.22 (1H, m), 7.41 (1H, s), 7.50 (1H, dd). | 514 |

TABLE G-continued

| Example | Structure | Name | 1H NMR | LCMS [M + H]+ |
|---|---|---|---|---|
| 153 | 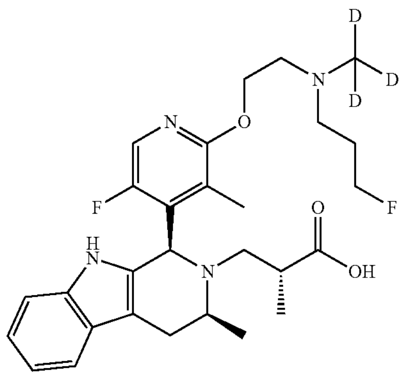 [SMILES: [2H]C([2H])([2H])N(CCCF)CCOc1ncc(F)c([C@@H]2c3[nH]c4ccccc4c3C[C@H](C)N2C[C@@H](C)C(=O)O)c1C] | (R)-3-((1R,3R)-1-(5-fluoro-2-(2-((3-fluoropropyl)(methyl-d3)amino)ethoxy)-3-methylpyridin-4-yl)-3-methyl-1,3,4,9-tetrahydro-2H-pyrido[3,4-b]indol-2-yl)-2-methylpropanoic acid | ¹H NMR (500 MHz, CDCl₃, 27° C.) 1.04 (3H, d), 1.15 (3H, d), 1.78-1.94 (5H, m), 2.46-2.56 (1H, m), 2.56-2.73 (4H, m), 2.78 (1H, d), 3.01 (1H, ddd), 3.20 (1H, ddd), 3.70 (2H, q), 4.26 (1H, ddd), 4.39 (1H, t), 4.49 (1H, t), 4.66-4.77 (1H, m), 5.26 (1H, s), 7.12 (2H, dtd), 7.22 (1H, dd), 7.51 (2H, dd), 7.89 (1H, s). | 518 |
| 154 | 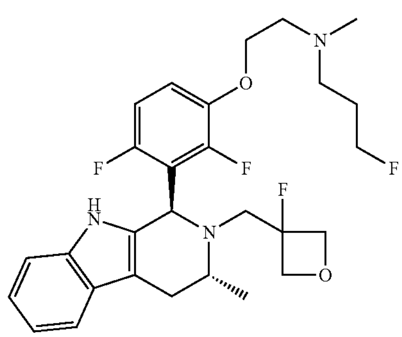 [SMILES: C[C@@H]1Cc2c([nH]c3ccccc23)[C@@H](c2c(F)ccc(OCCN(C)CCCF)c2F)N1CC1(F)COC1] | N-(2-(2,4-difluoro-3-((1R,3R)-2-((3-fluorooxetan-3-yl)methyl)-3-methyl-2,3,4,9-tetrahydro-1H-pyrido[3,4-b]indol-1-yl)phenoxy)ethyl)-3-fluoro-N-methylpropan-1-amine | ¹H NMR (300 MHz, DMSO-d₆, 27° C.) 1.10 (3H, d), 1.66-1.84 (2H, m), 2.21 (3H, s), 2.45 (2H, t), 2.58 (1H, dd), 2.67 (2H, t), 2.70-2.86 (2H, m), 3.15-3.30 (1H, m), 3.33-3.42 (1H, m), 4.05 (2H, t), 4.22-4.58 (6H, m), 5.26 (1H, s), 6.90-7.02 (3H, m), 7.11-7.22 (2H, m), 7.40 (1H, d), 10.59 (1H, s). | 520 |

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

The invention claimed is:

1. A compound of Formula (IH):

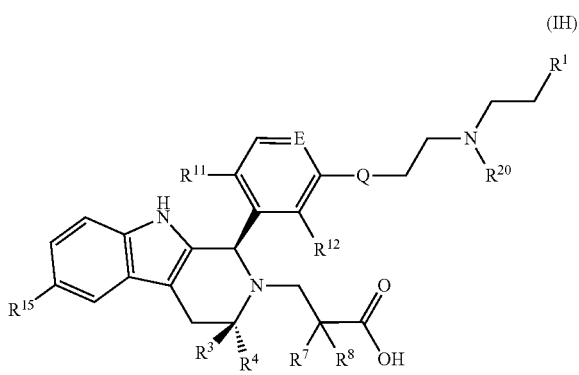

(IH)

wherein:

E is CH or N;

Q is O, NH or NMe;

$R^1$ is $CH_2F$ or $CHF_2$;

$R^3$ is H or Me;

$R^4$ is $C_{1-3}$ alkyl, $CHF_2$ or $CF_3$;

$R^7$ is H, Me or F;

$R^8$ is H, Me or F; or $R^7$ and $R^8$ taken together with the carbon atom to which they are attached form a cyclobutyl ring;

$R^{11}$ is H, F, Cl, or OMe;

$R^{12}$ is H, F, Cl, $CHF_2$, or Me;

$R^{15}$ is H or F; and $R^{20}$ is H or Me;

or a pharmaceutically acceptable salt thereof.

2. The compound of Formula (IH) or a pharmaceutically acceptable salt thereof, as claimed in claim 1, wherein E is CH.

3. The compound of Formula (IH) or a pharmaceutically acceptable salt thereof, as claimed in claim 1, wherein E is N and $R^1$ is $CH_2F$.

4. The compound of Formula (IH) or a pharmaceutically acceptable salt thereof, as claimed in claim 1, wherein the compound is a compound of Formula (IJ):

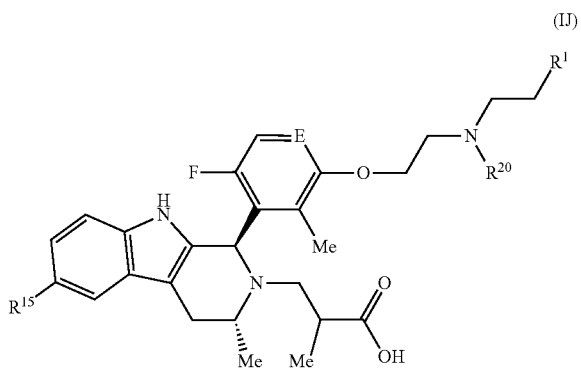

(IJ)

wherein:

E is CH or N;

$R^1$ is $CH_2F$ or $CHF_2$;

$R^{15}$ is H or F; and $R^{20}$ is H or Me.

5. The compound of Formula (IJ) or a pharmaceutically acceptable salt thereof, as claimed in claim 4, wherein $R^{15}$ is H.

6. The compound of Formula (IJ) or a pharmaceutically acceptable salt thereof, as claimed in claim 4, wherein E is N.

7. A compound of Formula (IJ) or a pharmaceutically acceptable salt thereof, as claimed in claim 4, wherein E is CH.

8. The compound of Formula (IJ) or a pharmaceutically acceptable salt thereof, as claimed in claim 4, wherein E is N and $R^1$ is $CH_2F$.

9. The compound of Formula (IJ) or a pharmaceutically acceptable salt thereof, as claimed in claim 4, wherein $R^1$ is $CH_2F$.

10. The compound of Formula (IJ) or a pharmaceutically acceptable salt thereof, as claimed in claim 4, wherein $R^1$ is $CHF_2$.

11. The compound of Formula (IH) or a pharmaceutically acceptable salt thereof, as claimed in claim 1, wherein the compound is selected from the group consisting of:

(S)-3-((1R,3R)-1-(5-(2-((3-fluoropropyl)amino)ethoxy)-2-methoxyphenyl)-3-methyl-1,3,4,9-tetrahydro-2H-pyrido[3,4-b]indol-2-yl)-2-methylpropanoic acid;

(S)-3-((1R,3R)-1-(6-chloro-2-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(2,6-difluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;

(S)-3-((1R,3R)-1-(2,6-difluoro-3-(2-((3-fluoropropyl)amino)ethoxy)phenyl)-6-fluoro-3-methyl-1,3,4,9-tetrahydro-2H-pyrido[3,4-b]indol-2-yl)-2-methylpropanoic acid;

3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid;

(R)-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid;

2,2-difluoro-3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)propanoic acid;

3-((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2,2-dimethylpropanoic acid;
1-(((1R,3R)-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)methyl)cyclobutane-1-carboxylic acid;
(R)-3-((1R,3R)-6-fluoro-1-(6-fluoro-3-(2-((3-fluoropropyl)amino)ethoxy)-2-methylphenyl)-3-methyl-1,3,4,9-tetrahydro-2H-pyrido[3,4-b]indol-2-yl)-2-methylpropanoic acid;
(S)-3-((1R,3R)-3-ethyl-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid;
(R)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid;
(S)-3-((1R,3R)-1-(3-(2-((3,3-difluoropropyl)amino)ethoxy)-6-fluoro-2-methylphenyl)-3-methyl-1,3,4,9-tetrahydro-2H-pyrido[3,4-b]indol-2-yl)-2-methylpropanoic acid;
(S)-3-((1R,3R)-1-(2-(difluoromethyl)-6-fluoro-3-(2-((3-fluoropropyl)amino)ethoxy)phenyl)-3-methyl-1,3,4,9-tetrahydro-2H-pyrido[3,4-b]indol-2-yl)-2-methylpropanoic acid;
3-((1R,3R)-1-(2-chloro-6-fluoro-3-(2-((3-fluoropropyl)amino)ethoxy)phenyl)-3-methyl-1,3,4,9-tetrahydro-2H-pyrido[3,4-b]indol-2-yl)-2,2-dimethylpropanoic acid;
(S)-3-((1R,3R)-1-(2-(2-((3-fluoropropyl)amino)ethoxy)-3-methylpyridin-4-yl)-3-methyl-1,3,4,9-tetrahydro-2H-pyrido[3,4-b]indol-2-yl)-2-methylpropanoic acid;
(S)-3-((1R,3R)-1-(3-chloro-5-fluoro-2-(2-((3-fluoropropyl)amino)ethoxy)pyridin-4-yl)-3-methyl-1,3,4,9-tetrahydro-2H-pyrido[3,4-b]indol-2-yl)-2-methylpropanoic acid;
(S)-3-((R)-1-(6-fluoro-3-(2-((3-fluoropropyl)amino)ethoxy)-2-methylphenyl)-3,3-dimethyl-1,3,4,9-tetrahydro-2H-pyrido[3,4-b]indol-2-yl)-2-methylpropanoic acid;
(S)-3-((1R,3R)-1-(6-fluoro-3-((2-((3-fluoropropyl)amino)ethyl)amino)-2-methylphenyl)-3-methyl-1,3,4,9-tetrahydro-2H-pyrido[3,4-b]indol-2-yl)-2-methylpropanoic acid;
(S)-3-((1R,3R)-1-(6-fluoro-3-((2-((3-fluoropropyl)amino)ethyl)(methyl)amino)-2-methylphenyl)-3-methyl-1,3,4,9-tetrahydro-2H-pyrido[3,4-b]indol-2-yl)-2-methylpropanoic acid;
(S)-3-((1R,3S)-3-(difluoromethyl)-1-(6-fluoro-3-(2-((3-fluoropropyl)amino)ethoxy)-2-methylphenyl)-1,3,4,9-tetrahydro-2H-pyrido[3,4-b]indol-2-yl)-2-methylpropanoic acid;
(S)-3-((1R,3S)-1-(2-chloro-6-fluoro-3-(2-((3-fluoropropyl)amino)ethoxy)phenyl)-3-(difluoromethyl)-1,3,4,9-tetrahydro-2H-pyrido[3,4-b]indol-2-yl)-2-methylpropanoic acid;
(S)-3-((1R,3S)-1-(3-chloro-5-fluoro-2-(2-((3-fluoropropyl)amino)ethoxy)pyridin-4-yl)-3-(difluoromethyl)-1,3,4,9-tetrahydro-2H-pyrido[3,4-b]indol-2-yl)-2-methylpropanoic acid;
(S)-3-((1R,3S)-1-(6-fluoro-3-(2-((3-fluoropropyl)amino)ethoxy)-2-methylphenyl)-3-(trifluoromethyl)-1,3,4,9-tetrahydro-2H-pyrido[3,4-b]indol-2-yl)-2-methylpropanoic acid;
(S)-3-((1R,3S)-1-(2-chloro-6-fluoro-3-(2-((3-fluoropropyl)amino)ethoxy)phenyl)-3-(trifluoromethyl)-1,3,4,9-tetrahydro-2H-pyrido[3,4-b]indol-2-yl)-2-methylpropanoic acid;
(S)-3-((1R,3S)-1-(3-chloro-5-fluoro-2-(2-((3-fluoropropyl)amino)ethoxy)pyridin-4-yl)-3-(trifluoromethyl)-1,3,4,9-tetrahydro-2H-pyrido[3,4-b]indol-2-yl)-2-methylpropanoic acid;
(S)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;
(S)-3-((1R,3R)-1-(2,6-difluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid;
(S)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;
(S)-3-((1R,3R)-6-fluoro-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;
(S)-3-((1R,3R)-1-(6-fluoro-3-((2-((3-fluoropropyl)(methyl)amino)ethyl)(methyl)amino)-2-methylphenyl)-3-methyl-1,3,4,9-tetrahydro-2H-pyrido[3,4-b]indol-2-yl)-2-methylpropanoic acid;
(S)-3-((1R,3R)-1-(2-(difluoromethyl)-6-fluoro-3-(2-((3-fluoropropyl)(methyl)amino)ethoxy)phenyl)-3-methyl-1,3,4,9-tetrahydro-2H-pyrido[3,4-b]indol-2-yl)-2-methylpropanoic acid;
(S)-3-((1R,3S)-1-(6-fluoro-3-(2-((3-fluoropropyl)(methyl)amino)ethoxy)-2-methylphenyl)-3-(trifluoromethyl)-1,3,4,9-tetrahydro-2H-pyrido[3,4-b]indol-2-yl)-2-methylpropanoic acid;
(S)-3-((1R,3R)-1-(6-fluoro-3-(2-((3-fluoropropyl)(methyl-d3)amino)ethoxy)-2-methylphenyl)-3-methyl-1,3,4,9-tetrahydro-2H-pyrido[3,4-b]indol-2-yl)-2-methylpropanoic acid;
(R)-3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)-2-methylpropanoic acid;
(R)-3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;
(R)-3-((1R,3R)-1-(5-fluoro-2-(2-((3-fluoropropyl)(methyl-d3)amino)ethoxy)-3-methylpyridin-4-yl)-3-methyl-1,3,4,9-tetrahydro-2H-pyrido[3,4-b]indol-2-yl)-2-methylpropanoic acid;
(2R)-3-[(1R,3R)-6-fluoro-1-[5-fluoro-2-[2-[3-fluoropropyl(methyl)amino]ethoxy]-3-methyl-4-pyridyl]-3-methyl-1,3,4,9-tetrahydropyrido[3,4-b]indol-2-yl]-2-methyl-propanoic acid;
3-((1R,3R)-6-fluoro-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid;
3-((1R,3R)-1-(5-fluoro-2-(2-((3-fluoropropyl)(methyl)amino)ethoxy)-3-methylpyridin-4-yl)-3-methyl-1,3,4,9-tetrahydro-2H-pyrido[3,4-b]indol-2-yl)propanoic acid;
(R)-3-((1R,3R)-6-fluoro-1-(6-fluoro-3-(2-((3-fluoropropyl)(methyl)amino)ethoxy)-2-methylphenyl)-3- methyl-1,3,4,9-tetrahydro-2H-pyrido[3,4-b]indol-2-yl)-2-methylpropanoic acid;

(R)-3-((1R,3R)-1-(2-(2-((3-fluoropropyl)(methyl)amino)ethoxy)-3-methylpyridin-4-yl)-3-methyl-1,3,4,9-tetrahydro-2H-pyrido[3,4-b]indol-2-yl)-2-methylpropanoic acid;

(R)-3-((1R,3R)-1-(3-(2-((3,3-difluoropropyl)amino)ethoxy)-6-fluoro-2-methylphenyl)-6-fluoro-3-methyl-1,3,4,9-tetrahydro-2H-pyrido[3,4-b]indol-2-yl)-2-methylpropanoic acid; and 3-((1R,3R)-1-(6-fluoro-3-(2-((3-fluoropropyl)(methyl)amino)ethoxy)-2-methylphenyl)-3-methyl-1,3,4,9-tetrahydro-2H-pyrido[3,4-b]indol-2-yl)propanoic acid.

12. A pharmaceutical composition comprising a compound of Formula (IH) or a pharmaceutically acceptable salt thereof, as claimed in claim 1, and a pharmaceutically acceptable excipient.

* * * * *